US007141656B2

(12) United States Patent
Rhode et al.

(10) Patent No.: US 7,141,656 B2
(45) Date of Patent: Nov. 28, 2006

(54) MHC COMPLEXES AND USES THEREOF

(75) Inventors: Peter R. Rhode, Miami, FL (US); Jin-An Jiao, Fort Lauderdale, FL (US); Martin Burkhardt, Miami, FL (US); Hing C. Wong, Fort Lauderdale, FL (US)

(73) Assignee: Altor Bioscience Corporation, Miramar, FL (US)

( * ) Notice: Subject to any disclaimer, the term of this patent is extended or adjusted under 35 U.S.C. 154(b) by 0 days.

(21) Appl. No.: 09/848,164

(22) Filed: May 3, 2001

(65) Prior Publication Data

US 2002/0034513 A1    Mar. 21, 2002

Related U.S. Application Data

(63) Continuation of application No. 09/067,615, filed on Apr. 28, 1998, now Pat. No. 6,309,645, which is a continuation of application No. 08/596,387, filed on Jan. 31, 1996, now Pat. No. 5,869,270.

(51) Int. Cl.
*C07K 16/46* (2006.01)
*C07K 14/74* (2006.01)

(52) U.S. Cl. .................. 530/403; 530/350; 530/391.7; 530/402

(58) Field of Classification Search ................ 530/350, 530/402, 403, 391.7; 435/69.7; 424/193.1
See application file for complete search history.

(56) References Cited

U.S. PATENT DOCUMENTS

| 5,130,297 | A | | 7/1992 | Sharma et al. |
| 5,194,425 | A | | 3/1993 | Sharma et al. |
| 5,260,422 | A | | 11/1993 | Clark et al. |
| 5,284,935 | A | | 2/1994 | Clark et al. |
| 5,583,031 | A | | 12/1996 | Stern |
| 5,827,737 | A | | 10/1998 | Peterson et al. |
| 5,869,270 | A | * | 2/1999 | Rhode et al. |
| 6,232,445 | B1 | | 5/2001 | Rhode et al. |

FOREIGN PATENT DOCUMENTS

| WO | WO 89/12458 | 12/1989 |
| WO | WO 92/18150 | 10/1992 |
| WO | WO 93/10220 | 3/1993 |
| WO | WO 93/09810 | 5/1993 |
| WO | WO 93/16191 A | 8/1993 |
| WO | WO 93/17095 A | 9/1993 |
| WO | WO 94/18998 | 9/1994 |
| WO | WO 94/25054 | 11/1994 |
| WO | WO 95/23814 | 9/1995 |
| WO | WO 95/23814 A | 9/1995 |
| WO | WO 96/04314 | 2/1996 |
| WO | WO 96/05228 | 2/1996 |
| WO | WO 96/40944 A | 12/1996 |
| WO | WO 97/28191 | 8/1997 |

OTHER PUBLICATIONS

Janeway et al Immunobiology, Fourth Edition, 1999, Garland Press NY London, pp. 119 and 136-137.*
Germain, RN. in Fundamental Immunology, Fourth Edition, ed. by WE Paul. Lippincott-Raven, Philadelphia. [1999] pp. 287-340.*
Kozono, et al.; *Nature*; Production of Soluble MHC Class II Proteins with Covalently Bound Single Peptides; 369:151-154; May 12, 1994.
Godeau,. et al.; *Journal of Biological Chemistry*; Purification and Ligand Binding of a Soluble Class I Major Histocompatibility Complex Module Consisting of the First Three Domains of H-2K$^d$ Fused to $\beta_2$-Microglobulin Expressed in the Baculovirus-Insect Cell System; 267:24223-242295; Dec. 5, 1992.
H. Konozo, et al., *Nature*, 369:151-154 (1994).
J. Altman, et al., *Proc. Natl. Acad. Sci, USA*, 90:10330-10334 (1993).
L. Stern, et al., *Nature*, 368:215-221 (1994).
S. Sharma, et al., *Proc. Natl. Acad. Sci. USA*, 88:11465-11469 (1991).
J. Guery, et al., *Critical Reviews in Immunology*, 13(3/4):195-206 (1993).
M. Nicolle, et al., *J. Clin. Invest.*, 93:1361-1369 (1994).
D. Harlan, et al., *Proc. Natl. Acad. Sci. USA*, 91:3137-3141 (1994).
E. Evahold, et al., *Immunology Today*, 14(12):602-609 (1993).
R. Chicz, et al., *Immunology Today*, 15(4):155-160 (1994).
R. Tisch, et al., *Proc. Natl. Acad. Sci. USA*, 91:437-438 (1994).
*Science*, 259:1691-1692 (1993).
J. Ulmer, et al., *Science*, 259:1745-1749 (1993).
H. Ploegh, et al., *Nature*, 364:16-17 (1993).
J. Brown, et al., *Nature*, 364:33-39 (1993).
D. O'Sullivan, et al., *Journal of Immunology*, 147:2663-2669 (1991).
J. Hammer, et al., *J. Exp. Med.*, 176:1007-1013 (1992).
L. Stern, et al., *Cell*, 68:465-477 (1992).
K. Webber, et al., *Molecular Immunology*, 32: 249 (1995).
Y. Reiter, et al., *The Journal of Biological Chemistry*, 269: 18327 (1994).
K. O'Neil, et al. *Science*, 249: 774-778.
Rhode, P.R., et al., *Single-Chain MHC Class II Molecules Induce T Cell Activation and Apoptosis*, The American Association of Immunologists, 1996.
U.S. Appl. No. 08/283,302, filed Jul. 29, 1994, Wong et al.
U.S. Appl. No. 08/382,454, filed Feb. 1, 1995, Rhode et al.
U.S. Appl. No. 09/766,378, filed Jan. 19, 2001, Rhode et al.
U.S. Appl. No. 09/900,379, filed Jul. 6, 2001, Rhode et al.

* cited by examiner

*Primary Examiner*—Christina Chan
*Assistant Examiner*—F. Pierre VanderVegt
(74) *Attorney, Agent, or Firm*—Peter F. Corless; Edwards Angell Palmer and Dodge LLP

(57) ABSTRACT

The present invention relates to novel complexes of major histocompatibility complex (MHC) molecules and uses of such complexes. In one aspect, the invention relates to loaded MHC complexes that include at least one MHC molecule with a peptide-binding groove and a presenting peptide non-covalently linked to the MHC protein. In another aspect, the invention features single chain MHC class II peptide fusion complexes with a presenting peptide covalently linked to the peptide binding grove of the complex. MHC complexes of the invention are useful for a variety of applications including: 1) in vitro screens for identification and isolation of peptides that modulate activity of selected T cells, including peptides that are T cell receptor antagonists and partial agonists, and 2) methods for suppressing or inducing an immune response in a mammal.

28 Claims, 69 Drawing Sheets

FIG. 1A
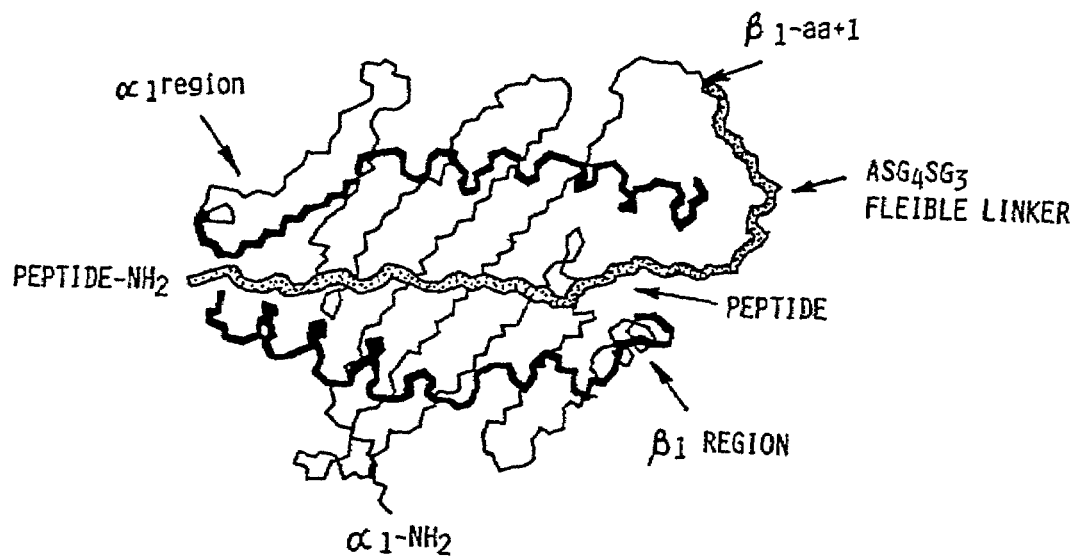
FIG. 1B
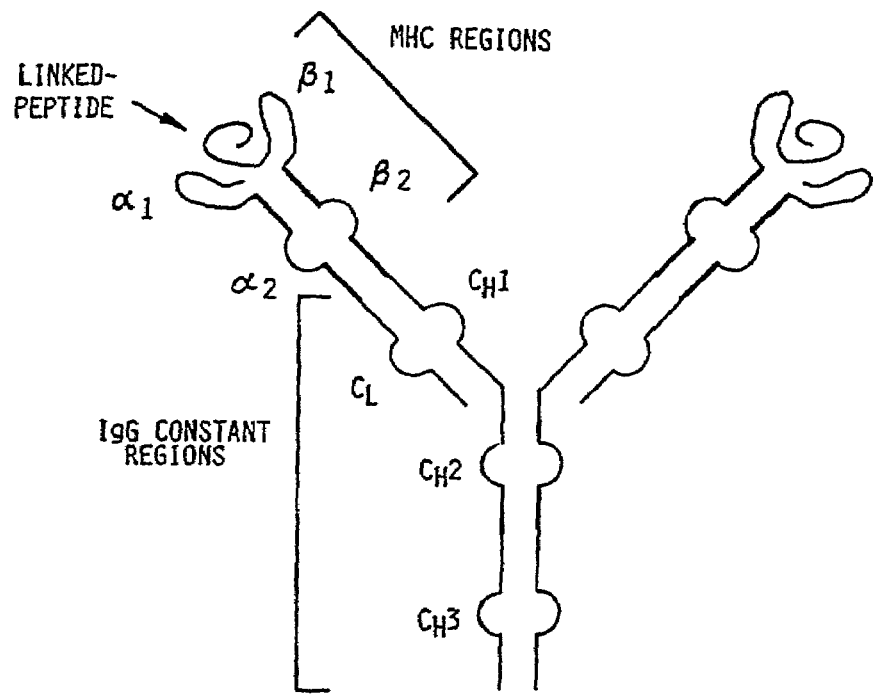
FIG. 1C

I-A$^d$/I-A$^s$ PCR PRIMERS AND CLONING OLIGONUCLEOTIDES
(RESTRICTION SITE ARE UNDERLINED).

OPR100
5'-GGG GGG GC<u>C ATG G</u>CC GAA GAC GAC GAC ATT GAG GCC GAC-3'

OPR101
5'-GCG GCG <u>ACT AGT</u> CCA GTG TTT CAG AAC CGG CTC-3'

OPR107
5'-CCC CCC <u>GAT ATC</u> TCA GCT TCC AGC AGT GGA GAC GAC ATT GAG GCC G-3'

OPR108
5'-CCC CCC <u>CGG CCG</u> CTA CTT ACG TTT CCA GTG TTT CAG AAC CGG C-3'

OPR102
5'-GGG GGG <u>GCC ATG G</u>CC GGA AAC TCC GAA AGG CAT TTC G-3'

OPR104
5'-GCG GCG <u>ACT AGT</u> CCA CTC CAC AGT GAT GGG GC-3'

OPR106
5'-CCC CCC <u>CGG CCG</u> TAC CTG AGG ACC ACT CCA CAG TGA TGG-3'

OPR112
5'-CCC CCC <u>GAT ATC</u> ACA GGT GTC TTA AGT GCT AGC GGA GGG GGC GGA AGC GGC GGA GGG GGA AAC TCC GAA AGG CAT TTC-3'

OPR119
5'-<u>AGC</u> TTG ATA TCA CAG GTG TCT TAA GTG GA<u>G</u>-3'.

OPR120-2
5'-<u>CTA GCT</u> CCA CTT AAG ACA CCT GTG ATA TC<u>A</u>-3'

VW310
5'-TCC GGA GGC GGC GGA GAC TCC GAA AGG CAT TTC G-3'

VW309
5'-CGA TCG <u>CTA GCG</u> GCG GTG GTG GTT CCG GTG GCG GCG GAG-3'

OPR136
5'-CCC CCC <u>AGG CTT</u> <u>CCC GGG</u> CCA CCA TGC CGT GCA GCA GAG CTC TG-3'

OPR139
5'-CCC CCC <u>GAG CTC</u> <u>GAA TTC</u> TCA TAA AGG CCC TGG GTG TCT G-3'

OPR132
5'-CCC CCC <u>AAG CTT</u> <u>CCC GGG</u> CCA CCA TGG CTC TGC AGA TCC CAG C-3'

OPR133
5'-CCC CCC <u>ACT TAA GGT</u> CCT TGG GCT GCT CAG CAC C-3'

OPR134
5'-CCC CCC <u>CCA TCA CTG TGG</u> AGT GGA GGG-3'

OPR135
5'-CCC CCC <u>GAG CTC</u> <u>GAA TTC</u> TCA CTG CAG GAG CCC TGC TGG-3'

FIG. 8A

HLA-DRI PCR PRIMERS AND CLONING OLIGONUCLEOTIDES.

DRIA-F
5'-GGG GGG AAG CTT ATG ATC AAA GAA GAA CAT GTG ATC ATC-3'

DRIA-B
5'-GCG GCG GGA TCC GTT CTC TGT AGT CTC TGG GAG AGG-3'

DRIB-F
5'-GGG GGG AAG CTT ATG GGG GAC ACC CGA CCA CGT TTC TTG TGG CAG C-3'

AF-N
5'-GGG GGG GCC ATG GCC ATC AAA GAA GAA CAT GTG ATC ATC-3'

AB-S
5'-GCG GCG ACT AGT GTT CTC TGT AGT CTC TGG GAG AGG-3'

OPR124
5'-GGG GGG AAG CTT GAT ATC TCA GCT TCC AGC AGT AGT ATC AAA GAA GAA CAT GTG ATC-3'

OPR125
5'-GGG GGG CGG CCG CTA CTT ACG TTT CTC TGG GAG AGG GCT TGG AGC-3'

DRIB-B
5'-GCG GCG GGA TCC CTT GCT CTG TGC AGA TTC AGA CC-3'

BF-NN
5'-GGG GGG GCC ATG GCC GGA TCC GCT AGC GGG GAC ACC CGA CCA CGT TTC TTG-3'

BB-S
5'-GCG GCG ACT AGT CTT GCT CTG TGC AGA TTC AGA CCG-3'

OPR121
5'-GTT GTC TTA AGT GGA GCT AGC GGA GGG GGC GGG TCC GGA GGT GGT GGG GAC ACC CG-3'

OPR122
5'-GAA ATG ACA TTC AAA CTT CAG CTG CCA CAA GAA ACG TGG TCG GGT GTC CCC ACC ACC-3'

OPR123
5'-GGG GGG CGG CCG TAC CTG AGG ACT TGC TCT GTG CAG ATT CAG-3'

FIG. 8B

PEPTIDE OLIGONUCLEOTIDES.

Ova 323-339
OPR110
5'-TTA AGT ATC TCT CAG GCT GTT CAC GCT GCT CAC GCT GAA ATC AAC GAA GCT GGT CGT G-3'

OPR111
5'-CTA GCA CGA CCA GCT TCG TTG ATT TCA GCC TGA GCA GCG TGA ACA GCC TGA GAG ATA C-3'

Ova H331R
OPR115
5'-TTA AGT ATC TCT CAG GCT GTT CAC GCT GCT CGG GCT GAA ATC AAC GAA GCT GGT CGT G-3'

OPR116
5'-CTA GCA CGA CCA GCT TCG TTG ATT TCA GCC CGA GCA GCG TGA ACA GCC TGA GAG ATA C-3'

Ova A332Y
OPR117
5'-TTA AGT ATC TCT CAG GCT GTT CAC GCT GCT CAC TAC GAA ATC AAC GAA GCT GGT CGT G-3'

OPR116
5'-CTA GCA CGA CCA GCT TCG TTG ATT TCA TAG TGA GCA GCG TGA ACA GCC TGA GAG ATA C-3'

HEL 74-86
OPR140
5'-TTA AGT AAC CTG TGC AAC ATC CCC TGC AGC GCC CTG CTG AGC TCC G-3'

OPR141
5'-CTA GCG GAG CTC AGC AGG GCG CTG CAG GGG ATG TTG CAC AGG TTA C-3'

NP 404-415
OPR128
5'-TTA AGT CAG ATC AGC GTG CAG CCC GCC TTC AGC GTG CAG G-3'

FIG. 8C

OPR129
5'-<u>CTA GCC</u> TGC ACG CTG AAG GCG GGC TGA ACG CTG ATC TGA <u>C</u>-3'

HA 307-319
OPR130
5'-<u>TTA AGT</u> CCC AAG TAC GTG AAG CAG AAC ACC CTG AAG CTG GCC ACC <u>G</u>-3'

OPR131
5'-<u>CTA GCG</u> GTG GCC AGC TTC AGG GTG TTC TGC TTC ACG TAC TTG GGA <u>C</u>-3'

MBP 91-103
VW315
5'-<u>TTA AGT</u> CAC TAT GGC TCC CTG CCG CAG AAG TCC CAG CAC GGG CGC <u>G</u>-3'

VW316
5'-<u>CTA GCG</u> CGC CCG TGC TGG GAC TTC TGC GGC AGG GAG CCA TAG TGA <u>C</u>-3'

PLP 139-151
VW313
5'-<u>TTA CAT</u> CAC TCC CTG GGC AAG TGG CTG GGC CAC CCG GAC AAG TTC <u>G</u>-3'

VW314
5'-<u>CTA GCG</u> AAC TTG TTC GGG TGG CCC AGC CAC TTG CCC AGG GAG TGA <u>C</u>-3'

MBP 1-14
VW317
5'-<u>TTA AGT</u> ATG GCA TCC CAG AAG CGC CCG TCC CAG CGC TCC AAG TAC CTG <u>G</u>-3'

VW316
5'-<u>CTA GCC</u> AGG TAC TTG GAG CGC TGG GAC GGG CGC TTC TGG GAT GCC ATA <u>C</u>-3'

FIG. 8D

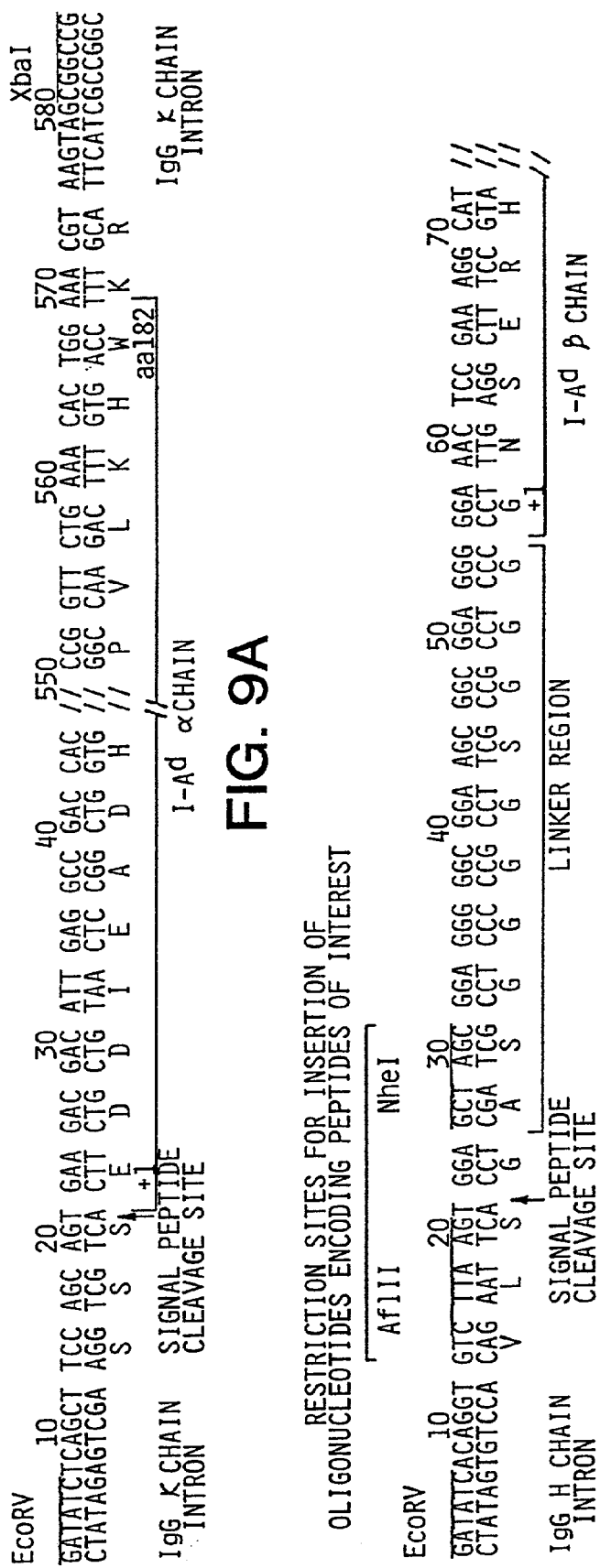

FIG. 9C

```
EcoRV
        10           20            30            40              550          560          570        XbaI
                                                                                                      580
GATATCTCAGCT TCC AGC AGT GAA GAC ATT GAG GAC CAC CCG GTT CTG AAA CAC TGG AAA AGTAGCGGCCG
CTATAGAGTCGA AGG TCG TCA CTT CTG TAA CTC CGG GTG // GGC CAA GAC TTT GTG ACC TGG GCA TTCATCGGCCGG
              S   S   S   E   D   I   E   D   H   P   V   L   K   H   W   K   R
IgG κ CHAIN        +1                                                                                 IgG κ CHAIN
INTRON           SIGNAL PEPTIDE                                                                       INTRON
                 CLEAVAGE SITE
                                                    I-AS α CHAIN                         aa182
```

RESTRICTION SITES FOR INSERTION OF
                  OLIGONUCLEOTIDES ENCODING PEPTIDES OF INTEREST

FIG. 9D

```
EcoRV           AflIII         NheI
        10           20            30            40            50            60            70
GATATCACAGGT GTC TTA AGT GGA GCT AGC GGT GGT TCC GGT GGC GGA GGC TCC GAA AGG CAT //
CTATAGTGTCCA CAG AAT TCA CCT CGA TCG CCA CCA AGG CCA CCG CCT CCG AGG CTT TCC GTA //
              V   L   S   G   A   S   G   G   S   G   G   G   G   S   E   R   H
                 SIGNAL PEPTIDE                                                         I-AS β CHAIN
                 CLEAVAGE SITE             LINKER REGION

XbaI
     610         620          630
ATC ACT GTG GAG CTC TGG TCC TCA GGT ACGGGCCGCC
TAG TGA CAC CTC GAG ACC AGG AGT CCA TGCCGGCGG
 I   T   V   E   L   W   S   S
                                              IgG H CHAIN
                                              INTRON
                           aa189
 I-AS β CHAIN
```

| PRIMER LIST | SEQUENCE |
|---|---|
| PMC-33 | [5'GCTCAGCTGTCTTGTTTCAGTACTGATC3'] |
| PMC-77 | [5'GTAAGTAGCGGCCG3'] |
| PMC-111 | [5'GGTATGTAAAAATAAACATCACAG3'] |
| PMC-114 | [5'GCTTTGCTTACGGAGTTACTC3'] |

```
        XbaI
              10              20              30              40              50
        CCCGGGCCAC C ATG CCG TGC AGC AGA GCT CTG ATT CTG GGG GTC CTC GCC
        GGGCCCGGTG G TAC GGC ACG TCG TCT CGA GAC TAA GAC CCC CAG GAG CGG
                     M   P   C   S   R   A   L   I   L   G   V   L   A
                                    I-Aᵈ α CHAIN SIGNAL PEPTIDE
            KOZAK
          CONSENSUS 60              70              80              90
        CTG AAC ACC ATG CTC AGC CTC TGC GGA GGT GAA GAC GAC ATT GAG //
        GAC TTG TGG TAC GAG TCG GAG ACG CCT CCA CTT CTG CTG TAA CTC //
         L   N   T   M   L   S   L   C   G   G   E   D   D   I   E
                                                ↑ +1
        ──────────────────────────────  ─────────────────────────────
        I-Aᵈ α CHAIN SIGNAL PEPTIDE     SIGNAL PEPTIDE
                                       CLEAVAGE SITE
                                                                  EcoRI
              750             760             770             780
        CGA TCA GGT GGC ACC TCC AGA CAC CCA GGG CCT TTA TGA GAATTC
        GCT AGT CCA CCG TGG AGG TCT GTG GGT CCC GGA AAT ACT CTTAAG
         R   S   G   G   T   S   R   H   P   G   P   L   *
                                                        STOP
        ────────────────────────────────────────
                  I-Aᵈ α CHAIN
                                FIG. 18A
```

```
              HindIII XmaI
                    10            20          30          40          50
              AAGCTTCCCG GGCCACC ATG GCT CTG CAG ATC CCC AGC CTC CTC CTC TCA GCT
              TTCGAAGGGC CCGGTGG TAC CGA GAC GTC TAG GGG TCG GAG GAG GAG ACT CGA
                                  M   A   L   Q   I   P   S   L   L   L   S   A
                  KOZAK             I-A^d β CHAIN SIGNAL PEPTIDE
                CONSENSUS AflII
                   60          70          80          90           100
              GCT GTG GTG GTG CTG ATG GTG CTG AGC AGC CCA AGG ACC TTA AGT ATC
              CGA CAC CAC CAC GAC TAC CAC GAC TCG TCG GGT TCC TGG AAT TCA TAG
               A   V   V   V   L   M   V   L   S   S   P   R   T   L   S   I
                     I-A^d β CHAIN SIGNAL PEPTIDE              SIGNAL PEPTIDE
                                                               CLEAVAGE SITE 110         120         130         140
              TCT CAG GCT GTT CAC GCT GCT CAC GCT GAA ATC AAC GAA GCT GGT CGT
              AGA GTC CGA CAA GTG CGA CGA GTG CGA CTT TAG TTG CTT CGA CCA GCA
               S   Q   A   V   H   A   A   H   A   E   I   N   E   A   G   R
                                            Ova PEPTIDE NheI
              150         160         170         180         190
              GCT AGC GGA GGG GGC GGA AGC GGC GGA GGG GGA AAC TCC GAA AGG //
              CGA TCG CCT CCC CCG CCT TCG CCG CCT CCC CCT TTG AGG CTT TCC //
               A   S   G   G   G   G   S   G   G   G   G   N   S   E   R  //
                                                         +1
                         LINKER REGION                  I-A^d β CHAIN EcoRI    SacI
              870         880         890          900
              CCT CCT CCA GCA GGG CTC CTG CAG TGA GAATTCGAGCTC
              GGA GGA GGT CGT CCC GAG GAC GTC ACT CTTAAGCTCGAG
               P   P   P   A   G   L   L   Q   *
                                                STOP
                              I-A^d β CHAIN

FIG. 18B
```

OPR132
I-A$^d$ β signal peptide front primer with Kozak consensus for CellTech vector - HindIII/XmaI sites
5'-CCC CCC <u>AAG CTT</u> <u>CCC GGG</u> CCA CCA TGG CTC TGC AGA TCC CAG C-3'

OPR133
I-A$^d$ β signal peptide back primer with Kozak consensus for CellTech vector - AflII site
5'-CCC CCC <u>ACT TAA</u> GGT CCT TGG·GCT GCT CAG CAC C-3'

OPR134
I-A$^d$ β transmembrane front primer for CellTech vector - BstXI sites
5'-CCC CCC <u>CCA</u> TCA CTG <u>TGG</u> AGT GGA GGG-3'

OPR135
I-A$^d$ β transmembrane back primer for CellTech vector - SstI, EcoRI sites
5'-CCC CCC <u>GAG CTC</u> <u>GAA TCC</u> TCA CTG CAG GAG CCC TGC TGG-3'

OPR136
I-A$^d$ α signal peptide front primer with Kozak consensus for CellTech vector - HindIII/XmaI sites
5'-CCC CCC <u>AAG CTT</u> <u>CCC GGG</u> CCA CCA TGC CGT GCA GCA GAG CTC TG-3'

OPR139
I-A$^d$ α transmembrane primer for CellTech vector - SstI/EcoRI sites
5'-CCC CCC <u>GAG CTC</u> <u>GAA TCC</u> TCA TAA AGG CCC TGG GTG TCT G-3'

B7-1-2F
Murine B7-1 front primer with Kozak consensus for CloneTech vector - NotI site
5'-CCC CCC <u>CCG CGG CCG CCC</u> CAC CAT GGG ACT GAG TAA CAT TCT C-3'

B7-1-2B
Murine B7-1 BACK primer for CloneTech vector - NotI site
5'-CCC CCC <u>GCG GCC GCT</u> TTA AAA ACA TGT ATC ACT TTT-3'

FIG. 20

JLA-005
5'-CCCCCCGCCATGGCCGCTAGCGGAGGGGGCGGAAGC-3'

JLA-007
5'-CCCGGGGCCTCGAGTGAAGACGACATTGAGGCCGAC-3'

JLA-009
5'-CCCCCCACTAGTCCACTCCACAGTGATGGGGCT-3'

JLA-010
5'-CCCCCCCCCGGGACCAGTGTTTCAGAACCGGCTCCTC-3'

JLA-301
5'-TCGAGGAACCGCCACCGCCAGAACCGCCGCCACCGGA-
ACCACCACCGCCGCTGCCACCGCCACCA-3'

JLA-302
5'-CTAGTGGTGGCGGTGGCAGCGGCGGTGGTGGTTCCGG-
TGGCGGCGGTTCTGGCGGTGGCGGTTCC-3'

OPR-142
5'-CTTGGGAATCTTGACTAAGAGG-3'

JS-305
5'-CAGGTCGAATTCTCATTCCATCGGCATGTACTCTTCTT-
CCTCCCAGTGTTTCAGAACCGG-3'

FIG.26

```
       10           20           30           40           50
        *            *            *            *            *
CCACC ATG GCT CTG CAG ATC CCC AGC CTC CTC CTC TCA GCT GCT GTG GTG
GGTGG TAC CGA GAC GTC TAG GGG TCG GAG GAG GAG AGT CGA CGA CAC CAC
       M   A   L   Q   I   P   S   L   L   L   S   A   A   V   V>
      <--------------- I-Ad β-CHAIN LEADER ---------------------

60           70           80           90
        *            *            *            *
GTG CTG ATG GTG CTG AGC AGC CCA AGG ACC TTA AGT ATC TCT CAG GCT
CAC GAC TAC CAC GAC TCG TCG GGT TCC TGG AAT TCA TAG AGA GTC CGA
 V   L   M   V   L   S   S   P   R   T   L   S   I   S   Q   A>
-----------------------------------------------------------------

100          110          120          130          140
   *            *            *            *            *
GTT CAC GCT GCT CAC GCT GAA ATC AAC GAA GCT GGT CGT GCT AGC GGA
CAA GTG CGA CGA GTG CGA CTT TAG TTG CTT CGA CCA GCA CGA TCG CCT
 V   H   A   A   H   A   E   I   N   E   A   G   R   A   S   G>
------ OVA 323-339 ---------------------------><----------

150          160          170          180          190
        *            *            *            *            *
GGG GGC GGA AGC GGC GGA GGG GGA AAC TCC GAA AGG CAT TTC GTG GTC
CCC CCG CCT TCG CCG CCT CCC CCT TTG AGG CTT TCC GTA AAG CAC CAG
 G   G   G   S   G   G   G   G   N   S   E   R   H   F   V   V>

-- 10 AMINO ACID LINKER--><-------- I-Ad β-1 DOMAIN ----------

200          210          220          230          240
        *            *            *            *            *
CAG TTC AAG GGC GAG TGC TAC TAC ACC AAC GGG ACG CAG CGC ATA CGG
GTC AAG TTC CCG CTC ACG ATG ATG TGG TTG CCC TGC GTC GCG TAT GCC
 Q   F   K   G   E   C   Y   Y   T   N   G   T   Q   R   I   R>
-----------------------------------------------------------------

250          260          270          280          290
        *            *            *            *            *
CTC GTG ACC AGA TAC ATC TAC AAC CGG GAG GAG TAC GTG CGC TAC GAC
GAG CAC TGG TCT ATG TAG ATG TTG GCC CTC CTC ATG CAC GCG ATG CTG
 L   V   T   R   Y   I   Y   N   R   E   E   Y   V   R   Y   D>
-----------------------------------------------------------------
```

FIG.27A

```
      300            310            320            330
       *              *              *              *
AGC GAC GTG GGC GAG TAC CGC GCG GTG ACC GAG CTG GGG CGG CCA GAC
TCG CTG CAC CCG CTC ATG GCG CGC CAC TGG CTC GAC CCC GCC GGT CTG
 S   D   V   G   E   Y   R   A   V   T   E   L   G   R   P   D>
----------------------------------------------------------------

340            350            360            370            380
   *              *              *              *              *
GCC GAG TAC TGG AAC AGC CAG CCG GAG ATC CTG GAG CGA ACG CGG GCC
CGG CTC ATG ACC TTG TCG GTC GGC CTC TAG GAC CTC GCT TGC GCC CGG
 A   E   Y   W   N   S   Q   P   E   I   L   E   R   T   R   A>
----------------------------------------------------------------

390            400            410            420            430
   *              *              *              *              *
GAG GTG GAC ACG GCG TGC AGA CAC AAC TAC GAG GGG CCG GAG ACC AGC
CTC CAC CTG TGC CGC ACG TCT GTG TTG ATG CTC CCC GGC CTC TGG TCG
 E   V   D   T   A   C   R   H   N   Y   E   G   P   E   T   S>
----------------------------------------------------------------

440            450            460            470            480
   *              *              *              *              *
ACC TCC CTG CGG CGG CTT GAA CAG CCC AAT GTC GCC ATC TCC CTG TCC
TGG AGG GAC GCC GCC GAA CTT GTC GGG TTA CAG CGG TAG AGG GAC AGG
 T   S   L   R   R   L   E   Q   P   N   V   A   I   S   L   S>
---  I-Ad β-1 DOMAIN  -><-------  I-Ad β-2 DOMAIN  -------------

490            500            510            520            530
   *              *              *              *              *
AGG ACA GAG GCC CTC AAC CAC CAC AAC ACT CTG GTC TGT TCG GTG ACA
TCC TGT CTC CGG GAG TTG GTG GTG TTG TGA GAC CAG ACA AGC CAC TGT
 R   T   E   A   L   N   H   H   N   T   L   V   C   S   V   T>
----------------------------------------------------------------

540            550            560            570
       *              *              *              *
GAT TTC TAC CCA GCC AAG ATC AAA GTG CGC TGG TTC AGG AAT GGC CAG
CTA AAG ATG GGT CGG TTC TAG TTT CAC GCG ACC AAG TCC TTA CCG GTC
 D   F   Y   P   A   K   I   K   V   R   W   F   R   N   G   Q>
----------------------------------------------------------------
```

FIG. 27B

```
     580           590           600           610           620
      *             *             *             *             *
GAG GAG ACA GTG GGG GTC TCA TCC ACA CAG CTT ATT AGG AAT GGG GAC
CTC CTC TGT CAC CCC CAG AGT AGG TGT GTC GAA TAA TCC TTA CCC CTG
 E   E   T   V   G   V   S   S   T   Q   L   I   R   N   G   D>
------------------------------------------------------------------

630           640           650           660           670
      *             *             *             *             *
TGG ACC TTC CAG GTC CTG GTC ATG CTG GAG ATG ACC CCT CAT CAG GGA
ACC TGG AAG GTC CAG GAC CAG TAC GAC CTC TAC TGG GGA GTA GTC CCT
 W   T   F   Q   V   L   V   M   L   E   M   T   P   H   Q   G>
------------------------------------------------------------------

680           690           700           710           720
      *             *             *             *             *
GAG GTC TAC ACC TGC CAT GTG GAG CAT CCC AGC CTG AAG AGC CCC ATC
CTC CAG ATG TGG ACG GTA CAC CTC GTA GGG TCG GAC TTC TCG GGG TAG
 E   V   Y   T   C   H   V   E   H   P   S   L   K   S   P   I>
-------------------------------------- I-Ad β-2 DOMAIN ------

730           740           750           760           770
      *             *             *             *             *
ACT GTG GAG TGG ACT AGT GGT GGC GGT GGC AGC GGC GGT GGT GGT TCC
TGA CAC CTC ACC TGA TCA CCA CCG CCA CCG TCG CCG CCA CCA CCA AGG
 T   V   E   W   T   S   G   G   G   S   G   G   G   G   S>
-------------->< ------------------ 24 AMINO ACID LINKER -----

780           790           800           810
      *             *             *             *
GGT GGC GGC GGT TCT GGC GGT GGC GGT TCC TCG AGT GAA GAC GAC ATT
CCA CCG CCG CCA AGA CCG CCA CCG CCA AGG AGC TCA CTT CTG CTG TAA
 G   G   G   G   S   G   G   G   G   S   S   E   D   D   I>
                                            ------->< --------------

820           830           840           850           860
      *             *             *             *             *
GAG GCC GAC CAC GTA GGC TTC TAT GGT ACA ACT GTT TAT CAG TCT CCT
CTC CGG CTG GTG CAT CCG AAG ATA CCA TGT TGA CAA ATA GTC AGA GGA
 E   A   D   H   V   G   F   Y   G   T   T   V   Y   Q   S   P>
----- I-Ad α-1 DOMAIN --------------------------------------
```

FIG.27C

```
      870         880         890         900         910
       *           *           *           *           *
GGA GAC ATT GGC CAG TAC ACA CAT GAA TTT GAT GGT GAT GAG TTG TTC
CCT CTG TAA CCG GTC ATG TGT GTA CTT AAA CTA CCA CTA CTC AAC AAG
 G   D   I   G   Q   Y   T   H   E   F   D   G   D   E   L   F>
-----------------------------------------------------------------

920         930         940         950         960
       *           *           *           *           *
TAT GTG GAC TTG GAT AAG AAG AAA ACT GTC TGG AGG CTT CCT GAG TTT
ATA CAC CTG AAC CTA TTC TTC TTT TGA CAG ACC TCC GAA GGA CTC AAA
 Y   V   D   L   D   K   K   K   T   V   W   R   L   P   E   F>
-----------------------------------------------------------------

970         980         990        1000        1010
        *           *           *           *           *
GGC CAA TTG ATA CTC TTT GAG CCC CAA GGT GGA CTG CAA AAC ATA GCT
CCG GTT AAC TAT GAG AAA CTC GGG GTT CCA CCT GAC GTT TTG TAT CGA
 G   Q   L   I   L   F   E   P   Q   G   G   L   Q   N   I   A>
-----------------------------------------------------------------

1020        1030        1040        1050
         *           *           *           *
GCA GAA AAA CAC AAC TTG GGA ATC TTG ACT AAG AGG TCA AAT TTC ACC
CGT CTT TTT GTG TTG AAC CCT TAG AAC TGA TTC TCC AGT TTA AAG TGG
 A   E   K   H   N   L   G   I   L   T   K   R   S   N   F   T>
----------------------------- I-Ad α-1 DOMAIN --------

1060        1070        1080        1090        1100
   *           *           *           *           *
CCA GCT ACC AAT GAG GCT CCT CAA GCG ACT GTG TTC CCC AAG TCC CCT
GGT CGA TGG TTA CTC CGA GGA GTT CGC TGA CAC AAG GGG TTC AGG GGA
 P   A   T   N   E   A   P   Q   A   T   V   F   P   K   S   P>
------------><------ I-Ad α-2 DOMAIN ----------------------

1110        1120        1130        1140        1150
      *           *           *           *           *
GTG CTG CTG GGT CAG CCC AAC ACC CTT ATC TGC TTT GTG GAC AAC ATC
CAC GAC GAC CCA GTC GGG TTG TGG GAA TAG ACG AAA CAC CTG TTG TAG
 V   L   L   G   Q   P   N   T   L   I   C   F   V   D   N   I>
-----------------------------------------------------------------
```

FIG.27D

```
        1160            1170            1180            1190            1200
          *               *               *               *               *
TTC CCA CCT GTG ATC AAC ATC ACA TGG CTC AGA AAT AGC AAG TCA GTC
AAG GGT GGA CAC TAG TTG TAG TGT ACC GAG TCT TTA TCG TTC AGT CAG
 F   P   P   V   I   N   I   T   W   L   R   N   S   K   S   V>
-----------------------------------------------------------------

1210            1220            1230            1240            1250
          *               *               *               *               *
ACA GAC GGC GTT TAT GAG ACC AGC TTC CTC GTC AAC CGT GAC CAT TCC
TGT CTG CCG CAA ATA CTC TGG TCG AAG GAG CAG TTG GCA CTG GTA AGG
 T   D   G   V   Y   E   T   S   F   L   V   N   R   D   H   S>
-----------------------------------------------------------------

1260            1270            1280            1290
           *               *               *               *
TTC CAC AAG CTG TCT TAT CTC ACC TTC ATC CCT TCT GAT GAT GAC ATT
AAG GTG TTC GAC AGA ATA GAG TGG AAG TAG GGA AGA CTA CTA CTG TAA
 F   H   K   L   S   Y   L   T   F   I   P   S   D   D   D   I>
-----------------------------------------------------------------

1300            1310            1320            1330            1340
      *               *               *               *               *
TAT GAC TGC AAG GTG GAG CAC TGG GGC CTG GAG GAG CCG GTT CTG AAA
ATA CTG ACG TTC CAC CTC GTG ACC CCG GAC CTC CTC GGC CAA GAC TTT
 Y   D   C   K   V   E   H   W   G   L   E   E   P   V   L   K>
                                 -------- I-Ad α-2 DOMAIN --------

1350            1360            1370            1380
          *               *               *               *
CAC TGG TCC CGG GCT AGT CAC CAT CAC CAT CAT CAC TAG
GTG ACC AGG GCC CGA TCA GTG GTA GTG GTA GTA GTG ATC
 H   W   S   R   A   S   H   H   H   H   H   H   *>
-------><---------------- 6 X HIS tag ----->
```

FIG.27E

```
              10           20           30           40           50
              *            *            *            *            *
        CCACC ATG GCT CTG CAG ATC CCC AGC CTC CTC CTC TCA GCT GCT GTG GTG
        GGTGG TAC CGA GAC GTC TAG GGG TCG GAG GAG GAG AGT CGA CGA CAC CAC
               M   A   L   G   I   P   S   L   L   L   S   A   A   V   V>
              <--------------- I-Ad β CHAIN LEADER -------------------
```

```
           60           70           80           90
           *            *            *            *
        GTG CTG ATG GTG CTG AGC AGC CCA AGG ACC TTA AGT ATC TCT CAG GCT
        CAC GAC TAC CAC GAC TCG TCG GGT TCC TGG AAT TCA TAG AGA GTC CGA
         V   L   M   V   L   S   S   P   R   T   L   S   I   S   Q   A>
        ----------------------------------------------------><---------
```

```
        100          110          120          130          140
         *            *            *            *            *
        GTT CAC GCT GCT CAC GCT GAA ATC AAC GAA GCT GGT CGT GCT AGC GGA
        CAA GTG CGA CGA GTG CGA CTT TAG TTG CTT CGA CCA GCA CGA TCG CCT
         V   H   A   A   H   A   E   I   N   E   A   G   R   A   S   G>
        ------ OVA 323-339 ---------------------------------><---------
```

```
        150          160          170          180          190
         *            *            *            *            *
        GGG GGC GGA AGC GGC GGA GGG GGA AAC TCC GAA AGG CAT TTC GTG GTC
        CCC CCG CCT TCG CCG CCT CCC CCT TTG AGG CTT TCC GTA AAG CAC CAG
         G   G   G   S   G   G   G   G   N   S   E   R   H   F   V   V>
        -- 10 AMINO ACID LINKER --><------ I-Ad β-1 DOMAIN ---------
```

```
        200          210          220          230          240
         *            *            *            *            *
        CAG TTC AAG GGC GAG TGC TAC TAC ACC AAC GGG ACG CAG CGC ATA CGG
        GTC AAG TTC CCG CTC ACG ATG ATG TCC TTG CCC TGC GTC GCG TAT GCC
         Q   F   K   G   E   C   Y   Y   T   N   G   T   Q   R   I   R>
        ---------------------------------------------------------------
```

```
        250          260          270          280          290
         *            *            *            *            *
        CTC GTG ACC AGA TAC ATC TAC AAC CGG GAG GAG TAC GTG CGC TAC GAC
        GAG CAC TGG TCT ATG TAG ATG TTG GCC CTC CTC ATG CAC GCG ATG CTG
         L   V   T   R   Y   I   Y   N   R   E   E   Y   V   R   Y   D>
        ---------------------------------------------------------------
```

FIG.28A

```
          300           310           320           330
           *             *             *             *
   AGC GAC GTG GGC GAG TAC CGC GCG GTG ACC GAG CTG GGG CGG CCA GAC
   TCG CTG CAC CCG CTC ATG GCG CGC CAC TGG CTC GAC CCC GCC GGT CTG
    S   D   V   G   E   Y   R   A   V   T   E   L   G   R   P   D>
   ----------------------------------------------------------------

340           350           360           370           380
       *             *             *             *             *
   GCC GAG TAC TGG AAC AGC CAG CCG GAG ATC CTG GAG CGA ACG CGG GCC
   CGG CTC ATG ACC TTG TCG GTC GGC CTC TAG GAC CTC GCT TGC GCC CGG
    A   E   Y   W   N   S   Q   P   E   I   L   E   R   T   R   A>
   ----------------------------------------------------------------

390           400           410           420           430
          *             *             *             *             *
   GAG GTG GAC ACG GCG TGC AGA CAC AAC TAC GAG GGG CCG GAG ACC AGC
   CTC CAC CTG TGC CGC ACG TCT GTG TTG ATG CTC CCC GGC CTC TGG TCG
    E   V   D   T   A   C   R   H   N   Y   E   G   P   E   T   S>
   ----------------------------------------------------------------

440           450           460           470           480
             *             *             *             *             *
   ACC TCC CTG CGG CGG CTT GAA CAG CCC AAT GTC GCC ATC TCC CTG TCC
   TGG AGG GAC GCC GCC GAA CTT GTC GGG TTA CAG CGG TAG AGG GAC AGG
    T   S   L   R   R   L   E   Q   P   N   V   A   I   S   L   S>
   --- I-Ad β-1 DOMAIN -><-------- I-Ad β-2 DOMAIN ------------

490           500           510           520           530
          *             *             *             *             *
   AGG ACA GAG GCC CTC AAC CAC CAC AAC ACT CTG GTC TGT TCG GTG ACA
   TCC TGT CTC CGG GAG TTG GTG GTG TTG TGA GAC CAG ACA AGC CAC TGT
    R   T   E   A   L   N   H   H   N   T   L   V   C   S   V   T>
   ----------------------------------------------------------------

540           550           560           570
             *             *             *             *
   GAT TTC TAC CCA GCC AAG ATC AAA GTG CGC TGG TTC AGG AAT GGC CAG
   CTA AAG ATG GGT CGG TTC TAG TTT CAC GCG ACC AAG TCC TTA CCG GTC
    D   F   Y   P   A   K   I   K   V   R   W   F   R   N   G   Q>
   ----------------------------------------------------------------
```

FIG.28B

```
580         590         600         610         620
 *           *           *           *           *
GAG GAG ACA GTG GGG GTC TCA TCC ACA CAG CTT ATT AGG AAT GGG GAC
CTC CTC TGT CAC CCC CAG AGT AGG TGT GTC GAA TAA TCC TTA CCC CTG
 E   E   T   V   G   V   S   S   T   Q   L   I   R   N   G   D>
---------------------------------------------------------------

630         640         650         660         670
         *           *           *           *           *
TGG ACC TTC CAG GTC CTG GTC ATG CTG GAG ATG ACC CCT CAT CAG GGA
ACC TGG AAG GTC CAG GAC CAG TAC GAC CTC TAC TGG GGA GTA GTC CCT
 W   T   F   Q   V   L   V   M   L   E   M   T   P   H   Q   G>
---------------------------------------------------------------

680         690         700         710         720
         *           *           *           *           *
GAG GTC TAC ACC TGC CAT GTG GAG CAT CCC AGC CTG AAG AGC CCC ATC
CTC CAG ATG TGG ACG GTA CAC CTC GTA GGG TCG GAC TTC TCG GGG TAG
 E   V   Y   T   C   H   V   E   H   P   S   L   K   S   P   I>
---------------------------------- I-Ad β-2 DOMAIN ------

730         740         750         760         770
         *           *           *           *           *
ACT GTG GAG TGG ACT AGT GGT GGC GGT GGC AGC GGC GGT GGT GGT TCC
TGA CAC CTC ACC TGA TCA CCA CCG CCA CCG TCG CCG CCA CCA CCA AGG
 T   V   E   W   T   S   G   G   G   G   S   G   G   G   G   S>
-------------><------------------ 24 AMINO ACID LINKER ----

780         790         800         810
              *           *           *           *
GGT GGC GGC GGT TCT GGC GGT GGC GGT TCC TCG AGT GAA GAC GAC ATT
CCA CCG CCG CCA AGA CCG CCA CCG CCA AGG AGC TCA CTT CTG CTG TAA
 G   G   G   G   S   G   G   G   G   S   S   E   D   D   I>
-----------------------------------------------><--------------

820         830         840         850         860
 *           *           *           *           *
GAG GCC GAC CAC GTA GGC TTC TAT GGT ACA ACT GTT TAT CAG TCT CCT
CTC CGG CTG GTG CAT CCG AAG ATA CCA TGT TGA CAA ATA GTC AGA GGA
 E   A   D   H   V   G   F   Y   G   T   T   V   Y   Q   S   P>
----- I-Ad α-1 DOMAIN ------------------------------------
```

FIG.28C

```
        870         880         890         900         910
         *           *           *           *           *
GGA GAC ATT GGC CAG TAC ACA CAT GAA TTT GAT GGT GAT GAG TTG TTC
CCT CTG TAA CCG GTC ATG TGT GTA CTT AAA CTA CCA CTA CTC AAC AAG
 G   D   I   G   Q   Y   T   H   E   F   D   G   D   E   L   F>
------------------------------------------------------------------

920         930         940         950         960
         *           *           *           *           *
TAT GTG GAC TTG GAT AAG AAG AAA ACT GTC TGG AGG CTT CCT GAG TTT
ATA CAC CTG AAC CTA TTC TTC TTT TGA CAG ACC TCC GAA GGA CTC AAA
 Y   V   D   L   D   K   K   K   T   V   W   R   L   P   E   F>
------------------------------------------------------------------

970         980         990        1000        1010
         *           *           *           *           *
GGC CAA TTG ATA CTC TTT GAG CCC CAA GGT GGA CTG CAA AAC ATA GCT
CCG GTT AAC TAT GAG AAA CTC GGG GTT CCA CCT GAC GTT TTG TAT CGA
 G   Q   L   I   L   F   E   P   Q   G   G   L   Q   N   I   A>
------------------------------------------------------------------

1020        1030        1040        1050
         *           *           *           *
GCA GAA AAA CAC AAC TTG GGA ATC TTG ACT AAG AGG TCA AAT TTC ACC
CGT CTT TTT GTG TTG AAC CCT TAG AAC TGA TTC TCC AGT TTA AAG TGG
 A   E   K   H   N   L   G   I   L   T   K   R   S   N   F   T>
-------------------------------------- I-Ad α-1 DOMAIN --------

1060        1070        1080        1090        1100
    *           *           *           *           *
CCA GCT ACC AAT GAG GCT CCT CAA GCG ACT GTG TTC CCC AAG TCC CCT
GGT CGA TGG TTA CTC CGA GGA GTT CGC TGA CAC AAG GGG TTC AGG GGA
 P   A   T   N   E   A   P   Q   A   T   V   F   P   K   S   P>
----------->< ----- I-Ad α-2 DOMAIN -----------------------

1110        1120        1130        1140        1150
         *           *           *           *           *
GTG CTG CTG GGT CAG CCC AAC ACC CTT ATC TGC TTT GTG GAC AAC ATC
CAC GAC GAC CCA GTC GGG TTG TGG GAA TAG ACG AAA CAC CTG TTG TAG
 V   L   L   G   Q   P   N   T   L   I   C   F   V   D   N   I>
------------------------------------------------------------------
```

FIG.28D

```
      1160          1170          1180          1190          1200
       *             *             *             *             *
TTC CCA CCT GTG ATC AAC ATC ACA TGG CTC AGA AAT AGC AAG TCA GTC
AAG GGT GGA CAC TAG TTG TAG TGT ACC GAG TCT TTA TCG TTC AGT CAG
 F   P   P   V   I   N   I   T   W   L   R   N   S   K   S   V>
------------------------------------------------------------------

1210          1220          1230          1240          1250
          *             *             *             *             *
ACA GAC GGC GTT TAT GAG ACC AGC TTC CTC GTC AAC CGT GAC CAT TCC
TGT CTG CCG CAA ATA CTC TGG TCG AAG GAG CAG TTG GCA CTG GTA AGG
 T   D   G   V   Y   E   T   S   F   L   V   N   R   D   H   S>
------------------------------------------------------------------

1260          1270          1280          1290
          *             *             *             *
TTC CAC AAG CTG TCT TAT CTC ACC TTC ATC CCT TCT GAT GAT GAC ATT
AAG GTG TTC GAC AGA ATA GAG TGG AAG TAG GGA AGA CTA CTA CTG TAA
 F   H   K   L   S   Y   L   T   F   I   P   S   D   D   D   I>
------------------------------------------------------------------

1300          1310          1320          1330          1340
  *             *             *             *             *
TAT GAC TGC AAG GTG GAG CAC TGG GGC CTG GAG GAG CCG GTT CTG AAA
ATA CTG ACG TTC CAC CTC GTG ACC CCG GAC CTC CTC GGC CAA GAC TTT
 Y   D   C   K   V   E   H   W   G   L   E   E   P   V   L   K>
-------------------------------- I-Ad α-2  DOMAIN --------

1350          1360          1370          1380          1390
       *             *             *             *             *
CAC TGG GAA CCT GAG ATT CCA GCC CCC ATG TCA GAG CTG ACA GAA ACT
GTG ACC CTT GGA CTC TAA GGT CGG GGG TAC AGT CTC GAC TGT CTT TGA
 H   W   E   P   E   I   P   A   P   M   S   E   L   T   E   T>
-------><-------- I-Ad α-TM DOMAIN ------------------------

1400          1410          1420          1430          1440
       *             *             *             *             *
GTG GTG TGT GCC CTG GGG TTG TCT GTG GGC CTT GTG GGC ATC GTG GTG
CAC CAC ACA CGG GAC CCC AAC AGA CAC CCG GAA CAC CCG TAG CAC CAC
 V   V   C   A   L   G   L   S   V   G   L   V   G   I   V   V>
------------------------------------------------------------------
```

FIG.28E

```
         1450          1460          1470          1480          1490
           *             *             *             *             *
GGC ACC ATC TTC ATC ATT CAA GGC CTG CGA TCA GGT GGC ACC TCC AGA
CCG TGG TAG AAG TAG TAA GTT CCG GAC GCT AGT CCA CCG TGG AGG TCT
 G   T   I   F   I   I   Q   G   L   R   S   G   G   T   S   R>
-----------------------------------------------------------------

CAC CCA GGG CCT TTA TGA
GTG GGT CCC GGA AAT ACT
 H   P   G   P   L   *>
- I-Ad α-TM DOMAIN ->
```

FIG.28F

```
           10           20            30            40            50
            *            *             *             *             *
CCACC ATG GCT CTG CAG ATC CCC AGC CTC CTC CTC TCA GCT GCT GTG GTG
GGTGG TAC CGA GAC GTC TAG GGG TCG GAG GAG GAG AGT CGA CGA CAC CAC
       M   A   L   Q   I   P   S   L   L   L   S   A   A   V   V>
      <--------------- I-Ad β CHAIN LEADER ------------------

60            70            80            90
           *             *             *             *
GTG CTG ATG GTG CTG AGC AGC CCA AGG ACC TTA AGT ATC TCT CAG GCT
CAC GAC TAC CAC GAC TCG TCG GGT TCC TGG AAT TCA TAG AGA GTC CGA
 V   L   M   V   L   S   S   P   R   T   L   S   I   S   Q   A>
------------------------------------------------><-------------

100          110           120           130           140
  *            *             *             *             *
GTT CAC GCT GCT CAC GCT GAA ATC AAC GAA GCT GGT CGT GCT AGC GGA
CAA GTG CGA CGA GTG CGA CTT TAG TTG CTT CGA CCA GCA CGA TCG CCT
 V   H   A   A   H   A   E   I   N   E   A   G   R   A   S   G>
------ OVA 323-339 ------------------------------><----------

150           160           170           180           190
           *             *             *             *             *
GGG GGC GGA AGC GGC GGA GGG GGA AAC TCC GAA AGG CAT TTC GTG GTC
CCC CCG CCT TCG CCG CCT CCC CCT TTG AGG CTT TCC GTA AAG CAC CAG
 G   G   G   S   G   G   G   G   N   S   E   R   H   F   V   V>
-- 10 AMINO ACID LINKER --><------ I-Ad β-1 DOMAIN ---------

200           210           220           230           240
          *             *             *             *             *
CAG TTC AAG GGC GAG TGC TAC TAC ACC AAC GGG ACG CAG CGC ATA CGG
GTC AAG TTC CCG CTC ACG ATG ATG TGG TTG CCC TGC GTC GCG TAT GCC
 Q   F   K   G   E   C   Y   Y   T   N   G   T   Q   R   I   R>
-----------------------------------------------------------

250           260           270           280           290
          *             *             *             *             *
CTC GTG ACC AGA TAC ATC TAC AAC CGG GAG GAG TAC GTG CGC TAC GAC
GAG CAC TGG TCT ATG TAG ATG TTG GCC CTC CTC ATG CAC GCG ATG CTG
 L   V   T   R   Y   I   Y   N   R   E   E   Y   V   R   Y   D>
-----------------------------------------------------------
```

FIG.29A

```
        300             310             320             330
         *               *               *               *
AGC GAC GTG GGC GAG TAC CGC GCG GTG ACC GAG CTG GGG CGG CCA GAC
TCG CTG CAC CCG CTC ATG GCG CGC CAC TGG CTC GAC CCC GCC GGT CTG
 S   D   V   G   E   Y   R   A   V   T   E   L   G   R   P   D>
----------------------------------------------------------------

340             350             360             370             380
   *               *               *               *               *
GCC GAG TAC TGG AAC AGC CAG CCG GAG ATC CTG GAG CGA ACG CGG GCC
CGG CTC ATG ACC TTG TCG GTC GGC CTC TAG GAC CTC GCT TGC GCC CGG
 A   E   Y   W   N   S   Q   P   E   I   L   E   R   T   R   A>
----------------------------------------------------------------

390             400             410             420             430
   *               *               *               *               *
GAG GTG GAC ACG GCG TGC AGA CAC AAC TAC GAG GGG CCG GAG ACC AGC
CTC CAC CTG TGC CGC ACG TCT GTG TTG ATG CTC CCC GGC CTC TGG TCG
 E   V   D   T   A   C   R   H   N   Y   E   G   P   E   T   S>
----------------------------------------------------------------

440             450             460             470             480
        *               *               *               *               *
     ACC TCC CTG CGG CGG CTT GAA CAG CCC AAT GTC GCC ATC TCC CTG TCC
     TGG AGG GAC GCC GCC GAA CTT GTC GGG TTA CAG CGG TAG AGG GAC AGG
      T   S   L   R   R   L   E   Q   P   N   V   A   I   S   L   S>
     ---  I-Ad β-1 DOMAIN  -><------- I-Ad β-2 DOMAIN  ------------

490             500             510             520             530
             *               *               *               *               *
          AGG ACA GAG GCC CTC AAC CAC CAC AAC ACT CTG GTC TGT TCG GTG ACA
          TCC TGT CTC CGG GAG TTG GTG GTG TTG TGA GAC CAG ACA AGC CAC TGT
           R   T   E   A   L   N   H   H   N   T   L   V   C   S   V   T>
          ------------------------------------------------------------

540             550             560             570
                  *               *               *               *
               GAT TTC TAC CCA GCC AAG ATC AAA GTG CGC TGG TTC AGG AAT GGC CAG
               CTA AAG ATG GGT CGG TTC TAG TTT CAC GCG ACC AAG TCC TTA CCG GTC
                D   F   Y   P   A   K   I   K   V   R   W   F   R   N   G   Q>
               -------------------------------------------------------------
```

FIG.29B

```
     580           590           600           610           620
      *             *             *             *             *
GAG GAG ACA GTG GGG GTC TCA TCC ACA CAG CTT ATT AGG AAT GGG GAC
CTC CTC TGT CAC CCC CAG AGT AGG TGT GTC GAA TAA TCC TTA CCC CTG
 E   E   T   V   G   V   S   S   T   Q   L   I   R   N   G   D>
----------------------------------------------------------------

630           640           650           660           670
            *             *             *             *             *
TGG ACC TTC CAG GTC CTG GTC ATG CTG GAG ATG ACC CCT CAT CAG GGA
ACC TGG AAG GTC CAG GAC CAG TAC GAC CTC TAC TGG GGA GTA GTC CCT
 W   T   F   Q   V   L   V   M   L   E   M   T   P   H   Q   G>
----------------------------------------------------------------

680           690           700           710           720
            *             *             *             *             *
GAG GTC TAC ACC TGC CAT GTG GAG CAT CCC AGC CTG AAG AGC CCC ATC
CTC CAG ATG TGG ACG GTA CAC CTC GTA GGG TCG GAC TTC TCG GGG TAG
 E   V   Y   T   C   H   V   E   H   P   S   L   K   S   P   I>
----------------------------------------- I-Ad β-2 DOMAIN ------

730           740           750           760           770
            *             *             *             *             *
ACT GTG GAG TGG ACT AGT GGT GGC GGT GGC AGC GGC GGT GGT GGT TCC
TGA CAC CTC ACC TGA TCA CCA CCG CCA CCG TCG CCG CCA CCA CCA AGG
 T   V   E   W   T   S   G   G   G   G   S   G   G   G   G   S>
-------------><------------------ 24 AMINO ACID LINKER ------

780           790           800           810
            *             *             *             *
GGT GGC GGC GGT TCT GGC GGT GGC GGT TCC TCG AGT GAA GAC GAC ATT
CCA CCG CCG CCA AGA CCG CCA CCG CCA AGG AGC TCA CTT CTG CTG TAA
 G   G   G   G   S   G   G   G   G   S   S   S   E   D   D   I>
-------------------------------------------------><-------------

820           830           840           850           860
      *             *             *             *             *
GAG GCC GAC CAC GTA GGC TTC TAT GGT ACA ACT GTT TAT CAG TCT CCT
CTC CGG CTG GTG CAT CCG AAG ATA CCA TGT TGA CAA ATA GTC AGA GGA
 E   A   D   H   V   G   F   Y   G   T   T   V   Y   Q   S   P>
----- I-Ad α-1 DOMAIN -------------------------------------------
```

FIG.29C

```
         870           880           890           900           910
          *             *             *             *             *
    GGA GAC ATT GGC CAG TAC ACA CAT GAA TTT GAT GGT GAT GAG TTG TTC
    CCT CTG TAA CCG GTC ATG TGT GTA CTT AAA CTA CCA CTA CTC AAC AAG
     G   D   I   G   Q   Y   T   H   E   F   D   G   D   E   L   F>
    ------------------------------------------------------------------

920           930           940           950           960
          *             *             *             *             *
    TAT GTG GAC TTG GAT AAG AAG AAA ACT GTC TGG AGG CTT CCT GAG TTT
    ATA CAC CTG AAC CTA TTC TTC TTT TGA CAG ACC TCC GAA GGA CTC AAA
     Y   V   D   L   D   K   K   K   T   V   W   R   -L  P   E   F>
    ------------------------------------------------------------------

970           980           990          1000          1010
          *             *             *             *             *
    GGC CAA TTG ATA CTC TTT GAG CCC CAA GGT GGA CTG CAA AAC ATA GCT
    CCG GTT AAC TAT GAG AAA CTC GGG GTT CCA GCT GAC GTT TTG TAT CGA
     G   Q   L   I   L   F   E   P   Q   G   G   L   Q   N   I   A>
    ------------------------------------------------------------------

1020          1030          1040          1050
          *             *             *             *
    GCA GAA AAA CAC AAC TTG GGA ATC TTG ACT AAG AGG TCA AAT TTC ACC
    CGT CTT TTT GTG TTG AAC CCT TAG AAC TGA TTC TCC AGT TTA AAG TGG
     A   E   K   H   N   L   G   I   L   T   K   R   S   N   F   T>
    ------------------------------- I-Ad α-1 DOMAIN --------

1060          1070          1080          1090          1100
      *             *             *             *             *
    CCA GCT ACC AAT GAG GCT CCT CAA GCG ACT GTG TTC CCC AAG TCC CCT
    GGT CGA TGG TTA CTC CGA GGA GTT CGC TGA CAC AAG GGG TTC AGG GGA
     P   A   T   N   E   A   P   Q   A   T   V   F   P.  K   S   P>
    -----------><----- I-Ad α-2 DOMAIN -----------------------

1110          1120          1130          1140          1150
          *             *             *             *             *
    GTG CTG CTG GGT CAG CCC AAC ACC CTT ATC TGC TTT GTG GAC AAC ATC
    CAC GAC GAC CCA GTC GGG TTG TGG GAA TAG ACG AAA CAC CTG TTG TAG
     V   L   L   G   Q   P   N   T   L   I   C   F   V   D   N   I>
    ------------------------------------------------------------------
```

FIG.29D

```
       1160           1170          1180          1190          1200
        *              *             *             *             *
TTC CCA CCT GTG ATC AAC ATC ACA TGG CTC AGA AAT AGC AAG TCA GTC
AAG GGT GGA CAC TAG TTG TAG TGT ACC GAG TCT TTA TCG TTC AGT CAG
 F   P   P   V   I   N   I   T   W   L   R   N   S   K   S   V>
-----------------------------------------------------------------

1210          1220          1230          1240          1250
               *             *             *             *             *
ACA GAC GGC GTT TAT GAG ACC AGC TTC CTC GTC AAC CGT GAC CAT TCC
TGT CTG CCG CAA ATA CTC TGG TCG AAG GAG CAG TTG GCA CTG GTA AGG
 T   D   G   V   Y   E   T   S   F   L   V   N   R   D   H  ·S>
-----------------------------------------------------------------

1260          1270          1280          1290
                     *             *             *             *
TTC CAC AAG CTG TCT TAT CTC ACC TTC ATC CCT TCT GAT GAT GAC ATT
AAG GTG TTC GAC AGA ATA GAG TGG AAG TAG GGA AGA CTA CTA CTG TAA
 F   H   K   L   S   Y   L   T   F   I   P   S   D   D   D   I>
-----------------------------------------------------------------

1300          1310          1320          1330          1340
 *             *             *             *             *
TAT GAC TGC AAG GTG GAG CAC TGG GGC CTG GAG GAG CCG GTT CTG AAA
ATA CTG ACG TTC CAC CTC GTG ACC CCG GAC CTC CTC GGC CAA GAC TTT
 Y   D   C   K   V   E   H   W   G   L   E   E   P   V   L   K>
------------------------------ I-Ad α-2 DOMAIN --------

1350          1360          1370          1380
 *             *             *             *
CAC TGG GAG GAA GAA GAG TAC ATG CCG ATG GAA TGA
GTG ACC CTC CTT CTT CTC ATG TAC GGC TAC CTT ACT
 H   W   E   E   E   E   Y   M   P   M   E   *>
-------><-------- EE TAG ---------------->
```

FIG.29E

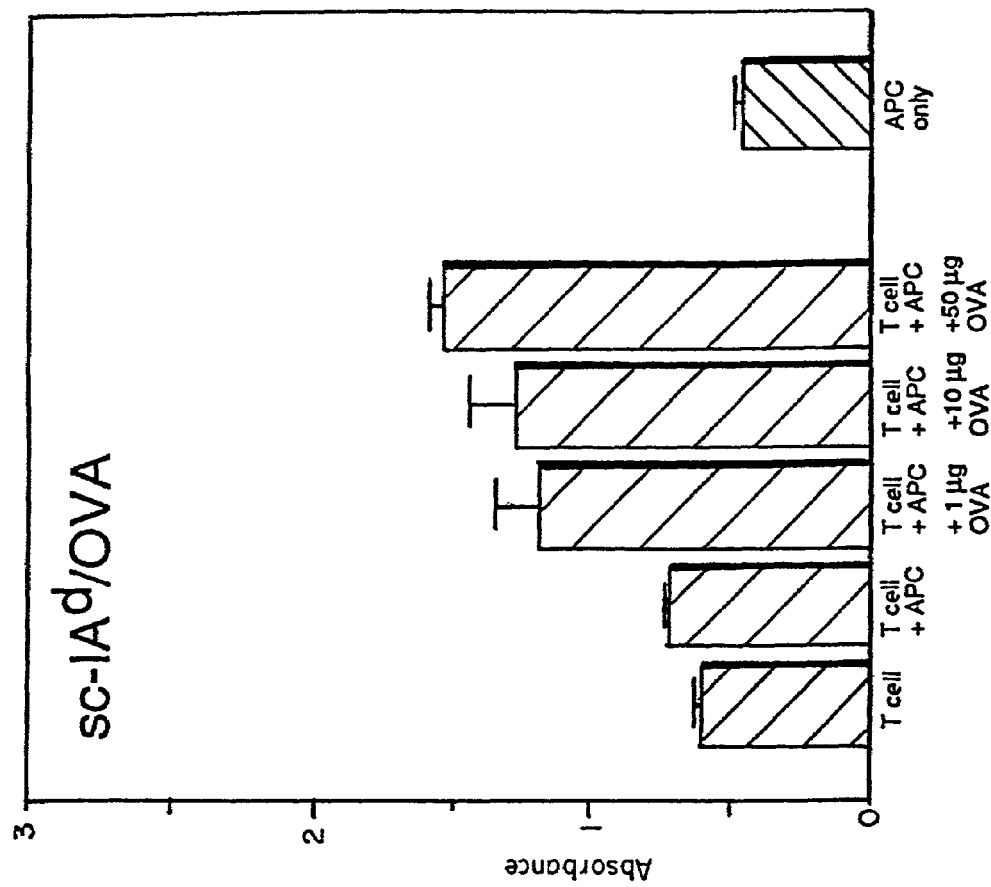
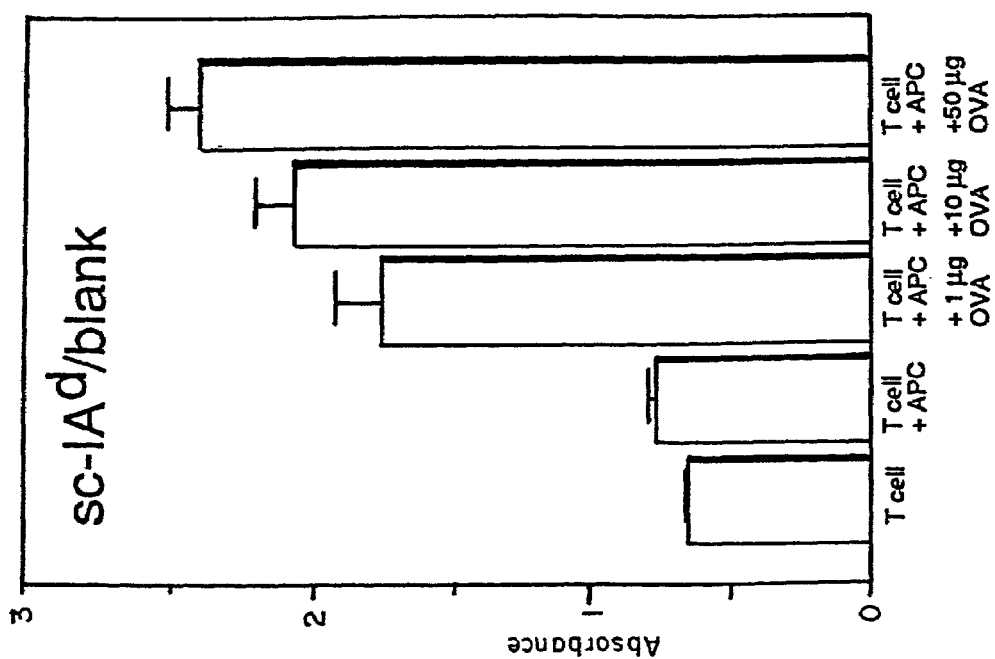
FIG. 36B
FIG. 36A

MHC COMPLEXES AND USES THEREOF

This is a continuation of application Ser. No. 09/067,615, filed Apr. 28, 1998, (Now U.S. Pat. No. 6,309,645) which application is a continuation of U.S. Ser. No. 08/596,387 filed on Jan. 31, 1996 (Now U.S. Pat. No. 5,869,270). The disclosures of said U.S. Ser. No. 09/067,615 (U.S. Pat. No. 6,309,645) and U.S. Pat. No. 5,869,270 are each incorporated herein by reference.

BACKGROUND OF THE INVENTION

1. Field of the Invention

The present invention relates to novel complexes of major histocompatibility complex (MHC) molecules and uses of such complexes. For example, in one aspect, the invention relates to empty MHC complexes that contain a MHC molecule with a peptide-binding groove and a presenting peptide non-covalently linked to the MHC protein. In another aspect, the invention relates to MHC class II-peptide fusion complexes which include a single chain MHC class II molecule and a presenting peptide covalently linked to the peptide binding groove of the MHC protein. MHC complexes of the invention are useful for a variety of applications including in vitro screens for identification and isolation of peptides that modulate activity of T cells.

2. Background

Antigen-specific T cell responses are invoked by antigenic peptides bound to the binding groove or cleft of major histocompatibility complex (MHC) glycoproteins as part of the mechanism of the immune system to identify and respond to foreign antigens. The bound antigenic peptides interact with T cell receptors and thereby modulate an immune response. The antigenic peptides are bound by non-covalent means to particular "binding pockets" comprised of polymorphic residues of the MHC protein's binding groove.

MHC class II molecules are heterodimeric glycoproteins consisting of α and β chains. The α1 and β1 domains of these molecules fold together to form a peptide binding grove. Antigenic peptides bind the MHC molecule through interaction between anchor amino acids on the peptide and the α1 and β1 domains. Crystal structure of human class II HLA-DR1 complex with an influenza virus peptide indicate that the N- and C-terminal ends of the bound peptide extend out of the binding groove such that the C-terminus of the peptide is proximal to the N-terminus of the β chain [J. Brown et al., Nature, 364:33–39 (1993); L. Stern et al., Nature, 368:215–221 (1994)]. MHC class I molecules have different domain organizations than MHC class II molecules, but generally similar structure with a peptide binding site or groove that is distal to membrane domains [see, e.g., A. Rudensky et al., Nature, 353:622–626 (1991)]. See also U.S. Pat. Nos. 5,284,935; 5,260,422; 5,194,425; 5,130,297; and WO 92/18150 and WO 93/10220 for discussions of MHC molecules.

The α and β chain transmembrane domains play an important role in the assembly and/or intracellular transport of MHC molecules. For example, amino acid changes in the TM domains can result in defective MHC molecules [P. Cosson et al., Science, 258:659 (1992); W. Wade et al., Immunology, 32:433 (1995); H. Kozono et al., Nature, 369:151 (1994)]. The α and β chain transmembrane and cytoplasmic domains have been disclosed [(see e.g., Brown, supra and references therein)].

MHC molecules complexed with antigenic peptides can induce selective immunosuppression by several different mechanisms [see, e.g., J. Guery et al., Critical Reviews in Immunology, 13(3/4):195–206 (1993)].

More specifically, it has been reported that peptide-MHC complexes on the surface of antigen presenting cells will only induce clonal expansion of a T cell line specific for the MHC bound peptide if the antigen presenting cells also deliver co-stimulatory signals. One proposed approach takes advantage of this requirement for T cell activation and reports inhibition of T cell development by interaction with the antigenic peptide bound to the MHC molecule in the absence of co-stimulatory signals [see M. Nicolle et al., J. Clin. Invest., 93:1361–1369 (1994); and S. Sharma et al., Proc. Natl. Acad. Sci. USA, 88:11465–11469 (1991)].

Another proposed approach inhibits T cell development with MHC molecules that contain a bound peptide that is an antagonist or partial agonist to a T cell receptor (TcR) [see B. Evavold et al., Immunology Today, 14(12):602–609 (1993)].

Modifications of the antigenic peptides bound to T cell receptors have been attempted to examine residues responsible for specific T cell responses. Determination of such "activating" amino acids of the antigenic peptides could provide insight of suitable sequence of a TcR partial agonist or antagonist. See Evavold, B. et al., supra.

It also has been speculated that new vaccines might be developed based on determination of the nature of various antigenic peptides bound to MHC molecules [see R. Chicz et al., Immunology Today, 15(4):155–160 (1994)].

SUMMARY OF THE INVENTION

The present invention relates to novel complexes of major histocompatibility complex (MHC) molecules (class I or II), e.g., empty single chain MHC class II complexes, loaded single chain MHC class II complexes, and single chain MHC class II peptide fusion complexes and the uses of such MHC complexes.

We have now discovered that single chain MHC class complexes without a covalently linked presenting peptide (i.e. an empty MHC complex) can be loaded by contacting a presenting peptide to the complex so that the presenting peptide non-covalently binds to the peptide binding groove of the complex. Generally, the presenting peptide will non-covalently bind to the peptide binding groove of the empty MHC complex via stable hydrogen bonding. The single chain MHC class complexes of the present invention, particularly single chain MHC class II complexes, are surprisingly stable and are useful in a variety of applications. For example, loaded single chain MHC class II complexes or single chain MHC class II peptide fusion complexes can be used to modulate various immune system responses in a mammal, e.g., T cell apoptosis, T cell anergy, T cell cytokine release, immunosuppression and induction of T cells. Empty MHC molecules, particularly empty single chain MHC class II molecules, are useful in, e.g., in vitro screens for detecting peptides that modulate the activity of T cells, including peptides which are T cell receptor antagonists and partial agonists.

We previously disclosed highly useful MHC class I and class II peptide fusion molecules in unpublished PCT Application No. PCT/US95/09816, filed Jul. 31, 1995 (sometimes referred to herein as said "PCT Application") as well as pending U.S. application Ser. No. 08/382,454, filed Feb. 1, 1995. The MHC fusion complexes comprise a presenting peptide covalently linked (ie. fused) to the MHC molecule.

The PCT Application No. PCT/US95/09816 and said U.S. application Ser. No. 08/382,454 are herein incorporated by reference in its entirety.

As used herein, the term "presenting peptide" refers to a peptide that is capable of modulating the activity of a T cell receptor, either to induce T-cell proliferation, to inhibit or inactivate T cell development such as determined by the assays disclosed below, including the assay that includes sequential steps of culturing T cells to proliferate same, and contacting the T cells with a single chain MHC peptide fusion complex of the invention or a loaded single chain MHC complex of the invention and then evaluating whether the complex inhibits further development of the T cells.

The term "empty" (particularly "empty MHC molecule" or similar phrase), as used herein, refers to an MHC molecule (class I or II) of the invention which lacks a covalently or non-covalently bound presenting peptide. Preferably, the empty MHC molecule is class II and is comprised of a single polypeptide chain, rather than separate polypeptides.

The term "loaded" (particularly "loaded MHC molecule" or similar phrase), as used herein, refers to an empty MHC molecule (class I or II) which includes a presenting peptide non-covalently bound to the peptide binding groove or cleft of the MHC molecule, preferably so that the loaded MHC molecule can modulate the activity of T cells. The non-covalent binding is suitably via stable hydrogen bonding between the presenting peptide and the peptide binding groove or cleft of the empty MHC molecule. The non-covalent binding can be performed in vitro or in vivo. Preferably, the loaded MHC molecule is class II and is comprised of a single polypeptide chain, rather than separate polypeptides.

Single chain MHC peptide fusion complexes of the invention as well as those disclosed in said PCT Application, provide a number of significant advantages. For example, prior practice required the purification of MHC molecules that had been previously loaded with peptides from antigen presenting cells. Such loaded peptides were generally tightly bound and could not be efficiently exchanged with the peptide of interest. In contrast, MHC complexes disclosed in said PCT application or the single chain MHC class II complexes of the invention can contain a single antigenic peptide, including such a peptide of known structure. Analysis of interactions with T cell receptors will be facilitated by use of such MHC molecules. Additionally, a wide variety of peptides can be presented for interaction with T cells by virtue of the fact that only a small number (ca. 4 to 6) of amino acids in the presenting peptide are important for binding to a particular MHC molecule. That is, a library of different peptides constrained only by the MHC anchor residues can be covalently linked to the MHC molecule for presentation of T cells. Further, for therapeutic applications, rather than administration of an MHC molecule to a subject, a DNA expression vector coding for the MHC molecule linked to the presenting peptide can be administered for in vivo expression of the MHC fusion complex. Such an approach avoids costly purification steps typically associated with preparation of recombinant proteins and avoids the complexities of antigen uptake and processing associated with conventional approaches.

Empty MHC molecules of the present invention also provide distinct advantages. For example, empty single chain MHC class II molecules can be readily combined with various suitable presenting peptides to form loaded MHC molecules. The ability to conveniently load empty MHC molecules of the invention enables the screening of many presenting peptides to evaluate the ability of each presenting peptide to modulate T cell receptor activity.

Empty MHC molecules of the invention, e.g., empty single chain MHC class II molecules, can be expressed as a stable polypeptide in a soluble form or on the surface of mammalian cells. In either form, the empty MHC molecule can be contacted by a suitable presenting peptide to form a loaded MHC molecule with desirable T cell modulating activity.

Single chain MHC peptide fusion molecules of the present invention and of said PCT application, e.g., single chain MHC class II peptide fusion molecules, include a presenting peptide covalently linked to the N-terminus of the α or β chain of the MHC protein. For example, a single chain MHC class II molecule has a presenting peptide covalently linked to the MHC α or β chain. Preferably, the presenting peptide is linked to the N-terminus of the α or β chain via a peptide linker.

Single chain MHC peptide fusion molecules of the present invention and of said PCT application may be truncated (particularly, not including a transmembrane portion), or may be, "full-length" and include a transmembrane portion, or portions thereof, and a cytoplasmic domain, or portions thereof. As discussed below in more detail, for some approaches, an MHC molecule that does not include a transmembrane portion is suitably employed, while for other applications MHC molecules are employed that contain a transmembrane portion and/or cytoplasmic portion and/or other such domains. In some instances where an MHC molecule does not include a transmembrane domain, or a portion thereof, one or more hydrophilic amino acids, preferably about one to ten histidines, can be added to the MHC molecule to increase solubility.

The single chain MHC fusion complexes of the present invention and of said PCT Application, e.g., single chain MHC class II peptide fusion complexes, preferably also include a flexible linker sequence interposed between the MHC protein and the presenting peptide. The linker sequence should allow effective positioning of the presenting peptide with respect to the MHC molecule binding groove so that the presenting peptide can modulate the activity of a T cell receptor, either to induce T-cell proliferation or to inhibit or inactivate T cell development as determined by the assays disclosed below, including the in vitro assays that includes sequential steps of culturing T cells to proliferate same, and contacting the T cells with a single chain MHC peptide fusion complex and then evaluating whether the MHC complex inhibits further development of the T cells.

As further disclosed in said PCT Application with respect to MHC peptide fusion complexes, MHC complexes of the present invention can be single-chain fusion proteins, i.e. where the α and β chain subunits are linked as a single chain fusion protein and the presenting peptide is preferably linked to the β chain of the fusion protein. Such a linked single-chain complex can provide a number of advantages. In particular, in reducing the complex to a single molecule, yields and stability of the molecules may be enhanced. That can be especially important for soluble molecules which may not be produced efficiently in active form. The single chain MHC complexes of the invention, e.g., single chain MHC class II peptide fusion complexes, are useful for the methods disclosed herein, including in vitro identification of peptides recognized by a T cell receptor, methods for suppressing an immune response (e.g. treatment of individuals with immune disorders such as autoimmune disorders or allergies) and methods for inducing a desired immune response, e.g., where a mammal is or is likely to become immunocompromised, e.g., where the immune system is suppressed by viral infection (e.g., as in AIDS) or chemotherapy (e.g., as in radiation therapy to treat cancer), and diagnostic methods such as HLA typing and in vivo diagnostic imaging. Direct administration of a DNA construct coding for a single-chain MHC class II peptide fusion complex is also preferred.

The invention also includes methods for in vitro identification of peptides recognized by a T cell receptor, including peptides that can induce T cell development as well as peptides that can antagonize T cell receptors, i.e. T cell receptor (TcR) antagonists or partial agonists.

The present invention also provides further methods for suppressing an immune response in a mammal, particularly a human, that comprises administering to the mammal an effective amount of a single chain MHC complex, preferably single chain MHC class II peptide fusion complexes or loaded single chain MHC class II complexes. The methods of the present invention include treatment of a mammal that suffers from or is susceptible to an autoimmune disorder such as multiple sclerosis, insulin-dependent diabetes mellitus or rheumatoid arthritis or, alternatively, a mammal who is susceptible to undesired immune response(s) such as a subject with chronic allergies or a patient undergoing transplant surgery such as organ or skin transplant surgery.

An immune response may be suppressed in accordance with the invention by one or a combination of alternative strategies. Thus, as disclosed in said PCT Application with respect to MHC peptide fusion complexes, the present invention provides treatment methods for suppression of an immune response by inducing anergy or apoptosis of T cells and provides for the administration of an effective amount of one or more MHC complexes of the invention, preferably single chain MHC class II peptide fusion complexes or loaded single chain MHC class II complexes, in the substantial absence of co-stimulatory signal(s). Typically a truncated MHC complex of the invention is employed, i.e. a soluble MHC complex that does not contain transmembrane and cytoplasmic domains of a full-length or intact MHC molecules, or portions thereof. Another method for suppression of an immune response provides for administration of an effective amount of one or more MHC fusion complexes or loaded MHC molecules that contain a presenting peptide that is a T cell antagonist or partial agonist.

As further disclosed in said PCT Application, with respect to MHC peptide fusion complexes containing a presenting peptide that is a T cell receptor antagonist or partial agonist, MHC molecules of the present invention comprising such presenting peptides can be administered as a soluble MHC fusion complex lacking co-stimulatory signals. Alternatively, administration can take the form of an effective amount of a DNA sequence comprising a vector coding for a "full-length" MHC fusion complex, i.e., a complex that contains full-length MHC proteins including the transmembrane portion and a presenting peptide with antagonist or partial agonist activity covalently linked to the MHC molecule.

The invention also provides methods for inducing an immune response in a mammal that in general comprise administrating an effective amount of a DNA sequence that comprises a vector coding for a "full-length" MHC fusion complex, i.e. a complex that contains full-length MHC proteins including the transmembrane portion and a presenting peptide covalently linked to the MHC molecule. Alternatively, the vector can encode an empty single chain MHC complex where the expressed complex is contacted with a suitable presenting peptide under conditions which form the loaded molecule. Preferably, DNA that codes for a full length MHC fusion complex is administered to a mammal together with a DNA sequence coding for a T cell costimulatory factor such as a gene coding for B7 or B7-2. As used herein, the term "T cell co-stimulatory factor" refers to a peptide that is capable of providing a co-stimulatory signal to thereby activate T cell proliferation in the presence of one or more MHC fusion complexes. Such activation of T cell proliferation can be determined by the assays disclosed herein, including the assay as exemplified in Example 9 and discussed below. Further provided are diagnostic methods including HLA typing and in vivo diagnostic imaging using MHC fusion complexes or loaded MHC molecules, including MHC fusion complexes or loaded MHC molecules that contain a radioactive label (e.g., $^{125}$I, $^{32}$P or $^{99}$Tc) or other detectable tag. Other aspects of the invention are discussed infra.

BRIEF DESCRIPTION OF THE DRAWINGS

FIGS. 1A and 1B each depict a MHC fusion complex that includes a linker sequence. FIG. 1C schematically shows a MHC fusion complex linked or fused to an immunoglobulin.

FIG. 8 specifies the oligonucleotide primers used in the depicted procedure.

FIG. 8 specifies the oligonucleotide primers used in the depicted procedure.

FIG. 8 specifies the oligonucleotide primers used in the depicted procedure.

FIG. 8 specifies the oligonucleotide primers used in the depicted procedure.

FIG. 8 specifies the oligonucleotide primers used in the depicted procedure.

FIG. 8 specifies the oligonucleotide primers used in the depicted procedure.

FIG. 8 (SEQ ID NOS: 26–74) shows the sequences of oligonucleotides used in constructing MHC fusion complexes.

In FIGS. 11A and 11B (and FIGS. 15, 16A and 16B) the reference "PE" designates promoter and enhancer, the reference "LS" designates leader sequence exon and the reference "HC" designates heavy chain.

FIGS. 18A and 18B (SEQ ID NOS: 103–109) shows DNA and amino acid sequences of full length MHC fusion complexes.

FIG. 20 depicts oligonucleotide primers used in the depicted cloning scheme.

FIG. 20 (SEQ ID NOS: 110–112) depicts sequences of oligonucleotide primers used in constructing MHC fusion complexes.

FIG. 26 (SEQ ID NOS: 113–120) depicts sequences of oligonucleotide primers used in constructing MHC fusion complexes.

FIG. 27 (SEQ ID NO: 121) shows the DNA and amino acid sequences of the SSC1 single-chain gene.

FIG. 28 (SEQ ID NO: 122) shows the DNA and amino acid sequences of the SCT1 single-chain gene.

FIG. 29 (SEQ ID NO: 123) shows the DNA and amino acid sequences of the SCE1 single-chain gene.

FIG. 34C demonstrates that a loaded sc-$IA^d$ molecule (middle box) induces T cells to a greater extent than the corresponding sc-fusion complex (right box).

FIGS. 36A and 36B are graphs demonstrating that in vivo expression of sc-$IA^d$/OVA suppresses T cell clonal expansion.

DETAILED DESCRIPTION OF THE INVENTION

Figure 2:
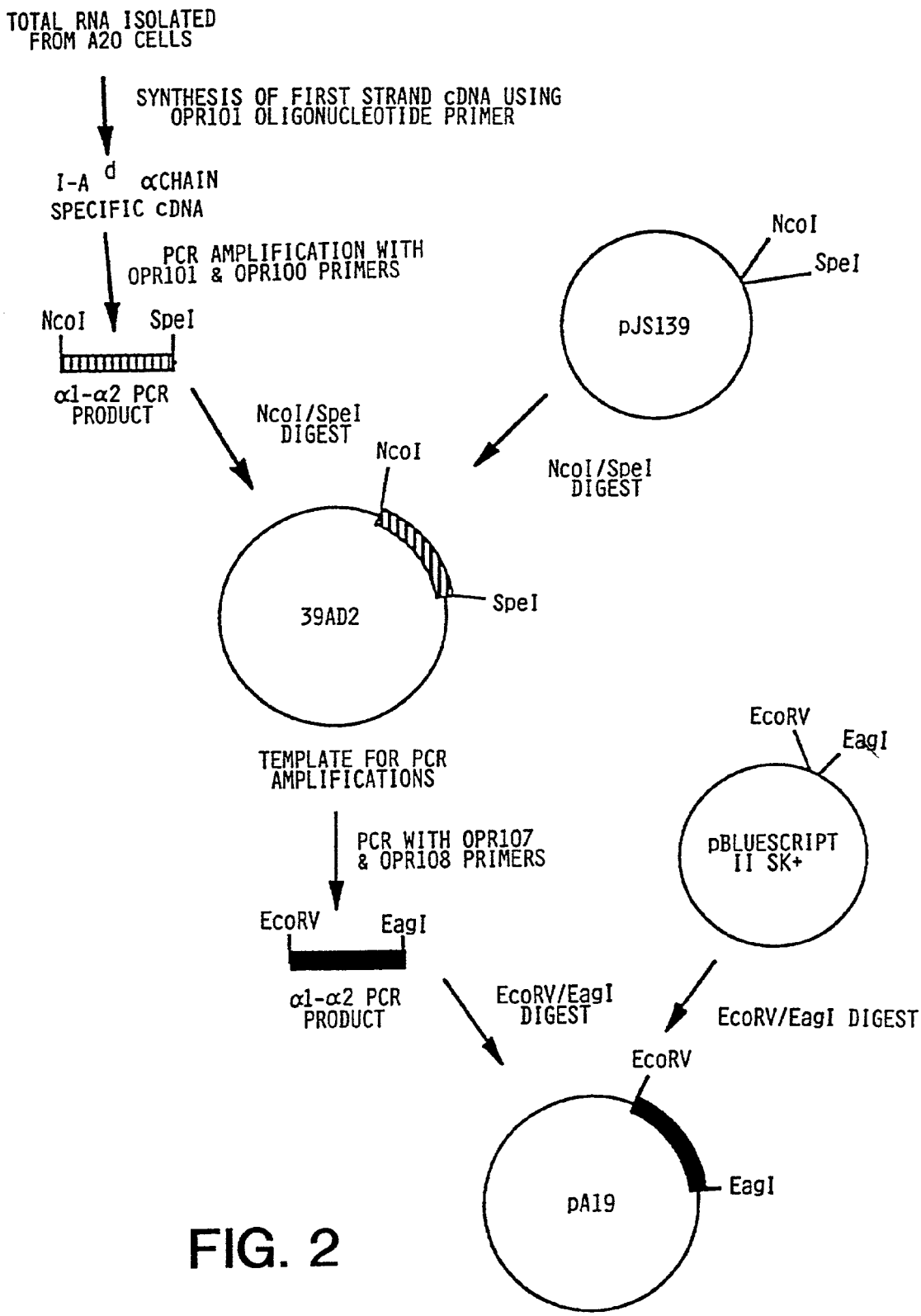
FIG. 2 shows the scheme for isolating the I-A$^d$ α1–β2 gene fragment and the cloning thereof.

As discussed above, and disclosed in said PCT Application No. PCT/US95/09816 (again the "PCT Application"), we have identified MHC class II peptide fusion complexes and expression vectors that encode such complexes and methods for use of such fusion complexes and expression vectors.

In general, preparation of MHC peptide fusion complexes can be accomplished by procedures disclosed herein and by recognized recombinant DNA techniques, i.e. preparation of plasmid DNA, cleavage of DNA with restriction enzymes, ligation of DNA, transformation or transfection of a host, culturing of the host, and isolation and purification of the expressed fusion complex. Such procedures are generally known and disclosed e.g. in Sambrook et al., *Molecular Cloning* (2d ed. 1989). As discussed more fully, infra, these methods are also suitable for the construction of empty and loaded MHC molecules of the invention. That is, to prepare empty and loaded MHC molecules of the present invention, the following procedures and examples for preparation of MHC fusion complexes can be employed except that the DNA sequence encoding the fused presenting peptide is not included in a gene construct coding for the empty/loaded molecule, or the formed fusion construct is treated by suitable recombinant techniques to remove the linked presenting peptide portion, as exemplified herein. Furthermore, the following discussions relating to the MHC fusion molecule, e.g. preferred present peptides, perferred linkers, molecule molecular weights, etc., are equally applicable to the empty and loaded MHC molecules of the present invention.

More specifically, DNA coding for a desired MHC protein is obtained from a suitable cell line as disclosed for instance in Example 1 which follows. Other sources of DNA coding for MHC protein are known, e.g. human lymphoblastoid cells. Once isolated, the gene coding for the MHC molecule can be amplified by the polymerase chain reaction (PCR) or other means known in the art. Suitable PCR primers to amplify the MHC peptide gene may add restriction sites to the PCR product. For example, for expression of a truncated fusion complex, specifically a soluble MHC fusion complex that does not contain transmembrane or cytoplasmic portions and is linked to an immunoglobulin such as IgG, the PCR product preferably includes IgG splice sites and leader sequences necessary for proper expression and secretion of the MHC-immunoglobulin fusion complex. The PCR product also preferably includes a sequence coding for the linker sequence, or a restriction enzyme site for ligation of such a sequence. Suitable primers, PCR conditions and expression vector construction techniques are e.g. disclosed in the examples which follow and the Drawings.

The presenting peptide linker sequence is preferably a nucleotide sequence that codes for a peptide that can effectively position the presenting peptide in the binding groove of the MHC molecule. As used herein, the phrase "presenting peptide is effectively positioned in the binding groove of an MHC molecule" or "MHC fusion complex capable of modulating the activity of a T cell", or other similar phrase, is intended to mean the presenting peptide linked to a MHC protein is positioned so that the presenting peptide and the fusion complex is capable of modulating the activity of a T cell receptor, either to induce T cell proliferation or to inhibit or inactivate T cell development as determined by an assay disclosed below, including the assay that includes sequential steps of culturing T cells to proliferate same, and contacting the T cells with a MHC fusion complex of the invention and then evaluating whether the MHC fusion complex inhibits further development of the T cells.

Preferably the presenting peptide linker sequence comprises from about 7 to 20 amino acids, more preferably from about 8 to 16 amino acids, still more preferably from about 8 to 12 amino acids. The linker sequence is preferably flexible so as not hold the presenting peptide in a single undesired conformation. The linker preferably predominantly comprises amino acids with small side chains, such as glycine, alanine and serine, to provide for flexibility. Preferably about 80 or 90 percent or greater of the linker sequence comprises glycine, alanine or serine residues, particularly glycine and serine residues. Preferably the linker sequence does not contain any proline residues, which could inhibit flexibility. For a MHC fusion complex that contains a MHC class II molecule, the linker sequence is suitably linked to the β chain of the MHC molecule, although the linker sequence also could be attached to the α chain of the MHC molecule. For covalently linking a presenting peptide to a MHC class II β chain molecule, the amino sequence of the linker should be capable of spanning approximately 30 angstroms from the N-terminal residue of the MHC class II β chain to the C-terminal residue of the presenting peptide. See for example FIGS. 1A and 1B of the Drawings. When such a β+peptide chain is expressed along with the α chain, the linked presenting peptide should fold into the α1 and β1 binding groove resulting in a functional MHC molecule as generally depicted in FIG. 1C. One suitable linker sequence is ASGGGGSGGG (SEQ ID NO: 1) (i.e., Ala Ser Gly Gly Gly Gly Ser Gly Gly Gly), preferably linked to the first amino acid of the β1 domain of the MHC class II protein. Different linker sequences could be used including any of a number of flexible linker designs that have been used successfully to join antibody variable regions together [see M. Whitlow et al., *Methods: A Companion to Methods in Enzymology*, 2:97–105 (1991)]. Suitable linker sequences can be readily identified empirically. For example, a DNA construct coding for a MHC fusion complex that includes a linker sequence can be cloned and expressed, and the fusion complex tested to determine if the complex is capable of modulating the activity of a T cell receptor, either to induce T-cell proliferation or to inhibit or inactivate T cell development as determined by the assay disclosed below. Suitable size and sequences of linker sequences also can be determined by conventional computer modeling techniques based on the predicted size and shape of the MHC molecule.

Preferably restriction sites are engineered in the DNA construct comprising the fused nucleotide sequences coding for the linker sequence and MHC protein so that essentially any nucleotide sequence coding for a presenting peptide of interest (e.g. either an antigenic or an antagonist presenting peptide) can be attached to the construct. For example, in one preferred system exemplified in the examples which follow, suitable restriction sites (e.g., AflII and NheI sites) are included between the end of the leader sequence and the beginning of the linker to facilitate insertion of a wide variety of presenting peptides to the β chain gene of the MHC molecule. See, for example, FIG. 3 of the Drawings. The nucleotide and amino acid sequences of specifically preferred leader sequences are depicted in FIGS. 18A and 18B of the Drawings.

The presenting peptide component of a MHC fusion complex should be capable of modulating the activity of a T cell as discussed above. For a MHC fusion complex that contains a class II MHC molecule, preferably the presenting peptide has from about 4 to 35 amino acids, more preferably about 6 to about 30 amino acids, still more preferably from about 8 to about 25 amino acids. For a MHC fusion complex that contains a class I MHC molecule, preferably the presenting peptide has from about 4 to 25 amino acids, more preferably about 6 to about 20 amino acids, still more preferably from about 6 to about 15 amino acids, even more preferably 8 to about 10 amino acids. Class I and class II MHC molecules show preferential binding toward different peptide sequences. Recently, anchor residues defining MHC allele-specific peptide motifs have been identified in class II binding peptides [F. Sinigaglia et al., *Curr. Opin. in Immun.*, 6:52–56 (1994)]. For example, in human class II HLA-DR1 molecules, an aromatic amino acid (e.g., Tyr, Phe, or Trp) is usually found near the amino terminus of the peptide (position 1), a hydrophobic residue (e.g., Met or Leu) at position 4 and a small amino acid (e.g., Ala or Gly) at position 6. Other MHC molecules have different motifs, e.g., for class II molecules, see Sinigaglia., supra; for class I molecules [see K. Parker et al., *J. Immunol.*, 152:163–175 (1994)]. Preferred presenting peptides include the desired MHC binding motif in order to facilitate optimum MHC binding. Thus, for example, in human class II HLA-DR1 MHC molecules, an aromatic amino acid (e.g., Tyr, Phe, or Trp) is preferably located near the amino terminus of the presenting peptide (position 1), a hydrophobic residue (e.g., Met or Leu) is at position 4 of the presenting peptide, and a small amino acid (e.g., Ala or Gly) is at position 6 of the presenting peptide. For the immunosuppression methods of the invention (e.g., to treat autoimmune diseases or allergies, or otherwise suppress an unwanted T cell response), the presenting peptide preferably may be the same as or homologous to (e.g., at least greater than about 80 or 90% shared sequence) a peptide known or suspected to be responsible for activating T cells in the targeted disorder. Thus, for example, the MPB peptide 80–105 is recognized by over 30% of MPB-specific T cells isolated from multiple sclerosis patients [see E. Meinl et al., *J. Clin. Invest.*, 92:2633–2643 (1993)] and should be a suitable as a presenting peptide in MHC fusion complexes used for immunosuppression applications as disclosed herein. Additionally, the activity of a particular presenting peptide, i.e. antigenic or antagonist or partial agonist, can be readily determined empirically by the methods disclosed herein, including the in vivo assays disclosed below.

To make the vector coding for a MHC fusion complex, the sequence coding for the MHC molecule is linked to a sequence coding for the presenting peptide by use of suitable ligases. DNA coding for the presenting peptide can be obtained by isolating DNA from natural sources or by known synthetic methods, e.g. the phosphate triester method. See, e.g., Oligonucleotide Synthesis, IRL Press (M. Gait, ed., 1984). Synthetic oligonucleotides also may be prepared using commercially available automated oligonucleotide synthesizers. A nucleotide sequence coding for a MHC molecule may be directly joined to a DNA sequence coding for the presenting peptide or, more typically, a DNA sequence coding for the linker sequence as discussed above may be interposed between the sequence coding for the MHC molecule and the sequence coding for the presenting peptide and joined using suitable ligases.

Other nucleotide sequences also can be included in the gene construct. For example, a promoter sequence, which controls expression of the sequence coding for the MHC peptide fused to the presenting peptide, or a leader sequence, which directs the MHC fusion complex to the cell surface or the culture medium, can be included in the construct or present in the expression vector into which the construct is inserted. An immunoglobulin or CMV promoter is particularly preferred. See the examples which follow. A strong translation initiation sequence also can be included in the construct to enhance efficiency of translational initiation. A preferred initiation sequence is the Kozak consensus sequence (CCACCATG) (SEQ ID NO: 2). See also FIGS. 18A and 18B of the Drawings.

Preferably a leader sequence included in a DNA construct contains an effectively positioned restriction site so that an oligonucleotide encoding a presenting peptide of interest can be attached to the MHC molecule. Suitably the restriction site can be incorporated into the 3-end of the leader sequence, sometimes referred to herein as a junction sequence, e.g. of about 2 to 10 codons in length, that is positioned before the coding region for the presenting peptide. A particularly preferred restriction site is the AflII site, although other cleavage sites also can be incorporated before the presenting peptide coding region. As discussed above, use of such a restriction site in combination with a second restriction site, typically positioned at the beginning of the sequence coding for the linker, enables rapid and straightforward insertion of sequences coding for a wide variety of presenting peptides into the DNA construct for the MHC fusion complex. Preferred leader sequences contain a strong translation initiation site and a cap site at the 3'-end of their mRNA. Preferably a leader sequence is attached to the α domain of a class I MHC molecule, and preferably a leader sequence is attached to the β domain of a class II MHC molecule. Preferred leader sequences provides for secretory expression of the MHC fusion complex.

As disclosed in said PCT Application, a number of strategies can be employed to express MHC fusion complexes of the invention. For example, the MHC gene fusion construct described above can be incorporated into a suitable vector by known means such as by use of restriction enzymes to make cuts in the vector for insertion of the construct followed by ligation. The vector containing the gene construct is then introduced into a suitable host for expression of the MHC fusion peptide or complex. See, generally, Sambrook et al., supra. Selection of suitable vectors can be made empirically based on factors relating to the cloning protocol. For example, the vector should be compatible with, and have the proper replicon for the host that is being employed. Further the vector must be able to accommodate the DNA sequence coding for the MHC fusion complex that is to be expressed. Suitable host cells include eukaryotic and prokaryotic cells, preferably those cells that can be easily transformed and exhibit rapid growth in culture medium. Specifically preferred hosts cells include prokaryotes such as *E. coli, Bacillus subtillus*, etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See Sambrook, supra. Stable transformed or transfected cell lines can then be selected. Cells expressing a MHC fusion complex can be determined by known procedures. For example, expression of a MHC fusion complex linked to an immunoglobulin can be determined by an ELISA specific for the linked immunoglobulin and/or by immunoblotting.

In one preferred protocol for preparation of soluble MHC fusion complexes, DNA sequences encoding the presenting peptide and β1–β2 domains of the MHC molecule (class II) are arranged such that the C-terminal end of the presenting peptide is attached to an initial amino acid of the β1 domain, preferably the first amino acid of the β1 domain by a flexible linker sequence. Such a construct is depicted in FIGS. 1A and 1B of the Drawings. For a class I MHC molecule, preferably the DNA sequence encoding the presenting peptide is attached to the α domain of the MHC molecule, preferably such that the presenting peptide will be linked to the N-terminus end of that α chain. As discussed above, preferably restriction sites are engineered between the end of the leader sequence and the beginning of the linker so that essentially any oligonucleotide encoding a presenting peptide of interest (i.e. antigenic or antagonist) can be attached to the β chain gene. For soluble expression, the α1–α2 and peptide-linked β1–β2 domains are suitably fused to an immunoglobulin, preferably to the constant domains of the immunoglobulin kappa and heavy chains, respectively, as depicted in FIG. 1C. Preferred immunoglobulins for such fusion to α and β for soluble expression include, e.g., the light chain constant domains and CH2–CH3 domains of IgG2b.

An expressed MHC fusion complex can be isolated and purified by known methods. Typically the culture medium is centrifuged and then the supernatant is purified by affinity or immunoaffinity chromatography, e.g. Protein-A or Protein-G affinity chromatography or an immunoaffinity protocol comprising use of monoclonal antibodies that bind the expressed fusion complex such as a linked MHC or immunoglobulin region thereof. For example, MHC fusion complexes containing human HLA-DR1 sequences can be purified by affinity chromatography on a monoclonal antibody L243-Sepharose column by procedures that are generally known and disclosed, e.g., see Harlow, E. et al., Antibodies, A Laboratory Manual (1988). The L243 monoclonal antibody is specific to a conformational epitope of the properly folded HLA-DR1 molecule [J. Gorga et al., *J. Biol. Chem.*, 262: 16087–16094], and therefore would be preferred for purifying the biologically active MHC fusion complex. The MHC fusion complex also may contain a sequence to aid in purification; see, e.g., Example 17 which follows which discloses use of a 6xHis tag.

Truncated MHC fusion complexes contain a MHC molecule that is sufficiently truncated so the MHC fusion complex can be secreted into culture medium (e.g. physiological conditions; in the substantial or complete absence of detergent or the like) after expression. Thus, a truncated MHC fusion complex will not include regions rich in hydrophobic residues, typically the transmembrane and cytoplasmic domains of the MHC molecule, although at least portions of those domains may be suitably present provided the MHC molecule can be secreted as discussed. Thus, for example, for a preferred truncated DR1 MHC molecule, preferably from about residues 199 to 237 of the β chain and from about residues 193 to 230 of the α chain of the MHC molecule are not included in the truncated MHC fusion complex. See the examples which follow. In addition to the sequences disclosed herein, sequences of domains of MHC class I and II molecules have been disclosed previously (see, e.g., the above mentioned publications). Truncated MHC fusion complexes of course also can be readily identified empirically, i.e. by examining if the MHC complex is secreted into culture medium after expression as discussed. Truncated MHC fusion complexes can be prepared be several means, e.g. expression of a soluble MHC molecule or enzymatic (e.g. papain) cleavage of at least portions of transmembrane and/or cytoplasmic domains of a full length MHC fusion complex.

Full length MHC molecules include a transmembrane portion and/or cytoplasmic domain and/or other cellular membranes or substantial portions thereof (e.g. greater than about 80 or 90 percent of such sequences). For a full length MHC class II molecule, generally both the α and β chains are linked to transmembrane and cytoplasmic domains, although only one of the α and β chains may be linked to transmembrane and cytoplasmic domains, particularly in the case of single chain MHC molecules. As discussed below, full length MHC molecules can be anchored to cell membranes through hydrophobic membrane spanning domains or alternatively through post-translational attachment of other anchor domains such as covalently linked glycosylated form of phosphatidylinositol.

Figure 24:
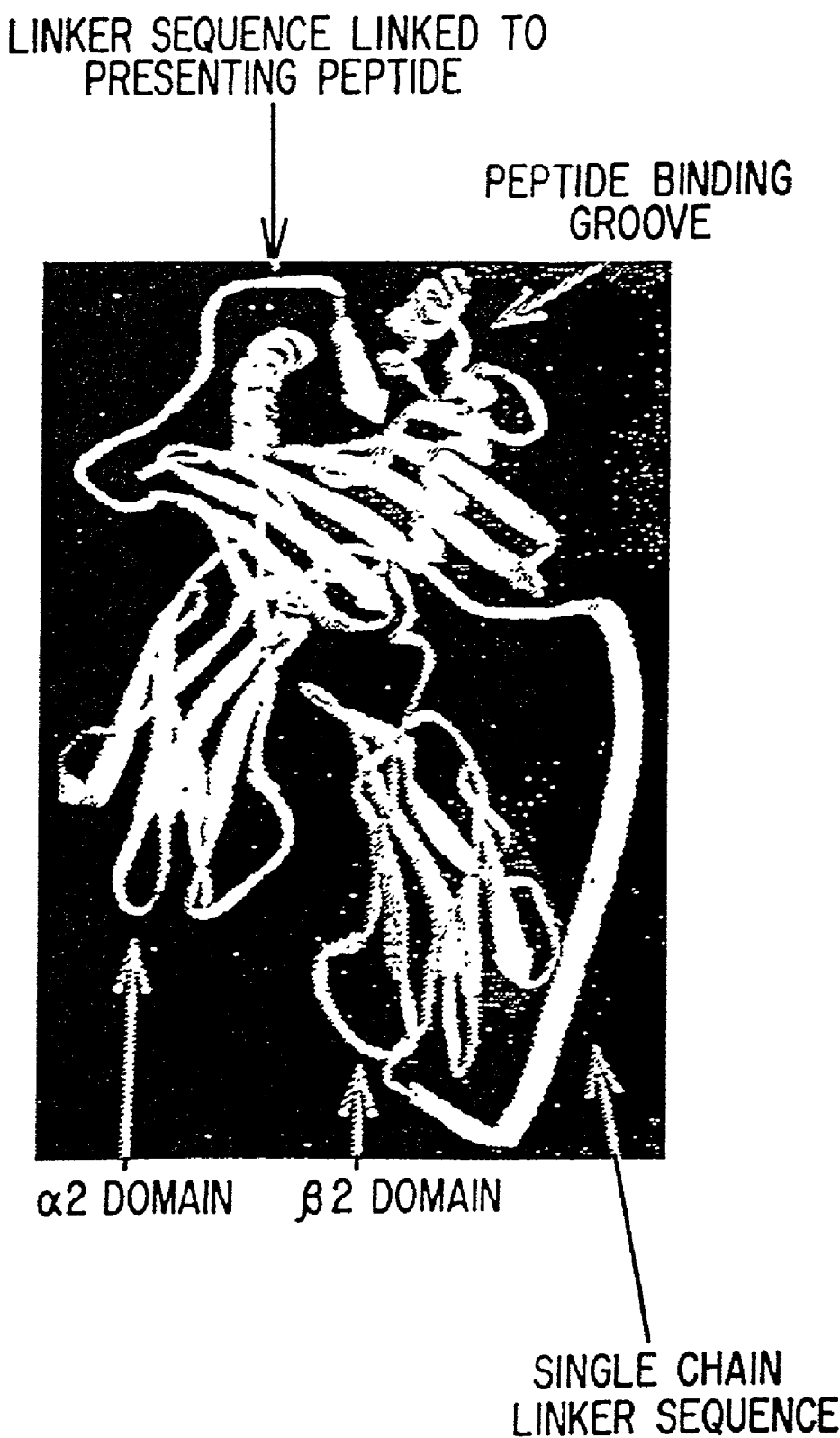
FIG. 24 depicts a single-chain MHC fusion complex.
Figure 25A:
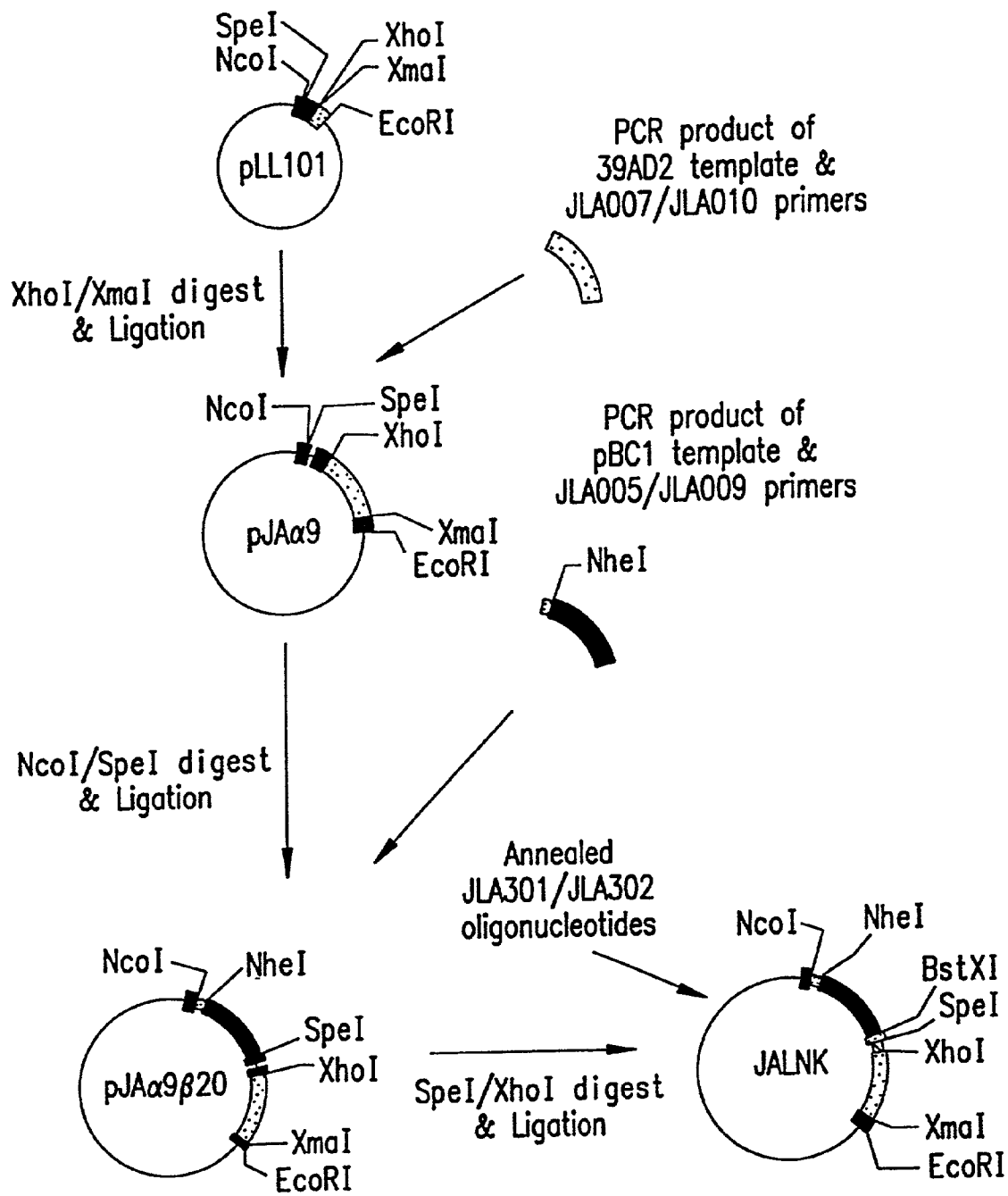
FIG. 25 (total of 4 sheets) shows the cloning scheme carried out in Example 17 which follows.
Figure 25B:
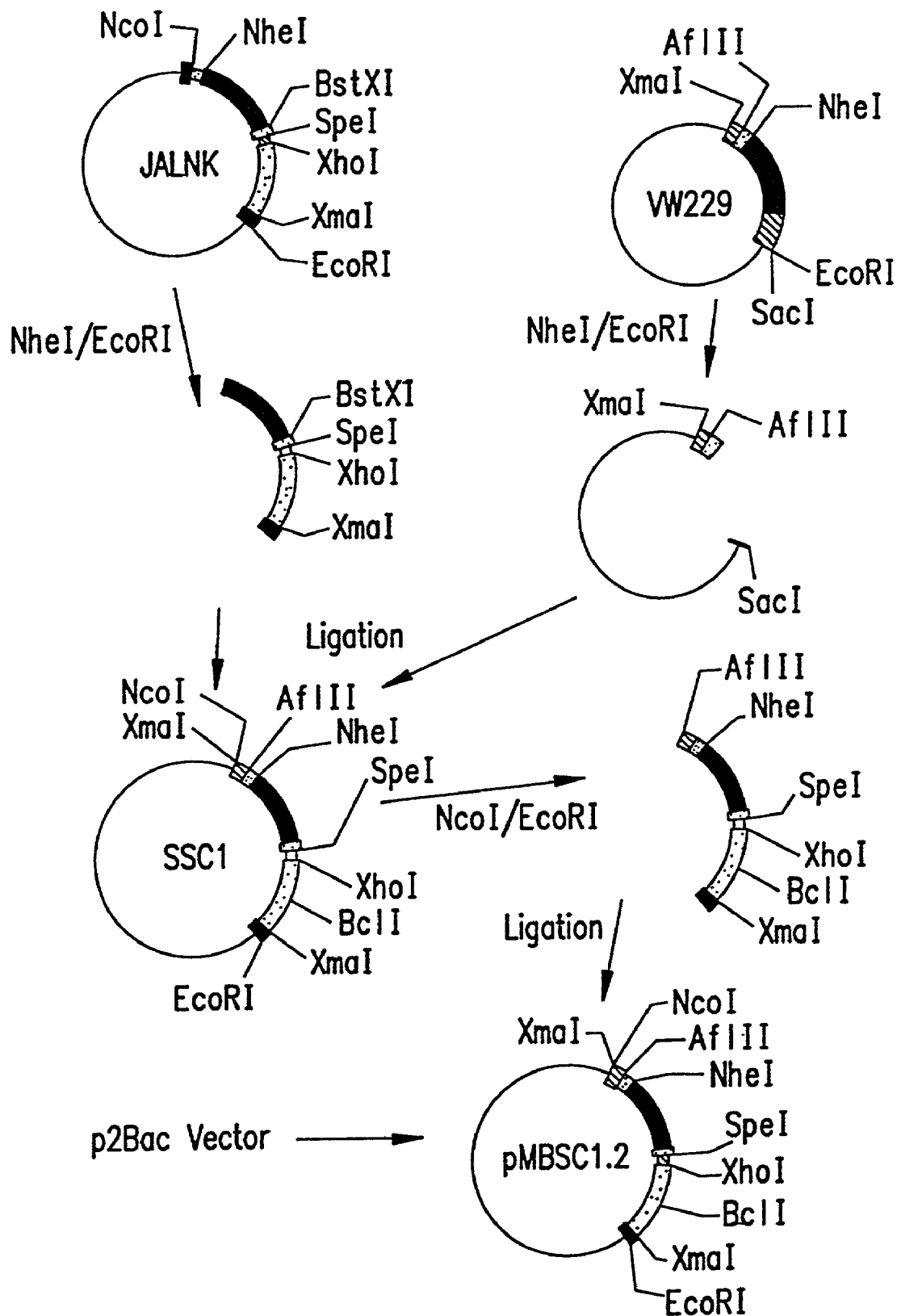
Figure 25C:
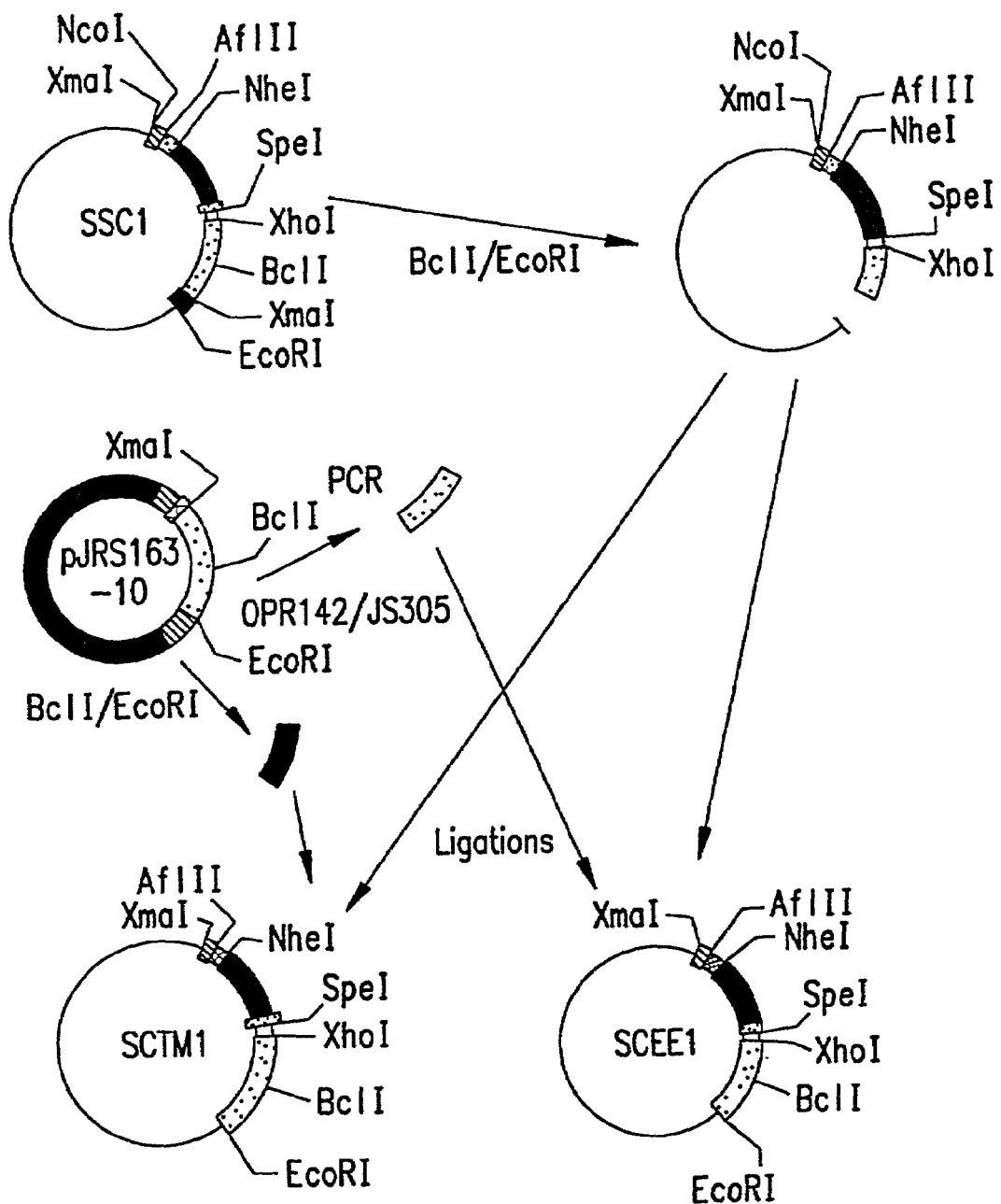
Figure 25D:
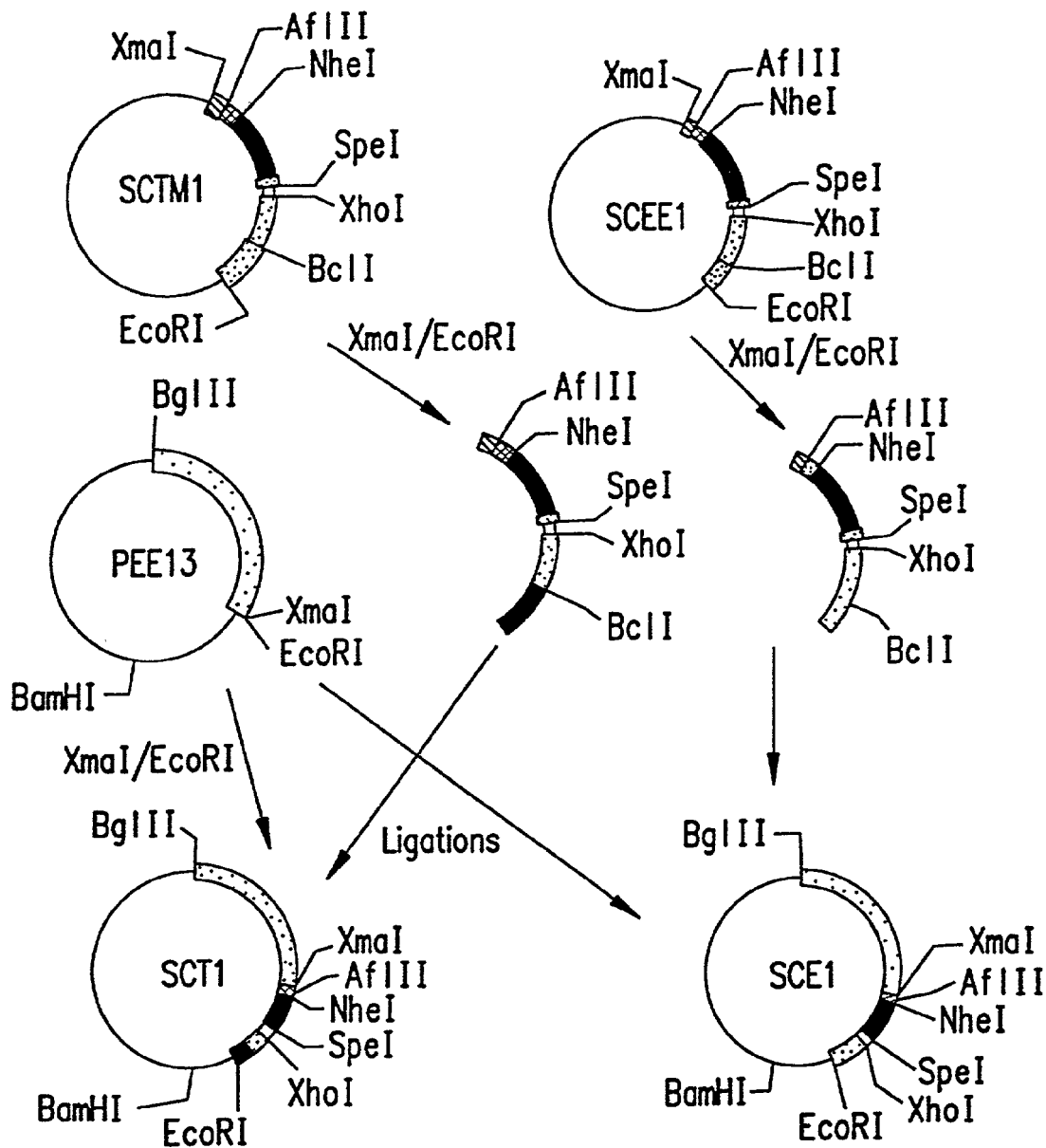
Figure 30:
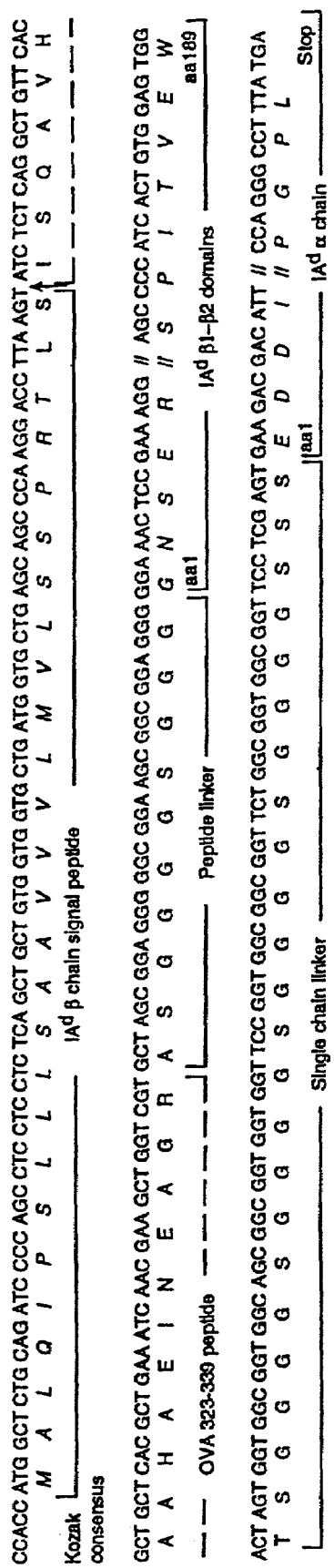
FIG. 30 (SEQ ID NO: 122) is a schematic representation of the gene encoding the single chain $IA^d$/OVA 323–229 MHC fusion molecule (i.e., sc-$IA^d$/OVA). The Kozak consensus sequence is indicated. The arrow designates the signal peptidase cleavage site. "//" in the $IA^d$ β1–β2 and $IA^d$ ∝ domains represents amino acid and nucleotide sequences in FIG. 28 omitted for clarity. The OVA 323–339 peptide (dashed line) is absent in the sc-$IA^d$/blank MHC molecule.

As discussed above and in said PCT Application, single chain MHC fusion complexes are desirable, i.e. a fusion complex that consists of a single polypeptide rather than a multiple chain aggregate such the native heterotrimeric class II/peptide complex where α and β chains and a peptide are associated through non-covalent interactions. In the case of a single chain MHC class II complex, the α and β chain subunits are linked as a single chain fusion protein with the presenting peptide preferably linked to the β chain of the chain fusion protein. Such a preferred single chain MHC molecule is depicted in FIG. 24 and FIG. 30. Preferably a linker sequence is used to link the α and β chains. Such a linker sequence used to link domains of an MHC molecule is sometimes referred to herein as a "single chain linker sequence" and is thereby distinguished from the linker sequence discussed above that is interposed between and covalently links a presenting peptide and an MHC molecule.

Preferably a single chain MHC class II complex is linked between the carboxyl terminus of the β2 domain and the amino terminus of the α1 domain, although multiple domains of a MHC complex may be linked through other positions.

The single chain linker sequence should enable the linked MHC molecule to fold to an active form, i.e. a form where the MHC molecule can modulate the activity of a T cell. Such effective single chain linker sequences can be readily determined empirically. Thus, e.g., a DNA construct coding for a single chain MHC molecule where the α and β chains are linked by a linker sequence can be cloned and expressed, and the single chain MHC molecule tested to determine if the complex is capable of modulating the activity of a T cell receptor, either to induce T-cell proliferation or to inhibit T cell development as determined by the assays disclosed below.

Both length and composition of the single chain linker sequence can in general vary. For example, the length of a suitable single chain linker sequence may vary with the positions at which the linker sequence is linked to polypeptide chains of the MHC complex; in other words the length of the linker sequence may vary with the geometry of the "gap" between polypeptides which the linker sequence bridges.

The single chain linker sequence preferably also should be flexible to permit folding of the single chain molecule to an active form. The linker sequence thus preferably predominantly comprises amino acids with small side chains, such as glycine, alanine and serine, to provide for flexibility. Preferably about 80 or 90 percent or greater of the linker sequence comprises glycine, alanine or serine residues, particularly glycine and serine residues. Preferably this linker sequence between the α and β chains does not contain any proline residues, which could inhibit flexibility. Preferably a linker sequence positioned between the carboxyl terminus of a β2 domain and the amino terminus of the α1 domain will comprise about 15 to 40 amino acids, more preferably about 15 to 30 amino acids. A particularly preferred linker sequence is disclosed in Example 17 which follows. Suitable size and sequence of single chain linker sequences also can be determined by conventional computer techniques; see Example 17 which follows.

Single chain MHC complexes ban be prepared as discussed above and in said PCT Application, as well as the examples which follow, including Examples 17–19 and 25. For example, DNA coding for a desired MHC protein can be obtained from a suitable cell line, and the isolated gene can be amplified by PCR or other means. In the case of a MHC class II molecule, an α1–α2 gene fragment can be cloned into a vector, followed by cloning of a gene fragment cloning for the β1–β2 domains with an interposed single chain linker sequence. The single vector is then expressed in a suitable host and the single chain molecule harvested and purified if desired. See the examples which follow, including Examples 17–19. See also U.S. Pat. No. 5,260,203 to Ladner et al., which discusses preparation of single chain antibodies, which methods can be generally employed to the single chain MHC fusion complexes of this invention.

In a preferred preparation method, coding regions of the α and β chains of the MHC class II molecules are obtained, particularly by isolating the coding regions by PCR from a B cell line or other MHC molecule source. A sequence encoding a single-chain β-α fusion MHC fusion molecule can be constructed by replacing sequences encoding the transmembrane spanning domain of the β chain gene with a single chain linker sequence as discussed above which joins the β chain gene to the mature α chain (particularly at the first codon of the α chain gene). The α chain gene may suitably contain its transmembrane region for membrane bound expression of the single chain fusion complex, or the α chain gene may be truncated at the end of the extracellular region for soluble expression of the single chain MHC fusion complex. A suitable restriction site and linker for the presenting peptide is preferably included between the β chain leader and the first codon of the β chain. The coding region of essentially any presenting peptide can then be introduced as an oligonucleotide into the created restriction site. The resulting construct is then suitably placed under the control of mammalian or bacterial promoters, including those specific promoters disclosed herein. One such preferred MHC class I single-chain construct contains linked nucleotide sequences encoding in sequence: β chain leader/presenting peptide/linker sequence/β1–β2 extracellular region/single chain linker sequence/α1–α2) extracellular region. The MHC single-chain DNA constructs are suitably introduced into bacterial, baculoviral-insect cell and mammalian expression systems, including those specific expression systems disclosed herein, then expressed and purified if desired.

The single chain MHC molecule may be either full length, i.e. the MHC molecule is associated with cellular domains and contains e.g. complete or substantial amounts (e.g. greater than 80% of the sequences) of transmembrane and/or cytoplasmic portions of an α or β chain, or be truncated as discussed above for soluble expression. Such truncated and full length single chain MHC molecules may be produced as described above and in the examples for multiple polypeptide MHC complexes. For an MHC class II molecule, a full length molecule may have only one of the α and β chains linked to transmembrane and cytoplasmic domains, preferably the α chain. A preferred full-length single chain fusion MHC class II complex comprises covalently linked in sequence: 1) the presenting peptide, 2) the class II β chain lacking transmembrane and cytoplasmic domains, 3) a single chain linker sequence, and 4) the class II α chain containing transmembrane and cytoplasmic domains or a membrane anchor domain. A preferred soluble single chain fusion MHC class II complex comprises covalently linked in sequence: 1) the presenting peptide, 2) the class II β chain lacking transmembrane and cytoplasmic domains, 3) a single chain linker sequence, and 4) the class II α chain lacking transmembrane and cytoplasmic domains.

With respect to the full length MHC complexes (both single chain and non-single chain molecules) the MHC proteins can be anchored to cell membranes through hydrophobic membrane spanning domains (transmembrane domains) as well as through post-translational attachment of the covalently linked glycosylated form of phosphatidylinositol (GPI membrane anchor). Typically for the α and β chains of the MHC class II molecule, the transmembrane domain consists of approximately 25 hydrophobic amino acids connected to the carboxyl terminal side of the α2 and β2 domains. These residues allow the protein to span the membrane. The transmembrane region ends with about 10–15 residues comprising the cytoplasmic tail at the carboxyl terminal end of each of these chains. It has been demonstrated that these transmembrane and cytoplasmic regions can be replaced with sequences signaling GPI linkage and that the chimeric GPI-anchored class II molecules are membrane bound [D. Wettstein et al., *J. Exp. Med.*, 174:219–228 (1991)]. GPI-linked membrane anchor domains have been defined in a number of proteins including decay accelerating factor (DAF), CD59 and humans placental alkaline phosphatase (HPAP) [D. Wettstein et al., *J. Exp. Med.*, 174:219–228 (1991); D. Kooyman et al.]. For example, the 38 carboxyl terminal amino acids of HPAP are sufficient to act as a signal sequence for GPI linkage. If the DNA sequence encoding this domain is linked to a secreted molecule such as the soluble portion of the MHC class II α or β chain, a membrane bound chimeric molecule is formed [D. Wettstein et al., *J. Exp. Med.*, 174:219–228 (1991)], and such an approach can be employed to anchor peptide-linked single chain II MHC molecules to a cell membrane.

Molecular weights of MHC fusion molecules as well as the empty and loaded MHC molecules of the present invention will vary, particularly depending on whether the molecule is soluble or full length (membrane bound). A soluble MHC class II fusion complex generally will have a molecular weight of greater than about 45 kDa, and mature α and β chains without trans-membrane and cytoplasmic domains each will have a molecular weight of greater than about 20 kDa, more typically between about 21 to about 26 kDa. Typically, mature single-chain MHC class II molecules without trans-membrane and cytoplasmic domains will have a molecular weight of about 48 to about 50 kDa. For full length (membrane bound) molecules, mature α and β chains generally will have a molecular weight of greater than about 25 kDa, preferably between about 26 and about 30 kDa. Typically, mature single-chain MHC class II fusion molecules with a single (linked to (α or β chain) transmembrane or membrane anchor domain will have a molecular weight of greater than about 49 kDa, preferably between about 50 and 52 kDa. All of the above mentioned molecular weights are by a SDS-PAGE determination.

Multivalent MHC fusion complexes or empty or loaded MHC molecules are desirable for a number of applications. The valence of a MHC-antigenic peptide complex influences the effect of the complex on T cell receptor(s). For example, activation of the 3DT52.5 T cell hybridomas requires a MHC-antigenic molecule that has been made multivalent. Monovalent, soluble MHC complexes are incapable of stimulating this T cell [J. McCluskey et al., *J. Immunology*, 141:1451–1455 (1988)]. Desired multivalent MHC fusion complexes include those linked to an immunoglobulin, e.g., IgG, IgM or Fab'$_2$. Chemically cross-linked MHC complexes (for example cross-linked to dendrimers) are also suitable multivalent species. For example, the MHC complex can be genetically modified by including sequences encoding amino acid residues with chemically reactive side chains such as Cys or His. Such amino acids with chemically reactive side chains may be positioned in a variety of positions of a MHC complex, preferably distal to the presenting peptide and binding domain of the MHC complex. For example, the C-terminus of the β chain of a MHC molecule distal from the presenting peptide suitably may contain such reactive amino acid(s). Suitable side chains can be used to chemically link two or more MHC fusion complexes to a suitable dendrimer particle to give a multivalent MHC fusion complex. Dendrimers are synthetic chemical polymers that can have any one of a number of different functional groups of their surface [D. Tomalia, *Aldrichimica Acta*, 26:91:101 (1993)]. Exemplary dendrimers for use in accordance with the present invention include e.g. E9 starburst polyamine dendrimer and E9 combburst polyamine dendrimer, which can link cysteine residues.

It may be desirable to construct a single expression vector that expresses both chains of an MHC fusion complex of the invention or an empty or loaded molecule of the invention, i.e. sequences that code for both the α and β chains of an MHC fusion complex are each connected to a single expression vector, even if not a single chain molecule. Such an expression vector may provide better results than where separate vectors are used for each chain of a MHC fusion complex, particularly where selection is difficult for cells into which the vector has been introduced. It also may be desirable to construct a single expression vector that codes for both chains of a MHC fusion complex as well as other agents, particularly a T cell costimulatory factor such as B7 or B7-2, i.e. sequences that code for both chains of an MHC fusion complex and sequence(s) that code for a costimulatory factor are each connected to a single expression vector, to enable a single transformation procedure. Again, this approach would avoid potentially difficult selection for cells that have been transformed or transfected two or more times.

The MHC molecules of the fusion complexes and the empty and loaded molecules of the present invention suitably correspond in amino acid sequence to naturally occurring MHC molecules, e.g. MHC molecules of a human (class I or class II), mouse or other rodent, or other mammal. Preferably at least about 70 percent of the amino acid sequence of a MHC molecule of the fusion complex will be the same as the amino acid sequence of a naturally occurring MHC molecule such as those mentioned above, more preferably at least about 90 percent amino acid sequence of a MHC molecule of the fusion complex will be the same as the amino acid sequence of a naturally occurring MHC molecule, and even more preferably about 98 percent to all of the amino acid sequence of a MHC molecule of the fusion complex will be the same as the amino acid sequence of a naturally occurring MHC molecule.

An empty MHC molecule of the invention, particularly an empty single chain MHC class II molecule, can be made according to any suitable method described above, except that the presenting peptide is not covalently linked to the molecule. For example, in Example 1B, steps which join an oligonucleotide encoding the OVA presenting peptide (OPR110 and OPR111) to the linker-β1–β2 gene fragment can be omitted. In another example, a presenting peptide can be excluded from an MHC molecule of the invention which already has a covalently linked presenting peptide by using standard recombinant DNA manipulations. For example, DNA encoding the sc-IA$^d$/OVA presenting peptide can be removed with a suitable restriction enzyme (e.g., AFII and Nhe I). As an illustrative example, the construction of a soluble empty single chain IA$^d$MHC molecule (i.e. sc-IA$^d$/blank) is discussed in Examples 25–27.

As disclosed in said PCT Application, MHC fusion complexes can be used in the detection and characterization of recombinant peptides. For example, the invention includes a method that can be used to map an uncharacterized epitope for T cells as follows: sequences encoding either a library of random peptides or selected peptides can be cloned into the presenting peptide position of an expression vector system of the invention such as those identified above that contains a DNA sequence encoding a MHC molecule and, optionally, a DNA sequence coding for a linker sequence. Suitably restriction fragments of an appropriate cDNA or genomic DNA library (see Sambrook, et al., supra) are used as the source of the sequences inserted into the expression vector or, alternatively, selected oligonucleotides such as synthetic oligonucleotides of known sequence are used as the inserted sequences. Suitable hosts, such mammalian cells and others identified above, are transformed or transfected with the vector containing the gene fusion, i.e. the sequence coding for the MHC molecule linked to sequence coding for the additional peptide. Transformants are cultured under suitable conditions and the cells screened for expression of fusion complex of interest that reacts with T cell clones as determined by assays disclosed below. Reactive colonies can then be picked and the vectors isolated. Sequence analysis of the DNA insert would reveal which of the cloned peptide sequences corresponded to the epitope(s) recognized by the T cell clone. Empty MHC molecules of the invention can be used in the same way except that the peptides are loaded onto the empty molecule rather than ingesting the peptide via recumbent methods.

The ability of a MHC fusion complex or loaded MHC molecules of the present invention to modulate the activity of a T cell receptor (including inactivation of the T cell responses) can be readily determined by an in vitro assay. Typically T cells for the assays will be provided by transformed T cell lines such as T cell hybridomas or T cells which are isolated from a mammal, e.g., from a human or from a rodent such as a mouse. Other suitable T cells include: 1) T cell hybridomas which are publicly available or can be prepared by known methods, 2) T helper cells, and 3) T cytotoxic cells, preferably cytotoxic CD4$^+$ cells. T cells can be isolated from a mammal by known methods. See, for example, R. Shimonkevitz et al., *J. Exp. Med.*, 158:303 (1983) and Examples 4 and 5 which follow.

A suitable assay to determine if a MHC fusion complex or a loaded MHC molecule of the present invention is capable of modulating the activity of T cells is conducted as follows, by the sequential steps 1–4 below. T cells suitably express a marker that can be assayed and that indicates T cell activation, or modulation of T cell activity after activation. Thus, e.g., as disclosed in Example 4 below, the murine T cell hybridoma DO 11.10 that express interleukine-2 (IL-2) upon activation can be employed. IL-2 concentrations can be measured to determine if a particular presenting peptide is capable of modulating activity of this T cell hybridoma. Such a suitable assay is conducted by the following sequential steps:

1. T cells carrying the T cell receptor specific to the peptide/MHC complex are obtained such as from a T cell hybridoma of interest or by isolating from a mammal.
2. The T cells are cultured under conditions that allow proliferation.
3. The proliferating T cells are contacted with a selected MHC fusion complex (or loaded molecule).
4. The T cell are contacted with the antigen presenting cells to provide signal necessary for activation and assayed for a marker, e.g. IL-2 production is measured. A decrease in IL-2 production, e.g., a 40 percent or greater decrease in IL-2 production after a period of 24 hrs., more typically a 50 percent or greater decrease in IL-2 production after a period of 24 hrs., indicates the MHC fusion complex (or loaded molecule) modulates the activity of the T cells and can suppress an immune response. Example 4 which follows exemplifies such an assay. The assay is suitably employed for analysis of activity of soluble "truncated" MHC complexes that do not contain a transmembrane portion. In addition, the assay is suitably employed for identification of MHC fusion complexes that contain a covalently linked presenting peptide (or loaded molecule) that functions as a T cell receptor antagonist or partial agonist. The assay is also conveniently adapted for use with loaded MHC complexes of the invention as mentioned above.

The T cells employed in the assays are incubated under conditions suitable for proliferation. For example, a DO11.10 T cell hybridoma is suitably incubated at about 37° C. and 5% $CO_2$ in complete culture medium (RPMI 1640 supplemented with 10% FBS, penicillin/streptomycin, L-glutamine and 5×10$^{-5}$ M 2-mercaptoethanol). Serial dilutions of MHC fusion complex can be added to the T cell culture medium. Suitable concentrations of the MHC fusion complex added to the T cells typically will be in the range of from 10$^{-12}$ to 10$^{-6}$ M. T cell activation signals are provided by antigen presenting cells that have been loaded with the appropriate antigenic peptide. It is believed that use of antigen dose and APC numbers giving slightly submaximal T cell activation is preferred to detect inhibition of T cell responses with MHC fusion complexes. A decrease in production of IL-2 following contact with the MHC fusion complex indicates the fusion complex modulates activity of the T cells and can suppress immune response.

Alternatively, rather than measurement of an expressed protein such as IL-2, modulation of T cell activation can be suitably determined by changes in antigen-dependent T cell proliferation as measured by radiolabelling techniques as are recognized in the art. For example, a labeled (e.g., tritiated) nucleotide may be introduced to an assay culture medium. Incorporation of such a tagged nucleotide into DNA serves as a measure of T cell proliferation. See Example 5 which follows, where such a procedure is specifically described. This assay is not suitable for T cells that do not require antigen presentation for growth, e.g., T cell hybridomas. It is suitable for measurement of modulation by the MHC fusion complexes (or loaded MHC molecules) of T cell activation for untransformed T cells isolated from mammals. A decrease in the level of T cell proliferation following contact with the MHC fusion complex, (or loaded MHC molecules) indicates the complex modulates activity of the T cells and can suppress immune response, e.g., see Example 5 which follows. The in vitro T cell proliferation assay is preferred for measuring the effects of MHC fusion complexes (or loaded MHC molecules) on antigen-specific changes in T cell clonal expansion in vivo. Such an assay is specifically described in Example 7 which follows.

These in vitro assays can be employed to select and identify peptide(s), coded by DNA from a random library or other oligonucleotides, that are capable of modulating the activity of T cell receptor (including activation or inhibition of T cell development). Specifically, DNA sequences encoding either a library of random peptides or selected peptides can be cloned into the presenting peptide position of an expression vector system such as those identified above that contains a DNA sequence encoding a MHC molecule and, optionally, a DNA sequence coding for a linker sequence. Suitably, restriction fragments of an appropriate cDNA of genomic DNA library (see Sambrook, et al., supra) are used as a source of the sequences inserted into the expression vector or, alternatively, selected oligonucleotides such as synthetic oligonucleotides of known sequence are used as the inserted sequence. Suitable hosts, such as a mammalian cells and others identified above, are transformed with the vector containing the gene fusion, e.g., the sequence coding for the MHC molecule linked to sequence coding for the presenting peptide. Transformants are cultured under suitable conditions and the cells are screened for expression of the MHC fusion complex (or loaded MHC molecules) of interest by contacting same with selected T cells. Assays described above, e.g., measurement of IL-2 production or T cell proliferation, are employed to determine if contact with the MHC fusion complex (or loaded MHC molecules) modulated T cell activation. For example, a decrease in IL-2 production of APC-stimulated T cells identifies those MHC fusion complexes that modulate activity of the T cells and suppress the immune responses. Alternatively, the in vitro assays can be employed to identify multivalent MHC fusion complexes (or loaded MHC molecules) described above, that contained presenting peptides that increase T cell responses.

In vivo assays also may be suitably employed to determine the ability of a MHC fusion complex (or loaded MHC molecules) to modulate the activity of T cells, including the ability to inhibit or inactivate T cell development. For example, an MHC fusion complex (or loaded MHC molecules) can be assayed for its ability to inhibit immunoglobulin class switching (i.e. IgM to IgG) [see, e.g., P. Linsley et al., Science, 257:792–795 (1992)]. Such an assay is specifically described in Example 6 which follows.

Diagnostic methods using MHC fusion molecules are also provided including in vivo diagnostic imaging and HLA typing [see, e.g., A. K. Abbas, Cellular and Molecular Immunology, page 328 (W. B. Saunders Co. 1991)]. For in vivo imaging applications, a MHC fusion molecule or loaded molecule that has a radioactive label (e.g., $^{125}$I, $^{32}$P, $^{99}$Tc) or other detectable tag can be administered to a mammal and the subject scanned by known procedures for binding of the MHC molecule or loaded molecule. Such an analysis of the mammal could aid in the diagnosis and treatment of a number of disorders including e.g. undesired immune responses as disclosed herein.

An empty MHC molecule of the invention, particularly an empty single chain MHC class II molecule, can be used to screen for presenting peptides which non-covalently bind the peptide binding groove or cleft of the MHC molecule. Such screens are useful for identifying those presenting peptides which can bind particular MHC molecules e.g., MHC class II molecules such as IA$^d$, DR1, IE, DP, and DQ. As an illustrative example, the sc-IA$^d$/blank molecule can be modified with a detectable tag (e.g., I$^{125}$, biotin or another protein tag disclosed herein) and then used to screen a random peptide library. Procedures for tagging proteins and screening libraries are well known [see, e.g., Sambrook et al., supra, and Ausubel et al., Current Protocols in Molecular Biology, John Wiley & Sons, New York, 1989; herein incorporated by reference]. Any one of several random peptide libraries can be suitably employed [see, e.g., J. Scott et al., Science, 249:386 (1990); J. Devlin et al., Science, 249:404 (1990); S. Cwirla et al., PNAS (USA), 87:6378 (1990); J. Hammer et al., J. Exp. Med., 176:1007 (1992); D. O'Sullivan et al., J. Immunol., 147:2663 (1991)]. Peptides which bind the sc-IA$^d$/blank molecule can be used to make the corresponding loaded molecule. The loaded molecule could then be tested in any T cell assay described herein to see if the identified peptide is capable of modulating T cell activity.

Assays also may be employed to evaluate the potential use of an MHC complex for treatment of an immune disorder. For example, experimental allergic encephalomyelitis (EAE) is an autoimmune disease in mice and a recognized model for multiple sclerosis. A suitable mouse strain can be treated to develop EAE and then a MHC fusion complex or loaded molecule administered and the animal evaluated to determine if EAE development is inhibited or prevented after administration of the MHC fusion complex or loaded molecule. Such an assay is specifically described in Examples 8 and 11 which follow.

The ability of a MHC fusion complex to induce an immune response, including vaccination against a targeted disorder, may be readily determined by an in vivo assay. For example, a MHC fusion complex of the invention, or DNA coding for a MHC fusion complex, can be administered to a mammal such as a mouse, blood samples obtained from the mammal at the time of initial administration and several times periodically thereafter (e.g. at 2, 5 and 8 weeks after administration of the fusion complex or DNA). Serum is collected from the blood samples and assayed for the presence of antibodies raised by the immunization. Antibody concentrations may be determined. Example 9 which follows specifically describes such an assay.

As discussed in said PCT Application, direct administration of a DNA construct coding for an MHC fusion complex can be suitably accomplished for expression of the fusion complex within cells of the subject. Preferably, DNA carrying the coding regions of the MHC-presenting peptide fusion, suitably under the control of an appropriate promotor such as the CMV promoter, is injected directly to skeletal muscle of the subject. To ensure the display of the MHC fusion molecules will induce an immune response in the subject, DNA vectors that code for a co-stimulatory factor is preferably co-administered to the subject with the DNA coding for the MHC-presenting peptide fusion. Preferred co-administered DNA vectors include e.g. those that comprise either the coding region of B7-1 or B7-2 under the control of the CMV promoter. The expressed B7-1 and B7-2 protein can provide the co-stimulatory signal to assist the initiation of the immune response.

Such an approach for induction of an immune response in a subject such as a mammal offers significant advantages over prior approaches. The initial step in the presentation of a foreign protein antigen is the binding of the native antigen to an antigen presenting cell (APC). After binding to APCs, antigens enter the cells, either by phagocytosis, receptor-mediated endocytosis or pinocytosis. Such internalized antigens become localized in intracellular membrane-bound vesicles called endosomes. After endosome-lysosome fusion, the antigens are processed into small peptides by cellular proteases located in lysosomes. The peptides become associated with the α and β chains of MHC class II molecules within these lysosomes. These MHC class II molecules, previously synthesized in the rough endoplasmic reticulum, are sequentially transported to the Golgi complexes and then to the lysosomal compartment. The peptide-MHC complex is presented on the surface of APCs for T and B cell activation. Therefore, the accessibility of proteolytic processing sites within the antigen, the stability of the resultant peptides in the lysosome and the affinities of the peptides for MHC molecules are determining factors for the immunogenicity of a particular epitope. These factors can not be changed by administration of adjuvants. Direct expression of the MHC fusion complexes (i.e. MHC directly covalently linked to the presenting peptide), however, should bypass such complications and induce immune response against the epitope carried on the MHC fusion molecules.

Also, as disclosed in said PCT Application, rather than directly administering DNA coding for an MHC fusion complex to a subject, host compatible antigen presenting cells into which such DNA has been introduced may be administered to the subject. That is, DNA coding for one or more MHC fusion complexes may be introduced into host compatible antigen presenting cells and such transformed or transfected antigen presenting cells can be administered to the targeted host, and with the site targeted where the most efficient interaction with the appropriate T cell would take place. See, for instance, the Examples 13 and 14 which follow. Upon administration to a subject, such engineered cells can then express in vivo on the cell surface the MHC fusion complex coded for by the DNA. Such engineered cells can be administered to a subject to induce an immune response or alternatively to suppress an immune response, as disclosed herein, depending on the expression of other co-stimulatory signals of the cells. That is, if upon administration the cells can provide an MHC fusion complex in the absence of an effective amount of co-stimulatory signal(s), or provide a MHC fusion complex that contains a presenting peptide with antagonist or partial agonist activity, the cells can be administered to a host to suppress an immune response. Alternatively, if the cells can provide a MHC fusion complex in the presence of an effective amount of co-stimulatory signal(s), e.g. if a T cell co-stimulatory factor such as B7 or B7-2 is expressed on the surface of the cells, the cells can be administered to a mammal host to induce an immune response in the mammal, as disclosed herein. It may be preferred to construct a single expression that codes for both chains of a MHC fusion complex as well as for a T-cell costimulatory factor if employed, as discussed above, and introduce that vector into a host compatible APC to prepare the cells for administration. As will be recognized by those in the art, the term "host compatible" antigen presenting cells means antigen presenting cells that are of the same haplotype as that of the subject or "host" to which the cells are administered. Preferably the transformed host compatible antigen presenting cells are those that can migrate to lymph nodes of the subject to which the cells have been administered and, at that site, express the MHC fusion complex.

As discussed above and in said PCT Application, MHC fusion complexes and DNA constructs that encode such fusion complexes have a number of therapeutic applications; loaded MHC molecules may also be used for such applications as discussed herein. For example, MHC fusion complexes or loaded complexes that do not contain a transmembrane portion (see, e.g., the soluble complex of Example 2 which follows) can be administered to suppress an immune response of a mammal, e.g., to treat a mammal including a human that suffers from or is susceptible to an autoimmune disorder such as e.g. multiple sclerosis, insulin-dependent diabetes mellitus, rheumatoid arthritis and the like. Also suitable for treatment are those subjects suffering or likely to suffer from an undesired immune response e.g. patients undergoing some type of transplant surgery such as transplant of heart, kidney, skin or other organs. In such situations, a treatment protocol may suitably be commenced in advance of the surgical procedure.

As disclosed in said PCT Application, to suppress an immune response, an MHC fusion complex is administered that is linked to an immunoglobulin, e.g., fused to the constant domains of an immunoglobulin molecule such as an IgG, IgM or IgA immunoglobulin or fragment. See FIG. 1C of the Drawings and the examples which follow.

A number of distinct approaches can be employed to suppress an immune response of a mammal in accordance with the invention.

Specifically, as discussed above, it has been shown that a MHC molecule will only induce clonal expansion of a T cell line specific if co-stimulatory signal(s) such as from antigen presenting cells are also delivered. In the absence of co-stimulatory signals, or at least in the absence delivery of an T cell proliferation effective amount of such T cell co-stimulatory signal(s), the T cells will be induced to a state of anergy or apoptosis resulting in clonal deletion.

Accordingly, one treatment method for suppression of an immune response provides for the administration of an effective amount of one or more MHC fusion complexes or loaded molecules in the substantial absence of any costimulatory signal(s) to thereby induce anergy for specific T cells and effectively suppress an undesired immune response. Preferably, a "truncated" soluble MHC complex is administered, i.e. the MHC complex does not contain a transmembrane portion. The presenting peptide of the administered soluble MHC fusion complex or loaded MHC molecule can be selected that are specific for T cells of an undesired immune response to induce a state of anergy with respect to those T cells. Such presenting peptides can be readily identified and selected by the in vitro protocols identified above.

Soluble MHC fusion complexes or loaded molecules suitably can be administered to a mammal by injection, e.g., intraperitoneal or intravenous injection. Topical administration, e.g., eye drops, and administration through nasal and lung inhalers also should be possible. A MHC fusion complex, at least those complexes used in therapeutic applications, should be produced in mammalian cells and purified prior to use so it is essentially or completely free of any bacterial or pyrogens. The optimal dose for a given therapeutic application can be determined by conventional means.

MHC fusion complexes or loaded molecules may be suitably administered to a subject (particularly mammal such as human or livestock such as cattle) in treatment or pharmaceutical compositions which comprise the fusion complex or loaded molecule. Such pharmaceutical compositions of the invention are prepared and used in accordance with procedures known in the art. For example, formulations containing a therapeutically effective amount of an MHC fusion complex or loaded molecules may be presented in unit-dose or multi-dose containers, e.g., sealed ampules and vials, and may be stored in a freeze dried (lyophilized) condition requiring only the addition of the sterile liquid carrier, e.g. water for injections, immediately prior to use. Liposome formulations also may be preferred for many applications. Other compositions for parenteral administration also will be suitable and include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents.

Another treatment method for suppression of an immune response provides for administration of a MHC fusion complex that contains a covalently linked presenting peptide that is a T cell receptor antagonist or partial agonist or loaded MHC molecule that contains a presenting peptide that is such a T cell receptor antagonist or partial agonist [see A. Sette et al., *Annu. Rev. Immunol.*, 12:413–431 (1994)]. The MHC fusion complex or loaded MHC molecule may be a truncated form and be administered as a soluble protein as described above. Alternatively, the MHC fusion complex or loaded MHC molecule may be full length, i.e. will contain a transmembrane portion. Treatment with these complexes will comprise administration to a mammal an effective amount of a DNA sequence that comprises a DNA vector encoding the full length MHC fusion complex of the invention and a presenting peptide that is a TcR antagonist or partial agonist. See, e.g., the discussion above and Examples 3, 10 and 11 which follow for suitable means of preparation of such MHC fusion complexes and use of same for immunosuppressive therapy. Presenting peptides that are TcR antagonists or partial agonists can be readily identified and selected by the in vitro protocols identified above. A MHC fusion complex that contains a presenting peptide that is a T cell receptor antagonist or partial agonist is particularly preferred for treatment of allergies and autoimmune diseases such as multiple sclerosis, insulin-dependent diabetes mellitus and rheumatoid arthritis.

Further, as discussed above and in said PCT Application, host compatible antigen presenting cells into which DNA coding for an MHC fusion complex has been introduced may be administered to a subject to suppress an immune response. Upon administration the cells express a MHC fusion complex in the absence of an effective amount of T cell co-stimulatory signal(s), i.e. such that T cell anergy is induced, and/or the administered cells express an MHC fusion complex that contains a linked presenting peptide with antagonist or partial agonist activity.

Different immunosuppressive therapies of the invention also may be used in combination as well as with other known immunosuppressive agents such as anti-inflammatory drugs to provide a more effective treatment of a T cell-mediated disorder. For example, immunosuppressive MHC fusion complexes or loaded MHC molecules that can be used in combination with anti-inflammatory agents such as corticosteroids and nonsteroidal drugs for the treatment of autoimmune disorders and allergies.

The invention also provides methods for invoking an immune response in a mammal such as a human, including vaccinating a mammal such as a human against an infectious agent or a targeted disorder such as cancer, particularly a melanoma cancer, or other disorder such as malaria.

As disclosed in said PCT Application these methods include administering to a mammal an effective amount of a DNA sequence that comprises a DNA vector that codes for an MHC fusion complex of the invention that contains a transmembrane portion, and/or administration of such a MHC fusion complex that contains a transmembrane portion and/or administration of host compatible antigen presenting cells that contain such DNA that code for such MHC fusion complexes. Preparation of expression vectors of MHC fusion complexes is described above and in Examples 3 and 12 which follow. Methods for administration of plasmid DNA, uptake of that DNA by cells of the administered subject and expression of protein has been reported [see J. Ulmer et al., *Science*, 259:1745–1749 (1993)].

Preferably the DNA that codes for a full length MHC fusion complex is administered to a mammal together with a DNA sequence coding for a T cell costimulatory factor such as DNA coding for B7 or B7-2. The B7 gene and expression thereof is described in D. Harlan et al., *Proc. Natl. Acad. Sci. USA*, 91:3137–3141 (1994). Upon uptake of that DNA by the cells of the subject, the T cell co-stimulatory factor will be expressed and can provide the co-stimulatory signal(s) and thereby assist in the initiation of the immune response. See Examples 3 and 12 which follow and disclose the construction of expression vectors containing B7 or B7-2 genes.

While administration of DNA coding for an MHC fusion complex to a mammal such as a human as discussed above is a preferred method for invoking an immune response in the subject, MHC fusion complexes also may be suitably administered by other routes. Thus, as discussed above, host compatible antigen presenting cells into which DNA coding for an MHC fusion complex has been introduced may be administered to a subject to induce an immune response. Upon administration the cells express an MHC fusion complex in the presence of an effective amount of T cell co-stimulatory signal(s) such as B7 or B7-2 genes to invoke an immune response, and/or the administered cells express a full length MHC fusion complex that is capable of invoking an immune response, e.g. as shown by an increase in T cell proliferation such as by procedures detailed in Examples which follow. Although typically less preferred than approaches discussed above, MHC fusion complexes that are capable of invoking an immune response also may be directly administered to a subject, e.g. a full length MHC fusion complex that contains a covalently linked antigenic presenting peptide which can stimulate or induce T cell proliferation.

Methods of the invention for inducing an immune response, including vaccinating a subject against a targeted disorder, may be used in combination with known methods for inducing an immune response. For example, a single chain MHC class II complex, or DNA construct coding for such a MHC complex, may be administered to a subject in coordination or combination with administration of a vaccine composition, in order to boost or prolong the desired effect of such vaccine composition.

As disclosed in said PCT Application, DNA vectors that encode MHC fusion complexes are suitably administered to a mammal including a human preferably by intramuscular injection. Administration of cDNA to skeletal muscle of a mammal with subsequent uptake of administered expression vector by the muscle cells and expression of protein encoded by the DNA has been described by Ulmer et al. and represents an exemplary protocol [J. Ulmer et al., *Science*, 259:1745–1749]. The optimal dose for a given therapeutic application can be determined by conventional means.

Additionally, MHC fusion complexes, DNA vectors that encode such complexes and host compatible antigen presenting cells that contain such DNA vectors each suitably may be administered to a subject by a variety of other routes. For example, to induce an immune response, it may be preferable to administer DNA vectors that encode antigenic MHC fusion complexes, alone or together with DNA coding for a co-stimulatory factor, intradermally to a subject, by procedures known to those skilled in the art. Such administration can result in transformation of intradermal antigen presenting cells (e.g., dendritic cells) and T cell proliferation. See the results of Example 16 which follows. MHC fusion complexes and DNA vectors encoding such fusion complexes also may be administered to a subject by other routes, e.g., orally or transdermally.

In addition to treatment of human disorders, MHC fusion complexes and DNA constructs that encode such fusion complexes or loaded MHC molecules will have significant use for veterinary applications, e.g., treatment of disorders of livestock such as cattle, sheep, etc. and pets such as dog and cats.

While MHC fusion complexes or DNA constructs coding for such fusion complexes, or loaded MHC molecules, may be administered alone to a subject, they also each may be used as part of a pharmaceutical composition. Pharmaceutical compositions in general comprise one or more MHC fusion complexes or DNA constructs coding for such fusion complexes or loaded MHC molecules together with one or more acceptable carriers. The carriers must be "acceptable" in the sense of being compatible with other ingredients of the formulation and not deleterious to the recipient thereof. For example, for parenteral administration such as by an injection formulation, a sterile solution or suspension with water may be prepared, or other pharmaceutically acceptable solutions. Such pharmaceutical compositions are suitably prepared by methods known in the art.

Actual preferred amounts of a given MHC fusion complex or DNA construct coding for same or loaded MHC molecules used in a given therapy will vary to the particular active compound or compounds being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests conducted e.g. with regard to the foregoing guidelines and the assays disclosed herein.

Empty single chain MHC complexes of the invention, preferably empty single chain MHC class II complexes, can be combined with a suitable presenting peptide to form a loaded single chain MHC complex of the invention. It will be appreciated that such loaded complexes can be suitably employed where administration of a MHC peptide fusion complex is indicated, as described above. In instances where a DNA construct encoding a MHC peptide fusion complex is used, one or more DNA constructs encoding a suitable empty single chain MHC complex may be employed, provided that approriate conditions are provided for non-covalently binding a suitable presenting peptide to the peptide binding groove or cleft of the empty MHC molecule. Examples of conditions for binding a suitable presenting peptide to an empty single chain MHC molecule are discussed more fully, infra. Loaded MHC complexes, particularly loaded MHC class II complexes, have use in the treatment of human, livestock and pet disorders as described above.

It will also be appreciated that the single chain MHC fusion complexes described above and in said PCT Application, can be used to construct transgenic mouse strains (see Example 31, infra). Such mouse strains are useful as, e.g., model systems in which the activity of T cells such as T helper cells can be modulated.

All documents mentioned herein are incorporated herein by reference in their entirety.

The following non-limiting examples are illustrative of the invention.

EXAMPLES 1A–1F

Construction of Soluble MHC Fusion Complexes of the Invention

MHC class II-peptide fusion vectors for expressing soluble MHC class II molecules with covalently linked presenting peptides were prepared as described below in Examples 1A–1F. The MHC class II genes used to prepare the following, MHC fusion complex constructs were isolated by PCR amplification of cDNA generated from the appropriate Antigen Presenting Cell (APC), as shown in FIGS. 2–8 of the Drawings.

EXAMPLE 1A

Figures 9E, 9F:
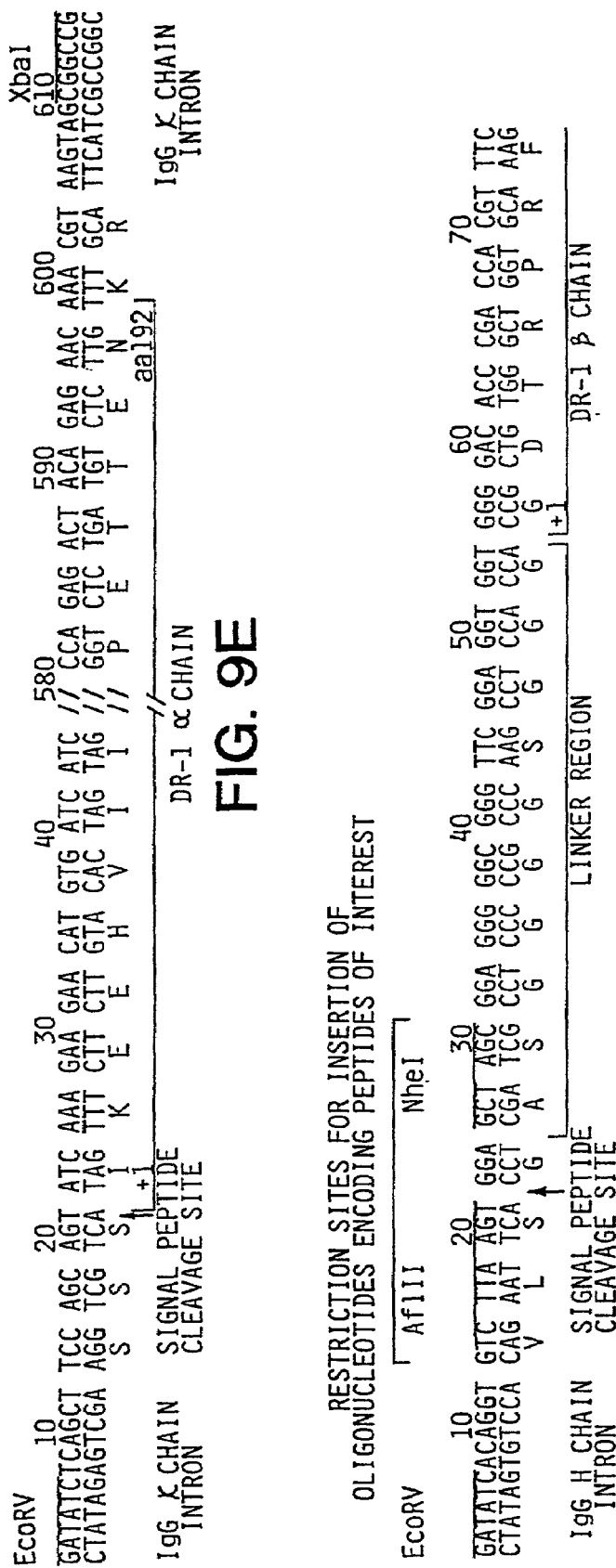
FIG. 9 (which includes FIGS. 9A–9F) (SEQ ID NOS: 75–98) shows nucleotide and amino acid sequences of soluble MHC fusion complexes.

For the I-$A^d$ genes, total RNA was isolated from the mouse B cell lymphoma A20 cell line. Briefly, 1×10$^8$ A20 cells (ATCC TIB 208) were homogenized in 6 ml of ice cold 4 M guanidinium thiocyanate, 0.1 M Tris-Hcl, Ph 7.5 using a Tissue Tearer homogenizer for 5 minutes. Following homogenization, sarcosyl was added to a final concentration of 0.5% and the solution was mixed thoroughly. The homogenate was centrifuged at 5000 g for 10 minutes and the supernatant was brought up to 10 mls with 4 M guanidinium thiocyanate, 0.1 M Tris-Hcl, Ph 7.5, 0.5% sarcosyl buffer. The supernatant was gently layered on top of a 3.5 ml cushion of 5.7 M CsCl, 0.01 M EDTA, pH 7.5 in an SW41 clear ultracentrifuge tube. The samples were centrifuged in an SW41 rotor at 32,000 rpm for 24 hours at 20° C. Following centrifugation, the supernatant was carefully removed and the RNA pellet was washed with 70% ethanol. The RNA was dissolved in 350 µl of DEPC-treated water containing 40 units of RNasin (Promega). The RNA was precipitated with 35 µl of 3 M sodium acetate and 970 µl of ethanol. This procedure yielded approximately 370 µg of total RNA. The RNA was resuspended to 5 µg/µl with DEPC-treated water and was used for RT-PCR cloning of the I-$A^d$ genes. FIG. 2 of the Drawings shows the strategy for isolating the I-Ad$^d$ α1–α2 gene fragment (encoding aa1 to 182) and FIG. 8 of the Drawings lists the oligonucleotides primers used. The A20 total RNA (5 µg) was converted to cDNA by using Superscript-MLV Reverse Transcriptase (GIBCO-BRL) and α2-specific priming according to manufacturer's procedures. Of the 20 µl of cDNA generated, 2 µl was used as template DNA for PCR. Typical PCR amplification reactions (100 µl) contained template DNA, 10 pmoles of the appropriate primers (OPR100 and OPR101), 2.5 units of Taq polymerase, 100 µM dNTP, 50 mM KCl, 10 mN Tris HCl, pH 8.3, 1.5 mM MgCl$_2$, 0.01% gelatin. The template was denatured by an initial incubation at 96° C. for 5 minutes during which the Taq polymerase was added to hot-start the reaction. The desired products were amplified by 10 thermal cycles of 55° C. for 1 minute, 70° C. for 1 minute, then 96° C. for 1 minute followed by 25 step cycles of 70° C. for 1 minute, then 96° C. for 1 minute. The initial α1–α2 PCR product (approximately 550 bp) was designed to be cloned into the bacterial expression vector, pJRS139. The PCR products from 5 reactions were pooled, precipitated with 2 volumes of ethanol/0.3 M sodium acetate, and the resulting products (about 0.2 µg of DNA) were resuspended in water. The α1–α2 gene fragment was digested with NcoI and SpeI, resolved by agarose gel electrophoresis and purified by elution from the agarose gel. The purified digested PCR products were then ligated into NcoI/SpeI digested pJRS139. The α1–α2 gene fragment cloned in pJRS139 was designated 39AD2 and served as the template for PCR amplification to add the restriction sites and flanking sequences necessary for cloning and expression in the mammalian expression vectors. In these reactions, 0.5 ng of NcoI-digested 39AD2 was used as a template, OPR107 and OPR108 were the primers and the PCR conditions were 5 thermal cycles of 60° C. for 1 minute, 70° C. for 1 minute, and 96° C. for 1 minute followed by 20 step cycles of 70° C. for 1 minute and 96° C. for 1 minute. The α1–α2 PCR product (approximately 590 bp) contains a 5' EcoRV site and a 3' EagI site for cloning between the leader intron and J-region intron of the IgG kappa chain shuttle vector (see FIG. 9A of the Drawings). In addition, PCR product has the IgG splice sites and leader sequences necessary for proper expression of the MHC-IgG fusion protein. The PCR products were digested with EcoRV and EagI and gel-purified. The purified digested PCR products were then ligated into EcoRV/EagI digested pBlueScript II SK+ (Stratagene) resulting in the pA19 construct. This vector was digested with EcoRV and EagI and the resulting α1–α2 gene fragment was subcloned into the pJW003 IgG shuttle vector as described in Example 2 below.

EXAMPLE 1B

Figure 3A:
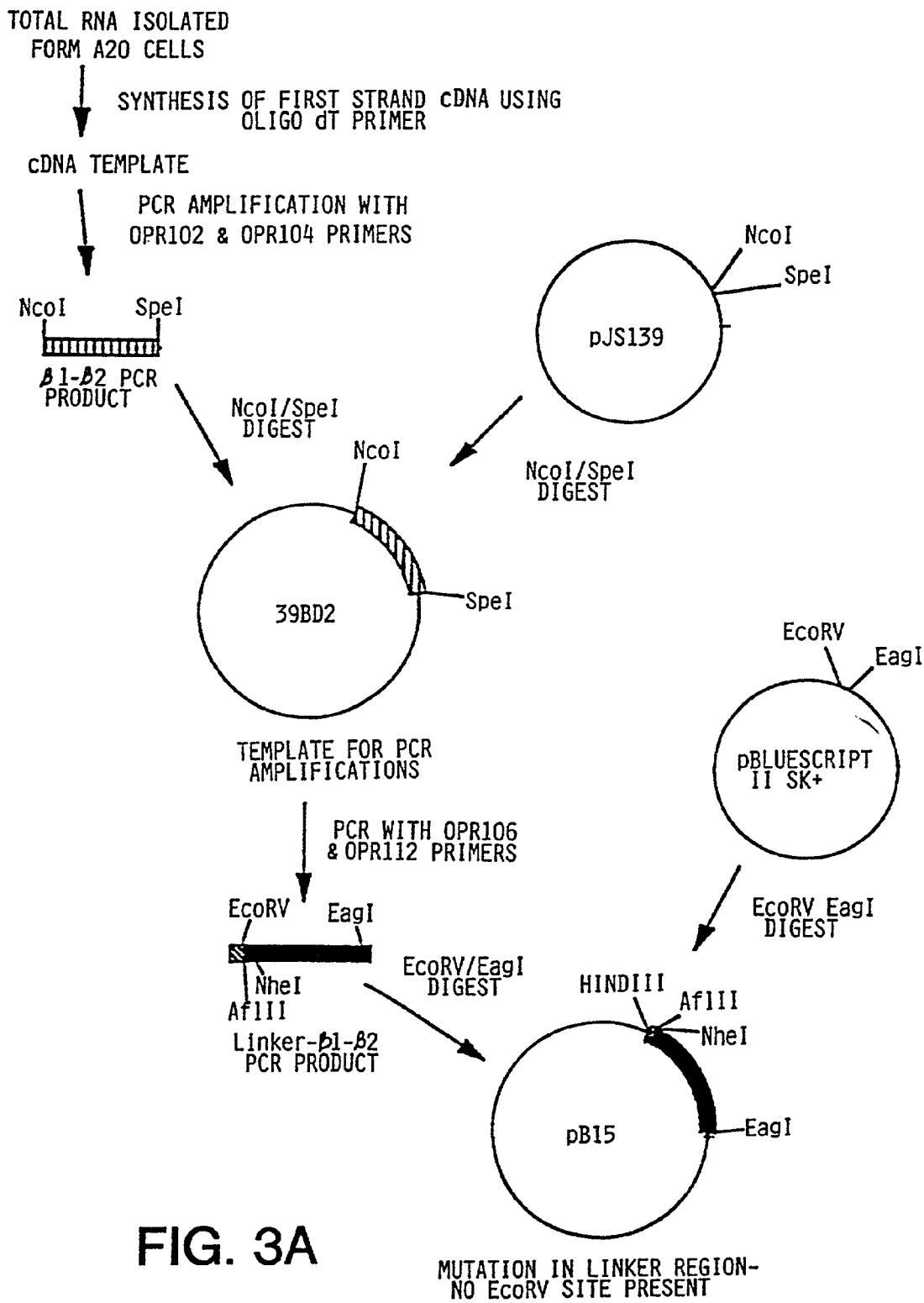
FIG. 3 shows the scheme for isolating the I-A$^d$ β1–β2 gene fragment, attaching the linker sequence and inserting the oligonucleotides encoding the antigenic peptides.
Figure 3B:
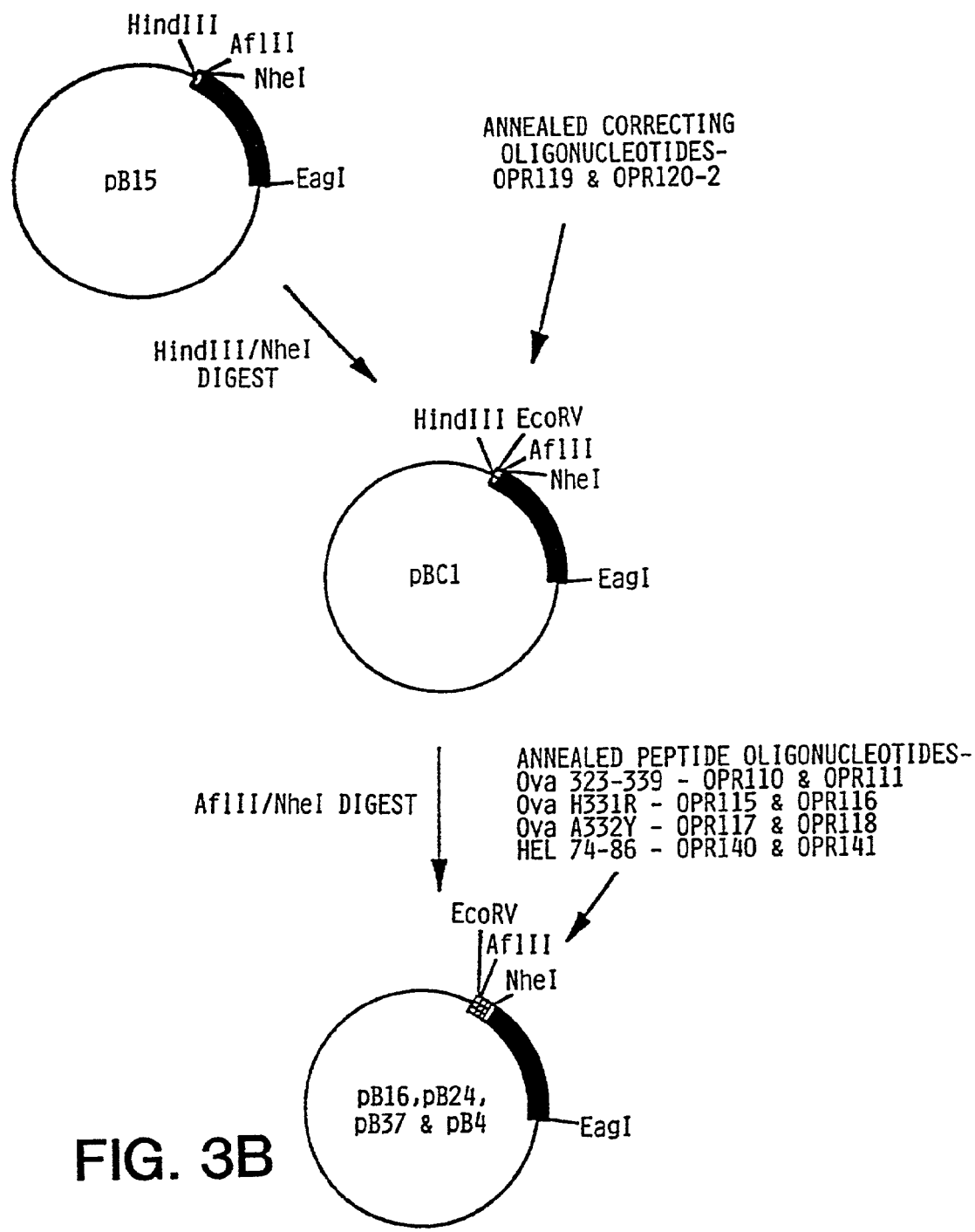

The following approach was employed to isolate the I-A$^d$ β1–β2 gene fragment (encoding aa1 to 189), attaching the linker sequence and inserting the oligonucleotides encoding the antigenic peptides. This approach also is depicted in FIG. 3 of the Drawings. The A20 total RNA (10 μg) was converted to cDNA by using Superscript-MLV Reverse Transcriptase (GIBCO-BRL) and oligo dT-specific priming according to manufacturer's procedures. Of the 20 μl of cDNA generated, 2 μl was used as template DNA for PCR. The reactions were carried out as described above except oligonucleotide primers were OPR102 and OPR104 (see FIG. 8 of the Drawings) and the PCR conditions were 10 thermal cycles of 60° C. for 1 minute, 70° C. for 1 minute, and 96° C. for 1 minute followed by 40 step cycles of 70° C. for 1 minute and 96° C. for 1 minute. The initial β1–β2 PCR product (approximately 570 bp) was designed to be cloned into the bacterial expression vector, pJRS139. The PCR products were digested with NcoI and SpeI and gel-purified in the same manner as described above. The purified digested PCR products were then ligated into NcoI/SpeI digested pJRS139. The β1–β2 gene fragment cloned in pJRS139 was designated 39BD2 and served as the template for PCR amplification to add the linker sequence and restriction sites and flanking sequences necessary for cloning and expression in the mammalian expression vectors. In these reactions, 0.5 ng of NcoI-digested 39AB2 was used as a template, OPR107 and OPR108 were the primers and the PCR conditions were 5 thermal cycles of 60° C. for 1 minute, 70° C. for 1 minute, and 96° C. for 1 minute followed by 20 step cycles of 70° C. for 1 minute and 96° C. for 1 minute. The linker-β1–β2 PCR product (approximately 640 bp) contains a 5' EcoRV site and a 3' EagI site for cloning between the leader intron and J-region intron of the IgG heavy chain shuttle vector (FIG. 9B). In addition, PCR product has the IgG splice sites and leader sequences necessary for proper expression of the MHC-IgG fusion protein. To allow for cloning of the antigenic peptide sequences, an AflII site was engineered into the end of the signal sequence and an NheI site was present at the beginning of the linker. The PCR products were digested with EcoRV and EagI and gel-purified. The purified digested PCR products were then ligated into EcoRV/EagI digested pBlueScript II SK+ (Stratagene) resulting in the pB15 construct. Sequence and restriction analyses indicated that this construct contained a mutation in the EcoRV site. To correct this mutation, two oligonucleotides (OPR119 and OPR120-2) were annealed and ligated into HindIII/NheI digested pB15, resulting in the vector, pBC1. To insert sequences encoding the class II I-A$^d$ binding peptides, oligonucleotides were annealed and ligated into AflII/NheI digested pBC1. The Ova 323–339 peptide (SISQAVHAAILSEINEAGR) (SEQ ID NO: 3) was encoded by oligonucleotides OPR110 and OPR111, Ova:H331R (SISQAVHAARAEINEAGR) (SEQ ID NO: 4) by OPR115 and OPR116, Ova A331Y (SISQAVHAAHYEINEAGR) (SEQ ID NO: 5) by OPR117 and OPR118, and HEL 74–86 (NLCNIPCSALLSS) (SEQ ID NO: 6) by OPR140 and OPR141. The respective constructs in the pBC1 backbone were designated pB16, pB24, pB37 and pB4. These vectors were digested with EcoRV and EagI and the resulting peptide-linker-β1–β2 gene fragment was subcloned into the pJW009 IgG shuttle vector as described in Example 2 which follows.

EXAMPLE 1C

Figure 4A:
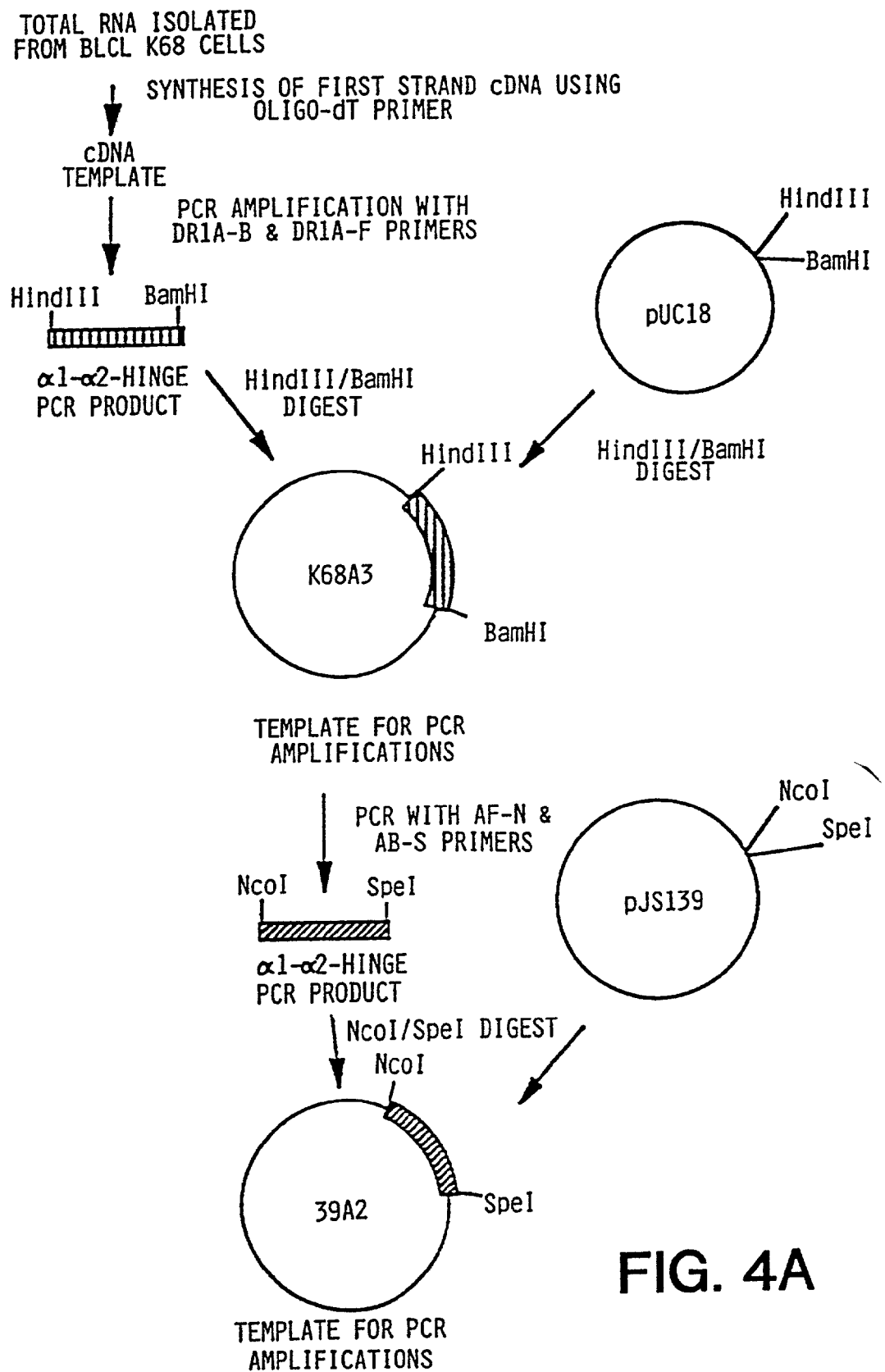
FIG. 4 shows the cloning scheme for human HLA-DR1 α1–β2.
Figure 4B:
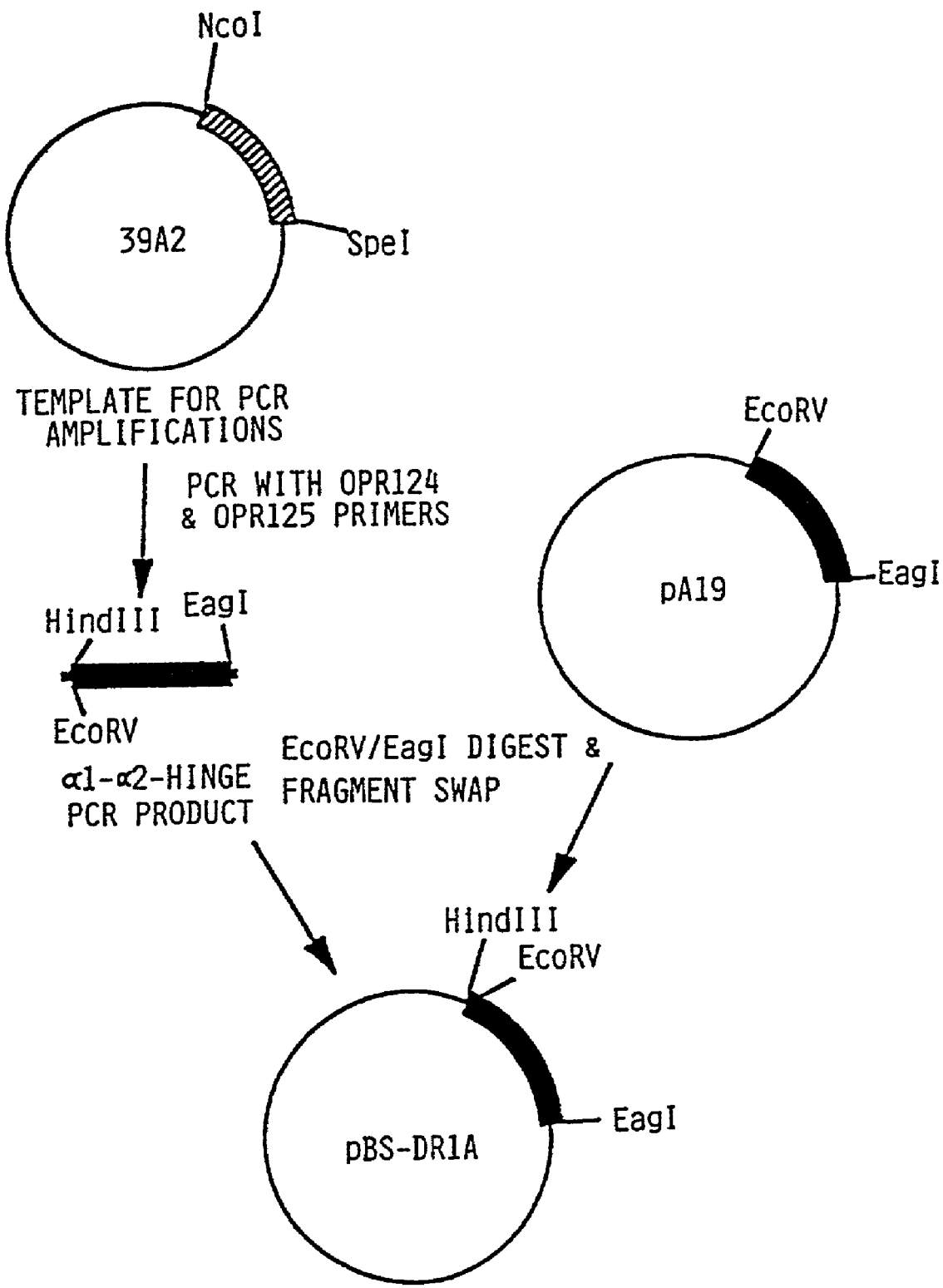

The following approach was employed to isolate the human HLA-DR1 α1–α2-hinge gene fragment (encoding aa1-192) and is depicted in FIG. 4 of the Drawings. Total cellular RNA was made by the procedure described above from 3×10$^6$BLCL-K68 cells obtained from a HLA-DR1 homozygous individual. Total RNA was converted to cDNA (20 μl) by using Superscript-MLV Reverse Transcriptase (GIBCO-BRL) and oligo dT-specific priming according to manufacturer's procedures. The initial PCR reactions were design to add restriction sites necessary for cloning the α1–α2-hinge gene fragment into bacterial expression vectors (for work that is not relevant to this application). PCRs were performed as described above except 5 μl of the template cDNA was used, the primers were DR1A-F and DR1A-B (FIG. 8) and the PCR conditions were 10 thermal cycles of 55° C. for 1 minute, 70° C. for 1 minute, and 96° C. for 1 minute followed by 20 step cycles of 70° C. for 1 minute and 96° C. for 1 minute. The α1–α2-hinge PCR product (approximately 570 bp) was digested with HindIII and BamHI, gel-purified and ligated into HindIII/BamHI digested pUC18, resulting in the K68A3 vector. This vector (0.5 ng) served as a template for further PCR amplifications using AF-N and AB-S oligonucleotides as primers. The resulting α1–α2-hinge PCR product was digested with NcoI and SpeI, gel-purified and ligated into NcoI/SpeI digested pJRS139, resulting in the 39A2 vector. This vector served as the template for PCR amplification to add the linker sequence and restriction sites and flanking sequences necessary for cloning and expression in the mammalian expression vectors. PCRs were performed as described above except 10 ng of the NcoI-digested 39A2 template DNA was used, the primers were OPR124 and OPR125 (sequences thereof set forth in FIG. 8 of the Drawings) and the PCR conditions were 5 thermal cycles of 50° C. for 1 minute, 70° C. for 1 minute, and 96° C. for 1 minute followed by 10 step cycles of 70° C. for 1 minute and 96° C. for 1 minute. The α1–α2-hinge PCR product (approximately 610 bp) contains a 5' EcoRV site and a 3' EagI site for cloning between the leader intron and J-region intron of the IgG kappa chain shuttle vector (see FIG. 9E of the Drawings). In addition, PCR product has the IgG splice sites and leader sequences necessary for proper expression of the MHC-IgG fusion protein. The PCR products were digested with EcoRV and EagI and gel-purified. The purified digested PCR products were then ligated into EcoRV/EagI digested pA19 resulting in the pBS-DR1A construct. This vector was digested with EcoRV and EagI and the resulting HLA-DR1 α1–α2-hinge gene fragment will be subcloned into the pJW003 IgG shuttle vector as described in Example 2 which follows.

EXAMPLE 1D

Figure 5A:
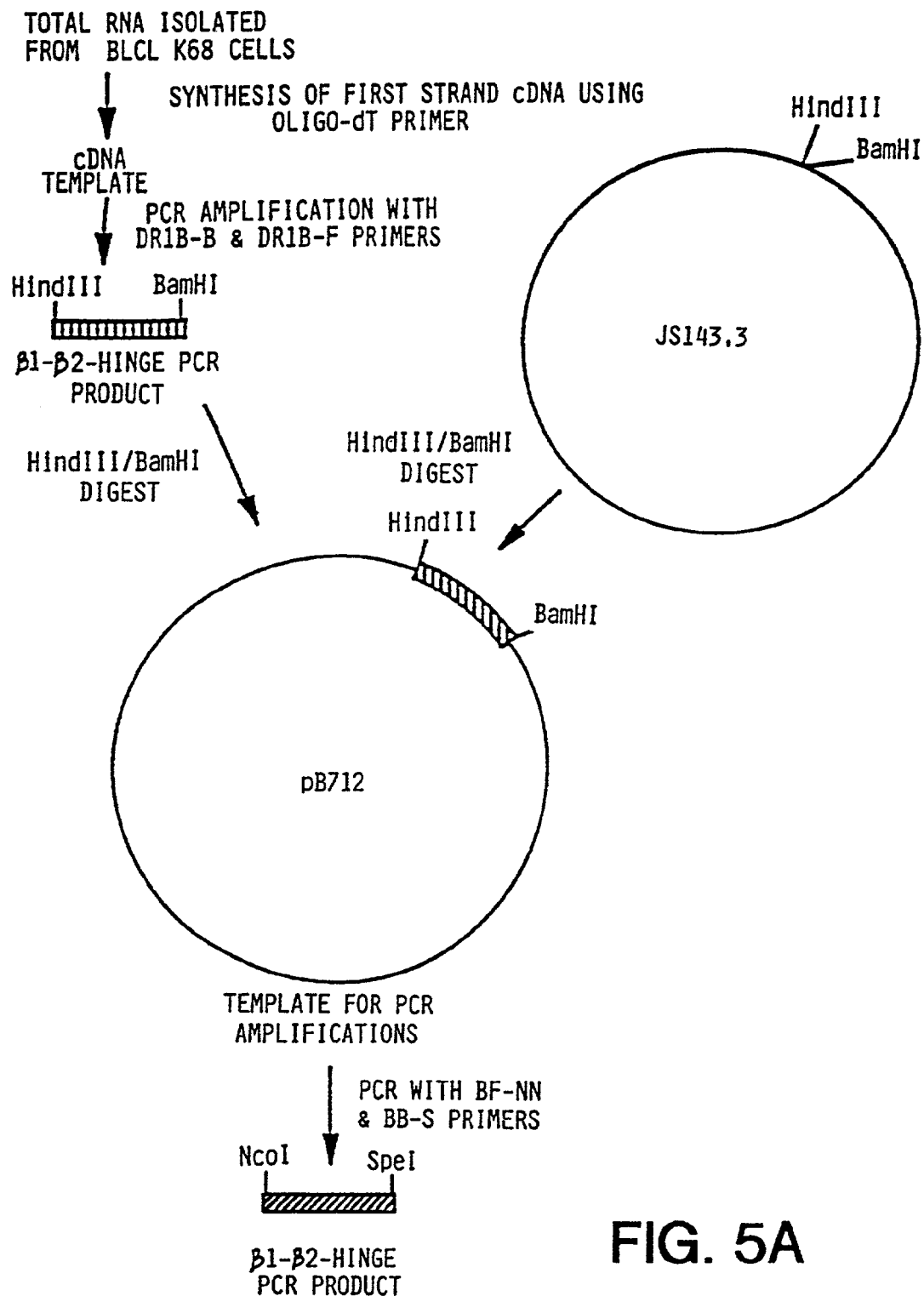
FIG. 5 shows the cloning scheme for human HLA-DR1 β1–β2 chain.
Figure 5B:
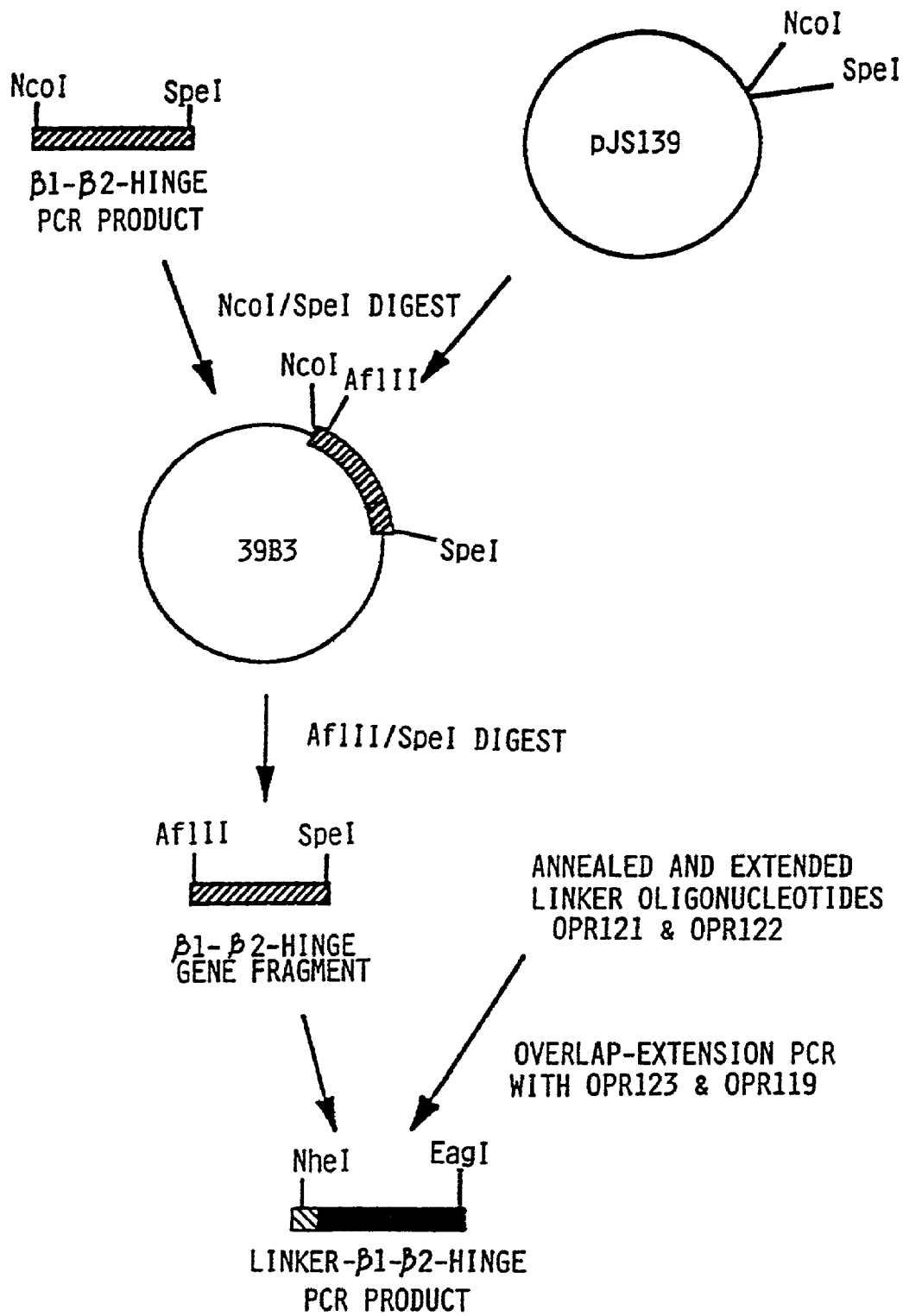
Figure 5C:
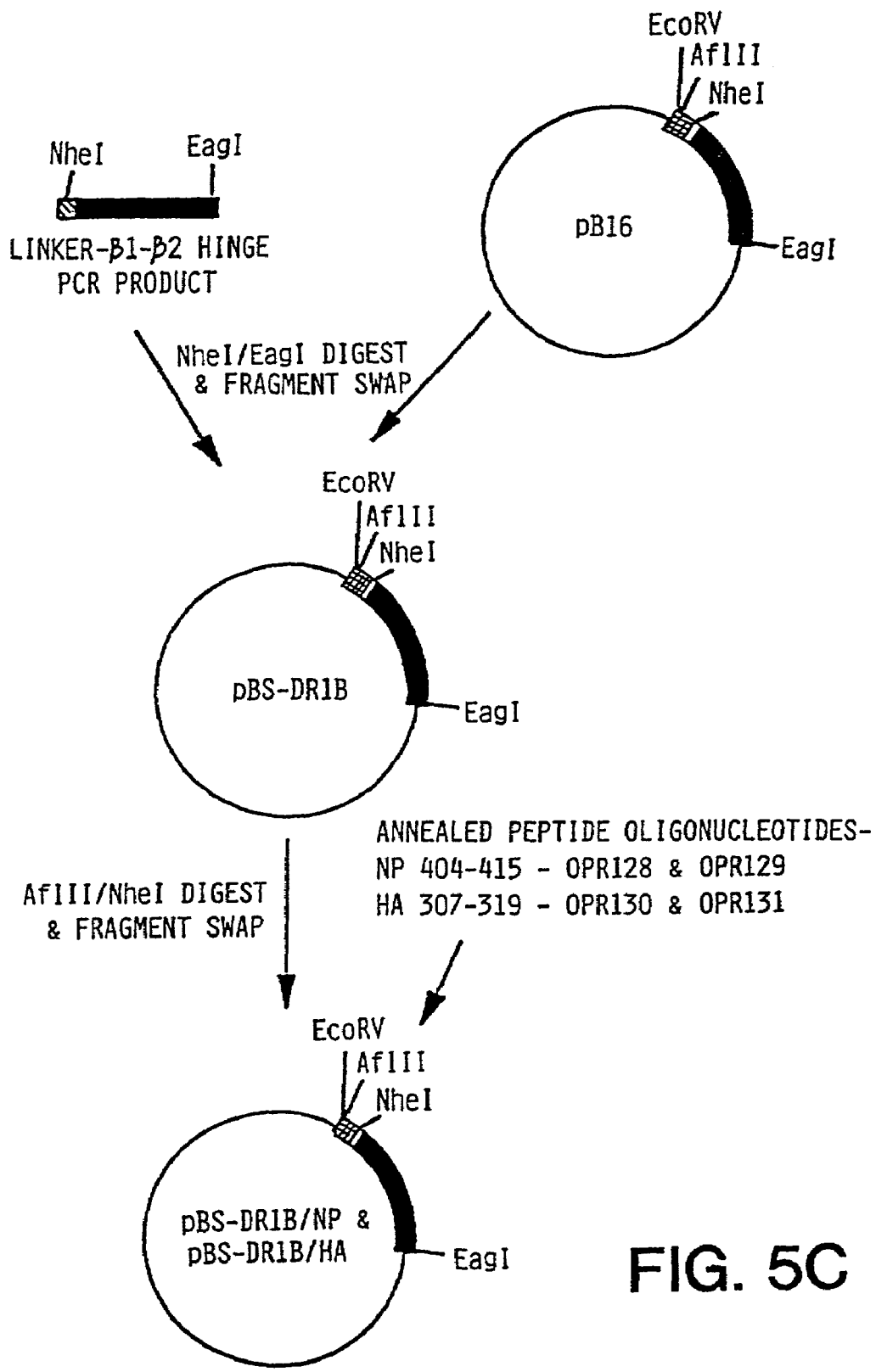

The following approach was employed to isolate the human HLA-DR1 β1–β2-hinge gene fragment (encoding aa1-198), attaching the linker sequence and inserting the oligonucleotides encoding the antigenic peptides. This approach also is depicted in FIG. 5 of the Drawings. Total cellular RNA was made by the procedure described above from $3 \times 10^6$ BLCL-K68 cells obtained from a HLA-DR1 homozygous individual. Total RNA was converted to cDNA (20 μl) by using Superscript-MLV Reverse Transcriptase (GIBCO-BRL) and oligo dT-specific priming according to manufacturer's procedures. The initial PCR reactions were design to add restriction sites necessary for cloning the β1–β2-hinge gene fragment into bacterial expression vectors (for work that is not relevant to this application). PCRs were performed as described above except 5 μl of the template cDNA was used, the primers were DR1B-F and DR1B-B (sequences of those primers set forth in FIG. 8 of the Drawings) and the PCR conditions were 10 thermal cycles of 55° C. for 1 minute, 70° C. for 1 minute, and 96° C. for 1 minute followed by 25 step cycles of 70° C. for 1 minute and 96° C. for 1 minute. The β1–β2-hinge PCR product (approximately 610 bp) was digested with HindIII and BamHI, gel-purified and ligated into HindIII/BamHI digested JS143.3, resulting in the pB712 vector. This vector (0.5 ng) served as a template for further PCR amplifications using BF-NN and BB-S oligonucleotides as primers. The resulting β1–β2-hinge PCR product was digested with NcoI and SpeI, gel-purified and ligated into NcoI/SpeI digested pJRS139, resulting in the 39B3 vector. This vector served as the template for PCR amplification to add the linker sequence and restriction sites and flanking sequences necessary for cloning and expression in the mammalian expression vectors. Overlap-extension PCR was used to mutate an AflII in the β1 region and add the linker sequence. The 39B3 vector was digested with AflII and SpeI and the AflII/SpeI β1–β2-hinge gene fragment was gel-purified. Two oligonucleotides coding for the linker and beginning of the β1 region (OPR121 and OPR122) were annealed, extended with Taq DNA polymerase resulting in a 78 bp fragment where the AflII in the β1 region is mutated without changing the amino acid specified. This fragment (5 ng) was mixed with the AflII/SpeI β1–β2-hinge gene fragment (5 ng) and overlap-extensions were carried out for 5 thermal cycles of 37° C. for 1 minute, 70° C. for 1 minute, and 96° C. for 1 minute. Following the addition of the PCR primers-OPR119 and OPR123, 5 additional thermal cycles of 37° C. for 1 minute, 70° C. for 1 minute, and 96° C. for 1 minute and 10 step cycles of 70° C. for 1 minute and 96° C. for 1 minute were carried out. The resulting linker-β1–β2-hinge PCR product (approximately 670 bp) contains a 5' EcoRV site and a 3' EagI site for cloning between the leader intron and J-region intron of the IgG heavy chain shuttle vector (see FIG. 9F of the Drawings). In addition, the PCR product has the IgG splice sites and leader sequences necessary for proper expression of the MHC-IgG fusion protein. To allow for cloning of the antigenic peptide sequences, an AflII site was engineered into the end of the signal sequence and an NheI site was present at the beginning of the linker. The PCR products were digested with NheI and EagI, gel-purified, and ligated into NheI/EagI digested pB16 (see above), in order to swap the β chain gene fragments. The resulting vector was designated pBS-DR1β. To insert sequences encoding the class II HLA-DR1 binding peptides, oligonucleotides are annealed and ligated into AflII/NheI digested pBS-DR1β. The NP 404–415 peptide having the sequence QISVQPAFSVQ (SEQ ID NO: 7) is encoded by oligonucleotides OPR128 and OPR129, and HA 307–319 having the sequence PKYVKQNTLKLAT (SEQ ID NO: 8) is encoded by OPR130 and OPR131. The sequences of OPR128, OPR129, OPR130 and OPR131 are set forth in FIG. 8 of the Drawings. The respective constructs in the pBS-DR1β backbone are designated pBS-DR1β/NP and pBS-DR1β/HA. These vectors are digested with EcoRV and EagI and the resulting peptide-linker-β1–β2-hinge gene fragment are subcloned into the pJW009 IgG shuttle vector as described in Example 2 which follows.

EXAMPLE 1E

Figure 6:
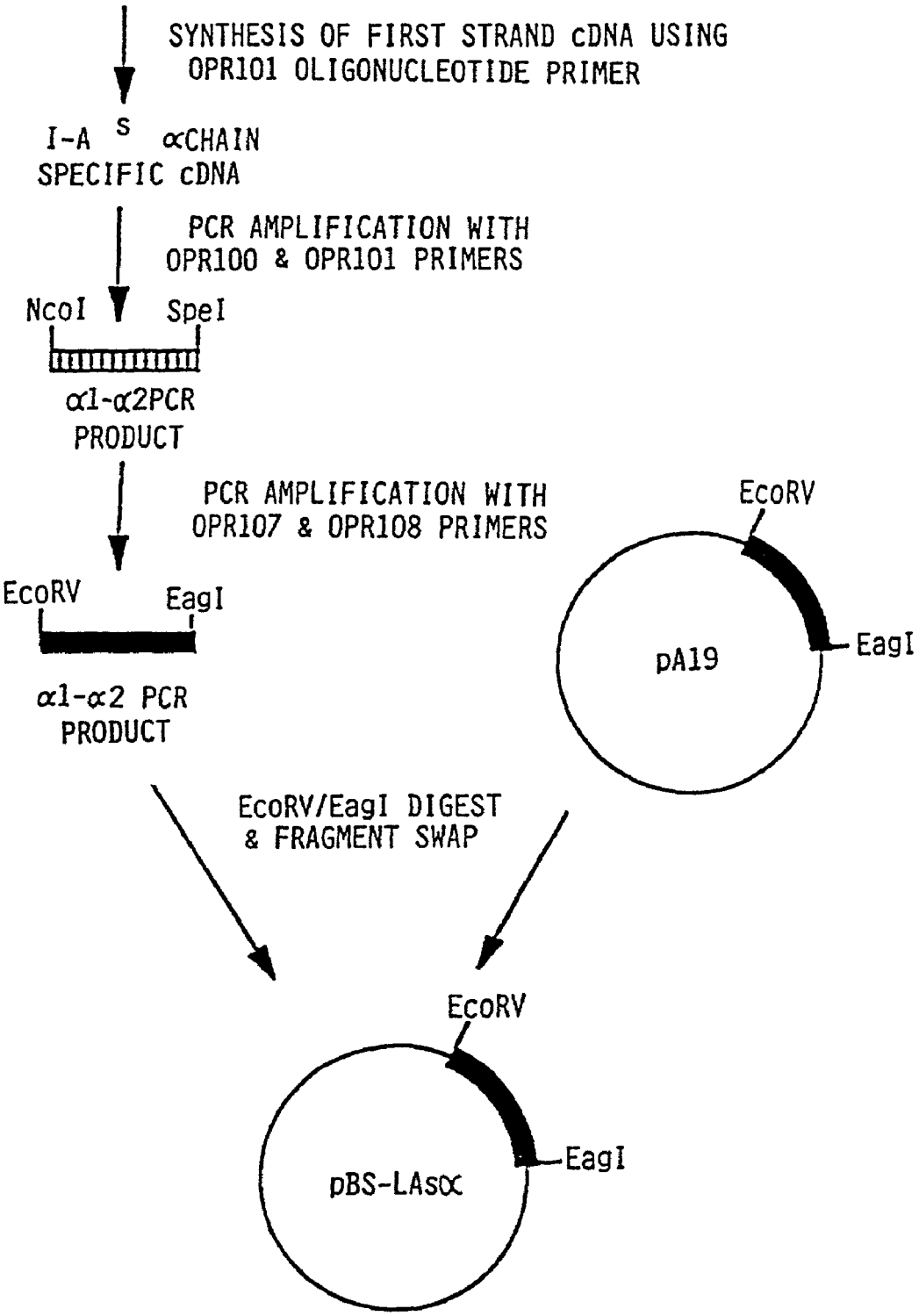
FIG. 6 shows the scheme for isolating the I-A$^s$ α1–α2 gene fragment and the cloning thereof.

The following approach is employed to isolate the I-A$^s$ α1–α2 gene fragment (encoding aa1 to 182). FIG. 8 lists the oligonucleotides primers used. FIG. 6 of the Drawings also depicts the protocol. The total RNA was prepared from the spleen of an SJL mouse by the same procedure used to prepare RNA from cell cultures. The RNA (10 μg) was converted to cDNA (50 μl) by using MLV Reverse Transcriptase (GIBCO-BRL) and α2-specific priming according to manufacturer's procedures. PCRs were performed as described above except 6 μl of the template cDNA was used, the primers were OPR100 and OPR101 (sequences thereof set forth in FIG. 8 of the Drawings) and the PCR conditions were 5 thermal cycles of 55° C. for 30 seconds, 72° C. for 30 seconds, and 96° C. for 1 minute followed by 20 step cycles of 72° C. for 1 minute and 96° C. for 1 minute. The initial α1–α2 PCR product (approximately 550 bp) was reamplified using the PCR primers OPR107 and OPR108 for 5 thermal cycles of 55° C. for 30 seconds, 72° C. for 30 seconds, and 96° C. for 1 minute followed by 10 to 15 step cycles of 72° C. for 1 minute and 96° C. for 1 minute. The resulting α1–α2 PCR product (approximately 590 bp) contains a 5' EcoRV site and a 3' EagI site for cloning between the leader intron and J-region intron of the IgG kappa chain shuttle vector (see FIG. 9C of the Drawings). In addition, the PCR product has the IgG splice sites and leader sequences necessary for proper expression of the MHC-IgG fusion protein. The PCR products were digested with EcoRV and EagI and gel-purified. The purified digested PCR products will be ligated into EcoRV/EagI digested pA19 (see above) in order to swap the α chain regions. The resulting vector, pBS-IASα is digested with EcoRV and EagI and the α1–α2 gene fragment is subcloned into the pJW003 IgG shuttle vector as described in Example 2 which follows.

EXAMPLE 1F

Figure 7:
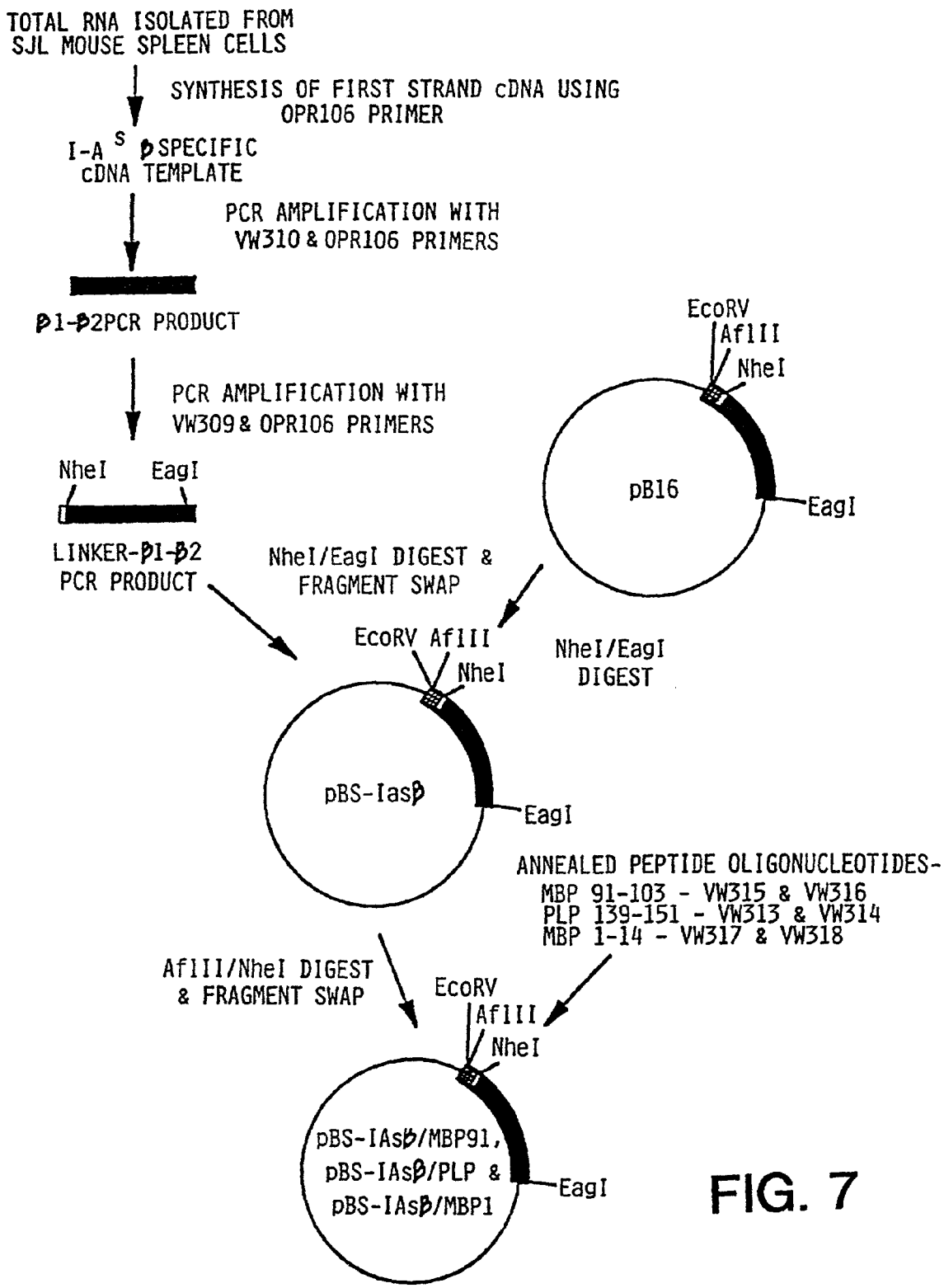
FIG. 7 shows the scheme for isolating the I-A$^s$ β1–β2 gene fragment, attaching the linker sequence and inserting the oligonucleotides encoding the antigenic peptides.

The following strategy is employed to isolate the I-A$^s$ β1–β2 gene fragment (encoding aa1 to 189), attaching the linker sequence and inserting the oligonucleotides encoding the antigenic peptides. This approach also is depicted in FIG. 7 of the Drawings. The SJL spleen total RNA (10 μg) was converted to cDNA by using MLV Reverse Transcriptase (GIBCO-BRL) and β2-specific priming according to manufacturer's procedures. Of the 50 μl of cDNA generated, 6 μl was used as template DNA for PCR. The reactions were carried out as described above except oligonucleotide primers were VW310 and OPR106 (FIG. 8) and the PCR conditions were 5 thermal cycles of 62° C. for 30 seconds, 72° C. for 30 seconds, and 96° C. for 1 minute followed by 21 step cycles of 72° C. for 1 minute and 96° C. for 1 minute. In order to add the linker sequences, the initial β1–β2 PCR product (approximately 570 bp) was reamplified using the PCR primers-VW309 and OPR106 for 3 thermal cycles of 50° C. for 30 seconds, 72° C. for 30 seconds, and 96° C. for 1 minute followed by 10 step cycles of 72° C. for 1 minute and 96° C. for 1 minute. See FIG. 8 for sequences of VW309 and OPR106 primers. The linker-β1–β2 PCR product (approximately 640 bp) was digested with NheI and EagI, gel-purified, and ligated into NheI/EagI digested pB16 (see above), in order to swap the β chain gene fragments. The resulting vector, designated pBS-IASβ, contains the EcoRV/EagI linker-β1–β2 fragment needed for cloning between the leader intron and J-region intron of the IgG kappa chain shuttle vector (see FIG. 9D of the Drawings). To insert sequences encoding the class II I-A$^s$ binding peptides, oligonucleotides are annealed and ligated into AflII/NheI digested pBS-IASβ. The MBP 91–103 peptide (HYGSLPQKSQHGR) (SEQ ID NO: 9) is encoded by oligonucleotides VW315 and VW316, PLP 139–151 (HSLGKWLGHPDKF) (SEQ ID NO: 10)) by VW313 and VW314 and MBP 1–14 (MASQKRPSQRSKYL) (SEQ ID NO: 11) by VW317 and VW318. Sequences of those oligonucleotides are set forth in FIG. 8 of the Drawings. The respective constructs in the pBS-IASβ backbone are designated pBS-IASβ/MBP91, pBS-IASβ/PLP and pBS-IASβ/MBP1. These vectors are digested with EcoRV and EagI and the resulting peptide-linker-β1–β2 gene fragment is subcloned into the pJW009 IgG shuttle vector as described in Example 2 which follows.

EXAMPLE 2

Preparation of Expression Vector of MHC Fusion Complex Linked to Immunoglobulin

The following protocol includes expression of soluble peptide-linked MHC class II/immunoglobulin molecules as chimeric protein. The objective is to construct an antibody-like molecule that has kappa constant domain plus the MHC class II α chain region and the murine IgG2b constant domain joined with the MHC class II β chain covalently linked to peptides of interest. These constructs are then cloned into separate mammalian expression vectors and used to transfect lymphoid derived cell lines, i.e. J558.

Figure 10A:
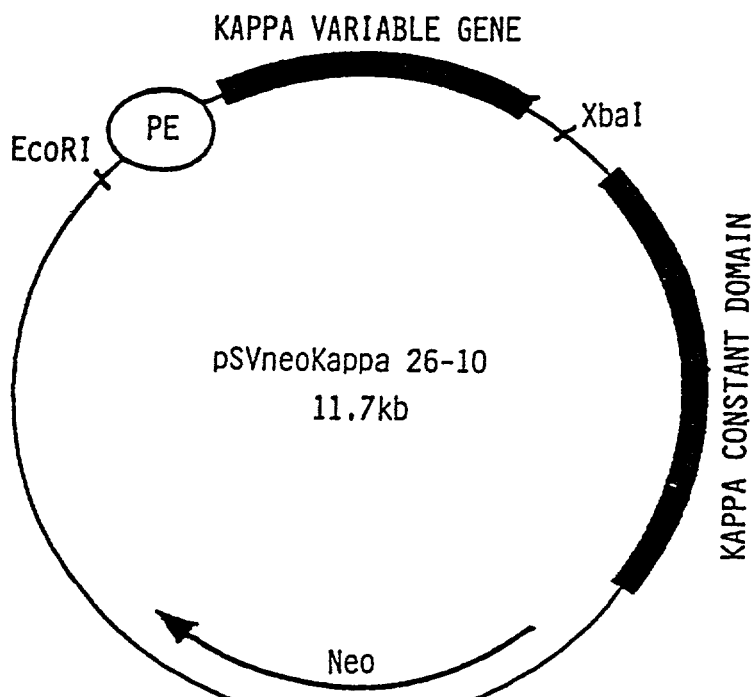
FIGS. 10A and 10B show mammalian cell expression vectors used in the Example 2 which follows.

Two commonly used mammalian expression vectors were modified so that the chimeric constructs could be cloned and expressed. The original vectors are described by Near et al., Molecular Immunology 27: 901–909 (1990). FIG. 10A of the Drawings shows the 11.7 Kb pSVneoKappa 26-10 light chain expression vector which contains pBR322 as backbone and the neomycin resistance gene. Furthermore, it has a 6.7 Kb piece of germline kappa DNA that was initially cloned as genomic DNA into lambda. A 2.7 Kb EcoRI-XbaI fragment contains the Ig kappa promoter and enhancer, the leader sequence and its intron, the variable region exon rearranged with JK1, the remaining JK exons and introns, and part of the major intron separating the variable region from kappa constant region as shown in FIG. 11A of the Drawings.

Figure 10B:
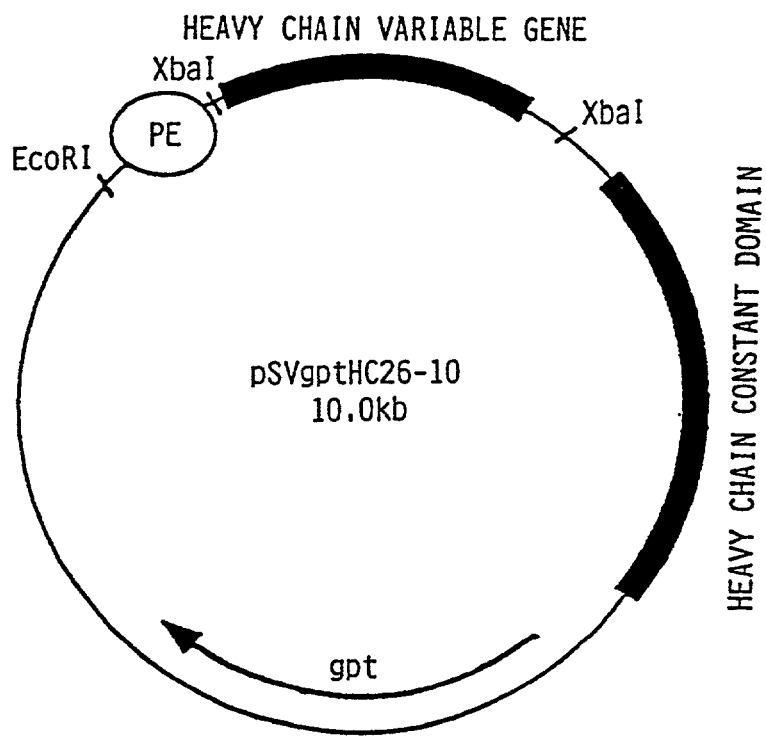

The peptide-linked β chain plus the IgG2b immunoglobulin constant region has been cloned into pSVgptHC 26-10 referred to as pJW010. This mammalian cell vector was originally described by Mulligan et al. (Science, 209:1422–1427, 1980); and later by Near et al., supra. Briefly, pSVgptHC 26-10, shown in FIG. 10B of the Drawings, is 10 Kb and contains the *E. coli* xanthine-guanine phosphoribosyl transferase gene (gpt) under the control of the SV40 early promoter. Germline murine IgG2b constant domain was cloned into pSVgpt as a BglII-XbaI fragment. Another change to the vector made by Near et al., supra, was cloning of a 0.7 Kb EcoRI-XbaI piece that contains the Ig heavy chain promoter/enhancer. These changes left the pSVgptHC 26-10 vector with an XbaI cloning site that was used to clone a 1.7 Kb XbaI fragment by Near et al. This 1.7 Kb insert contains an Ig heavy chain leader sequence and its intron, the variable exon linked to the JH4 domain, and part of the major intron residing between the V region and C region. Furthermore, the 1.7 Kb fragment is the target sequence DNA that has been mutated. In summary, to make cloning of the α and β chains possible several mutations to the 2.7 Kb and 1.7 Kb fragments had to be completed as described below.

Figure 11A:
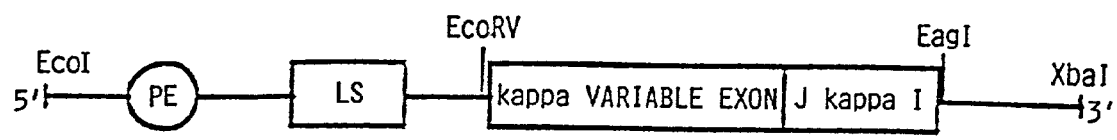
FIGS. 11A and 11B shows DNA constructs which are described in Example 2 which follows.
Figure 12:
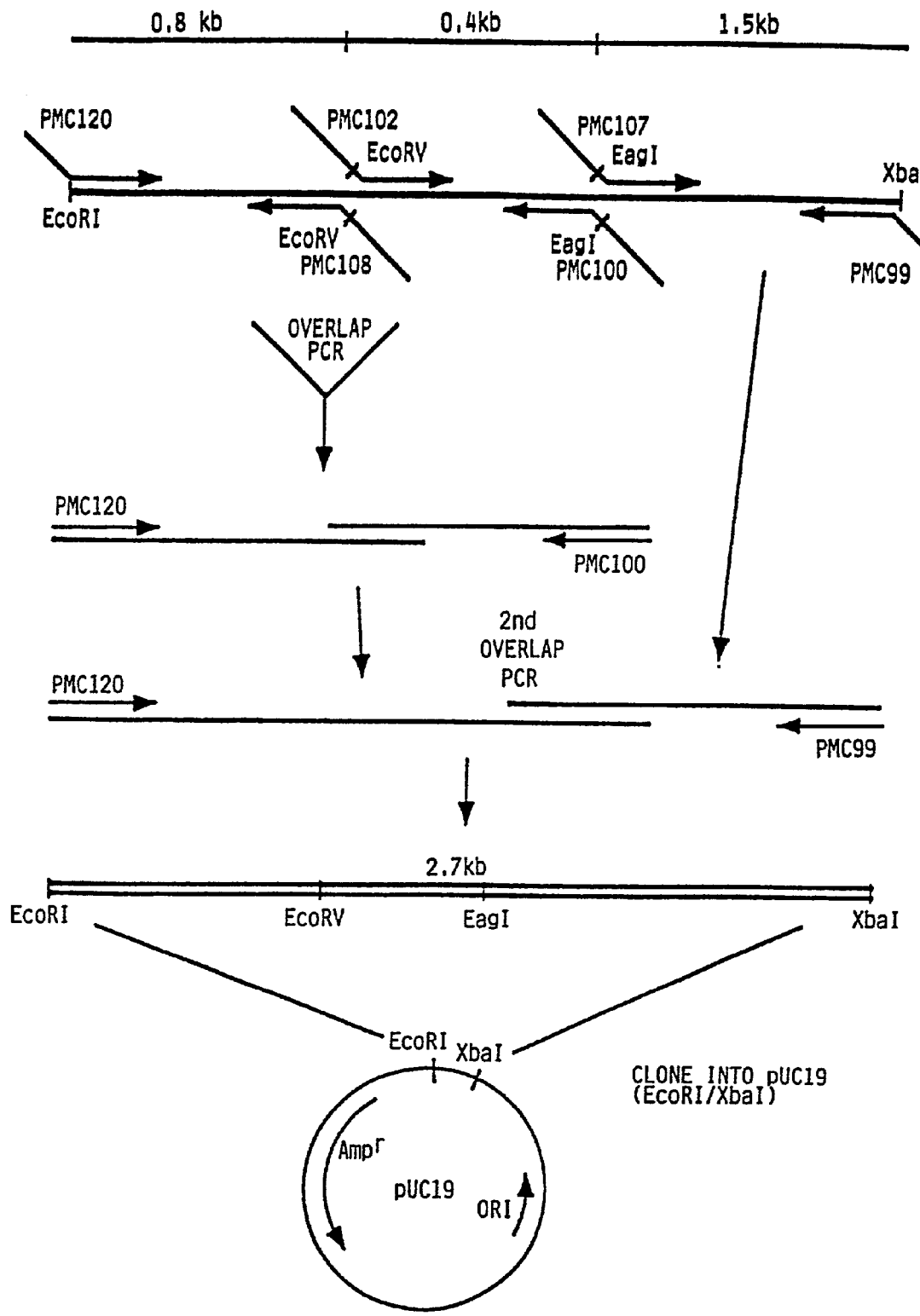
FIG. 12 shows the scheme for introducing restriction sites into the kappa chain 2.7 kb insert via PCR site directed mutagenesis.

The strategy for preparing the pJW004 vector for cloning and expression of the α chain gene was to make two site mutations within the 2.7 Kb insert is described in FIG. 11A. A sample of pJW004 has been deposited with the American Type Culture Collection (ATCC), Rockland, Md. U.S.A. and has received ATCC number 75832. An EcoRV site was created at eight nucleotides 5' of the kappa variable region while an EagI site was added at eight nucleotides 3' of the JK1 domain. These mutations would enable directional cloning of the MHC class II α gene into the vector for expression of the α chain/kappa constant region fusion molecule. Polymerase chain reaction (PCR) site directed mutagenesis was used to add these two restriction sites, and the primers and steps taken to make these changes are shown in FIG. 12 of the Drawings. The 2.7 Kb piece of DNA was cloned from pUC19 into M13 mp18 as an EcoRI-XbaI fragment that was linearized with EcoRI and used as template (5 ng/100 ul mixture) in the PCR reactions. The 2.7 Kb insert was divided into three PCR fragments by designing primers that would specifically amplify three different length PCR products, which included a 0.8 Kb EcoRI to EcoRV fragment, a 0.4 Kb EcoRV to EagI fragment, and a 1.5 Kb EagI to XbaI fragment. The PCR primers used to amplify each fragment are summarized and the underlined sequence corresponds to the restriction endonuclease site. Primers PMC 120 [5'GCAGAA GAATTCGAGCTCGGCCCCCAG3'] (SEQ ID NO: 12) containing an EcoRI site and PMC108 [5'GAT GATATCAGAGAGAAATACATACTAACACAC3'] (SEQ ID NO: 13) containing an EcoRV site were used to amplify the 0.8 Kb product, while primers PMC100 [5'GGAA-GAAAGAGACTTCGGCCGCTACTTAC3'] (SEQ ID NO: 14) containing an EagI site and PMC 102 [5'GTGTGTTAG-TATGTATTTCTCTCT GATATCTTCAGCTTCCAGCAGTG3'] (SEQ ID NO: 15) containing an EcoRV site were used to PCR the 0.4 Kb fragment. The final piece to be amplified was 1.5 Kb in length and was amplified using primers PMC 99 [5'TCT TCTAGAAGACCACGCTAC3'] (SEQ ID NO: 16) containing an XbaI site and PMC 107 [5'GATGATATC CGGCCGAAGTCTCTTTCTTCCGTTGTC3'] (SEQ ID NO: 17) containing an EagI site. Two overlapping PCR reactions were done with the three PCR products to construct the mutated 2.7 Kb insert. The first overlap PCR resulted in amplifying a 1.2 Kb product using primers PMC 100 and PMC 120 and the 0.8 Kb and 0.4 Kb fragments. A second overlapping PCR reaction was done using the gel purified 1.2 Kb DNA and the 1.5 Kb piece and primers PMC99 and 120. From this reaction, a 2.7 Kb fragment was produced that was later digested with EcoRI and XbaI and cloned into pUC19. DNA from ligation reaction mixtures was transformed into DG101 cells and 36 colonies were picked and screened by double digests using EcoRV-EagI and EcoRI-XbaI enzymes.

Figure 13:
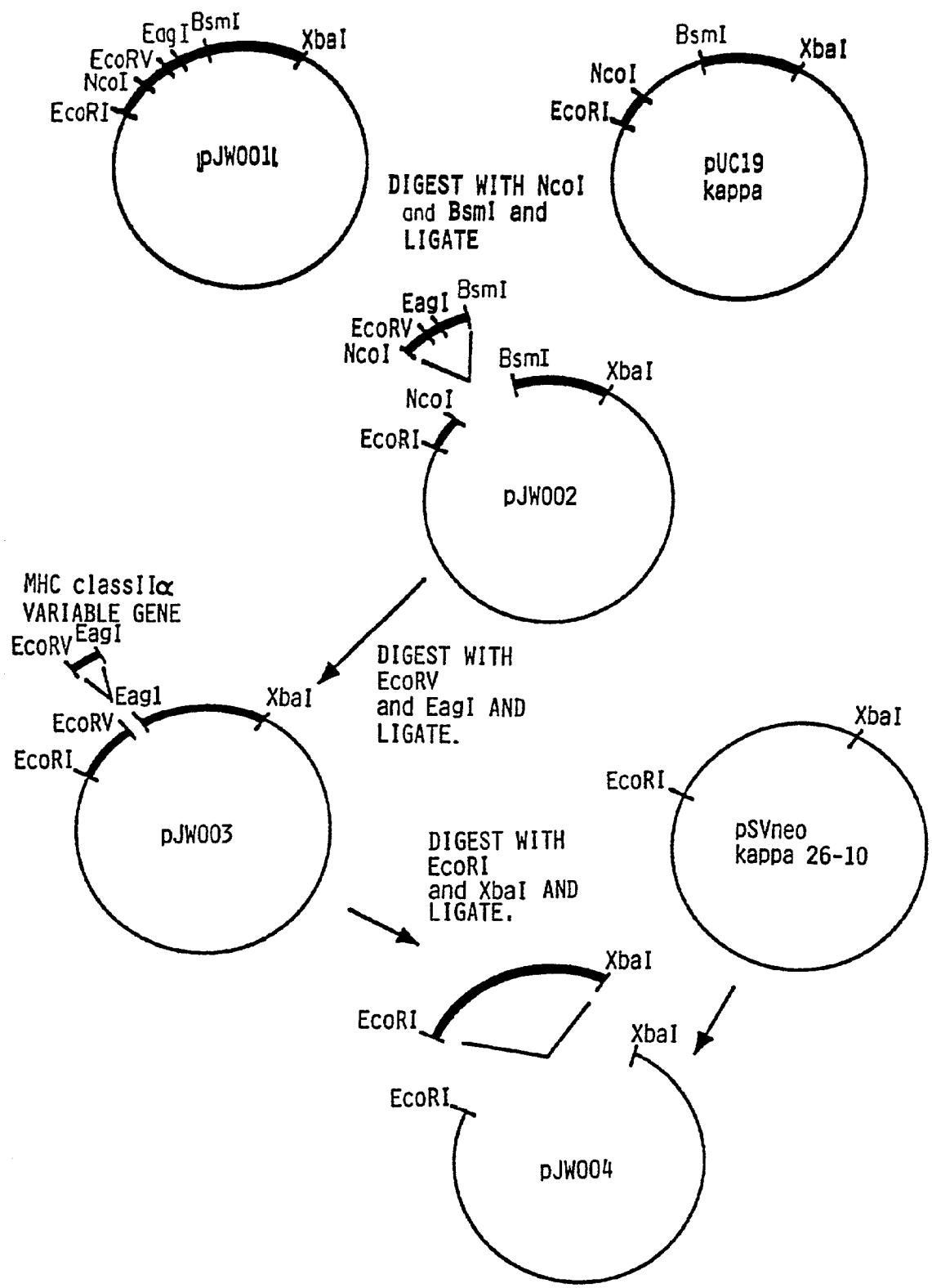
FIG. 13 shows the scheme for constructing a fusion gene encoding the MHC (class IIα)/kappa chain constant region in mammalian cell expression vector.

After detecting several positive clones by restriction mapping, three clones were chosen for sequencing. By using primers PMC-33, 77, 111, and 114 (sequences of those primers set forth in FIG. 14 of the Drawings), 900 bp of sequence data was obtained. The region where correct sequence was found to include 400 bp of DNA between the EcoRV and EagI sites and 300 bp 5' of the EcoRV site and 200 bp 3' of the EagI site. One clone, pJW001, had good sequence that was different from the consensus sequence at five bases. A disturbing observation made after restriction mapping and from reviewing sequence data generated using M13 universal primers was that insert DNA cloned into pUC19 and transformed into DG101 was deleted. These deleted sequences poised a problem since much of the transcriptional machinery was deleted along with the major intron located between the EagI site and XbaI. To salvage the piece of DNA that contained the mutated sites, EcoRV and EagI, clone #12 insert was digested with two unique cutters, NcoI and BsmI. The NcoI site is located about 300 bp 5' from the EcoRV site, and a BsmI site is present about 200 bp 3' of the EagI site. Therefore, as seen in FIG. 13 of the Drawings, the 0.9 Kb NcoI-BsmI piece was cut from pJW001 and cloned into pUC19/kappa 26-10 insert which did not have the EcoRV and EagI sites but did have the unique sites NcoI and BsmI. To confirm whether the correct size insert had been cloned into pJW002, an aliquot of pJW002 DNA was digested with three different pairs of restriction enzymes, EcoRI-XbaI, NcoI-BsmI, and EcoRV-EagI.

To prevent recombination events from occurring again, the strain of E.coli was changed from DG101 to XL1-B, a recA negative host. At this step, the insert DNA contained the two site mutations and cloning of the MHC class II α gene could proceed.

pJW002 DNA was digested with EcoRV and EagI, dephosphorylated with calf intestinal alkaline phosphatase (CIAP), and then gel purified. The isolated vector DNA was then used in ligations with the gel purified 577 bp EcoRV-EagI cut α chain I-A$^d$ gene. Ligation, transformation and screening of 10 colonies yielded a single positive clone which was digested with two pairs of enzymes, EcoRI-XbaI and EcoRV-EagI. The positive clone, pJW003 (pUC19 mutated kappa containing the a gene), was grown up and the DNA was Qiagen purified.

Figure 16A:
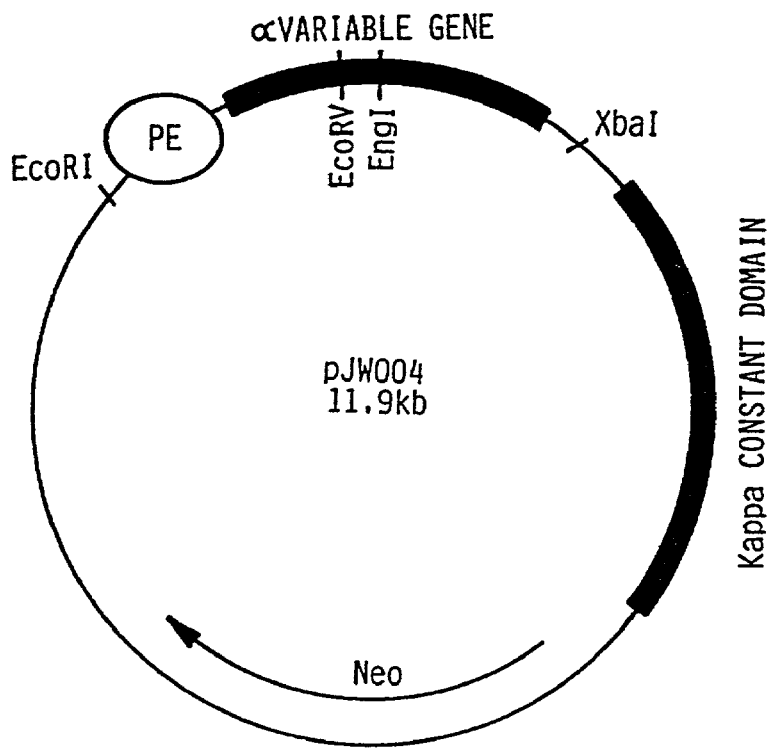
FIGS. 16A and 16B show vectors for expression of MHC II/Ig chimeric proteins.

A triple digest of pJW003 DNA was done using EcoRI, XbaI, and HindIII. The cut DNA was then treated with phenol chloroform, precipitated with ethanol, and washed with 70% ethanol after which the DNA was digested with ScaI and treated with CIAP. pUC19 DNA migrates at 2.7 Kb on an agarose gel which makes it difficult to separate pUC DNA from the desired insert DNA. However, pUC19 as a unique ScaI site that cuts and gives two smaller size fragments that can be separated on an agarose gel away from the 2.9 Kb insert DNA. After gel purification, the 2.9 Kb α I-A$^d$ gene insert was ligated in EcoRI-XaI gel purified pSVneo vector to make pJW004 (FIG. 16A). Ligations were transformed into DG103. Qiagen maxi-preparations were done to isolate large amounts of vector DNA so that pJW004 could be transfected into mammalian cells.

Figure 11B:
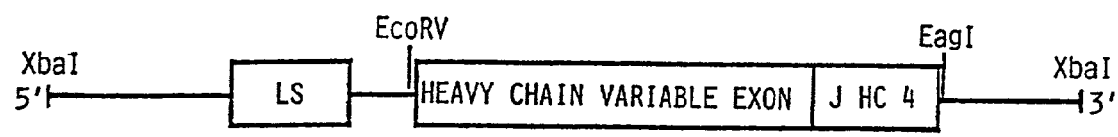

The strategy for cloning the MHC β variable gene into the pSVgpt expression vector was to make four mutations within the 1.7 Kb XbaI piece described in FIG. 11B. The four mutations included two EcoRV site deletions, one situated 68 nucleotides 5' of the leader sequence exon and the other site located at 27 nucleotides 5' of the variable region. The other two mutations were site additions and involved an EcoRV site eight nucleotides 5' of the variable region and an EagI site eight nucleotides 3' of the JH4 domain. M13 site directed mutagenesis was used to make the mutations on the 1.7 Kb insert. The approach was to subclone the 1.7 Kb XbaI fragment from pSVgptHC26-10 and clone it into M13. Site directed mutagenesis was done using the BioRad Muta-Gene in vitro Mutagenesis Kit that is based on the highly efficient and simple method of Kunkel. This method employs a special E. coli strain that is deficient for dUTPase (dut) and uracil-N-glycosylase (ung). These deficiencies allow random uracil substitutions for thiamine in the M13 ssDNA. When the double stranded DNA, or replicative form (RF), is transformed back into a wild type host strain the uracil-N-glycosylase degrades uracils present in the original template so that only the strand of DNA that carries the site specific mutation is replicated thereby generating a high efficiency of positive clones.

Figures 14, 15:
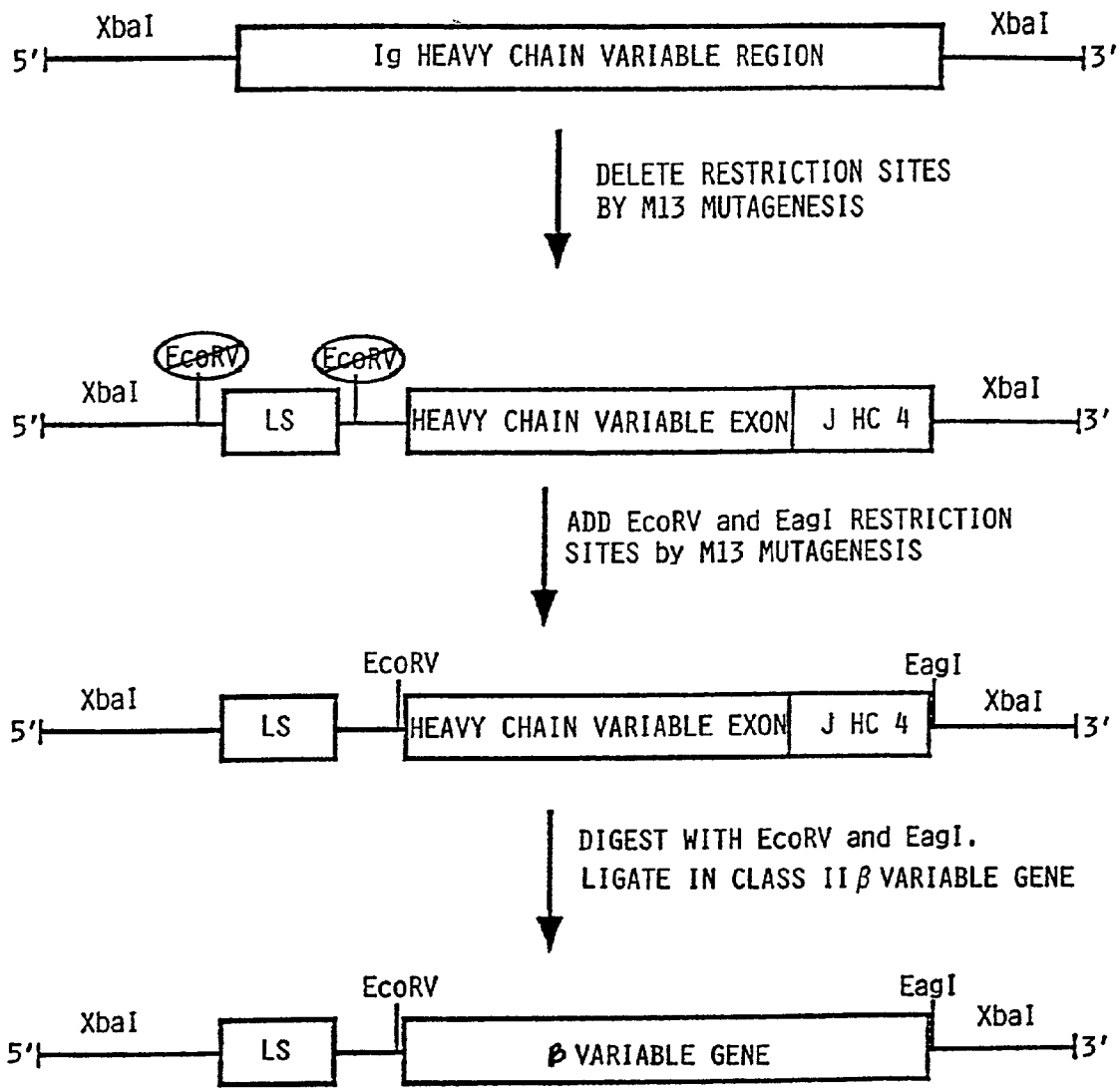
FIG. 14 (SEQ ID NOS: 99–102) shows primers used for sequencing mutated 2.7 kb fragment.
FIG. 15 shows the scheme for M13 mutagenesis and cloning of the MHC II β variable gene.

The steps taken in making the mutations are shown in FIG. 15. Briefly, primer PMC 26 [5'AGGG TTATCAACACCCTGAAAAC3'] (SEQ ID NO: 18) was used to delete the EcoRV site located 68 nucleotides 5' of the leader sequence exon, and contained a single base change, indicated by the underlined nucleotide, from A to T. The deletion of the second EcoRV site at 27 nucleotides 5' of the variable region was done with primer PMC 28 [5'GTCA-CAGTTATCCACTCTGTC3'] (SEQ ID NO: 19) and again was a simple point mutation change from A to T. Primer PMC 96 [5'CGTCTCCTCAGGTACGGCC GGCCTCTCCAGGTCTTCG3'] (SEQ ID NO: 20) contained the EagI site mutation, which consisted of four base changes indicated by the underlined nucleotides. Finally, primer PMC 97 [5'ACAGTTATCCACTCTGTCTTT GATATCACAGGTGTCCT3'] (SEQ ID NO: 21) was used to create the EcoRV site by changing four nucleotides as shown.

Figure 16B:
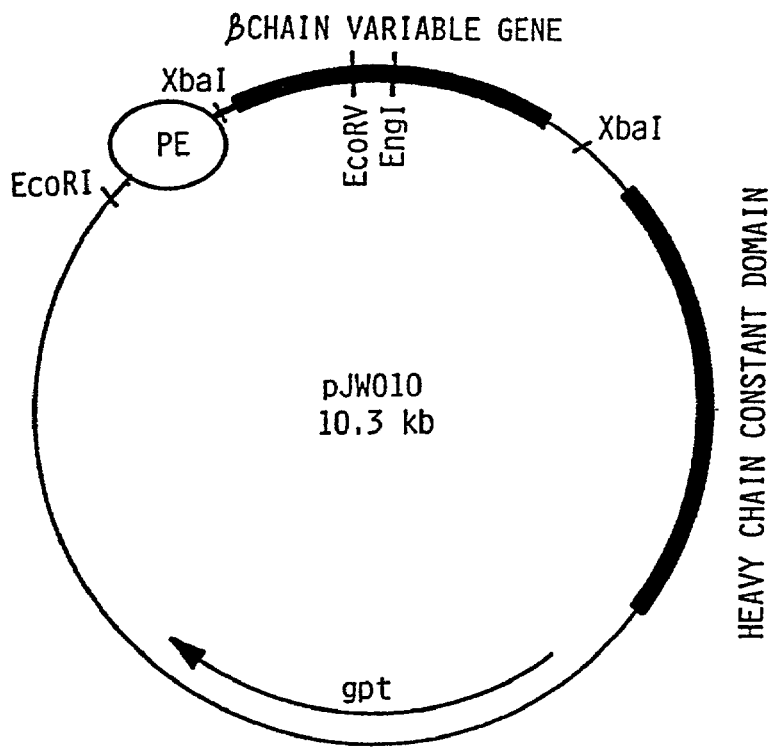

The mutated 1.7 Kb insert was then digested with EcoRV-EagI, CIAP treated, gel purified and used in ligations with the EcoRV-EagI cut, gel purified MHC class II β gene. Other variants, such as the Ova 323–339/I-A$^d$ β1–β2 gene fragment described in Example 1 above, were also cloned into the EcoRV-EagI site and grown up in M13. FIG. 15 of the Drawing describes the strategy for cloning the MHC class II β variable and variants into the vector pJW009. After cloning into pJW009, the DNA was digested with XbaI to drop out the XbaI fragments containing the various peptide-linked β variable gene and was subcloned into the mammalian expression vector pJW010 as shown in FIG. 16B. Since directional cloning was not possible, screening for positive clones was done by digesting with EcoRI-EcoRV. Positive clones containing the β genes and other peptide-linked β chain variants have been isolated and the DNA has been Qiagen purified. These have been designated pHB27, pHB310, pHB412 and pEB58 for the I-A$^d$ β chain construct containing no peptide, the Ova 323–339 peptide, the Ova: H331R peptide and the Ova:A331Y peptide, respectively (see Example 1B). Samples of pHB27, pHB310, pHB412 and pHB58 have been deposited with the American Type Culture Collection (ATCC), Rockville, Md. USA and have received ATCC numbers 75833, 75835, 75836 and 75834, respectively.

Transfection of lymphoid derived cells such as J558 and NS0 cells, can be done essentially as described by Near et al. 20 µg of both, pJW004 and pJW010, can be co-transfected into either J558 or NS0 cells by electroporation using the BioRad gene pulser. Stable cell lines are selected within 7 to 10 days. Expression of the chimeric MHC class II/Ig molecule is determined by an ELISA specific for detecting murine IgG2b constant region and/or a western blot analysis can be done. Finally, the expressed protein is purified by Protein-A or -G affinity chromatography.

EXAMPLE 3

Construction of the Full-length Peptide-linked MHC Expression Vectors and Expression Vectors for Co-stimulatory factors (B7-1 and B7-2)

Figure 17A:
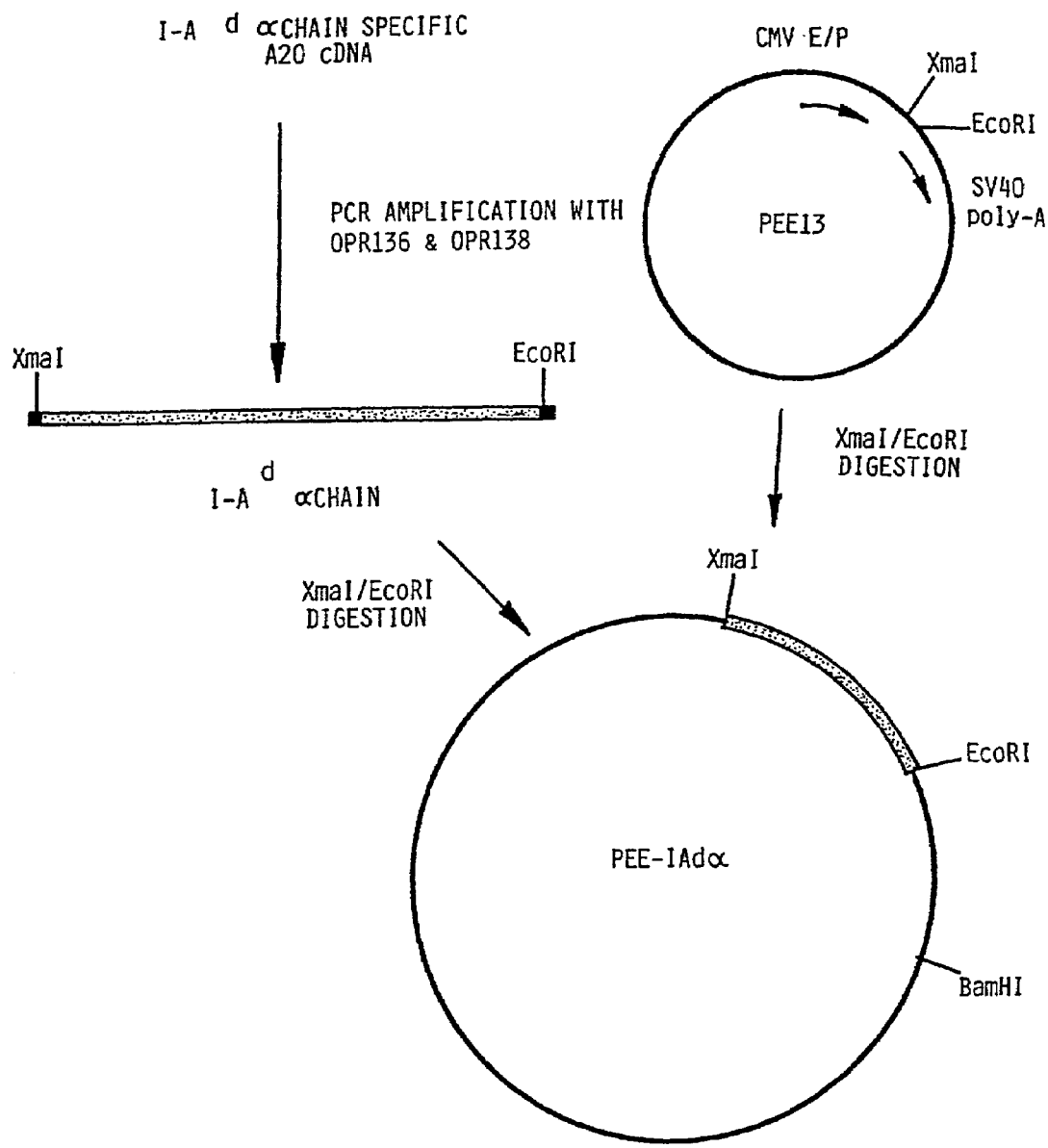
FIG. 17 shows the scheme for construction of a full length MHC fusion complex expression vector.
Figure 17B:
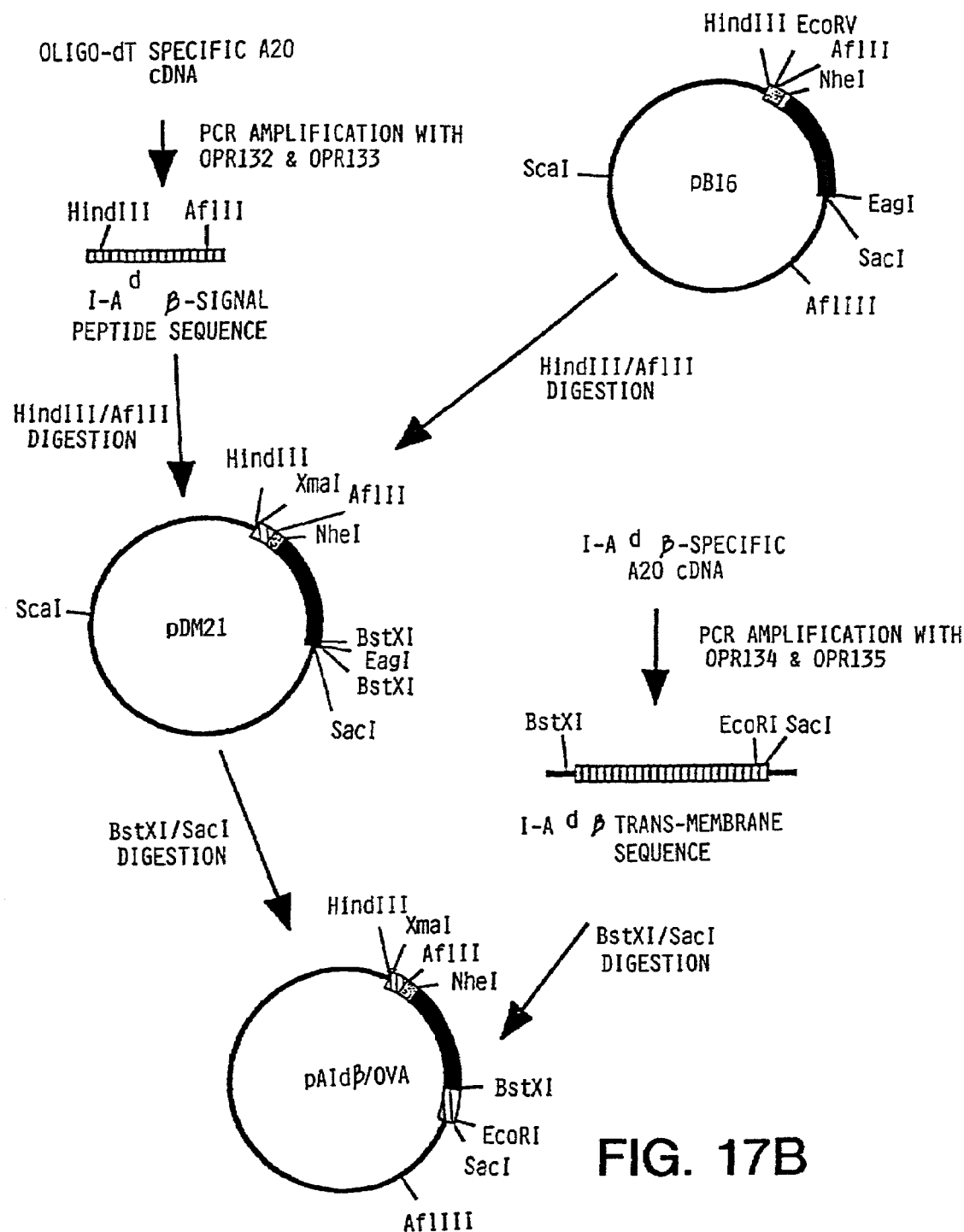
Figure 17C:
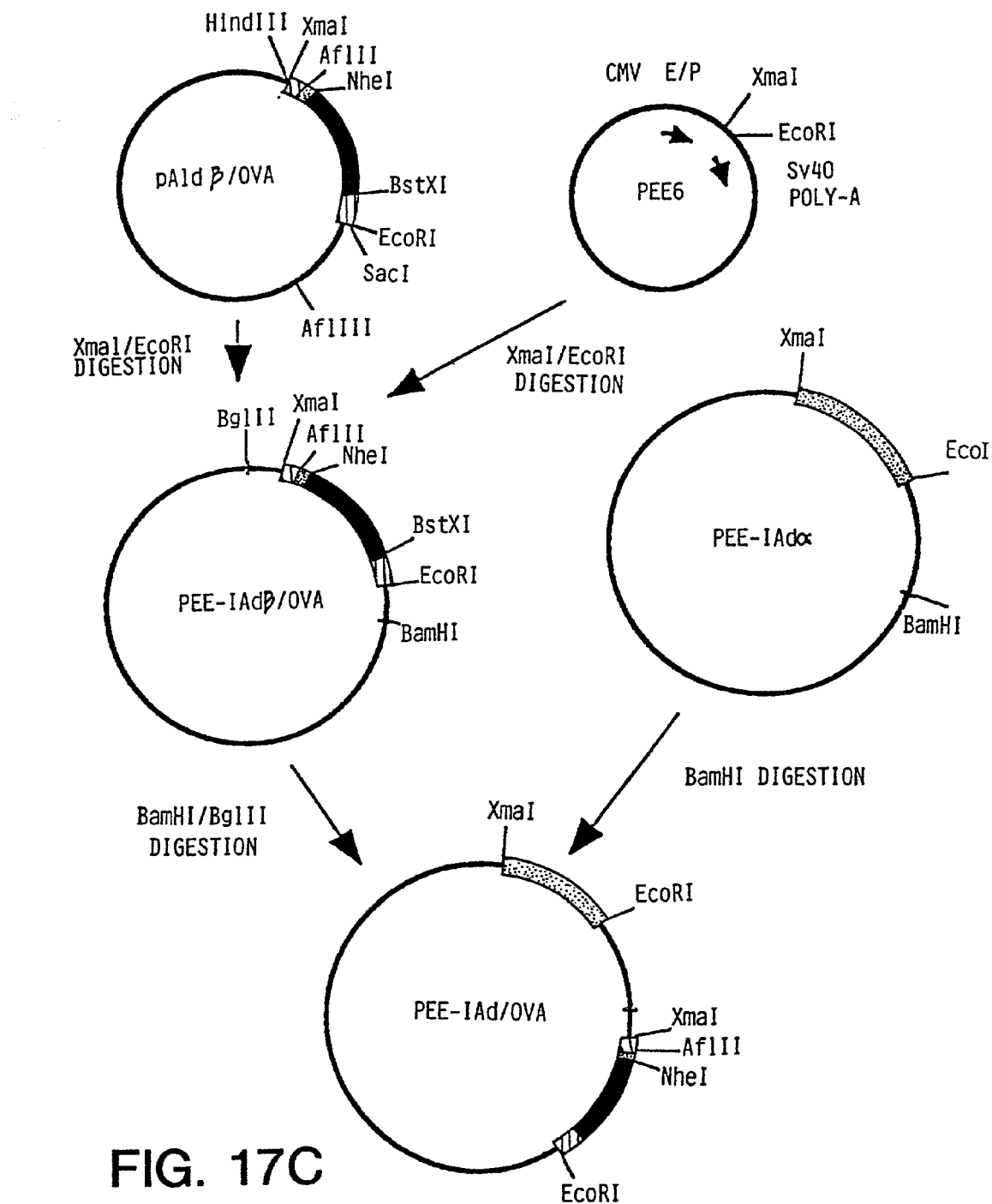
Figure 19A:
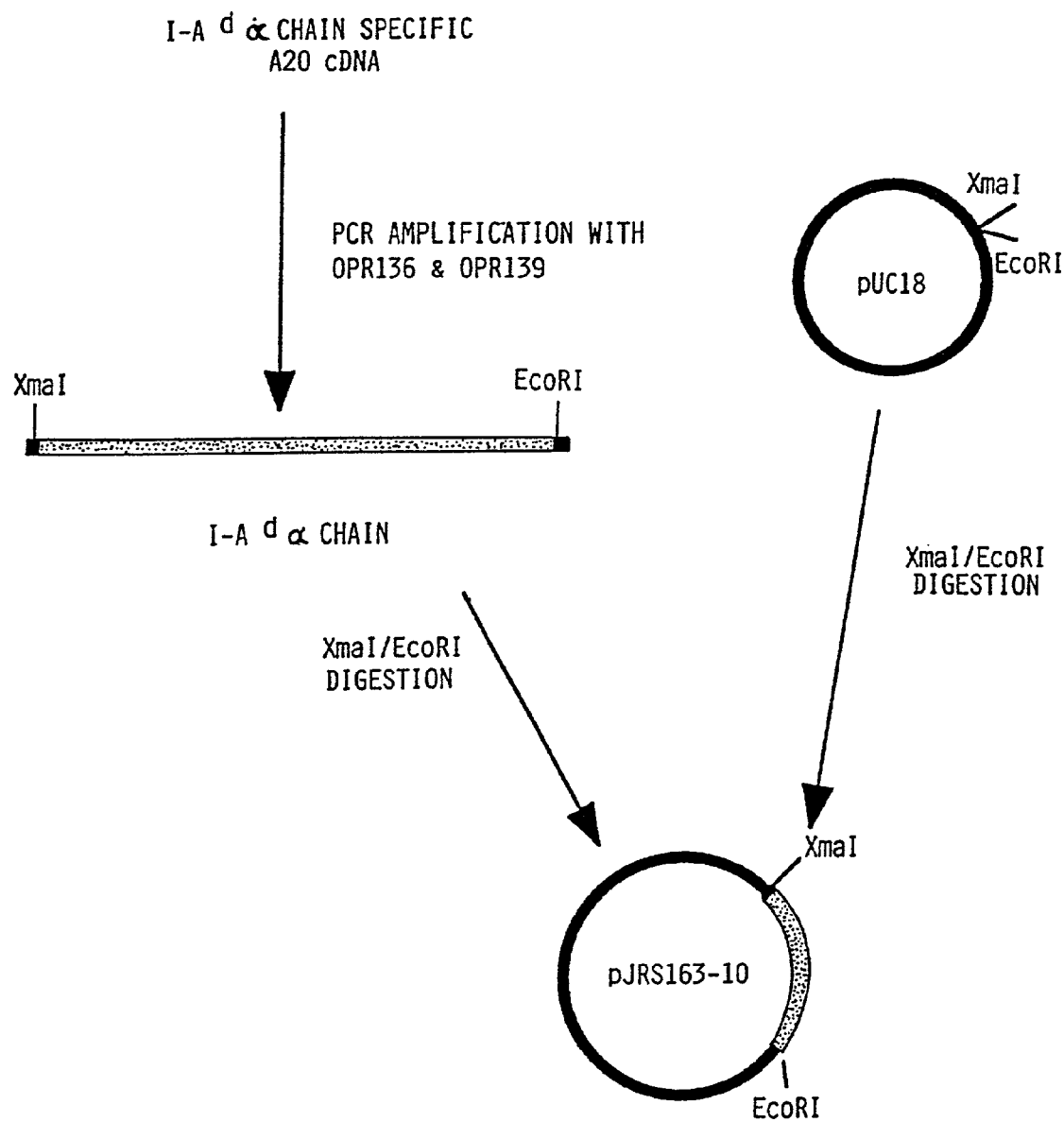
FIG. 19 (total of 7 sheets) shows the cloning scheme carried out in Example 12 which follows.
Figure 19B:
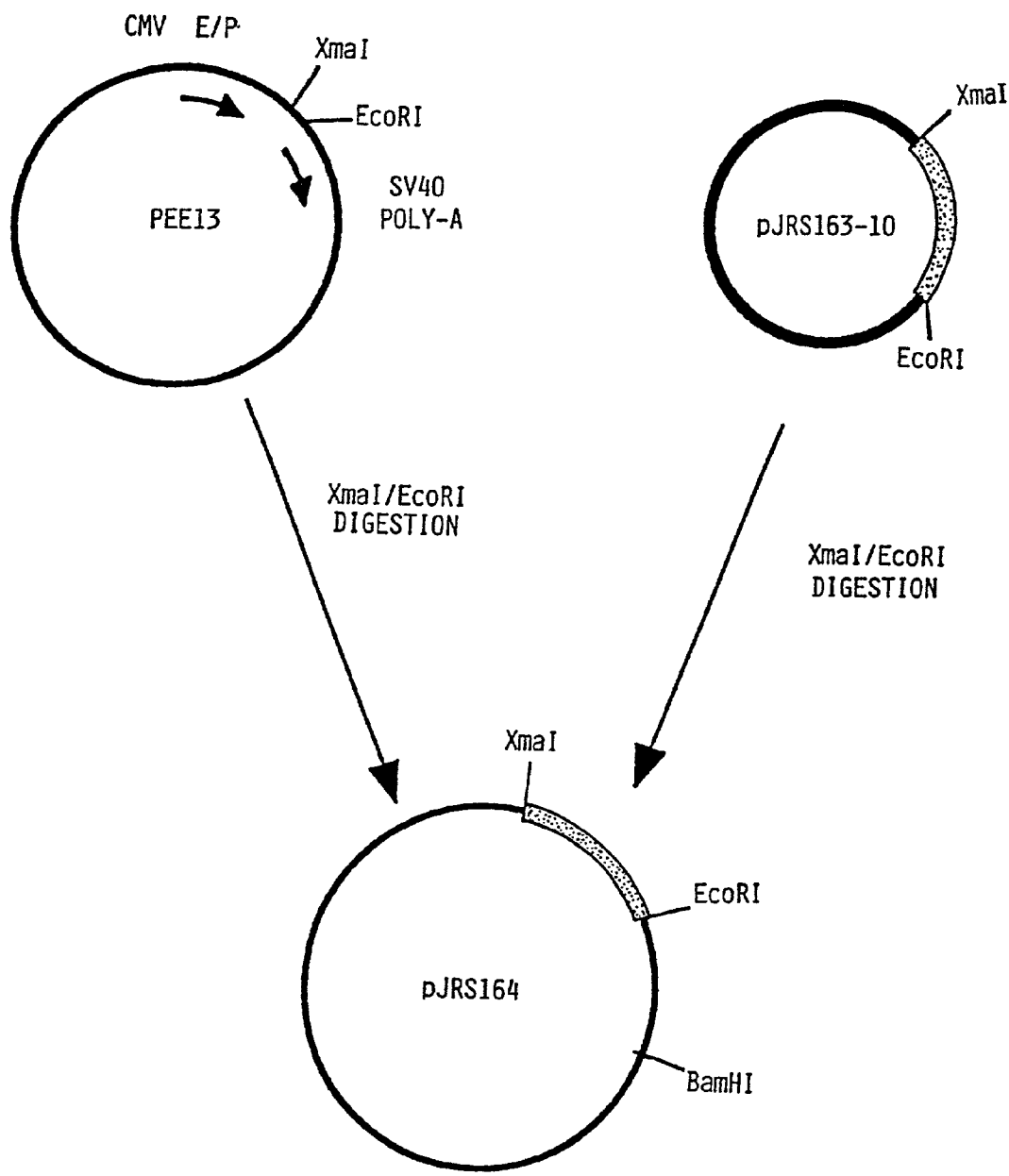
Figure 19C:
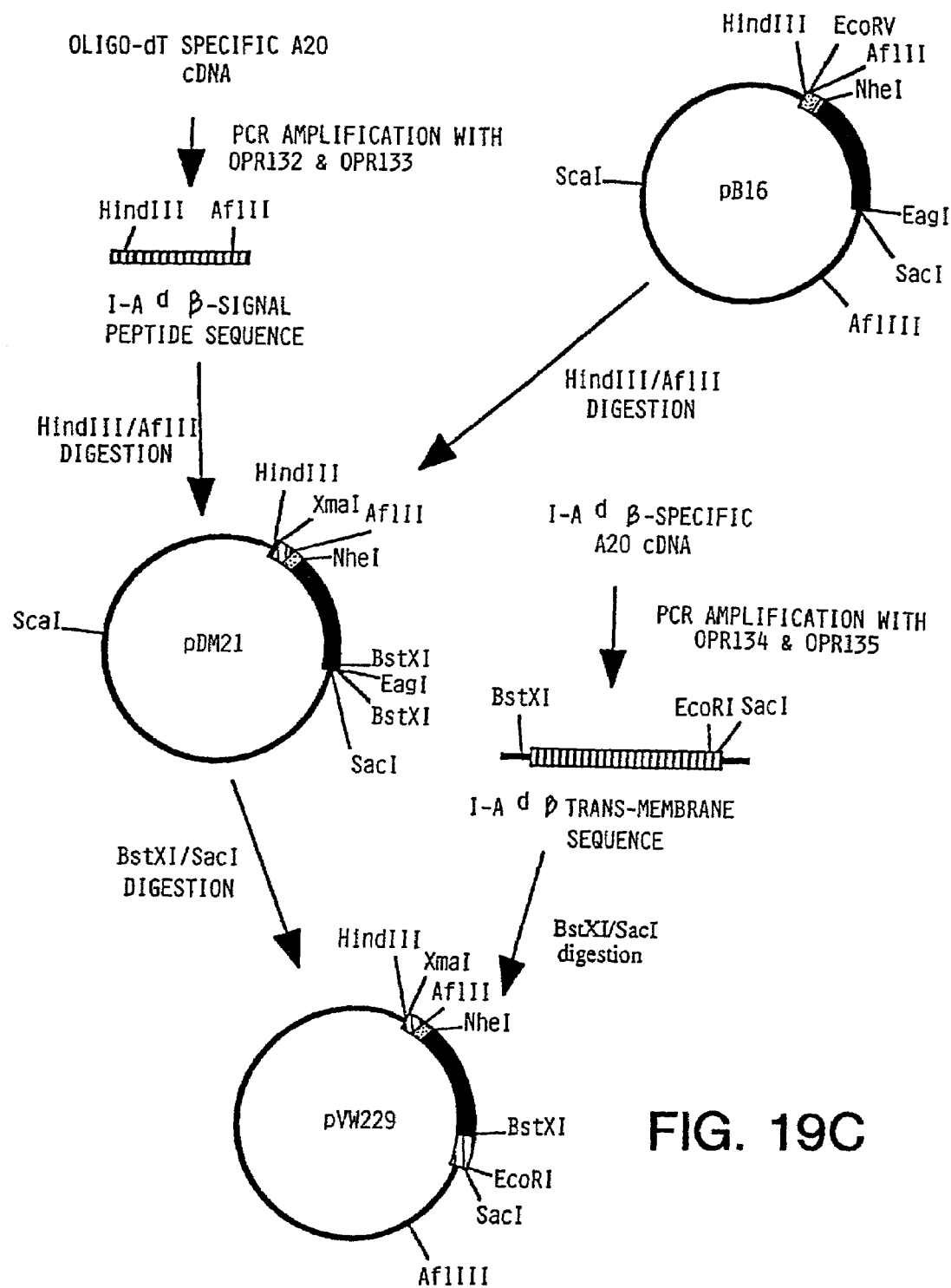
Figure 19D:
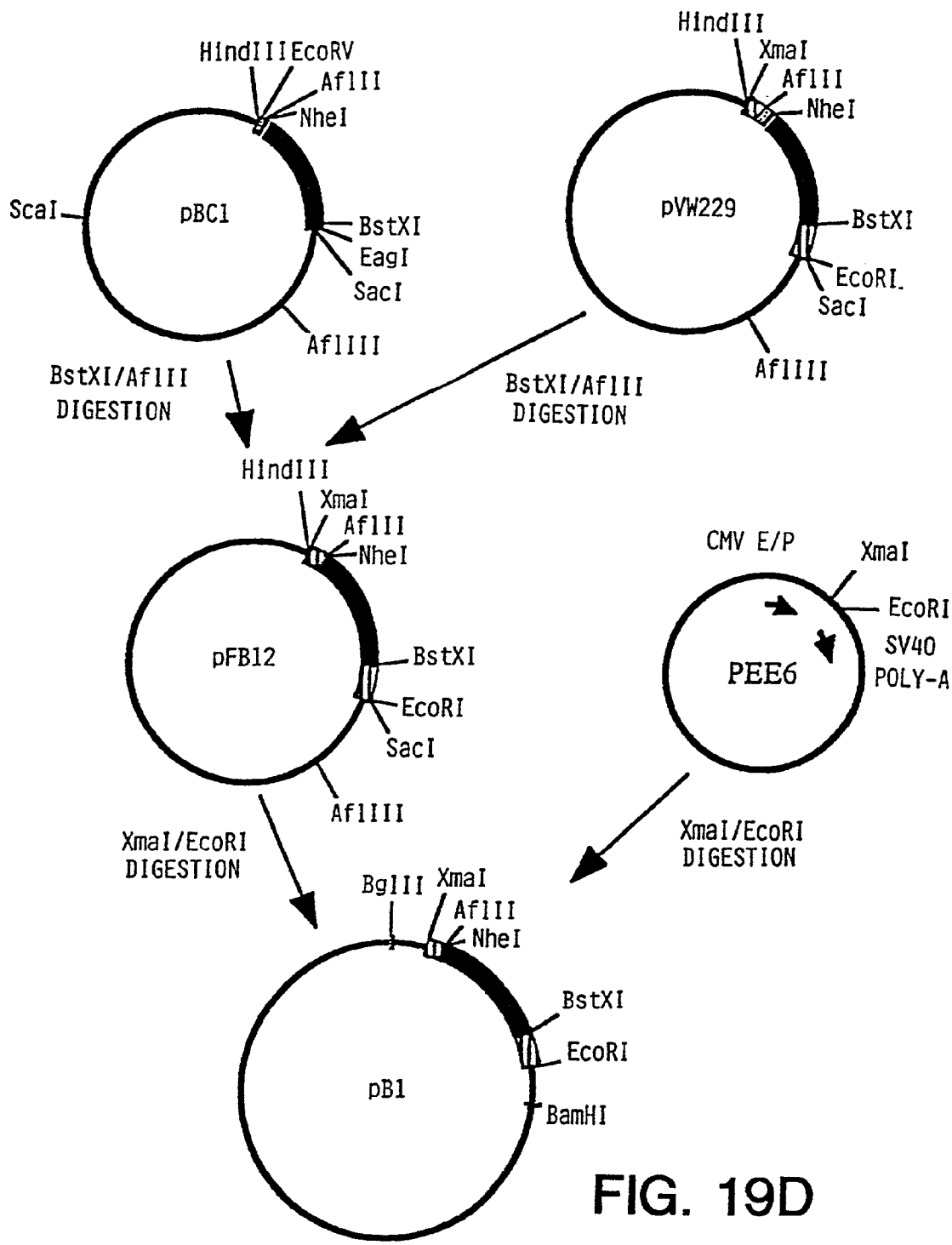
Figure 19E:
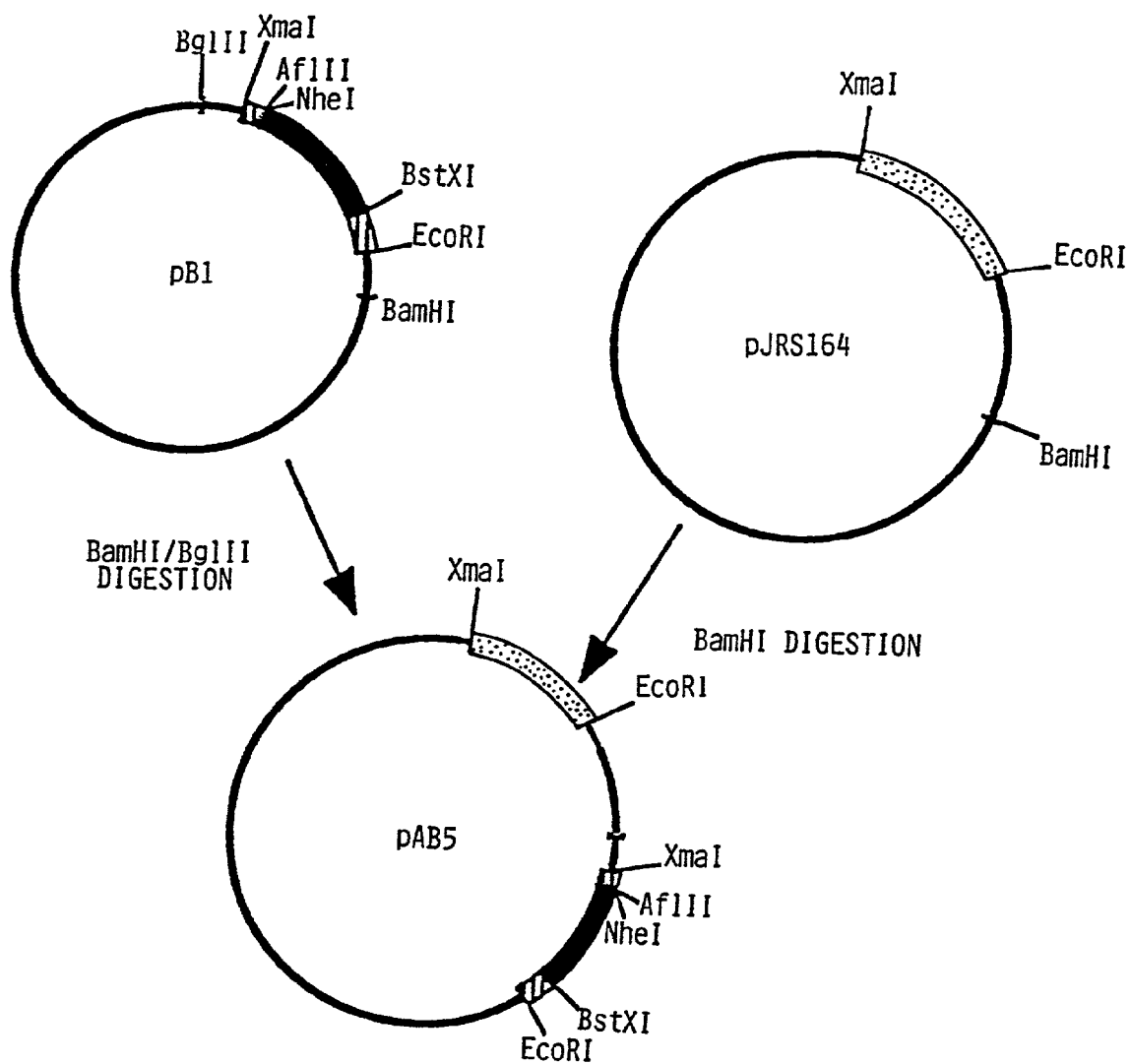
Figure 19F:
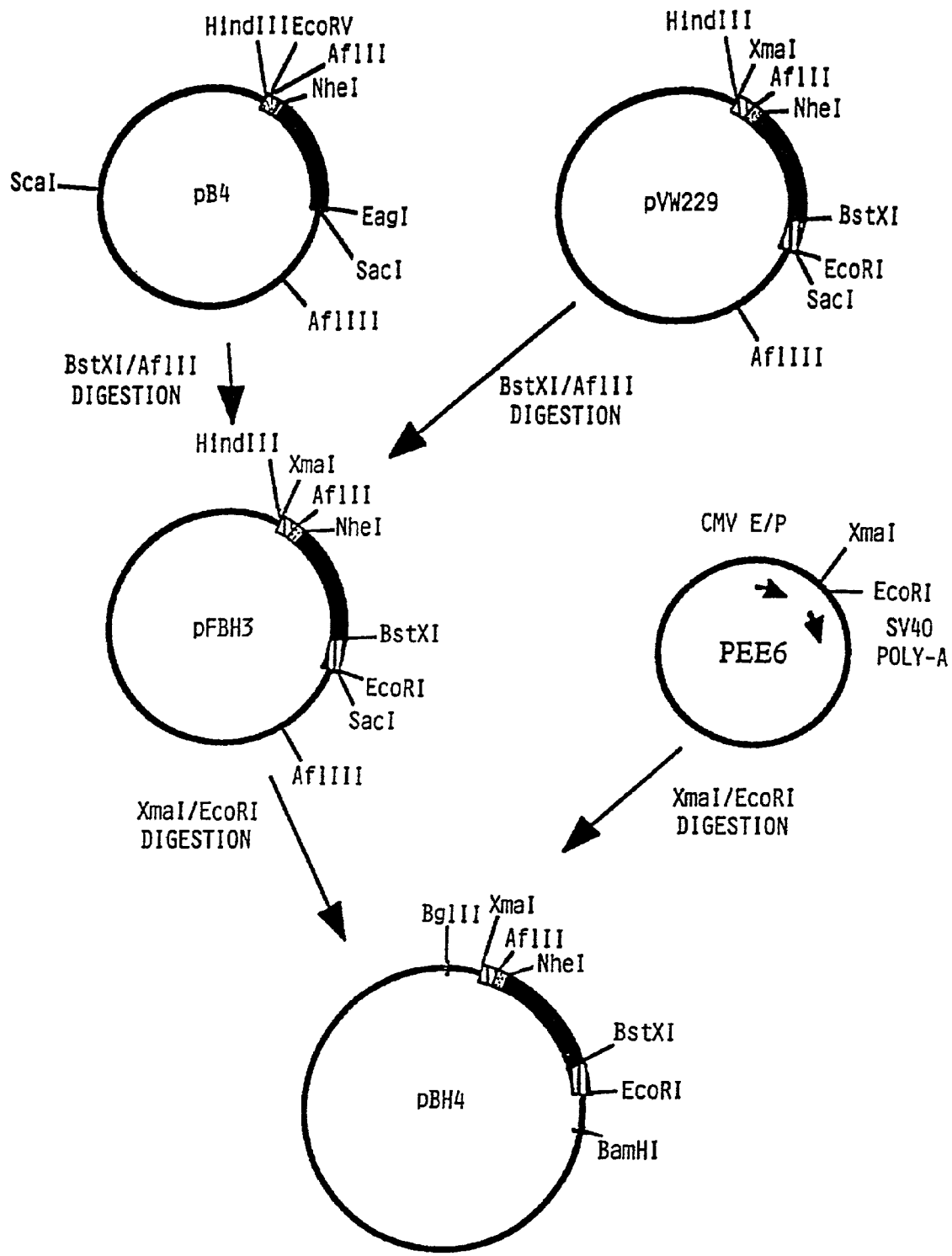
Figure 19G:
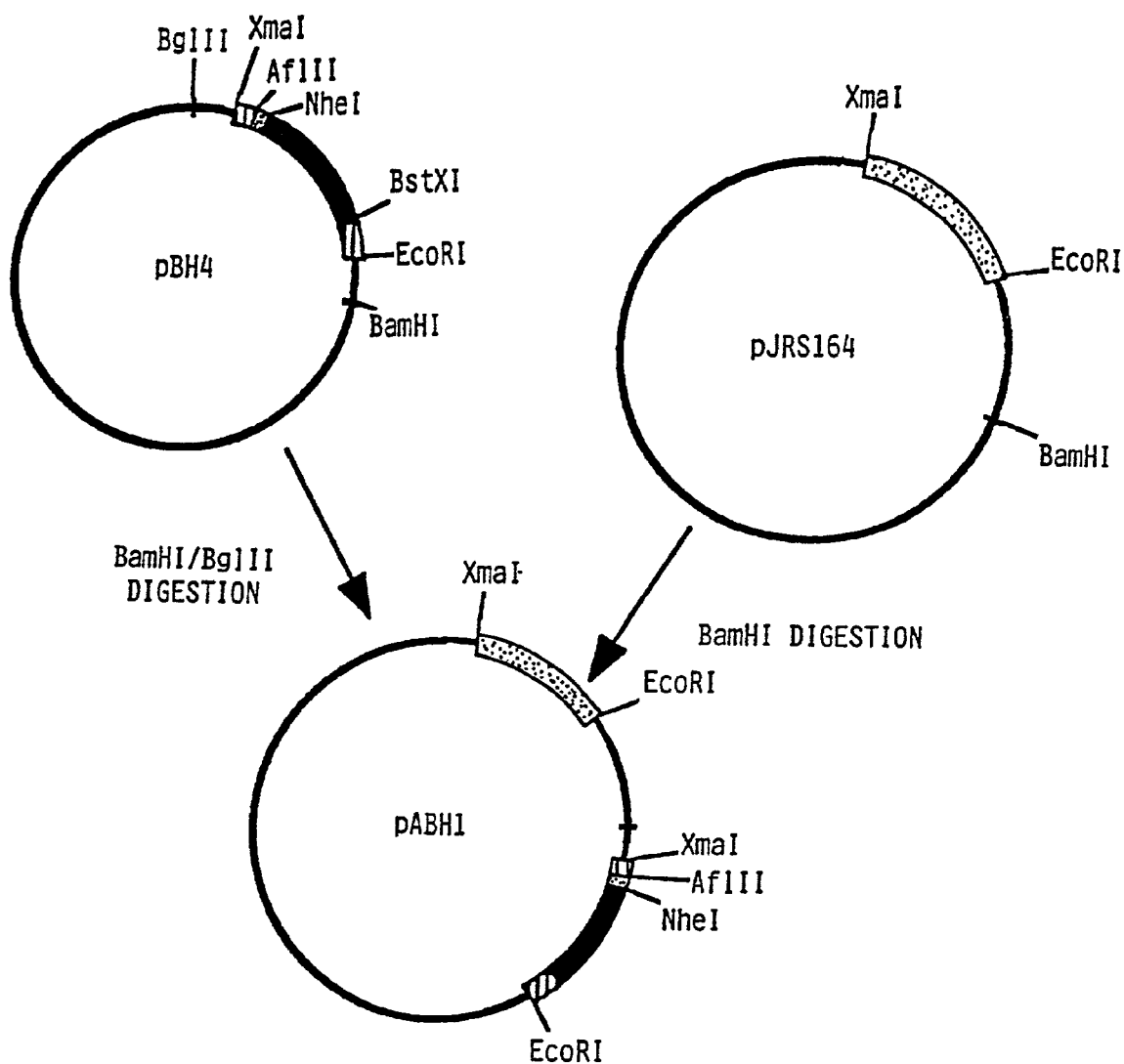

Vectors capable of co-expressing the full-length I-A$^d$ α chain and peptide-linked I-A$^d$ β chain molecules are suitably constructed by the procedures outlined in FIG. 17 of the Drawings. In order to isolate the full-length I-A$^d$ α chain, A20 total RNA (5 µg) was converted to cDNA by using Superscript-MLV Reverse Transcriptase (GIBCO-BRL) and α chain TM-specific priming according to manufacturer's procedures. This cDNA was used as the template for PCR amplification using an a chain leader-specific primer OPR136 (sequence of that primer set forth in FIG. 8) and an α chain TM-specific primer OPR139 (sequence of that primer set forth in FIG. 8) by the PCR conditions described in Example 1 above. The resulting PCR product has about 800 bp and contains a 5' XmaI site and a 3' EcoRI site for cloning between the CMV promoter and SV40 poly-A sites of the PEE13 mammalian expression vector (Celltech). In addition, this fragment carries a Kozak consensus sequence for efficient translational initiation (see FIG. 18A of the Drawings). The PCR product was digested with XmaI and EcoRI, gel-purified and ligated into XmaI/EcoRI digested PEE13, to give the PEE-IA$^d$ α vector. The full-length peptide-linked β chain fragment was constructed by inserting the leader and TM sequences into the Ova 323–339 and the HEL 74–86 peptide-linker-β1–β2 vectors (pB16 and pB4, respectively) described in Example 1 above. A20 total RNA (5 µg) was converted to cDNA by using Superscript-MLV Reverse Transcriptase (GIBCO-BRL) and either oligo dT-specific or β chain TM-specific priming according to manufacturer's procedures. These cDNAs were used as the template for PCR amplifications using either a pair of β chain leader-specific primers (OPR132/OPR133) (sequences of those primers set forth in FIG. 8 of the Drawings) or a pair of β chain TM-specific primers (OPR134/OPR135) (sequences of those primers set forth in FIG. 8 of the Drawings). The 110 bp β leader PCR product contains 5' HindIII and XmaI sites and a 3' AflII site for cloning into the pBC1 and pB16 peptide-linker-β1–β2 vectors. The inclusion of the AflII site changes the last two amino acids of the I-A$^d$ β chain leader to those found in the IgG leader. The β leader PCR product was digested with HindIII and XmaI, gel-purified and ligated into HindIII/AflII digested pB16, to give pDM21. The 180 bp β TM PCR product contains a 5' BstXI and sites and 3' XmaIII and EcoRI sites for cloning into pDM21. The β TM PCR product was digested with BstXI and EcoRI, gel-purified and ligated into BstXI/EcoRI digested pDM21, to give the pIA$^d$β/OVA vector, pVW229. The Ova peptide oligonucleotide was swapped with the HEL peptide oligonucleotide described in Example 1 above to generate the pIA$^d$β/HEL vector. These vectors were digested with XmaI and EcoRI to generate the full-length peptide linked β chain gene fragments for cloning between the CMV promoter and SV40 poly-A sites of the PEE6 mammalian expression vector (Celltech). These fragments also carry the Kozak consensus sequence for efficient translational initiation (FIG. 18B). The resulting vectors PEE-IA$^d$β/OVA and PEE-IA$^d$β/HEL were digested with BglII and BamHI. The CKMB promoter/peptide-β chain fragments were gel-purified and ligated into BamHI digested PEE-IA$^d$α, to generate the final PEE-IA$^d$/OVA and PEE-IA$^d$/HEL expression vectors. A vector without any peptide oligonucleotide, PEE-IA$^d$, was also constructed and used as a control.

In order to clone the B7-1 and B7-2 genes, cDNAs can be generated from total RNA isolated from activated mouse spleen cells or from mouse lymphoma cell lines. These cDNAs serve as templates for PCR amplification using either B7-1 or B7-2 specific primers. The PCR products generated carry 5' and 3' NotI sites for cloning between the CMV promoter and SV40 poly-A sites of pCMVβ mammalian expression vector (Clonetech). These fragments also carry the Kozak consensus sequence for efficient translational initiation.

EXAMPLES 4–11

Assays and Methods

General Comments

One or more of several assay systems are suitably employed to test the ability of the soluble MHC fusion complexes to modulate the activity of T cells and are exemplified in the examples which follow. In a first exemplary assay a mouse MHC class II I-A$^d$/Ig fusion molecule is linked to an antigenic peptide from hen egg lysozyme (HEL 74–86), chicken ovalbumin (Ova 323–339) or one of two single-substitution analogues of the Ova peptide—Ova H331R or Ova A332Y. The HEL 74–86, Ova 323–339 and Ova H331R peptides are known to bind I-A$^d$ whereas the Ova A332Y analogue will serve as a non-binding control [S. Buus et al., *Science*, 235:1353–1358 (1987); A. Sette et al., *Nature*, 328:395–399 (1987)]. The His$_{331}$ is believed to not be important for MHC binding but it is critical for T cell stimulation and the Ova H331R/I-A$^d$/Ig complex will serve as a TcR antagonist for T cell stimulation. The mouse DO 11.10 T-cell hybridoma specifically recognizes the Ova 323–339/I-A$^d$ complex and is stimulated to produce IL-2. The assay, outlined in Example 4 below, uses the soluble Ova 323–339/I-A$^d$/Ig to suppress T-cell stimulation by APCs loaded with the Ova peptide. Further effects of the soluble peptide-linked MHC/Ig molecules on Ova-specific T-cell proliferation are examined in Example 5. In addition, the effects of the soluble Ova 323–339/I-A$^d$/Ig and soluble HEL 74–86-A$^d$/Ig on T cell function in vivo can be examined as described in Examples 6 and 7. Mice are injected with the antigenic HEL and Ova peptides (linked to KLH carrier) and either the soluble Ova 323–339/I-A$^d$/Ig or soluble HEL 74–86/I-A$^d$/Ig molecules. Inhibition of in vivo T cell-dependent antibody responses and proliferation of Ova-specific T cells and HEL-specific T cells will be characterized as described in Examples 6 and 7.

A further model is exemplified by an assay that involves linking a peptide from the influenza nucleoprotein (NP 404–415) to the human class II HLA-DR1/Ig molecules (see Example 5). The soluble NP 404–415/DR1/Ig molecules are analyzed for their ability to inhibit APC/NP 404–415-dependent proliferation of a human T cell line, K68–36. Soluble DR1/Ig molecules linked to a different HLA-DR1 binding peptide (HA 307–319) is used as a negative control.

In an additional model system, the ability of soluble peptide-linked MHC/Ig molecules to suppress autoimmunity is examined. As an animal model for multiple sclerosis, SJL mice can be induce to develop experimental allergic encephalomyelitis (EAE) following immunization with encephalitogenic proteins or peptides or following adoptive transfer of $T_H$ cells specific to these antigens. As described below, the encephalitogenic regions of myelin basic protein (MBP 91–103) and of proteolipoprotein (PLP 139–151) are each linked to the mouse class II I-A$^s$/Ig molecule. The non-binding MBP 1–14 peptide serves as a negative control. The soluble peptide-linked I-A$^s$/Ig molecules is administered to EAE-induced mice. The ability to reduce the incidence and severity of EAE is determined as described in Example 8 which follows. In addition, the immuno-suppressive effects of TcR antagonistic PLP analogs linked to full length I-A$^s$ molecules in EAE-induced mice can be examined in this system. The peptide/MHC complexes will be produced in the muscle following injection with DNA carrying the appropriate gene constructs, as described in Example 11 which follows.

EXAMPLE 4

Effects of the soluble peptide-linked MHC/Ig molecules in an ovalbumin specific T cell hybridoma system.

One assay in accordance with the invention involves use of a murine T cell hybridoma, DO 11.10 [R. Shimonkevitz et al., *J. Exp. Med.*, 158:303 (1983)] which expresses on its surface a T cell receptor specific for a 21 amino acid peptide fragment (aa 323–339) derived from chicken egg ovalbumin (Ova). This peptide can be presented to DO 11.10 only by antigen presenting cells (APC) expressing the murine class II MHC molecule I-A$^d$. When the peptide is presented by the appropriate APC, DO 11.10 cells respond by producing IL-2, which can then be assayed as a measure of T cell activation. The cell line to employ to present the antigen is A20.1-11 [K. Kim et al., *J. Immunol.*, 122:549 (1979)], which expresses I-A$^d$ on its surface. Briefly, the A20.1-11 cells are incubated in the presence of the peptide fragment until their I-A$^d$ molecules are saturated (approximately 3 hours) with peptide and then washed to remove unbound peptide. DO 11.10 cells are incubated with or without the soluble peptide-linked MHC/Ig molecules for 3 hours (or more) and then washed extensively to remove unbound protein. As described in Example 1 above, the peptides linked to the I-A$^d$ β chain include Ova 323–339, one of two single-substitution analogs of the Ova peptide—Ova H331R or Ova A332Y, or a peptide from hen egg lysozyme (HEL 74–86). The Ova 323–339, Ova H331R, HEL 74–86 peptides are known to bind I-A$^d$ whereas the Ova A332Y analog will serve as a non-binding control [S. Buus et al., *Science*, 235:1353–1358 (1987): A. Sette et al., *Nature*, 328:395–399 (1987)]. The HEL 74–86 peptide serves as a non-specific negative control. Antigen-pulsed APC are then incubated with the treated DO 11.10 T cell hybridoma (2×10$^5$/well) for 24 hours at 37° C. in an atmosphere of 5% CO$_2$. Cultures are carried out in complete culture medium (RPMI 1640 supplemented with 10% FBS, penicillin/streptomycin, L-glutamine and 5×10$^{-6}$ M 2-mercaptoethanol) in 96 well flat bottom microtiter plates. After 24 hours, culture supernatant is assayed for the presence of IL-2 using the IL-2 dependent murine T cell line CTLL-2.

Serial twofold dilutions of each culture supernatant is prepared in completed medium in flat bottomed microtiter plates and 1×10$^4$ CTLL-2 cells is added to each well. After 16 to 20 hours the negative control wells (CTLL-2 cultured with medium alone) and positive control wells (CTLL-2 cells cultured with rIL-2) is examined microscopically and at the point at which negative control cells are 90% dead, while positive control cells are still actively proliferating, MTT (2 mg/ml; 25 μl/well) is added and the plates returned to the incubator for an additional 4 hours. At this time, blue crystals formed by MTT in actively metabolizing cells will be dissolved by addition of 150 μl per well of 0.4 N HCl in isopropanol per well. After careful mixing, the O.D. at 562 nm is determined using a ELISA plate reader (Ceres-LTV900HI). The concentration of IL-2 in experimental wells can be determined by extrapolation from an IL-2 standard curve and then comparison of IL-2 from cultures containing no recombinant protein molecules can be compared to those containing the molecules to be tested and an index of inhibition calculated.

It is believed that use of antigen dose and APC numbers giving slightly submaximal responses of peptide antigen and antigen presenting cells for activation of DO 11.10 is preferred to detect inhibition of the system by recombinant protein molecules. In view thereof, experiments preferably are at least initially conducted with peptide antigen pulse conditions of 100 μg/ml and 10 μg/ml and with APC concentrations of 0.5×10$^5$/well and 0.1×10$^5$/well.

Soluble peptide-linked MHC/Ig molecules are tested for their ability to block this system over a range of concentrations from 10$^{-12}$–10$^{-5}$ M. Testing is suitably performed with approximately a 10:1 to 1:1 molar ratio between the soluble peptide-linked MHC/Ig molecules and the MHC Class II expressed on either 0.5×10$^5$ or 0.1×10$^5$ A20.1-11 cells. Concentrations are adjusted as necessary depending on results of preliminary experiments. A decrease in DO 11.10 IL-2 production following preincubation with the soluble Ova 323–339/I-A$^d$/Ig or Ova H331R/I-A$^d$/Ig molecules compared to preincubation with Ova A332Y/I-A$^d$/Ig or HEL 74–86/I-A$^d$ molecules or no preincubation will indicate that the soluble peptide-linked MHC molecules can suppress immune responses in a peptide-specific manner.

This same assay also can be used to identify peptides that function as TcR antagonist or partial agonists as discussed above.

EXAMPLE 5

Effects of Soluble Peptide-linked MHC/Ig Molecules on Antigen Stimulated T Cell Proliferation A further assay in accordance with the invention examines whether the soluble peptide-linked MHC/Ig molecules are able to suppress immune responses in T cells isolated from mice or humans (rather than the T cell hybridoma described in Example 4 above).

The DO 11.10 T cell hybridoma is partially activated and does not require co-stimulatory signals for complete activation. On the other hand, non-transformed $T_H$ cells isolated from immunized mice require both a peptide/MHC signal as well as co-stimulatory signals in order to proliferate in culture. This system will be used as a sensitive measure of the effects of the soluble peptide-linked MHC/Ig molecules on $T_H$ cell responses. Ova-primed T cells will be obtained from BALB/c mice (MHC Class II:I-A$^d$) by immunizing with 50 μg of Ova 323–339-KLH in complete Freund's adjuvant, subcutaneously at the base of the tail. Two immunizations will be performed at 7 day intervals and, one week after the second injection, mice will be sacrificed and inguinal and paraaortic lymph nodes removed and rendered into a single cell suspension.

The suspension is depleted of antigen presenting cells by incubation on nylon wool and Sephadex G-10 columns, and the resulting purified T cell populations incubated either with Click's medium alone, or with soluble peptide-linked MHC/Ig molecules dissolved in Click's medium. T cells are cultured with the soluble peptide-linked MHC/Ig molecules (as described in Example 4 above) for 3 hours prior to washing and initiation of proliferation assay, however this time period may be increased up to 24 hours if necessary.

Activated B cells from BALB/c mice are used as antigen presenting cells in the proliferation assay. B cells are prepared by culturing spleen cells with 50 μg/ml of LPS for 48 to 72 hours at which time activated cells will be isolated by density gradient centrifugation on Lymphoprep. Activated B cells are then pulsed with ovalbumin peptide for 3 hours, washed extensively, fixed with paraformaldehyde to inhibit proliferation of B cells, and added to purified T cells.

The proliferation assay is carried out in 96 well round bottom microtiter plates at 37° C., 5% $CO_2$ for 3–5 days. Wells are pulsed with 1 μCi of $^3$H-thymidine for 18 hours prior to termination of cultures and harvested using a Skatron cell harvester. Incorporation of $^3$H-thymidine into DNA as a measure of T cell proliferation are determined using an LKB liquid scintillation spectrometer. A decrease in T cell proliferation following preincubation with the soluble Ova 323–339/I-A$^d$/Ig molecules, as compared to preincubation with Ova A332Y/I-A$^d$/Ig or HEL 74–86/I-A$^d$/Ig molecules or no preincubation, indicates the soluble peptide-linked MHC/Ig molecules can suppress immune responses in a peptide-specific manner.

Measurement of IL-2 concentrations in wells containing proliferating T cells at 24 and 48 hours may be a good alternative to carrying out the 3 to 5 day assay of proliferation. Initial experiments involve comparison of these two systems to determine which would be more sensitive to detection of inhibition. Because the detection of IL-2 measures an earlier activation event it may prove to be more useful in this situation.

Initial experiments carried out prior to testing of soluble peptide-linked MHC molecules will determine the optimum parameters for these systems, i.e., supramaximal, maximal and submaximal concentrations of peptide antigen for pulsing of antigen presenting cells, optimal and suboptimal dosages of APC/well, and optimum length of proliferation assay (3–5 days) or IL-2 production assay. As discussed above, it is believed that the system will be most sensitive to inhibition with recombinant proteins at a suboptimal level of T cell activation, so such conditions preferably are chosen for initial experiments.

The effects of soluble peptide-linked human class II MHC/Ig molecules on antigen-stimulated human T cell proliferation will also be examined. Soluble HLA-DR1/Ig molecules covalently attached to either the influenza nuclear protein—NP 404–415 or the influenza hemagglutinin protein HA 307–318 can be produced as described in Examples 1 and 2 above. Both peptides are known to bind the HLA-DR1 molecules. An NP 404–415/DR1 specific human T cell clone, K68-36, will be used to test the effects of preincubation of the soluble peptide-linked MHC/Ig molecules on $^3$H-thymidine incorporation stimulated by NP 404–415 loaded APCs (BLCL-K68 cells; EBV-transformed B cells from the same donor), as described above. Again, a decrease in T cell proliferation following preincubation with the soluble NP 404–415/DR1/Ig molecules compared to preincubation with HA 307–318/DR1/Ig molecules or no preincubation will indicate that the soluble peptide-linked MHC/Ig molecules can suppress human immune responses in a peptide-specific manner.

These assays also can be employed to determine indicate whether a peptide can function as a TcR antagonist or partial agonists as discussed above.

EXAMPLE 6

In Vivo Effects of the Soluble Peptide-linked MHC Molecules on Antibody Responses As discussed above, it has been shown that peptide-MHC complexes on the surface of APCs will only induce the clonal expansion of a reactive T cell line specific for the MHC bound peptide if the APCs also deliver co-stimulatory signals. In the absence of co-stimulatory signals delivered by APCs, these particular reactive $T_H$ cells will be induced to a state of anergy.

To test whether the soluble peptide-linked MHC/Ig molecules can induce $T_H$ cell anergy in vivo, the effects of such molecules on $T_H$ cell-dependent immunoglobulin class switching (i.e. IgM to IgG) and on clonal expansion of peptide-specific T cell lines (Example 7 which follows) can be examined.

In order to examine Ig class switching, three test groups are set up as follows:

(a) 15 BALB/c mice are injected intraperitoneally (IP) with 10–100 μg of Ova 323–339-KLH conjugate, in Complete Freund's adjuvant, in order to induce an immune response to the Ova 323–339 peptide. On the day before and the day of immunization with Ova-KLH, 5 of the mice are injected IP with 10–100 μg of the soluble Ova 323–339/MHC I-A$^d$/Ig in PBS. This soluble Ova fusion protein binds to the T cell receptor (TCR) displayed on the Ova 323–339 specific $T_H$ cells. Due to the absence of the co-stimulatory signal, these $T_H$ cells are induced to a state of anergy. The remaining 10 mice serve as control. 5 of them receive PBS and other 5 receive MHC I-A$^d$/Ig intraperitoneally.

(b) Identical experiments are performed with HEL-KLH conjugate and HEL 74–86/MHC I-A$^d$/Ig.

(c) 25 BALB/c mice are injected as described above with both Ova-KLH and HEL-KLH conjugates. 5 of these mice are injected intraperitoneally with Ova 323–339/MHC I-A$^d$/Ig and 5 of them will receive HEL 74–86/MHC I-A$^d$/Ig intraperitoneally. The other mice receive either PBS or MHC I-A$^d$/Ig as controls.

Ten days after the immunization, blood is collected from each mouse by tail bleeding. Mice are anesthetized with metafane in the following manner: cotton or gauze moistened with 20 to 25 drops of metafane and placed in a glass container with a metal or glass cover. The mouse is placed on top of a grate that is over the moistened cotton or gauze. When breathing slows down, the mouse is removed from the chamber and the toes pinched to check reflexes. Once the mouse is sufficiently anesthetized, the tail is held under a heat lamp to increase blood flow. After disinfecting the tail with isopropyl or ethyl alcohol, the tip is clipped off with sharp scissors. Blood is collected in an eppendorf tube. Bleeding can be enhanced by "milking" the tail. After collecting the blood, pressure is applied to the tip of the tail with a gauze pad. The blood is centrifuged at approximately 14,000 G for 3–5 minutes and the serum collected.

Assays are performed in 96-well microtiter plates (Maxisorp F8; Nunc,. Inc.) coated at 1–50 μg/ml with OVA-KLH or whole Ovalbumin using a Tris-HCl coating buffer, pH 8.5. A second set of plates are coated at 1–50 μ/ml of HEL-KLH or whole HEL. The plates are covered with pressure sensitive film (Falcon, Becton Dickinson, Oxnard, Calif.) and incubated overnight at 4° C. Plates are then washed with Wash solution (Imidazole/NaCl/0.4% Tween-20) and blocked by adding 100 μl/well of a 3% BSA solution. Following incubation on a plate rotator at room temperature for 30 minutes, the plates are washed five times with Wash solution. Mouse sera is diluted 1:500 in Sample/conjugate diluent (2% gelatin+0.1% Tween-20 in TBS) and then, in duplicate, serially diluted on the plate. Two identical plates are set up for each coating protein, one for determination of IgM titer and the other for IgG. Following incubation on a plate rotator at room temperature for 30 minutes, the plates are washed five times with Wash solution. Goat anti mouse IgM-HRP and goat anti mouse IgG-HRP conjugates (Boehringer Mannheim, Indianapolis, Ind., 1:100 dilution in Sample/conjugate diluent) are added to the appropriate plates. Following incubation on a plate rotator at room temperature for 30 minutes, the plates are washed five times with Wash solution and then incubated with 100 μl/well of ABTS developing substrate (Kirkgaard & Perry Laboratories, Inc., Gaithersburg, Md.) for 10 minutes on a plate rotator at room temperature. The reactions are stopped with 100 μl/well of Quench buffer (Kirkgaard & Perry Laboratories, Inc., Gaithersburg, Md.) and the absorbance value is read at 405 nm using an automated microtiter plate ELISA reader (Ceres UV900HI, Bioteck, Winooski, Vt.). The titer is determined by plotting the absorbance reading versus the log of the dilutions of the samples and determining the dilution at the mid-point (50% of the absorbance). The titers for IgM versus IgG are then compared. The sera is also checked for cross-reactivity.

EXAMPLE 7

$T_H$ Cell Stimulation in Mice Treated with Soluble Peptide-linked MHC/Ig Molecules The effects of soluble peptide-linked MHC/Ig molecules on clonal expansion of peptide-specific T cell lines in vivo can be suitably examined in accordance with the following assay.

The treatment groups (4 mice per group) are identical to those described in Example 6 above. The immunization protocol is as follows: mice are injected intraperitoneally with 10–100 μg of the soluble Ova 323–339/MHC I-$A^d$/Ig in PBS and 24 hours later injected subcutaneously at the base of the tail with 50 μg of Ova 323–339-KLH. These two injections are repeated 6 and 7 days later. Seven days after completion of the second set of injections, the mice are sacrificed. The inguinal and paraaortic lymph nodes are removed and rendered into a single cell suspension.

The suspension is depleted of antigen presenting cells by incubation on nylon wool and Sephadex G-10 columns, and the resulting purified T cell populations incubated with APCs pulsed with either the Ova 323–339 peptide or the HEL 74–86 peptide.

Activated B cells from BALB/c mice are used at antigen presenting cells in the proliferation assay. B cells are prepared by culturing spleen cells with 50 μg/ml of LPS for 48 to 72 hours at which time activated cells are isolated by density gradient centrifugation on Lymphoprep. Activated B cells are then pulsed with the Ova 323–339 peptide or the HEL 74–86 peptide for 3 hours, washed extensively, fixed with paraformaldehyde to inhibit proliferation of B cells, and added to purified T cells from each panel of mice.

The proliferation assay is carried out in 96 well round bottom microtiter plates at 37° C., 5% $CO_2$ for 3–5 days. Wells are pulsed with 1 μCi of $^3$H-thymidine for 18 hours prior to termination of cultures and harvested using a Skatron cell harvester. Incorporation of $^3$H-thymidine into DNA as a measure of T cell proliferation is determined using an LKB liquid scintillation spectrometer. The decree of peptide-reactive T cell proliferation is indicative of the $T_H$ cell responses (i.e. of clonal expansion) that took place in the mice following immunization.

EXAMPLE 8

Soluble Peptide-linked MHC/Ig-mediated Inhibition of EAE Induction in SJL Mice

Experimental allergic encephalomyelitis (EAE) is an autoimmune disease in mice and serves as an animal model for multiple sclerosis. Encephalitogenic regions of two proteins, myelin basic protein (MBP 91–103) and proteolipoprotein (PLP 139–151), have been defined. In the susceptible SJL mouse strain, EAE can be induced to develop following immunization with the encephalitogenic peptide or adoptive transfer of MBP-reactive T cells. To determine whether treatment with soluble MHC fusion complexes such as MBP 91–103/MHC I-$A^s$/Ig and PLP 139–151/MHC I-$A^s$/Ig complex will prevent EAE development after T-cell activation, SJL mice can be injected with the examined MHC fusion complex e.g. MBP 91–103 and PLP 139–151 reactive T-cell blasts in vivo.

To induce EAE in SJL mice with MBP 91–103, mice are immunized with 400 μg of MBP 91–103 in complete Freund's adjuvant on the dorsum. Ten to 14 days later, regional draining lymph node cells are harvested as described above and cultured in 24-well plates at a concentration of 6×10$^6$ cells per well in 1.5 ml of RPMI 1640 medium/10% fetal bovine serum/1% penicillin/streptomycin with the addition of MBP at 50 μg/ml. After a 4-day in vitro stimulation, MBP 91–103-reactive T cell blasts are harvested via Ficoll/Hypaque density gradient, washed twice in PBS, and 1.3×10$^7$ cells are injected into each mouse. Mice receiving encephalitogenic MBP 91–103-reactive T cells then receive either 100 μg of soluble MBP 91–103/I-$A^s$/Ig, 100 μg of MBP 1–14/I-$A^s$/Ig (the negative control), or normal saline on days 0, 3, and 7 i.v. (total dose 300 μg). Clinical and histological evaluations are performed to confirm that the MBP 91–103/I-$A^s$/Ig inhibited the development of EAE in these mice.

To induce EAE in SJL mice with PLP peptide 139–151, mice are immunized with PLP peptide 139–151 dissolved in PBS and mixed with complete Freund's adjuvant containing Mycobacterium tuberculosis H37Ra at 4 mg/ml in 1:1 ratio. Mice are injected with 150 μg of peptide adjuvant mixture. On the same day and 48 hours later, all animals are given 400 ng of pertussis toxin. Adoptive transfer of EAE are then performed as described above. PLP 139–151/I-$A^s$/Ig rather than MBP 91–103/I-$A^s$/Ig is then used to prevent the development of EAE.

EXAMPLE 9

Antibody Response in Mice Vaccinated with the Peptide-linked MHC Expression Vectors The following assay (illustrated with PEE-IA$^d$/OVA) shows how an immune response can be induced in a mammal in accordance with the invention by administration (e.g., IM) with one or more presenting peptide-linked MHC expression vectors, and that co-administration of DNA coding for co-stimulatory factor such as B7-1 (or B7-2) expression vector can be employed to further augment the immune response as discussed above. This system will provide a unique method for inducing immune responses (including to provide a vaccination against a targeted disorder) that bypasses the complexities of antigen uptake and processing.

BALB/c mice (five per group) are injected intramuscular (IM) in both hind legs with 100 μg of: (1) PEE-IA$^d$/OVA carrying the coding regions of Ova 323–339/I-A$^d$ under the control of the CMV promoter, (b) pCMV/B7-1 or pCMV/B7-2 containing the coding regions of B7-1 or B7-2 gene under the control of the CMV promoter, (c) PEE-IA$^d$/OVA and either pCMV/B7-1 or pCMV/B7-2, (d) PEE-IA$^d$/HEL bearing the coding region HEL 74–86/I-A$^d$ under the control of the CMV promoter, (e) PEE-IA$^d$/HEL and either pCMV/B7-1 or pCMV/B7-2 or (f) PEE-IA$^d$ containing the coding region of I-A$^d$ under the control of the CMV promoter. Injections are given at 0, 3, and 6 weeks.

At 0, 2, 5, and 8 weeks post initial injection, blood is collected from each mouse by tail bleeding as described in Example 6. The blood is centrifuged at approximately 14,000 G for 3–5 minutes and the serum collected.

Assays are performed in 96-well microtiter plates (Maxisorp F8; Nunc, Inc.) that have been coated at 1–50 μg/ml with OVA-KLH and HEL-KLH using a Tris-HCl coating buffer, pH 8.5. The plates are covered with pressure sensitive film (Falcon, Becton Dickinson, Oxnard, Calif.) and incubated overnight at 4° C. Plates are then washed with Wash solution (Imidazole/NaCl/0.4% Tween-20) and blocked by adding 100 μl/well of a 3% BSA solution. Following incubation on a plate rotator at room temperature for 30 minutes, the plates are washed five times with Wash solution. Mouse sera is diluted 1:500 in Sample/conjugate diluent (2% gelatin+0.1% Tween-20 in TBS) and then, in duplicate, serially diluted on the plate. Samples of mouse sera is run on both the OVA-KLH and HEL-KLH coated plates to test for cross-reactivity. Following incubation on a plate rotator at room temperature for 30 minutes, the plates are washed five times with Wash solution and then 100 μl of the goat anti-mouse IgG-HRP conjugates (Boehringer Mannheim, Indianapolis, Ind., 1:100 dilution in Sample/conjugate diluent) are added to the appropriate plates. Following incubation on a plate rotator at room temperature for 30 minutes, the plates are washed five times with Wash solution and then incubated with 100 μl/well of ABTS developing substrate (Kirkgaard & Perry Laboratories, Inc., Gaithersburg, Md.) for 10 minutes on a plate rotator at room temperature. The reactions are stopped with 100 μl/well of Quench buffer (Kirkgaard & Perry Laboratories, Inc., Gaithersburg, Md.) and the absorbance value at 405 nm read using an automated microtiter plate ELISA reader (Ceres UV900HI, Bioteck, Winooski, Vt.). The titer can be determined by plotting the absorbance reading versus the log of the dilutions of the samples and determining the dilution at the mid-point (50% of the absorbance).

EXAMPLE 10

Detection of Peptide Specific T Cells Following Induction of Immune Response with Peptide-linked MHC Expression Vectors In order to determine whether intramuscular injection of DNA has successfully immunized mice to mount a T helper cell response to ovalbumin, an ovalbumin specific T cell proliferation assay can be employed. Mice are immunized by the protocol described in Example 9 and T cells are prepared from the inguinal and paraaortic lymph nodes 7 days after the second immunization.

The suspension is depleted of antigen presenting cells by incubation on nylon wool and Sephadex G-10 columns, and the resulting purified T cell populations incubated with APCs pulsed with either the Ova 323–339 peptide or the HEL 74–86 peptide. Activated B cells from BALB/c mice are used as antigen presenting cells in the proliferation assay. B cells are prepared by culturing spleen cells with 50 μ/ml of LPS for 48 to 72 hours at which time activated cells are isolated by density gradient centrifugation on Lymphoprep. Activated B cells are then pulsed with either the Ova 323–339 peptide or the HEL 74–86 peptide for 3 hours, washed extensively, fixed with paraformaldehyde to inhibit proliferation of B cells, and added to purified T cells.

The proliferation assay is carried out in 96 well round bottom microtiter plates at 37° C., 5% $CO_2$ for 3–5 days. Wells are pulsed with 1 μCi of $^3$H-thymidine for 18 hours prior to termination of cultures and harvested using a Skatorn cell harvester. Incorporation of $^3$H-thymidine into DNA as a measure of T cell proliferation is determined using an LKB liquid scintillation spectrometer. The degree of peptide-reactive T cell proliferation is indicative of the $T_H$ cell responses (i.e. of clonal expansion) that took place in the mice following immunization.

EXAMPLE 11

Suppression of Autoimmune Disease in Mice Injected with TcR Antagonistic Peptide-linked MHC Expression Vectors Examples 3 and 9–10 above show methodologies to be used for stimulating immune responses via MHC fusion complexes. As discussed above, similar procedures can be employed to inhibit immune responses by using TcR antagonistic peptides linked to the MHC molecules, i.e. the presenting peptide covalently linked to the MHC peptide is a TcR antagonist or partial agonist. As described in Example 1, the PLP peptide 139–151 is capable of inducing EAE in SJL mice. Analogs of this peptide have been characterized for TcR antagonistic activity against a panel of I-A$^s$-restricted, PLP 139–151-specific T cell clones. Two different analogs, PLP-W144Y (HSLGKYLGHPDKF) (SEQ ID NO: 22) and PLP-W144L (HSLGKLLGHPDKF) (SEQ ID NO: 23), were found to be particularly useful for inhibiting in vitro T cell proliferation in most of the T cell clones tested [A. Franco et al., Eur. J. Immunol., 24:940–946] (1994). As a model system, vectors capable of co-expressing the PLP peptide analog-linked I-A$^s$ β chain and the full-length I-A$^s$ α chain molecules can be constructed. Vector construction is suitably similar to that outlined in Example 3 above. The native PLP 139–151 linked-MHC construct serves as a positive (antigenic) control. These vector DNAs (with and without the B7 or B7-2 expression vectors) are suitably injected IM into SJL mice (see Example 9 for injection procedures) prior to and during the induction of EAE. EAE can be induced by the adoptive-transfer of PLP 139–151 reactive $T_H$ cells by procedures as described in Example 8 above. Clinical and histological evaluations are performed to confirm that the PLP antagonist/I-A$^s$ expression vector injection inhibited the development of EAE in the mice.

EXAMPLE 12

Construction of Full-length Peptide-linked I-A$^d$ MHC Expression Vectors

Vectors capable of co-expressing the full-length I-A$^d$ α chain and peptide-linked I-A$^d$ β chain molecules were constructed as outlined in FIG. 19 of the Drawings and by the same or similar procedures as disclosed in Example 3 above. For the I-A$^d$ genes, total RNA was isolated from the mouse B cell lymphoma A20 cell line. Briefly, 1×10$^8$ A20 cells (American Type Collection Culture Accession No. TIB 208) were homogenized in 6 ml of ice cold 4 M guanidinium thiocyanate, 0.1 M Tris-HCl, pH 7.5 using a Tissue Tearer homogenizer for 5 minutes. Following homogenization, sodium sarcosyl was added to a final concentration of 0.5% and the solution was mixed thoroughly. The homogenate was centrifuged at 5000 g for 10 minutes and the supernatant was brought up to 10 ml with 4 M guanidinium thiocyanate, 0.1 M Tris-HCl, pH 7.5, 0.5% sodium sarcosyl buffer. The supernatant was gently layered on top of a 3.5 ml cushion of 5.7 M CsCl, 0.01 M EDTA, pH 7.5 in an SW41 clear ultracentrifuge tube. The samples were centrifuged in an SW41 rotor at 32,000 rpm for 24 hours at 20° C. Following centrifugation, the supernatant was carefully removed and the RNA pellet was washed with 70% ethanol. The RNA was dissolved in 350 μl of 3 M sodium acetate and 970 μl of ethanol. This procedure yielded approximately 370 μg of total RNA. The RNA was resuspended to 5 μg/μl with DEPC-treated water and was used for RT-PCR cloning of the I-A$^d$ genes.

To isolate the full-length I-A$^d$ α chain, A20 total RNA (5 μg) was converted to cDNA by using M-MLV Reverse Transcriptase (GIBCO-BRL) and α chain TM-specific priming (oligonucleotide OPR139) according to manufacturer's recommended procedures. This cDNA was used as the template for PCR amplification using an α chain leader-specific primer (OPR136) and an α chain TM-specific primer (OPR139). See FIG. 20 of the Drawings where the sequences of those OPR136 and OPR139 primers are disclosed. Typical PCR amplification reactions (100 μl) contained template DNA, 10 pmoles of the appropriate primers, 2.5 units of Taq polymerase, 100 μM dNTP, 50 mM KCl, 10 mM Tris-HCl, pH 8.3, 1.5 mM MgCl$_2$, 0.01% gelatin. The template was denatured by an initial incubation at 96° C. for 5 min during which the Taq polymerase was added to hot-start the reaction. The desired products were amplified by 10 thermal cycles of 58° C. for 30 sec, 72° C. for 1 minute, then 96° C. for 1 minute followed by 20 step cycles of 70° C. for 1.5 minute, then 96° C. for 1 minute. The resulting PCR product (~800 bp) contains a 5' XmaI site and a 3' EcoRI site for cloning. In addition, this fragment carries a Kozak consensus sequence for efficient translational initiation (see FIG. 18A of the Drawings where the sequence of the PCR product is disclosed). The PCR product was digested with XmaI and EcoRI, gel-purified and ligated into XamI/EcoRI digested pUC18, to give the vector pJRS163-10. Following sequence verification, the XmaI/EcoRI fragment was excised, purified and subcloned between the CMV promoter and SV40 poly-A-sites of the PEE13 mammalian expression vector (Celltech), resulting in the pJRS164 vector.

The full-length peptide-linked β chain fragment was constructed by inserting the leader and TM sequences into the OVA 323–339 peptide (SISQAVHAAHAEINEAGR) (SEQ ID NO: 24) linked β1–β2 vector (pB16) as described in Example 1 above. A20 total RNA (5 μg) was converted to cDNA by using Superscript-MLV or M-MLV Reverse Transcriptase (GIBCO-BRL) and either oligo dT-specific or β chain TM-specific priming (with OPR135, sequence thereof shown in FIG. 20) according to manufacturer's recommended procedures. These cDNAs were used as the template for PCR amplifications using either a pair of β chain leader-specific primers (OPR132/OPR133; sequences of those primers disclosed in FIG. 20 of the Drawings) and a pair of β chain TM-specific primers (OPR134/OPR135; sequences of those primers disclosed in FIG. 20 of the Drawings). PCR amplification conditions were similar to those described above in this example. Specifically, thermal cycling conditions for amplifying the leader sequence were 10 thermal cycles of 60° C. for 1 minute, 70° C. for 1 minute, and 96° C. for 1 minute followed by 30 step cycles of 70° C. for I minute and 96° C. for 1 minute, whereas conditions for amplifying the TM domain were 5 thermal cycles of 60° C. for 30 seconds, 72° C. for 30 seconds, and 96° C. for 1 minute followed by 25 step cycles of 70° C. for 1 minute and 96° C. for 1 minute. The 110 bp β leader PCR product contains 5' HindIII and XmaI sites and a 3' AflII site for cloning into the pB16 OVA peptide-linker-β1–β2 vector. The inclusion of the AflII site changes the last two amino acids of the I-A$^d$ β chain leader to those found in the IgG leader (see FIG. 18B of the Drawings). The β leader PCR product was digested with HindIII and XmaI, gel-purified and ligated into HindIII/AflII digested pB16, to give pDM21. The 180 bp β TM PCR product contains a 5' BstXI and sites and 3' XmaI and EcoRI sites for cloning into the pDM21 vector. The β TM PCR product was digested with BstXI and EcoRI, gel-purified and ligated into BstXI/EcoRI digested pDM21, to give the pVW229 vector. This vector was digested with XmaI and EcoRI to generate the full-length peptide linked β chain gene fragments for cloning between the CMV promoter and SV40 poly-A sites of the PEE6 mammalian expression vector (Celltech). These fragments also carry the Kozak consensus sequence (CCAC-CATG) (SEQ ID NO: 2) for efficient translational initiation (see FIG. 18A of the Drawings). The resulting pVW231 was digested with BglII and BamHI. The CMV promoter/peptide β chain fragments was gel-purified and ligated into BamHI digested pJRS164, to generate the final pJRS165.1 expression vector containing full length I-A$^d$ α and OVA-linked β chain genes.

Additional plasmids containing the full length I-A$^d$ α chain gene and either the β chain gene without a linked peptide or with the HEL 74–86 peptide (NLCNIP-SCALLSS) (SEQ ID NO: 25) were constructed as shown in the scheme of FIG. 19 of the Drawings and served as controls in the induction studies. The AflII/BstXI fragments of pBC1 and pB4 (as disclosed in Example 1 above) containing the linker-β1–β2 region and the HEL peptide-linker-β1–β2 region, respectively were excised, gel purified, and ligated into AflII/BstXI digested pVW229. The resulting vectors, pFB12 and pFBH3, have XmaI/EcoRI fragments contain the full length β chain gene linked either to no peptide or the HEL peptide, respectively. These fragments were excised, gel purified and ligated between the CMV promoter and SV40 poly-A sites of XmaI/EcoRI digested PEE6, resulting in pB1 and pBH4. These vectors were digested with BglII and BamHI and the CMV promoter/β chain fragments were gel purified and ligated into BamHI digested pJRS164, to generate pAB5, the expression vector containing full length I-$A^d$ α and β chain genes without a linked peptide, and pABH1, the expression vector containing full length I-$A^d$ α and HEL-linked β chain genes. Samples of aforesaid plasmids pJRS165.1, pAB5 and pABH1 (Accession Nos. 97301, 97032 and 97033 respectively) have been deposited with the American Type Culture Collection, Rockville, Md.

The murine B7-1 gene was amplified from a plasmid MB7-PCR2 template carrying the B7 gene (provided by E. Podack, Univ. of Miami). These reactions were carried out with Ultima polymerase (Perkin-Elmer) according to manufacturer's recommended procedures using the B7 specific primers B7-1-2F and B7-1-2B (sequences of those primers disclosed in FIG. 20 of the Drawings). Thermal cycling conditions were 20 thermal cycles of 60° C. for 30 seconds, 72° C. for 1.5 minute, and 96° C. for 1 minute followed by 10 step cycles of 72° C. for 1.5 minute and 96° C. for 1 minute. The PCR product generated carries 5' and 3' NotI sites for cloning. This fragment also carries the Kozak consensus sequence (CCACCATG) (SEQ ID NO: 2) for efficient translational initiation. The product was digested with NotI, gel purified and ligated between the CMV promoter and SV40 poly-A sites of NotI-digested pCMVβ mammalian expression vector (Clonetech). The resulting vector was designated pUB719.

EXAMPLE 13

Development of a Cell Line Expressing a Functional Fusion Complex on the Cell Surface As further detailed below, a murine B cell tumor (NSO; H-$2^d$ background) has been transfected with the pJRS165.1 construct (murine I-$A^d$/OVA 323–339 described in Example 12 above) and has been shown by flow cytometric analysis of the cell surface to express the MHC portion of the fusion complex. In addition, the fusion complex expressed on these cells was shown to be capable of modulating the activity of the appropriate T cell receptor (TcR) by inducing IL-2 production in the I-$A^d$ restricted, OVA peptide 323–339 specific T cell hybridoma, DO11.10. The results demonstrate, inter alia, that (1) the covalently linked fusion peptide can be loaded into the binding cleft of the MHC with preservation of the conformation of the MHC, (2) the peptide/MHC fusion preserves the functional integrity of the MHC molecule (i.e. it is able to bind the TcR and activate peptide specific T cells) and (3) the ordinary physiologic mechanisms for peptide loading of MHC molecules and subsequent antigen presentation can be bypassed through the present invention.

A. Generation of Transfected Lymphocytes

The NSO murine B cell tumor line was transfected according to the Celltech Glutamine Synthestase Gene Amplification System Manual with minor modifications. This method uses electroporation to transfect mammalian cells with a vector (PEE-13) containing the coding region for the glutamine synthetase. Transfected cells have the ability to synthesize glutamine, thereby surviving without an exogenous supply. Selection of transformed clones was accomplished by isolating the cells that grow in glutamine-free medium. Briefly, 1×$10^7$ NSO cells were washed twice in ice cold PBS and resuspended in 760 μl of cold PBS. Forty μg (40 μl at 1 μg/μl) of Sal I digested pJRS165.1 (See Example 12 above) plasmid DNA was added to the cells in an electroporation cuvette (0.4 cm). The cell/DNA mix was placed on ice for 5 minutes and the cells then electroporated using a Gene Pulser (Biorad) to deliver one pulse of 250 volts, 960 μFd. The pulsed cells were placed on ice for 2–5 minutes, removed from the cuvette, and added to 30 ml of non-selective medium (IMDM, 10% FBS, 2 mM L-glutamine, penicillin/streptomycin). Cells were plated in 96-well flat bottomed microtiter plates at 50 μl/well (4 plates, cell suspension in 30 ml of medium as above; 5 plates, cell suspension diluted 1:4; 5 plates, cell suspension diluted 1:20) and then incubated with 5% $CO_2$ at 37° C. For the negative control, the same procedure of electroporation and plating was followed except that the DNA was omitted. The next day, 150 μl of selective medium [IMDM, 10% dialyzed FBS, penicillin/streptomycin, nucleosides (6 μg/ml A, G, C and U; 2 μg/ml T), 60 μg/ml glutamate and asparagine] was added to each well. The plates were fed with selective medium on a weekly basis by removing 100 μl/well of used medium and adding 100 μl/well of fresh medium, allowing the cells to gradually deplete the medium of all residual glutamine. Only those cells that have been transformed will survive, colonies becoming evident in 14–21 days. The colonies, or clones, were expanded and screened for expression of conformationally correct surface MHC Class II fusion complex, as detailed below.

B. Conformation of MHC/peptide Fusion Construct

Clones generated in the above transfection were analyzed for expression of Class II MHC fusion complex at levels significantly higher than the parent cell, NSO. NSO/I$A^d$/OVA clones (1×$10^5$) or control cells, NSO or A20.1-11 [K. Kim et al., *J. Immunol.*, 122:549 (1979)], were incubated with FITC-conjugated anti-I$A^d$ antibody (Pharmingen, 1:100 dilution) in staining buffer (PBS/1% FBS) for 45 minutes at 4° C. in the dark. After washing three times in staining buffer, fluorescence was examined on a Beckton Dickinson FACScan flow cytometer. An isotype matched irrelevant antibody (FITC-conjugated anti-I$A^k$, Pharmingen 1:100) was used as negative control. I$A^d$ fluorescence intensity was compared to I$A^k$ expression to determine specific fluorescence (see results set forth in Table 1 below). In that Table, data are reported as peak channel green fluorescence which is a measure of fluorescence intensity and therefore the density of I$A^d$ molecules expressed on the cell surface. The negative control cell line (NSO) peaks at channel 67 and the positive control (A20.1-11) at channel 1322. Clones exhibiting peak fluorescence greater than channel 100 were chosen for further analysis of functionality of the fusion protein. The clones listed in Table 1 have been grown in bulk, frozen and banked for future use. Since the antibody recognize the conformational MHC molecule, this ability to detect the MHC fusion complex on the cell surface using antibody demonstrates the conformation of the MHC class II has been preserved in the recombinant fusion complex.

TABLE 1

I$A^d$ Expression on NSO/I$A^d$/OVA clones (in peak channel fluorescence)

| CLONE | I$A^d$ | I$A^k$ |
| --- | --- | --- |
| A20.1 (+ control) | 1322 | 5 |
| NSO (− control) | 67 | 5 |
| NSO/I$A^d$/OVA.B2 | 528 | 14 |
| NSO/I$A^d$/OVA.B5 | 209 | 10 |
| NSO/I$A^d$/OVA.B4 | 271 | 11 |
| NSO/I$A^d$/OVA.A4 | 153 | 34 |

C. Demonstration of Functional Activity of MHC Fusion Complex

To verify the biologically relevant activity of these recombinant protein molecules, the molecules' ability to interact with the appropriate T cell receptor in vitro in an antigen specific manner and cause activation of the T cell was evaluated.

A murine T cell hybridoma, DO11.10 [Shimonkevitz, R. et al. (1983) J. Exp. Med. 158: 303], was utilized which expresses on its surface a T cell receptor specific for a 21 amino acid peptide fragment (aa 323–339) derived from chicken egg ovalbumin (OVA). This peptide can be presented to DO11.10 only by antigen presenting cells (APC) expressing the murine Class II MHC molecule I-$A^d$. When the peptide is presented by the appropriate APC, DO11.10 cells will respond by producing IL-2, which can then be assayed as a measure of T cell activation. The cell line which served as a positive control was A20.1-11, which expresses I-$A^d$ on its surface. Briefly, the A20.1-11 cells ($1 \times 10^5$ well) were incubated together with peptide (1 μg/well) and DO11.10 cells ($2 \times 10^5$/well), for 24 hours at 37° C. in an atmosphere of 5% $CO_2$. NSO cells (as negative control) and NSO/$IA^d$/OVA clones ($1 \times 10^5$) were incubated with DO11.10 cells in the absence of peptide. Cultures were carried out in complete culture medium (RPMI 1640, 10% FBS, penicillin/streptomycin, 2 mM L-glutamine and $5 \times 10^{-5}$M 2-mercaptoethanol) in 96 well flat bottom microtiter plates. After 24 hours, culture supernatants were assayed for the presence of DO11.10 derived IL-2 using the IL-2 dependent murine T cell line CTLL-2, as described below.

Figure 21:
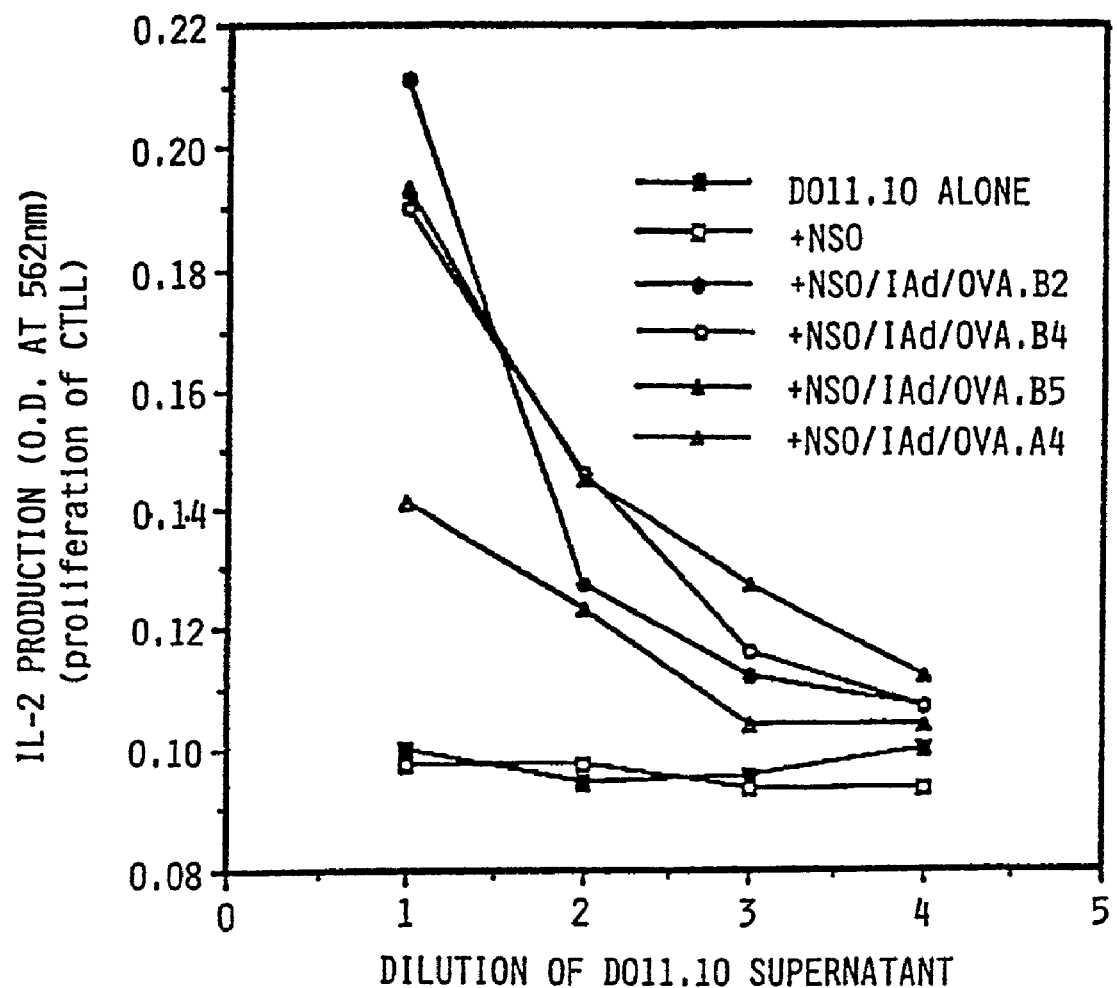
FIG. 21 shows graphically the functional activity of the four clones of Example 13 which follows along with negative control (NSO) and positive control (A20), where the O.D. value of the first four dilutions of DO11.10 culture supernatant is displayed.

Briefly, serial twofold dilutions of each culture supernatant were prepared in complete medium in flat bottomed microtiter plates and $1 \times 10^4$ CTLL-2 cells were added to each well. After 16–20 hours the negative control wells (CTLL-2 cultured with medium alone) and positive control wells (CTLL-2 cells cultured with rIL-2) were examined microscopically and at the point at which negative control cells were approximately 90% dead, while positive control cells were still actively proliferating MTT (2 mg/ml in PBS; 25 μl/well) was added and the plates returned to the incubator for an additional 4 hours. At this time, blue crystals of formazan formed in actively metabolizing cells were dissolved by addition of 150 μl of 0.4 N HCl in isopropanol per well. After careful mixing, the O.D. at 562 nm was determined using a Ceres-UV900HI plate reader. Data demonstrating the functional activity of the four clones discussed above along with appropriate negative (NSO) controls is shown in FIG. 21 of the Drawings and is represented in a graph displaying the O.D. value of the first four dilutions of DO11.10 culture supernatant, as a measure of T cell activation.

These results establish the MHC/peptide complex expressed on these transfected cells is biologically functional, in that it can engage the TcR on DO 11.10 and trigger the production of IL-2. These results indicate that such engineered cells expressing unique MHC/peptide constructs in the absence of co-stimulatory signals, can be of clinical importance in disease states in which an inappropriate immune response to a peptide has pathological consequences for the host, such as in allergy or in certain autoimmune disorders. This technique also has the potential, through further manipulation of the engineered cells, to serve as a vector to deliver a positive signal for immunization.

EXAMPLE 14

Assay for Immune Induction or Suppression by Cells Expressing MHC Fusion Complex The following assay can be employed to evaluate the capability of MHC fusion complex cell lines of the invention (i.e., cells that have introduced therein DNA coding for an MHC fusion complex) for inducing or suppressing an immune response in a host to which the cells have been administered.

The following exemplification of the assay utilizes an animal model of immunization with ovalbumin peptide 323–339 and manipulation of the response to the peptide using the engineered fusion complex expressing cells described in Example 13 above. The methodology of this example can be applied to a wide variety of MHC fusion complexes that contain a presenting peptide which can modulate (i.e., suppress or induce) an immune response in mammals and which can be linked to an MHC molecule such as by a flexible linker as disclosed above.

The cells that can be utilized in this assay (NSO/$IA^d$/OVA.B2, NSO/$IA^d$/OVA.B4, NSO/$IA^d$/OVA.B5 and NSO/$IA^d$/OVA.A4) are transfected with the MHC/OVA 323–339 fusion complex DNA, pJRS165.1 (see Examples 12 and 13 above). These cells express only low levels of costimulatory molecules (i.e., a non-effective T cell proliferation amount) and therefore are not capable of initiating the initial priming event for induction of immunity to the peptide (as is known in the art, B cells are capable of activating memory T cells, but, unlike "professional APC" are unable to deliver the signal required for induction of immunity). Injection of these cells into a histocompatible host can result in interaction with T cells in the absence of co-stimulatory molecules, and therefore induction of antigen specific unresponsiveness or T cell tolerance.

The assay can be specifically conducted as follows. BALB/c (IA$^d$) mice (3–4 per group) are injected i.v. in the tail or s.c. in the base of the tail with the cells or reagents listed in Table 2 below. Cells are washed in PBS, resuspended to $1 \times 10^8$/ml in PBS and injected into the tail vein (0.1 ml; $1 \times 10^7$ cells/mouse). Ovalbumin peptide (2 mg/ml in PBS) is mixed with complete Freund's adjuvant containing Mycobacterium tuberculosis H37Ra in a 1:1 v/v ratio. Fifty microliters are injected s.c. into each side of the base of the tail. Seven days after the last injection, lymph nodes (inguinal, paraaortic, cervical, axillary, brachial) are removed and homogenized to obtain a single cell suspension. Lymph nodes from individual mice within a group are processed separately. T cells are purified from lymph node populations by passage of cell suspensions over G-10 and nylon wool to remove accessory cells. Antigen presenting cells are prepared from the spleens of naive BALB/c mice by homogenizing spleens to obtain a single cell suspension, lysis of erythrocytes using Gey's solution, treatment with mitomycin C (100 μg/ml in RPMI 1640/1% FBS for 1 hour at 37° C.) to inhibit APC proliferation, and 3 washes to remove residual mitomycin C. Assays for induction of a T cell response are carried out in 96 well round bottom microtiter plates. Two to $4 \times 10^5$ T cells are mixed with $2–4 \times 10^5$ APC. Each T cell/APC combination is incubated, in triplicate, with and without OVA peptide (range 10–200 ng/well) for 3–5 days. Approximately 18 hr before termination of the culture 0.4 uCi of $^3$H-thymidine is added to each well. The wells are harvested using a Skatron cell harvester and $^3$H-thymidine incorporation (a measure of DNA synthesis and, therefore, T cell proliferation) is determined using a LKB liquid scintillation spectrometer.

A positive response is evident if the wells containing peptide incorporate significantly more DNA than those without peptide. Typically mice are considered positive where proliferation (in mean cpm) in response to peptide is more than about 3 standard deviations greater than the background proliferation without peptide. For each group, mean peptide specific proliferation is calculated by averaging values for each of the 3 mice. Suppression of immunization will typically be considered as having occurred when the experimental group mean is greater than about 3 standard deviations less than the positive control group mean.

Referring to Table 2 below, groups 1 (uninjected) and 4 (injection of NSO alone) serve as negative controls and should not respond to in vitro challenge with peptide. Group 2 receives 2 injections of peptide, the classical immunization protocol, and should respond optimally to in vitro peptide presentation. Group 3 receives one injection of peptide and can be expected to respond suboptimally in vitro. Group 5 receives NSO cells first and then peptide one week later. Injection of NSO cells should not interfere with priming by peptide, therefore results from this group should be similar to group 3 and serve as a negative control for tolerance induction (Group 7). Group 6 receives the cells expressing the fusion complex. Due to lack of expression of co-stimulatory molecules necessary for stimulation of naive T cells, this group serves as a negative control for Group 7. No response from this group could potentially mean either "no response" or "specific unresponsiveness". Group 7, which receives an initial injection of NSO/IA$^d$/OVA cells and then an injection of peptide, will differentiate between these two outcomes. A lack of response to in vitro challenge with peptide from this group will demonstrate the induction of specific unresponsiveness, or tolerance.

TABLE 2

| Group Number | Injection #1 (Day-14) | Injection #2 (Day-7) | in vitro challenge (Day-0) |
|---|---|---|---|
| 1 (neg control-a) | — | — | peptide |
| 2 (pos control-a) | peptide (s.c.) | peptide (s.c.) | — |
| 3 (pos control-a) | — | peptide (s.c.) | peptide |
| 4 (neg control-b) | NSO (i.v.) | — | peptide |
| 5 (pos control-c) (neg control-c) | NSO (i.v.) | peptide (s.c.) | peptide |
| 6 (experimental) (&neg cont-d) | NSO/IA$^d$/OVA (i.v.) | — | peptide |
| 7 (experimental) | NSO/IA$^d$/OVA (i.v.) | peptide (s.c.) | peptide |

EXAMPLE 15

T-cell Activation After Intramuscular (i.m.) Injection of DNA Coding for MHC Fusion Complex Alone or in Combination with DNA Coding for Costimulatory Molecules The skeletal muscle can play a role as an immunological microenvironment. Previous work has shown that foreign genes can be expressed in muscle cells [J. Wolff et al., *Science*, 247:1465 (1990)] and that an immune response is elicited against these antigens [J. Ulmer et al., *Science*, 259:1745 (1993)]. It also has been reported that stimulation of cultured human muscle cells (myoblasts) with interferon-γ (IFN-γ) leads to the expression of MHC class II complexes on these cells [N. Goebels et al., *J. Immunol.*, 149:661–667 (1992)].

Mouse muscle cells were injected with DNA coding for a specific murine OVA 323–339/IA$^d$MHCII fusion complex (pJRS165.1) and the costimulatory signal B7-1 (pUB719) to generate local antigen presenting cells (APCs) that express the fusion complex containing the ovalbumin peptide 323–339. These APCs will eventually activate T-cells. As detailed below, DNA coding for an MHC fusion complex and co-stimulatory molecule was injected (i.m.) into BALB/c mice in order to elicit a specific T-cell proliferation response to the peptide encoded by the DNA (illustrated with pJRS165.1 and pUB719).

Three groups of BALB/c mice (3 mice per group) were injected i.m. in both hind leg quadriceps with 50 µL sterile PBS containing the plasmids 1) pJRS165.1 carrying the encoding region of the murine OVA 323–339/I-A$^d$ MHCII under the control of the CMV promoter alone or 2) pJRS165.1 and pUB719 containing the coding region of the murine B7-1 gene under the control of the CMV promoter or 3) pUB719 alone. The mice were previously anesthetized-in a chamber saturated with Metophane® (Pitman-Moor, Mundelein, Ill.) according to the method disclosed in Example 6 above.

Within every group, 3 mice were injected with 100 µg DNA in 100 µL PBS at week 0 and a boost injection with the same DNA was performed at week 3. Ten days after the last injection, the inguinal and paraaortic lymph nodes were collected. Lymph node cells were isolated and submitted to an OVA specific T-cell proliferation assay as follows. The cells were washed 3 times in complete medium (RPMI-1640, 10% FBS, 2 mM L-glutamine, penicillin, streptomycin, and $5 \times 10^{-5}$ 2-mercaptoethanol) and resuspended at $5 \times 10^6$ cells/mL. One hundred microliters of the cell suspension were added to wells of a 96-well round bottomed microtiter plate. Dilutions of the OVA (323–339) peptide were prepared ranging from 0.8 µg/mL to 10 µg/mL and 100 µL/well was added to the cells in triplicate. Background proliferation was determined by omitting the peptide. The plates were incubated with 5% $CO_2$ at 37° C., for 3–5 days. Wells were pulsed with 0.4 µCi of $^3$H-thymidine for 18 hours prior to termination of cultures and harvested using a Skatron Cell Harvester. Incorporation of $^3$H-thymidine into DNA as a measure of T-cell proliferation was determined using an LKB liquid scintillation spectrometer. The degree of peptide reactive T-cell proliferation was indicative of the $T_h$-cell responses (i.e. of clonal expansion) that took place in the mice following immunization.

Figure 22:
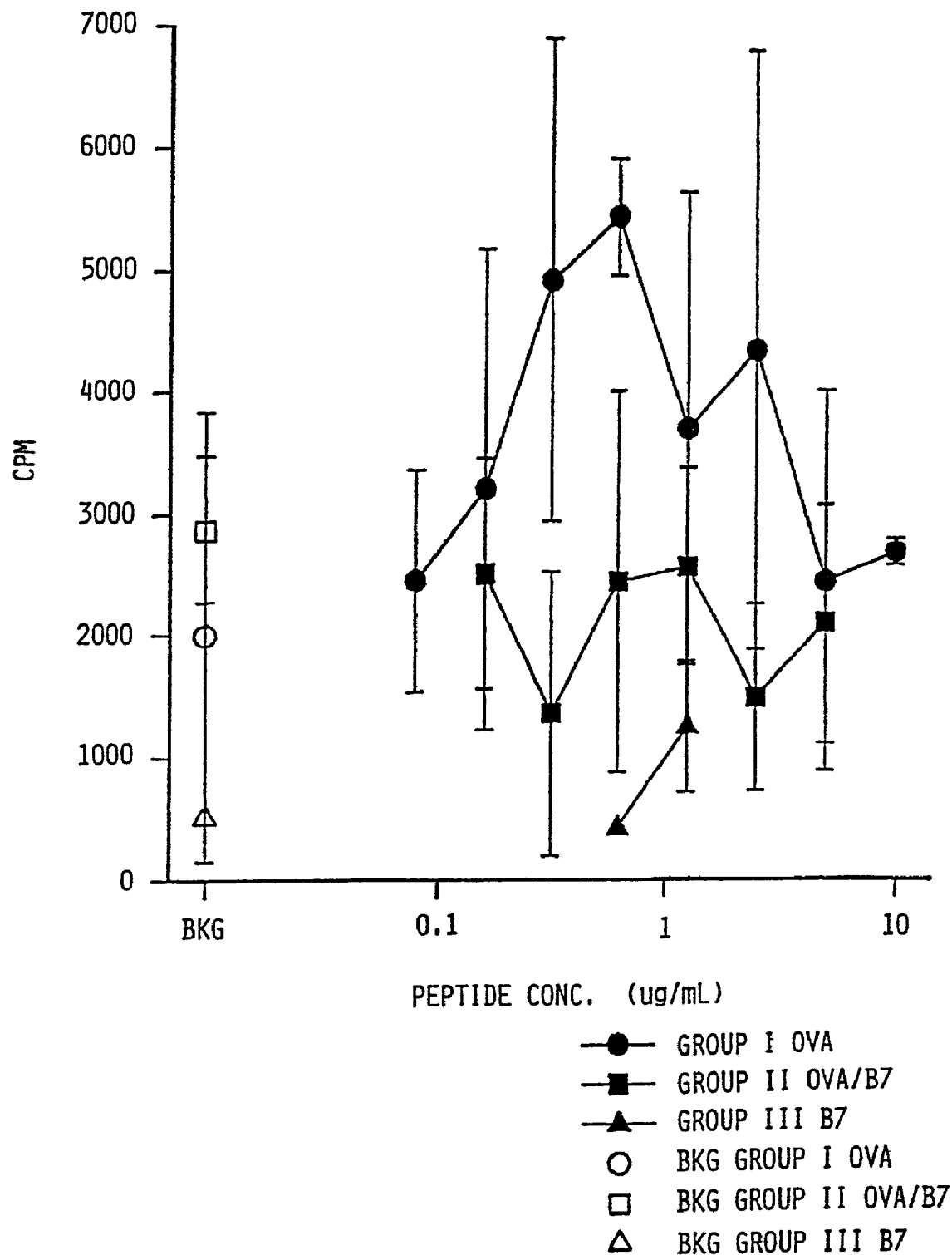
FIG. 22 shows graphically the results of the T cell proliferation assay of Example 15 which follows.

The results of the proliferation assay are shown in FIG. 22 of the Drawings. Specifically, injection of 100 µg DNA showed no significant OVA specific T-cell proliferation neither in the case of pJRS165.1 injection nor if pUB719 was coinjected. These results indicate that in this case administering DNA coding for OVA 323–339 MCHII fusion complexes alone or in combination with costimulatory molecule DNA intramuscularly does not induce an immune response against the OVA peptide. The limited proliferative response observed at high doses of injected pJRS165.1 DNA (i.e. 100 µg) may be the result of transforming intradermal dendritic cells (intradermal APCs) during the injection (see Example 16 below).

EXAMPLE 16

In vivo T Cell Activation After Intradermal (i.d.) Injection of DNA Coding for MHC Fusion Complex Dendritic cells are professional, intradermal antigen presenting cells (APCs). The transformation of these cells (illustrated in this example) or other cells (such as exemplified in Example 13 above) with specific MHC class II fusion complexes can induce a peptide specific T-cell response. These APCs already bear the costimulatory molecules (i.e. B7-1) which provide the second activation signal to T-cells.

Two groups of BALB/c mice (9 mice per group) were injected i.d. on the shaved back with 100 μl PBS containing 10 μg of 1) pJRS165.1 carrying the encoding region of the murine OVA 323–339/I-$A^d$ MHC class II fusion gene under the control of the CMV promoter or 2) pABH1 carrying the encoding region of the murine HEL 74–86/I-$A^d$ MHCII fusion complex under the control of the CMV promoter as a control group. Four, 7 and 14 days after the injection the inguinal and paraaortic lymph nodes were collected. Lymph node cells were isolated and submitted to an OVA specific T-cell proliferation assay as follows. Cells were washed 3 times in complete medium (RPMI-1640, 10% FBS, 2 mM L-glutamine, penicillin, streptomycin, and $5\times10^{-5}$ M 2-mercaptoethanol) and resuspended at $5\times10^6$ cells/mL. One hundred microliters of the cell suspension were added to wells of a 96-well round bottomed microtiter plate. Dilutions of the OVA (323–339) peptide were prepared ranging from 0.08 μg/mL to 10 μg/ml and 100 μL/well was added to the cells in triplicate. Background proliferation was determined by omitting the peptide. Plates were incubated with 5% $CO_2$ at 37° C., for 3–5 days. Wells were pulsed with 0.4 μCi of $^3$H-thymidine for 18 hours prior to termination of cultures and harvested using a Skatron Cell Harvester. Incorporation of $^3$H-thymidine into DNA as a measure of T-cell proliferation was determined using an LKB liquid scintillation spectrometer. The degree of peptide reactive T-cell proliferation was indicative of the $T_H$-cell responses (i.e. of clonal expansion) that took place in the mice following immunization.

Figure 23:
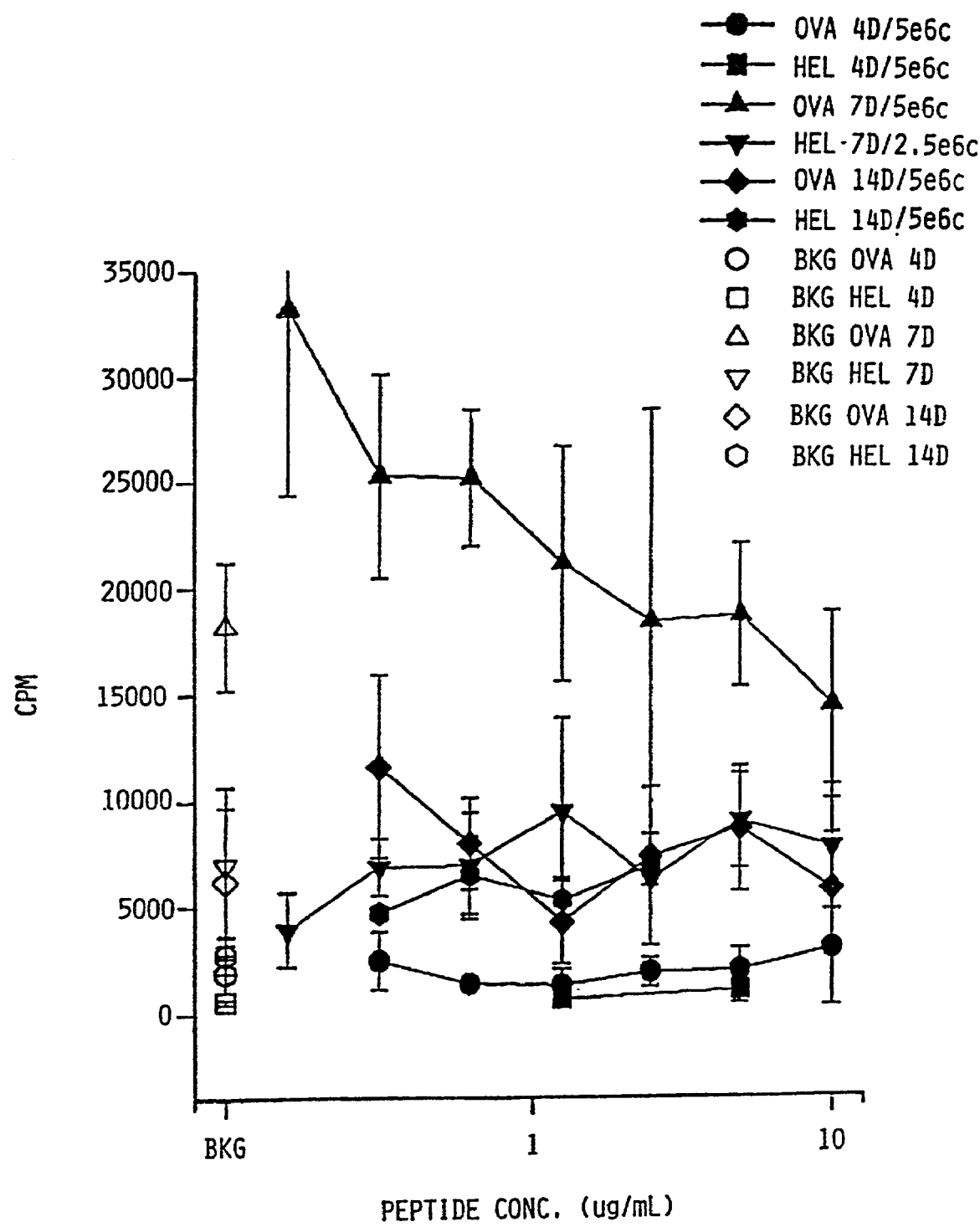
FIG. 23 shows graphically the results of the T cell proliferation assay of Example 16 which follows.

The results of the proliferation assays are shown in FIG. 23 of the Drawings. No significant specific T-cell proliferation is detected (approx. 2,500 cpm) 4 days post injection either in pJRS165.1 or pABH1 injected mice. Seven days after the injection, lymph node cells from pJRS165.1 injected mice show a 12 times higher proliferation at a stimulating peptide concentration of 0.31 μg/mL compared to day 4. Higher peptide concentrations reduced the proliferative response to approx 15,000 cpm. Cells, however, from pABH1 injected mice showed no significant increase in proliferation (approx. 7,000 cpm) at all 3 time points. The specific (OVA) proliferative response at 14 days post injection is 3 times lower than at day 7 indicating that the maximal stimulation period has elapsed. These results indicated that intradermal APCs have been transformed with functional OVA 323–3391/MHCII fusion complex and that OVA specific T-cells have been primed and expanded. Because of the absence of stimulus (HEL—peptide) the HEL specific T-cells (activated by pABH1 transformed APCs) do not proliferate in the test. A lag period of 4 days is observed prior to any T-cell activation.

EXAMPLE 17

Construction of Vectors for Expressing Soluble and Membrane-bound Single-chain MHC Class II Molecules with Specific Presenting Peptides The MHC class II genes used for these constructs were originally isolated by PCR amplification of cDNA generated from the appropriate APC as described in the above examples (see in particular Example 1 above). Fragments of the I-$A^d$ α and β chain genes were generated by PCR amplification using cloned genes as template DNA and were assembled in the cloning scheme shown in FIG. 25 of the Drawings resulting in a chimeric gene encoding the antigenic peptide, OVA 323–339, linked to a single-chain I-$A^d$ molecule. Briefly, the α1–α2 gene fragment cloned into 39AD2 served as the template for PCR amplification using primers JLA007 and JLA110 (all of the oligonucleotides used in cloning are listed in FIG. 26 of the Drawings), resulting in the addition of a 5' XhoI and a 3' XmaI restriction site. The α1–α2 PCR product was digested with XhoI and XmaI, gel-purified and subcloned into the pLL101 vector resulting in the pJAα9 construct. This vector adds sequence encoding a 6×His tag to the end of the α1–α2 protein to aid in protein to aid in protein purification.

The strategy for isolating the I-$A_d$ β1–β2 gene fragment and attaching the linker sequence has been described in the above examples. The 10 aa linker-β1–β2 gene fragment in pBC1 served as the template for PCR amplification using JLA005 and JLA009 primers to add NcoI and SpeI restriction sites necessary for subsequent cloning. The PCR products were digested with NcoI/SpeI digested pJAα9 resulting in the pJAα9β20 construct. In order to generate a single chain class II molecule, it was determined by computer modeling of the HLA-DR1 crystal structure that a flexible linker could be inserted between the carboxyl terminus of the 32 domain and the amino terminus of the α1 domain. Based on that the distance between these residues was 47 angstroms, a 24 amino acid linker primarily comprised of the (GGGGS) motif repeated four times was modeled and used. To insert sequences encoding this flexible peptide between the cloned β and α chain gene fragments, oligonucleotides, JA301 and JA302, were annealed and ligated into SpeI/XhoI digested pJAα9β20. The resulting construct was called pJALNK. pJALNK was digested with NheI and EcoRI and the β1β2-α1α2 single chain gene fragment was gel purified. This fragment was inserted into the pVW229 vector carrying the β chain leader sequence and the regions encoding the OVA 323–339 peptide as described in the above examples. The resulting construct SSC1 contains a chimeric gene encoding the β leader/OVA peptide/10 aa linker/β1–β2/20 aa linker/α1–α2/6×His tag. The sequence of this gene is shown in FIG. 27 of the Drawings.

To construct a vector for expression of soluble single-chain (sc) class II molecules in an insect cell expression system, the chimeric gene was removed from SSC1 by digestion with NcoI and EcoRI and gel purified. The fragment was ligated into NcoI/EcoRI-digested p2Bac vector (In Vitrogen—part number V1980-10) to created pMBSC1.2.

To generate a vector capable of expressing membrane bound sc class II molecules in mammalian cells, the BclI-EcoRI fragment of pJRS163-10 that encodes the α chain transmembrane (TM) domain was subcloned into BclI-EcoRI digested SSCI vector. The resulting vector, SCTM1, was digested with XmaI and EcoRI and the single-chain I-$A^d$-OVA cassette was inserted into the PEE13 mammalian expression vector, giving the SCT1 construct. The sequence of the chimeric gene is shown in FIG. 28 of the Drawings.

To generate a vector capable of expressing soluble sc-MHC molecules in mammalian cells, the α chain template DNA was amplified by PCR from pJRS163-10 using primers JS305 and OPR142, thereby adding sequence encoding the EE antibody tag to the 3' end of the gene fragment. The PCR product was digested with BclI and EcoRI and cloned into digested SSC1 vector. The resulting vector, SCEE1, was digested with BclI-EcoRI and the single-chain I-$A^d$-OVA cassette was inserted into the PEE13 mammalian expression vector, giving the SCE1 construct. The sequence of the chimeric gene is shown in FIG. 29 of the Drawings. Samples of the above single chain plasmids pMBSC1.2, SCT1 and SCE1 have been deposited with the American Type Culture Collection, Rockville, Md.

EXAMPLE 18

Production of Soluble Single Chain MHC Molecules (MHC II (I-$A^d$) in Insect Cells)

The purified pMBSC1.2 plasmid was used in a cotransfection and recombinant virus was enriched from wild type AcMNPV by limiting dilution (see D.R. O'Reilly et al., Baculovirus Expression Vectors: A Laboratory Manual. WH Freeman & Co. New York (1992)). SF9 cells were used throughout.

Supernatant from wells was tested by ELISA to identify virus producing recombinant product (sc I-$A^d$-OVA). The ELISA assay involves coating 100 ngs of M5/114 (ATCC TIB 120) anti-$IA^d$ onto wells of 96 well microtiter plates in 50 microliters of 0.1M carbonate buffer pH 8.2. Blocking was done with 200 μl of PBS 10% FBS (fetal bovine serum from Biowhittaker part number 14-901F) for at least 1 hour and plates were washed three times with 200 μls of wash buffer (PBS with 0.5 ml Tween 20/1). Samples were added at 100 μl/well and incubated 15 minutes at 37° C. Plates were washed four times with 200 μl wash buffer. Biotinylated AMS-32.1 anti-$IA^d$ (part number 06032D from Pharmingen) was added at 100 ng/well in 100 μl PBS 10% FBS. Following incubation for 15 minutes at 37° C., the plates were washed four times with wash buffer. Avidin peroxidase (Sigma) was added at 250 ng/well in 100 μl/well PBS 10% FBS and incubated for 15 minutes at 37° C. Plates were then washed eight times with 200 μl wash buffer and 100 μl of ABTS substrate (Kirkegaard and Perry part numbers 5060-00 or 50-60-01) was added per well. Absorbance was measured at 405 nm.

The cotransfection mix supernatant was tested for I-$A^d$ reactivity by the above ELISA. Mean absorbance of duplicate wells are shown in Table 3 below. The specificity of the signal observed shown to be due to secretion of sc I-$A^d$-OVA into culture supernatant by SF9 cells.

Limiting dilution subcloning was done on the cotransfection mix by diluting virus in complete media (TNMFH part number 51942 from JRH Biosciences supplemented with 10% FBS) and incubating virus dilutions with 2×10$^4$ SF9 cells/well in 96 well plates. Supernatant from wells that showed visible signs of infection but no polyhedra were tested in the $IA^d$ ELISA. Clones C6 (1.557), and F8 (1.446) are strongly positive. C12 is clearly negative (0.124).

Five hundred microliters of positive clone C6 was added to each of three one liter flasks containing SF9 cells at 1×10$^6$ cells/ml. Approximately 2200 mls of infection supernatant was used in the purification of sc I-$A^d$-OVA as described in Example 19 below. The thus purified single chain MHC II complex was assayed for ability to modulate the activity of DO11.10 T cell hybridoma as described in Example 20 below.

TABLE 3

I-$A^d$ ELISA of insect cell culture supernatants from cotransfections

| Sample dilution | Absorbance |
|---|---|
| Undiluted | 0.857 |
| 1:2 | 0.524 |
| 1:4 | 0.305 |
| 1:8 | 0.165 |

Negative controls including sample diluent (0.064) and supernatant from an infection done with a recombinant Baculovirus containing the gene for Neuron Specific Enolase (NSE) in SF9 cells showed negligible binding (0.098).

EXAMPLE 19

Purification of Single Chain MHC Molecules (MHC II (I-Ad) Expressed in Insect Cells)

The following steps were carried out in the preparation of soluble single-chain I-$A^d$-OVA from insect cell culture supernatants.

Ammonium Sulfate Fractionation: At 0–4° C., solid ammonium sulfate (0.436 g/ml) was slowly added into insect cell culture medium (2200 ml) while stirring the sample. Following the addition of ammonium sulfate, stirring of the sample was continued for 30 minutes. The mixture was then centrifuged at 26000 g and 4° C. for 30 minutes, the supernatant discarded, and the pellet resuspended in 100 ml of phosphate-buffered saline (PBS). The resuspended sample was dialyzed against 4000 ml of PBS at 4° C. for about 20 hours, with one change of fresh PBS after first 4.5–5 hours of dialysis. The volume of the dialyzed sample was measured and solid NaCl and 20% (v/v) Tween 20 was added to 0.5 NaOH, followed by filtration through a 0.8 micron filter.

Metal Chelate Affinity and Immunoaffinity Chromatography: All the following steps were done at room temperature.

Ni-IDA Sepharose: The sample provided by the above fractionation step was loaded onto a Ni-IDA Sepharose Fast Flow column (2.6×7.2 cm, 38.0 ml) that had been equilibrated with at least 5 bed volumes of PBS, 0.5 M NaCl, 0.2% (v/v) Tween 20, pH 8.0. The flow rate for loading sample was 3 ml/minute. Then the column was washed with at least 7–8 bed volumes of the above equilibration buffer, followed by 2.5–3 bed volumes of 20 mM $Na_2HPO_4$, pH 7.0, 0.2 M NaCl. The flow rate for washing was 5 ml/minute. I-$A^d$ protein was eluted with stepwise pH decreases effected by mixing different portions of Buffer A (20 mM $Na_2HPO_4$, pH 7.0, 0.2 M NaCl) and Buffer B (20 mM $Na_2HPO_4$, pH 3.0, 0.2 M NaCl) programmed in a FPLC controller. An ELISA assay using anti-I-$A^d$ monoclonal antibody (which recognize conformational epitopes of I-Ad molecules) indicated that I-Ad is present in fractions eluted by 90% and 100% Buffer B. Those $A_{280nm}$ peaks eluted by 90% and 100% Buffer B were pooled, immediately adjusting to pH 7.0 with 1 M Tris. The sample was concentrated and buffer-exchanged into 20 mM Tris-HCl, pH 8.0 by ultrafiltration.

Immunoaffinity Chromatography: The sample from the above step was first passed through a Protein A Sepharose Fast Flow column (1.6×5 cm, 10 ml) and then applied onto a column (1.6×3.4 cm, 6.8 ml) of Protein A Sepharose Fast Flow crosslinked with MKD 6, an anti-I-A$^d$ monoclonal antibody. The two columns had been previously equilibrated with 20 mM Tris-HCl, pH 8.0. Following sample application, the immunoaffinity column was washed with 20 mM Tris-HCl, pH 8.0 until A$_{280nm}$ baseline was reached. The antibody column was then washed with the same buffer containing 1 M NaCl as above to remove nonspecific bound proteins. The I-A$_d$ protein was then eluted with 50 mM glycine-NaOH, pH 11.0. The eluted protein peak (monitored by A$_{280nm}$) from the antibody column was immediately adjusted to pH 8.0 with 2M glycine, pH 2.0, concentrated and buffer-exchanged into 20 mM Tris-HCl, pH 8.0 by ultrafiltration. The purified sample was stored at 4–8° C. The purity and functionality of I-A$^d$ sample were tested by sodium dodecyl sulfate-polyacrylamide gel electrophoresis and T-cell activation assay (see below), respectively. Purified single-chain I-A$^d$-OVA from this preparation showed no contaminating bands on a Coommassie stained polyacrylamide gel and total protein was 125 µg/ml by total protein assay.

EXAMPLE 20

Activity of Single-chain MHC Complexes

It was determined whether purified single-chain I-A$^d$/OVA MHC complexes could activate the OVA-specific DO11.10 T cell hybridoma as measured by IL-2 and IL-4 production. This method involves coating single-chain I-A$^d$/OVA onto IMMULON II plates (Dynatech) in PBS overnight at 4° C. Wells were emptied, washed once with PBS and 1×10$^5$ DO11.10 cells were added per well in 200 µl RPMI 10% FBS. Following incubation overnight at 37° C. in a humid incubator with 10% CO$_2$, culture supernatants were harvested, cells were removed by centrifugation and IL-2 and IL-4 levels were determined by ELISA as follows.

The rat anti-mouse IL-2 ELISA capture antibody (Pharmingen part number 18161D) was coated at 100 ng/well in 50 µl 0.1 M carbonate pH 8.2. Blocking was done with 200 µl of PBS 10% FBS for at least 1 hour and the plates were washed three times with 200 µl of wash buffer (PBS with 0.5 ml Tween 20 per 1). Samples were added at 100 µl/well and incubated for 4 hours at room temperature or overnight at 4° C. Plates were washed four times with 200 µl wash buffer and biotinylated rat anti-mouse IL-2 (Pharmingen) was added at 100 ng/well in 100 µl PBS 10% FBS. Following incubation for 45 minutes at room temperature, the plates were washed four times with wash buffer. Avidin peroxidase (Sigma part number A-3151) was added at 250 ng/well in 100 µl/well PBS 10% FBS and incubated for 30 minutes at room temperature. Plates were then washed eight times with 200 µl wash buffer and 100 µl of ABTS substrate (Kirkegaard and Perry part number 5060-00 or 50-66-01) was added per well. Absorbance was measured at 405 nm. The IL-4 ELISA protocol was identical except for the use of IL-4 specific capture and probe antibodies (Pharmingen). The results of one activation assay is shown in Table 4 below. Neither DI11.10 cells alone nor DO11.10+A20 (I-A$^d$ positive) cells secreted any IL-2 or Il-4. The sc I-A$^d$-OVA resulted in the secretion of IL-2 and IL-4 by the DO11.10 T cell hybridoma. A second activation was done with lower doses of immobilized sc I-A$^d$-OVA. Secretion levels of IL-2 and IL-4 both titered down to zero, as shown in Table 5 below. In both experiments, IL-2 and IL-4 were secreted by DO11.10 cells in a dose dependent manner with regard to exposure to immobilized sc I-A$^d$-OVA.

TABLE 4

DO11.10 activation assay using immobilized purified sc I-A$^d$-OVA

| sc IA$^d$-OVA (ng/well) | IL-2 concentration in DO11 super (U/ml) | IL-4 concentration in DO11 super(U/ml) |
|---|---|---|
| 2500 | 143 | 23 |
| 1250 | 126 | 20 |
| 625 | 116 | 15 |
| 312 | 109 | 16 |
| 156 | 100 | 10 |
| 78 | 45 | 7 |
| 0 (DO11.10 only) | 0 | 0 |

TABLE 5

DO11.10 activation assay using immobilized purified sc IA$^d$-OVA-extended dilution

| scIA$^d$-OVA (ng/well) | IL-2 concentration in DO11 super (U/ml) | IL-r concentration in DO11 super (U/ml) |
|---|---|---|
| 625 | 38 | 2.0 |
| 312 | 35 | 1.5 |
| 156 | 24 | 0.9 |
| 78 | 17 | 0.8 |
| 39 | 0 | 0 |
| 0 (DO11.10 only) | 0 | 0 |

EXAMPLE 21

Production of Single-chain MHC Molecules (Class II) in Mammalian Cells

Transfection and selection of mammalian cell lines was carried out as follows: 1×10$^7$ NSO cells were washed twice in ice cold PBS, resuspended in 760 µl of cold PBS, and mixed with 40 µg (1 µg/µl) of SalI linearized plasmic SCE1 or SCT1 DNA. After 5 minutes incubation on ice, the cells were electroporated using a Gene Pulser (Biorad) to deliver one pulse of 250 volts, 960 µFd. The pulsed cells were placed on ice for 2–5 minutes and added to 30 ml of non-selective medium (IMDM, 10% FBS, 2 mM glutamine, 5000 units/ml penicillin, 5000 µg/ml streptomycin). Cells were plated in 96-well flat bottom tissue culture plates and 24 h later, 150 µl of selective medium (IMDM, 10% dialyzed FBS, 5000 units/ml penicillin, 5000 µg/ml streptomycin, 1×nucleosides, 1×glutamate+asparagine) was added to each well. The plates were fed with selective medium on a weekly basis by removing 100 µl/well used medium and adding 100 µl/well of fresh selective medium, allowing the cells to gradually deplete the medium of all residual glutamine. The glutamine synthetase gene carried on the SCE1 and SCT1 plasmids allows selective growth of the transfected cells in glutamine-free media. Colonies of the cells transfected with the plasmic became evident after 14–21 days. The transfectants carrying the SCT1 vector (i.e. membrane-bound form of the sc I-A$^d$-OVA molecules) were expanded and screened for expression of the MHC molecules by flow cytometry as described below.

Clones generated from the transfection/selection protocol were analyzed for surface expression of class II MHC molecules at levels significantly higher than the parental cell line. The cells were incubated with FITC-conjugated anti-I-A$^d$ antibody, AMS 32.1 (PharMingen, 1:100 dilution) in cold staining buffer (PBS, 1% FCS) for 45 minutes in the dark. After washing three times in staining buffer, fluorescence was examined of a FACScan flow cytometer (Beckton Dickinson). An isotype matched FITC-conjugated anti-I-$A^k$ antibody, 10-3.6 (PharMingen, 1:100 dilution) was used as a negative control. The results of such an assay, shown in Table 6 below for three independent SCT1 transfected cell lines, indicate that the transfected cells express the sc I-$A^d$-OVA on their cell surface.

The transfectants carrying the SCE1 vector (i.e. soluble form of the sc I-$A^d$ OVA molecules) were expanded and screened for expression and secretion of the MHC molecules by the I-Ad specific ELISA assays described in Example 18 above. The results of such an assay of the culture supernatant from two SCE1 transfected cell lines are shown in Table 7 below. These results indicate that the transfected cells produce and secrete the sc I-$A^d$-OVA molecule. This system could be used to generate large amounts of soluble peptide-linked single-chain MHC molecules.

TABLE 6

Surface expression of I-$A^d$ molecules on transfected cell lines

| Cell line | Mean Fluorescence | |
| --- | --- | --- |
| | I-$A^d$-specific | I-$A^k$-specific |
| NSO (parental) | 280.4 | 32.1 |
| T2 (SCT1-transfectant) | 612.8 | 22.0 |
| T6 (SCT1-transfectant) | 417.9 | 45.1 |
| T12 (SCT1-transfectant) | 911.1 | 45.9 |

TABLE 7

I-$A^d$ ELISA assay on SCE1 transfectant cell culture supernatants

| Culture Supernatant (undiluted) | Absorbance |
| --- | --- |
| NSO (parental cell line) | 0.444 |
| E10 (SCE1 transfectant) | 0.781 |
| E11 (SCE1 transfectant) | 0.960 |
| sc I-$A^d$-OVA from insect cell culture (positive control) | 2.44 |

EXAMPLE 22

Activity of the Single-chain I-$A^d$ Molecules Expressed on Mammalian Cells

Stimulation of IL-2 release from the OVA 323–339 specific I-$A^d$ restricted DO11.10 T cell hybridoma was carried out as described in Example 20 above. Briefly, 1×10$^5$ SCT1 transfectant cells or A20.11 were incubated together with (varying amounts) OVA peptide and 2×10$^5$/well DO11.10 cells at 37° C. in an atmosphere of 5% CO$_2$. Cultures were carried out in complete medium (RPMI 1640 supplemented with 10% FBS, penicillin/streptomycin, L-glutamine and 50 µM 2-mercaptoethanol) in 96 well flat bottom microtiter plates. After 24 hours, culture supernatants were assayed for the presence of DO11.10 derived IL-2 using the IL-2 ELISA assay described in Example 20 above or by measuring the growth of the IL-2 dependent murine T-cell line CTLL-2. In the latter test, serial twofold dilutions of each culture supernatant were prepared in complete medium in flat bottomed microtiter plates and 1×10$^4$ CTLL-2 cells were added to each well. A standard curve of (amounts) rIL-2 was run in parallel. After 16 to 20 h, MTT (2 mg/ml, 27 µl/well) was added and the plates incubated for 4 h. At this time, blue crystals formed by MTT in actively metabolizing cells were dissolved by addition of 150 µl of 0.4 N HCl in isopropanol. After mixing, the O.D. at 562 was determined using a Ceres-UV900HI plate reader. The absorbance corresponds to the level of CTLL cell growth supported by the IL-2 in the culture media.

The results of two such activation assay are shown in Tables 8 and 9 below. Similar results were obtained using the CTLL assay.

TABLE 8

DO11.10 T cell hybridoma activation by SCT1 transfected cell lines

| Antigen presenting cell assayed | IL-2 ELISA result (Absorbance) |
| --- | --- |
| NSO (parental cell line) | 0.047 |
| T2 (SCT1 transfectant) | 0.758 |
| T6 (SCT1 transfectant) | 0.307 |
| A20 + OVA 323–339 peptide (positive control) | 1.33 |

TABLE 9

DO11.10 T cell hybridoma activation by SCT1 transfected T12 cell

| Antigen presenting cell assayed | IL-2 ELISA result (Absorbance) |
| --- | --- |
| NSO (parental cell line) | 0.078 |
| T12 (SCT1 transfectant) | 1.03 |
| A20 + OVA 323–339 peptide (positive control) | 1.45 |

EXAMPLE 23

Immunosuppression Methods Using Soluble Peptide-linked Single-chain MHC Class II Molecules To test whether the soluble peptide-linked single-chain class II molecules can induce $T_H$ cell anergy in an animal model system, the effects of the molecules on $T_H$ cell-dependent immunoglobulin class switching (i.e. IgM to IgG) and on clonal expansion of peptide-specific T cell lines can be examined.

In order to examine Ig class switching, two test groups are set up as follows: (a) 10 BALB/c mice are injected with 100 µg of OVA 323–339 in Complete Freund's adjuvant H37Ra at the base of the tail and boosted again 7 days later, in order to induce an immune response to the OVA 323–339 peptide. On the day before the day of each immunization with OVA, 5 of the mice are injected IV with 10–100 µg of the soluble single-chain I-$A^d$ OVA in PBS. This soluble fusion protein will bind to the T cell receptor (TCR) displayed on the OVA 323–339 specific THE cells. Due to the absence of the co-stimulatory signal, these $T_H$ cells are induced to a state of anergy. Since the immunoglobulin class switching is a $T_H$ cell dependent process, it is expected that the induction of anti-OVA 323–339 IgG antibody will be reduced in the single-chain I-$A^d$-OVA treated mice. The remaining 5 mice serve as control and receive PBS.

Ten days after the second immunization, blood is collected from each mouse by tail bleeding. The blood is centrifuged at approximately 14,000 G for 3–5 minutes and the serum collected. Assays are performed in 96-well microtiter plates (Maxisorp F8; Nunc, Inc.) coated at 1–50 µg/ml with ovalbumin using a Tris-HCl coating buffer, pH 8.5. The plates are covered with pressure sensitive film (Falcon, Becton Dickinson, Oxnard, Calif.) and incubated overnight at 4° C. Plates are then washed with Wash solution (Imidazole/NaCl/0.4% Tween-20) and blocked by adding 100 µl/well of a 3% BSA solution. Following incubation on a plate rotator at room temperature for 30 minutes, the plates are washed five times with Wash solution. Mouse sera is diluted 1:500 in sample/conjugate diluent (2% gelatin+0.1% Tween-20 in TBS) and then, in duplicate, serially diluted on the plate. Two identical plates are set up for each coating protein, one for determination of IgM titer and the other for IgG. Following incubation at room temperature for 30 minutes, the plates are washed five times with Wash solution. Goat anti mouse IgM-HRP and goat anti mouse IgG-HRP conjugates (Boehringer Mannheim, Indianapolis, Ind., 1:100 dilution in Sample/conjugate diluent) are added to the appropriate plates. Following incubation at room temperature for 30 minutes, the plates are washed five times with Wash solution and then incubated with 100 µl/well of ABTS developing substrate (Kirkgaard & Perry Laboratories, Inc., Gaithersburg, Md.) for 10 minutes at room temperature. The reactions are stopped with 100 µl/well of Quench buffer (Kirkgaard & Perry laboratories, Inc., Gaithersburg, Md.) and the absorbance values are read at 405 nm using an automated microtiter plate ELISA reader (Ceres UV900HI, Bioteck, Winooski, Vt.). The titer is determined by plotting the absorbance reading versus the log of the dilutions of the samples. The titers for IgM is versus are then compared. As detailed above, soluble peptide-linked single-chain MHC class II molecules are expected to inhibit the IgG class switching in a peptide specific manner due to the anergy induced in the corresponding peptide-reactive $T_H$ cells.

The effects of soluble peptide-linked single-chain MHC molecules on clonal expansion of peptide-specific T cell lines in vivo can be examined as follows. Treatment groups (4 mice per group) are suitably the same as described above. The immunization protocol is suitably as follows: mice are injected IV with 10–100 µg of the soluble single-chain I-$A^d$-OVA fusion protein in PBS and 24 hours later injected subcutaneously at the base of the tail with 50 µg of OVA 323–339 in complete Freunds Adjuvant H37Ra. These two injections are repeated 6 and 7 days later. Seven days after completion of the second set of injections, the mice are sacrificed. The injected and paraaortic lymph nodes are removed and rendered into a single cell suspension.

The suspension is depleted of antigen presenting cells by incubation on nylon wool and Sephadex G-10 columns, and the resulting purified T cell populations incubated with APCs pulsed with the OVA 323–339 peptide. Spleenic B cells serve as antigen presenting cells. These cells are fixed with mitomycin C (50 to 100 µg/ml in a suspension of 4×10⁶ spleenocytes/ml) to inhibit proliferation of the B cells, washed extensively and added to purified T cells with various concentrations of the OVA 323–339 peptide. The proliferation assay is carried out in 96 well round bottom microtiter plates at 37° C., 5% $CO_2$ for 3–5 days. Wells are pulsed with 1 µCi of $^3$H-thymidine 18 hrs prior to termination of cultures and harvested using a Skatron cell harvester. Incorporation of $^3$H-thymidine into DNA as a measure of T cell proliferation is determined using an LKB liquid scintillation spectrometer. The degree of peptide-reactive T cell proliferation is indicative of the $T_H$ cell responses (i.e. of clonal expansion) that took place in the mice following immunization.

EXAMPLE 24

Immunosuppressive Approach by DNA Inoculation with Vectors Expressing Peptide-linked Single-chain MHC Molecules An example of a model system for testing the effects of the DNA inoculation approach (particularly intramuscular or intradermal) is outlined as follows. Three groups of BALB/c mice are injected intramuscular (IM) in both hind legs with 100 µg of: (1) SCE1, (b) SCT1, or (c) saline. Injections will be given at 0, 2, and 4 weeks. At 4 and 5 weeks after the initial DNA injection, OVA peptide 323–339 (100 µg/mouse in complete Freunds H37Ra adjuvant) is injected subcutaneously at the base of the tail. Two weeks later (week 8), blood is collected from each mouse by tail bleeding and serum obtained following centrifugation at approximately 14,000 G for 3–5 minutes. Titers of OVA-specific IgG and IgM antibodies is determined as described above. The degree of OVA-specific IgG antibody is indicative of the $T_H$ cell directed immunoglobulin class switching that took place in the mice following immunization with the peptide. Therefore, DNA inoculation with the peptide-linked single-chain MHC expression vectors may cause a reduction in the level of peptide-specific IgG antibodies without effecting IgM antibody levels.

An alternative assay is to measure OVA-specific $T_H$ cell clonal expansion or proliferation. Briefly, a cell suspension will be prepared from the inguinal and paraaortic lymph notes 7 days after the second OVA immunization. The suspension is depleted of antigen presenting cells by incubation on nylon wool and Sephadex G-10 columns, and the resulting purified T cell populations incubated with APCs pulsed with the OVA 323–339 peptide. Spleenic B cells serve as antigen presenting cells. These cells are fixed with mitomycin C (50 to 100 µg/ml in a suspension of 4×10⁶ spleenocytes/ml) to inhibit proliferation of the B cells, washed extensively and added to purified T cells with various concentrations of the OVA 323–339 peptide. The OVA-specific T cell proliferation assay is carried out as described above. The degree of peptide-reactive T cell proliferation is indicative of the $T_H$ cell responses (i.e. of clonal expansion) that took place in the mice following immunization with the peptide. Therefore, DNA inoculation with the peptide-linked single-chain MHC expression vectors may cause a reduction in the level of peptide-specific $T_H$ cell proliferation.

EXAMPLE 25

Construction and Cell Surface Expression of a Single-chain Class II MHC Molecule with One TM Domain (sc-IA$^d$/OVA)

In accordance with the above-described methods, the sc-IA$^d$ OVA fusion molecule (FIG. 30) was made by the following method:

Reverse transcriptase-polymerase chain reactions (RT-PCRs) were carried out to amplify IA$^d$ α and β chain gene fragments from total RNA isolated from A20-1.11 cells [K. Kim et al., *J. Immunol.*, 122:546 (1979)]. Suitable restriction enzyme sites were introduced at the each end of the gene fragments by PCR in order to facilitate cloning. DNA sequence encoding a 10 amino acid peptide linker was introduced into the 5' end of the β1–β2 gene fragment and the Kozak consensus sequence was introduced at the 5' end of the β signal sequences by PCR. The regions encoding the 24 amino acid linker and OVA antigenic peptide were generated from annealed oligonucleotides. Assembly of the PCR fragments and double-strand oligonucleotides in the pBlueScript-II vector (Stratagene) generated the sc-IA$^d$ fusion gene (see FIG. 30). For mammalian expression, the pSCT1 vector was generated by subcloning the sc/IA$^d$OVA gene (including the α chain TM and cytoplasmic regions) downstream of the CMV promoter of pEE13 (Cell Tech). The pEE13 vector also carries a selectable glutamate synthetase gene. To make soluble SC-IA$^d$ molecules, truncated sc-IA$^d$ constructs were made by replacing α chain TM and cytoplasmic regions (i.e., amino acids 183 to 233 inclusive) with an amino acid sequence encoding six consecutive histidines. These constructs were subcloned downstream of the baculovirus polyhedron promoter of pBluebac III (Invitrogen). The fusion genes were recombined into baculovirus following liposome-mediated cotransfection of SF9 insect cells with linearized wild-type AcMN-PV (Invitrogen). After cloning, purified recombinant virus stocks were prepared according to standard methods.

It is readily apparent that other antigenic peptides can be used as the covalently linked presenting peptide. For example, the HSV-1 gD peptide was used to create the sc-IA$^d$/gD fusion molecule by substituting the OVA 323–339 peptide coding sequence with the gD peptide coding sequence, infra. Preferably, the presenting peptide contains from about 6 to 30 amino acids (inclusive). For any single chain MHC fusion complex with a covalently linked presenting peptide, T cell activation assays, as described herein, can be used to determine whether the presenting peptide folds appropriately into the peptide binding groove or cleft of the complex.

The sc-IA$^d$/OVA fusion molecule was tested for cell surface expression by the following method: Plasmacytoma NS-0 cells transfected with an expression vector carrying the sc-IA$^d$/OVA fusion gene were selected and surface expression of class II molecules was examined by flow cytometry. The NS-0 cells were transfected by electroporation with linearized pSCT1 DNA carrying the sc-IA$^d$/OVA fusion gene. The cells were selected by growth in glutamine-free medium. Transfectants (i.e. T12 cells) became evident after 14–21 days and were analyzed for surface expression of class II MHC molecules. The cells were stained with FITC-conjugated anti-IA$^d$mAb (AMS-32.1 PharMingen) and fluorescence was examined by flow cytometry. An isotype matched FITC-conjugated anti-IA$^k$ mAb (10-3.6; PharMingen) was used as a negative control.

Figure 31A:
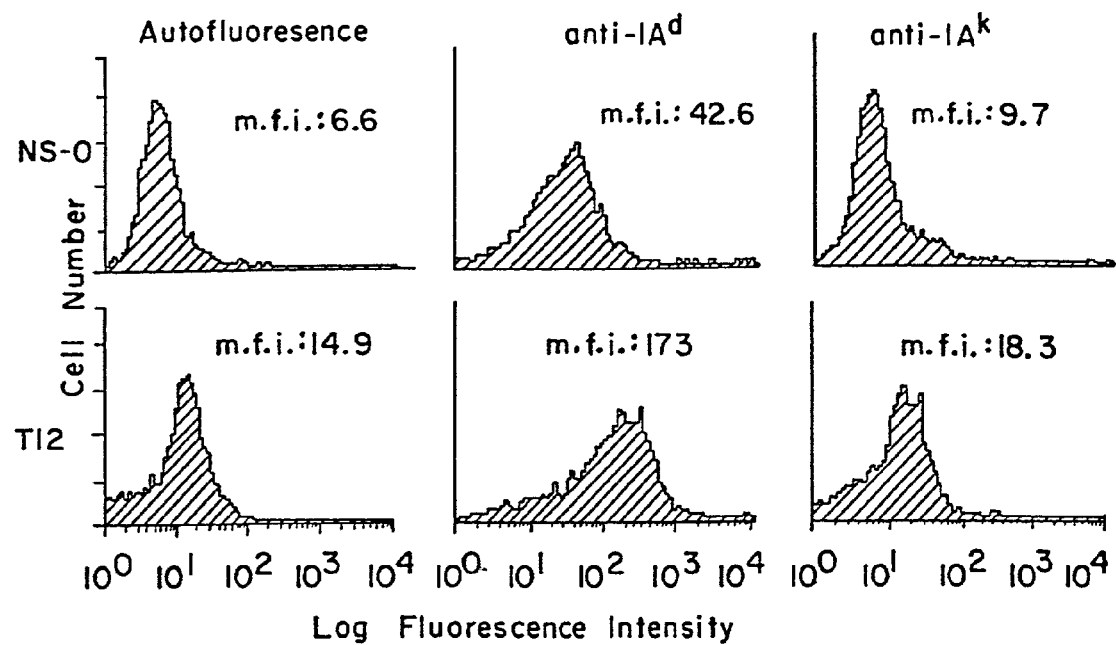
FIGS. 31A and 31B are graphs illustrating the cell surface expression (FIG. 31A) and T-cell inducing activity (FIG. 31B) of the sc-$IA^d$/OVA molecule.

FIG. 31A show the cell surface expression of a functional single-chain fusion molecule. Stable transfectants were analyzed by flow cytometry using-IA$^d$ and anti-IA$^k$ mAbs. Results shown for the T12 transfectant are similar to those seen for three other independent transfectants (m.f.i.=mean fluorescence intensity). The results demonstrate an increase in sc-IA$^d$/OVA expression on the surface of cells transfected with the sc-IA$^d$/OVA expression vector. An intact β TM domain is not required for cell surface expression of class II molecules; a flexible linker connecting the β and α chains can replace the function of the β TM domain. Finally, the results also demonstrate that covalently linking the presenting peptide to a single chain MHC class II molecule facilitates stable assembly and surface expression of the MHC molecule. Linking the presenting peptide to the β chain will also allow stable assembly and cell surface expression of a single chain MHC fusion molecule.

EXAMPLE 26

A cell Surface sc-IA$^d$/OVA Fusion Complex Induces a T Cell Response in vitro

Figure 31B:
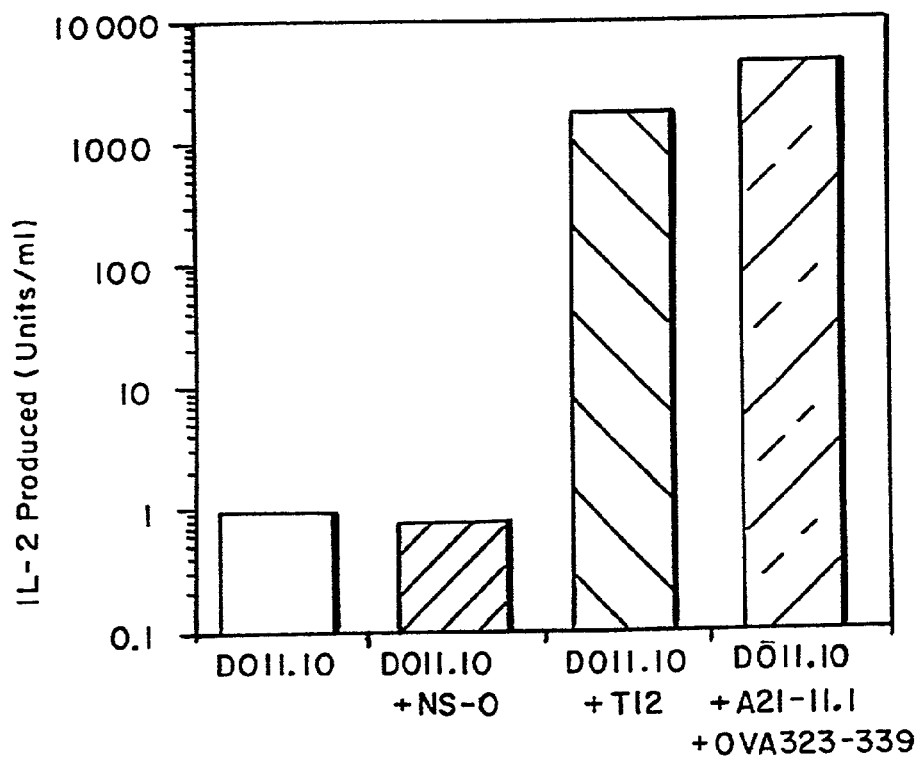

To check whether the OVA peptide folded properly into the sc-IA$^d$ fusion complex, sc-IA$^d$/OVA transfected cells were assayed for their ability to stimulate T cells. A murine T cell hybridoma (DO11.10) that expresses a T cell receptor (TCR) was used. The TCR recognizes the OVA 323–339 peptide in the context of IA$^d$. When the TCRs of these cells interact with the APCs (here, sc-IA$^d$/OVA transfectants) the DO11.10 cells secrete interleukin-2 (IL-2). DO11.10 cells (2×10$^5$/well) were cultured in the presence of NS-0 cells of the T12 transfectants (1×10$^5$/well) for 24 hours and IL-2 released into the culture medium was determined by an IL-2-specific ELISA (PharMingen). The murine IA$^d$-bearing B cell lymphoma, A20-1.11 (1×10$^5$/well) was pulsed with 2 mM OVA 323–339 served as a positive control for antigen presentation [K. Kim et al., *J. Immunol.*, 122:549 (1979)]. No IL-2 was detected in the culture medium of T12 cells alone. Results were similar to those observed for two other sc-IA$^d$/OVA transfectants. As shown in FIG. 31B, NS-0 cells (untransfected) failed to stimulate DO11.10 cells, whereas cells transfected with the sc-IA$_d$/OVA fusion gene strongly stimulated the release of IL-2 from DO11.10 cells. The extent of IL-2 secretion was comparable to those seen for IA$^d$-bearing APCs pulsed with OVA peptide. The results demonstrate that the OVA peptide folds properly within the sc-IA$^d$ fusion complex and that the folded OVA peptide in the context of IA$^d$ is recognized by the TCR on the surface of DO11.10 cells.

EXAMPLE 27

Soluble sc-IA$^d$/peptide Fusion Molecules Induce a T Cell Response in vitro

Soluble IA$^d$ heterodimers have been reported to be unstable (Kozono, H. et al. Nature 369, 151 (1994)). The results below show that the IA$^d$ molecule is stabilized by combining the dimers into a single chain. Stabilization of other MHC molecules (e.g., MHC class I, IE, DQ, DP or DR molecules) can also be achieved by combining the dimers, or fragments thereof, into a single chain molecule.

To demonstrate the stability of the single chain IA$^d$ MHC molecule, and to show that the OVA peptide could be replaced by other peptides, a baculovirus-insect cell system was used to produce a soluble sc-IA$^d$/peptide molecule. The chimeric genes which were made were generally the same as FIG. 30, except for the presenting peptide. For example, the chimeric genes included either a covalently linked OVA 323–339 peptide (sc-IVA$^d$/OVA), a peptide (gD 246–261) [APYSTLLPPELSETP] (SEQ ID NO: 124) [S. Grammer et al., *J. Immunol.*, 145:2249 (1990)] from HSV-1 glycoprotein D (sc-IA$^d$/gD) or no peptide (sc-IA$^d$/blank). In each case, the TM and cytoplasmic domains of the α chain gene were substituted with a sequence encoding a histidine tail (6×His) to allow soluble expression. Recombinant baculoviruses carrying the sc-IA$^d$ fusion genes were generated by standard procedures and then used to infect SF9 insect cells. The infected cells secreted soluble sc-IA$^d$ fusion molecules; these could be detected in the culture media by an IA$^d$-specific enzyme-linked immunosorbent assay (ELISA). The sc-IA$^d$ fusion molecules were then purified by immunoaffinity chromatography.

The protocol used to transfect the insect cells and purify sc-IA$^d$ fusion molecules was as follows: SF9 cells (1×10$^6$ cells/ml) in Hink's TMN-FH insect media plus 10% fetal bovine serum were infected at a multiplicity of infection of 10 with baculovirus carrying the sc-IA$^d$ genes. After 5 days, the culture supernatant was collected, adjusted to pH 8.0 with 1 M Tris and passed over a protein A Sepharose column. Unbound material was then applied to an MK-D6 mAb protein A Sepharose column. The column was washed with 20 mM Tris-HCl, pH 8.0 and 1 M NaCl, 20 mM Tris-HCl, pH 8.0. The sc-IA$^d$ fusion protein was eluted with 50 mM glycine-HCl, pH 11.0 and immediately neutralized to pH 8.0. The eluted protein was concentrated and exchanged into 20 mM Tris-HCl, pH 8.0 using Centricon 30. The SC-IA$^d$ molecules were detected by a sensitive IA$_d$ conformation-specific ELISA using M5/114 as the capture mAb and biotin-conjugated AMS-32.1 (PharMingen) as the probe mAb. Other mAbs (34-5-4,39-10-8) used to probe the sc-IA$^d$ proteins were obtained from PharMingen. Covalently linked OVA peptide was detected using polyclonal antisera from mice injected twice with 100 μg of OVA 323–339 in Complete Freund's adjuvant H37Ra). For a detailed protocol on how to prepare polyclonal antisera, see Ausbel, supra. Generally, the purification procedure yielded 200–300 μg of sc-IA$^d$/peptide per liter of medium.

Figure 32:
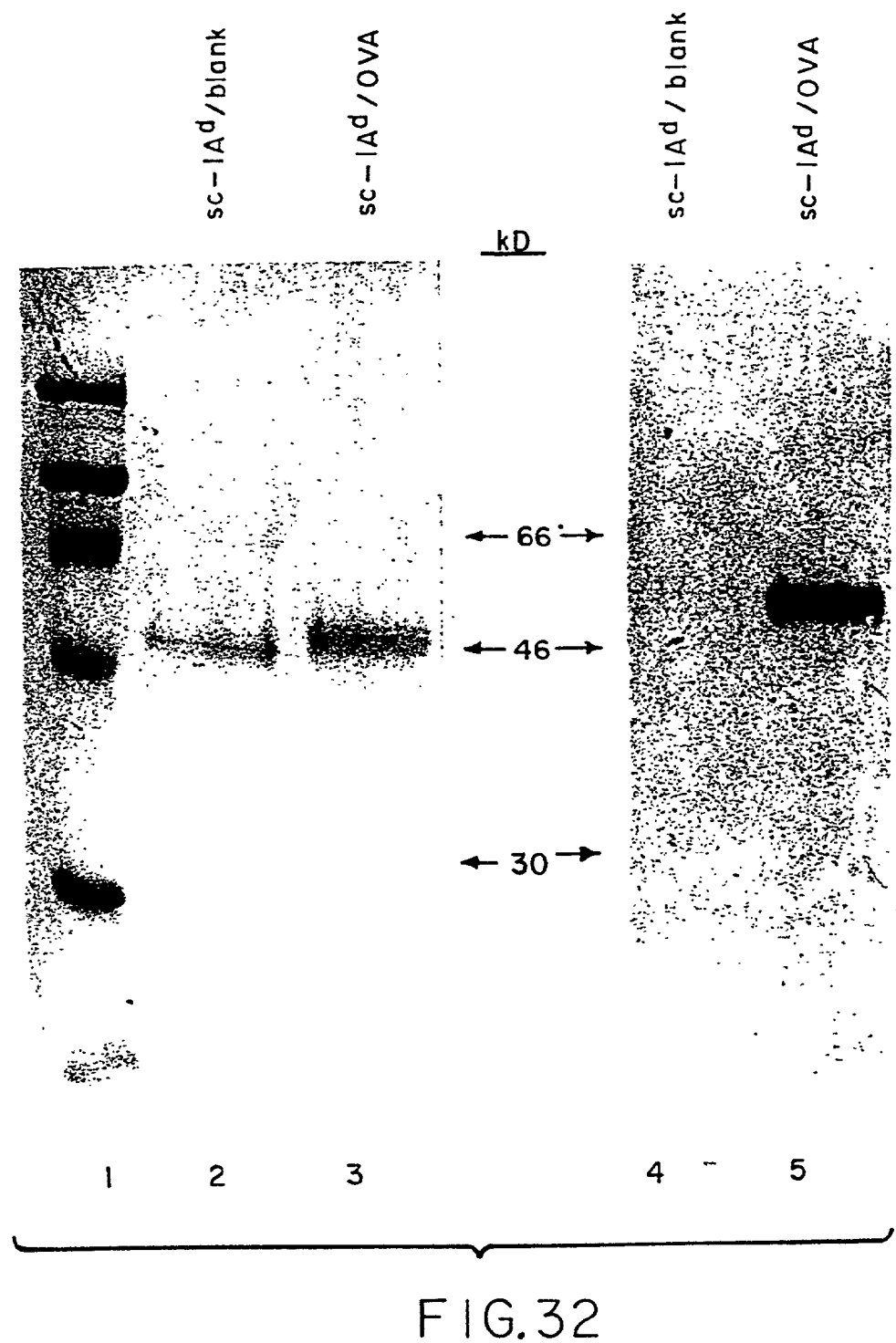
FIG. 32 is a photograph of two gels showing the expression of the sc-$IA^d$ MHC molecule with covalently linked OVA peptide (sc-$IA^d$/OVA) and without OVA peptide (sc-$IA^d$/blank) in insect cells.

FIG. 32 shows that the insect cells produced soluble single chain MHC class II molecules. SDS-polyacrylamide gel electrophoresis (SDS-PAGE) of the affinity column eluate showed a single major band of approximately 50 kDa (FIG. 32, lanes 2 and 3). Soluble sc-IA$^d$/OVA (lanes 3, 5) and sc-IA$^d$/blank (lanes 2 and 4) protein were expressed by baculovirus-infected SF9 cells and purified by immunoaffinity chromatography using immobilized anti-IA$^d$ MK-D6 mAbs. The samples were analyzed with 12% SDS-PAGE gel and stained with Coomassie Blue (lanes 1–3). Molecular weight standards (lane 1) are indicated. The sc-IA$^d$ proteins were also transferred to nylon membrane and probed with mouse anti-sera specific to the OVA 323–339 peptide (Western blot, lanes 4 and 5). Covalently linked OVA peptide was detected using polyclonal antisera from the mice injected OVA 323–339 in Complete Freund's adjuvant H37Ra.

The sc/IA$^d$ were glycosylated and showed differences in mass due to the linked peptide. Western blot analysis confirmed the presence of the OVA 323–339 peptide in the sc-IA$^d$/OVA samples (FIG. 32, lane 5). Both the purified sc-IA$^d$/OVA and the sc-IA$^d$/blank proteins were also recognized by monoclonal antibodies (mAbs) (MK-D6, M5/114, AM5-32.1, 39-10-8, and 34-5-4). These mAbs recognize epitopes on native IA$^d$.

Figure 33:
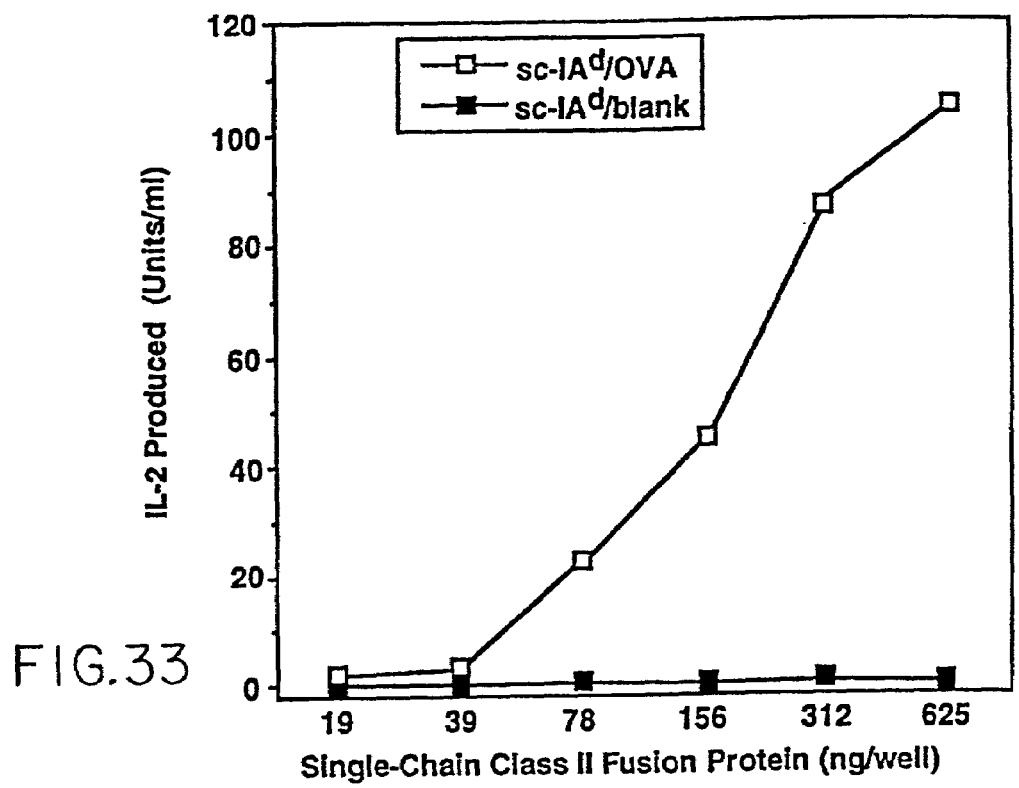
FIG. 33 is a graph showing that the sc-$IA^d$/OVA protein induces IL-2 expression in T cells.

FIG. 33 shows that the sc-IA$^d$/OVA molecule induced a dose-dependent release of IL-2 from D11.10 cells, confirming the functionality of the baculovirus produced molecules. D11.10 cells also produce IL-4 when stimulated by the sc-IA$^d$/OVA molecule. FIG. 33 also shows that DO11.10 cells did not respond to sc-IA$^d$/blank molecules.

It will be apparent that a single chain MHC fusion molecule can bear a covalently linked presenting peptide other than OVA 323–339. The choice of cells to be used to check for proper folding of the peptide within the fusion molecule will be guided by the particular presenting peptide employed. For example, the T cell hybridoma cell line GD12 recognizes the gD 246–261 peptide in the context of the IA$^d$ molecule [see, e.g., S. Grammer et al., *J. Immunol.*, 145: 2249 (1990)].

Figure 34C:
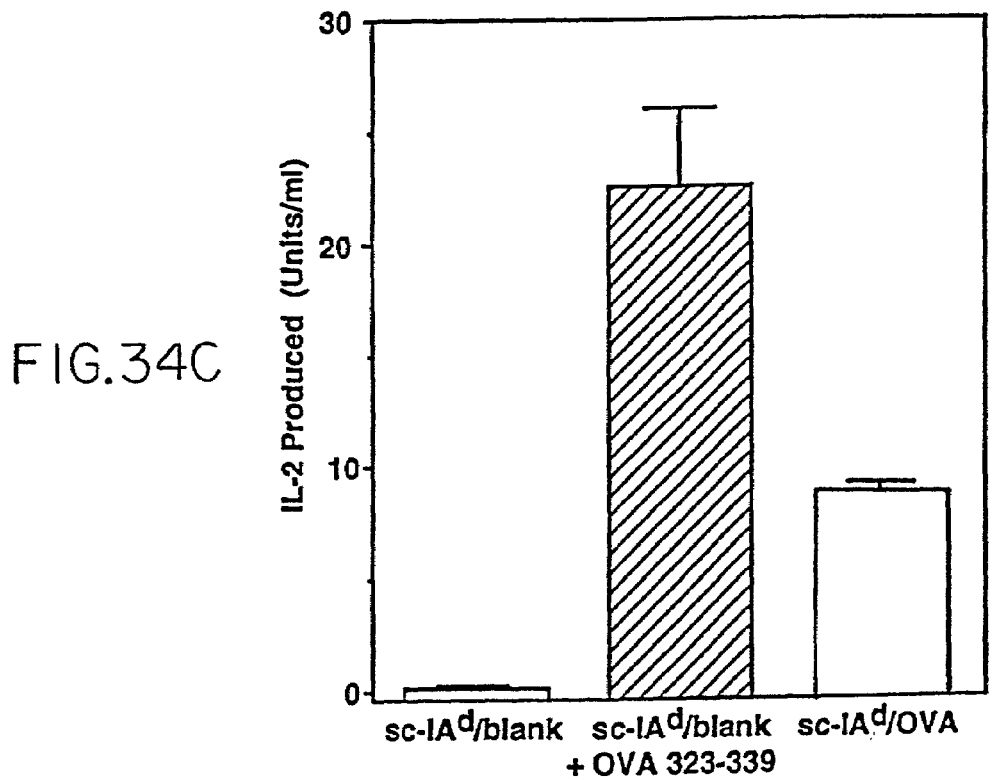
FIGS. 34A, 34B and 34C are graphs illustrating that sc-$IA^d$/OVA and sc-$IA^d$/gD induce IL-2 expression in T cells.
Figure 34A:
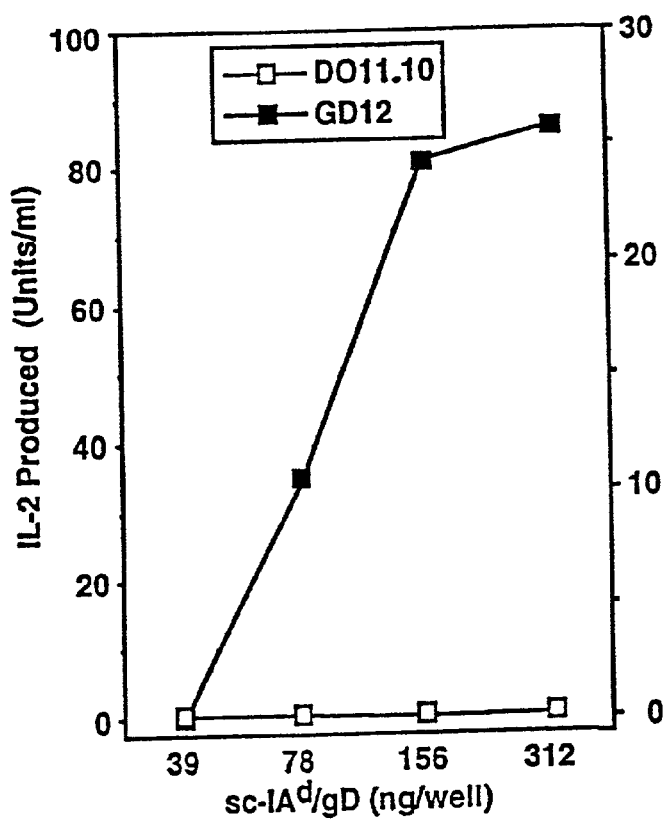
Figure 34B:
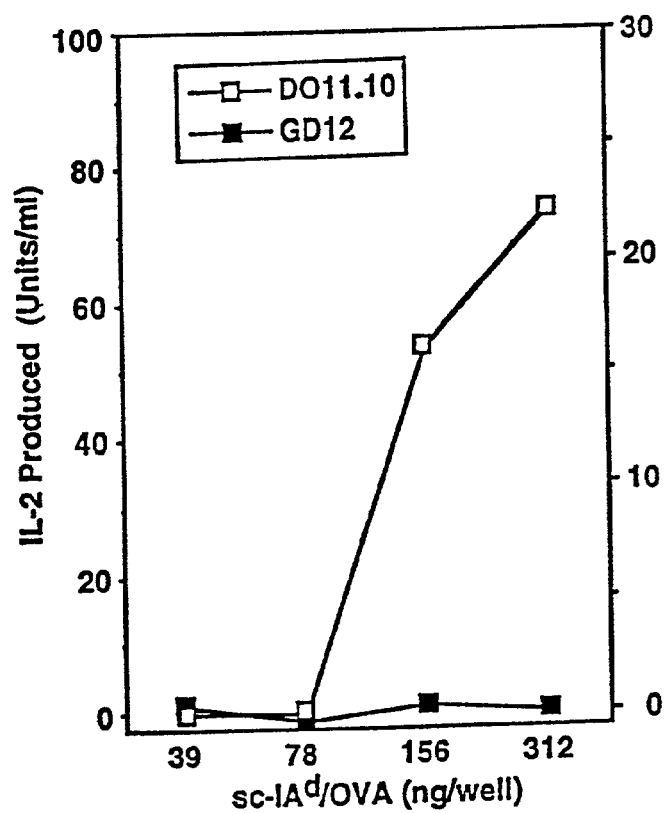

As an example, GD12 cells were used to demonstrate that the gD peptide folded properly in the sc-IA$^d$ fusion complex and that the sc-IA$^d$/gD molecule activated T cells. The T cell hybridoma GD12 responded well to immobilized sc-IA$^d$/gD but not to sc-IA$^d$/OVA (FIG. 34A). Conversely, the DO11.10 cell line responded well with the sc-IA$^d$/OVA peptide, but not with sc-IA$^d$/gD (FIG. 34B). In these experiments, GD12 (specific to gD 246–261 and IA$^d$) or DO11.10 cells, were each added individually at 1×10$^5$ to wells coated with sc-IA$^d$/gD or sc/IA$^d$/OVA. The plates were incubated overnight and the amount of supernatant IL-2 was determined by ELISA.

EXAMPLE 28

Construction and Use of Empty sc-IA$^d$ Fusion Complexes

It was found that the sc-IA$^d$/blank molecule could be loaded with the OVA 323–339 presenting peptide. As shown in FIG. 34C, the loaded fusion molecule unexpectedly activated DO11.10 cells to a greater extent than the sc-IA$^d$/OVA fusion molecule. FIG. 34C is explained as follows:

FIG. 34C. Immobilized sc-IA$^d$/blank protein (500 ng/well) was incubated for 20 hours at 37° C. in the absence (left bar) or presence (middle bar) of a 50 molar excess of OVA 323–339 peptide in citrate buffer, pH 5.0. Immobilized sc-IA$^d$/OVA protein (500 ng/well) was incubated without peptide to determine the effects of the binding conditions on antigen presentation (right bar). After removal of unbound peptide, all the sc-IA$^d$ molecules were tested for their ability to activate DO11.10 cells.

It will be apparent that other soluble empty single chain MHC class II complexes of the invention can effectively modulate immune system responses, e.g., T cell induction and cytokine release. For example, DNA encoding a soluble MHC/Ig molecule (Example 4) can be made, via standard methods, without the linked OVA peptide to produce DNA encoding the corresponding empty MHC/Ig molecule. The empty molecule can be suitably expressed and loaded with a presenting peptide, e.g., an OVA peptide described herein. The ability of the loaded soluble MHC/Ig molecule to induce T cells can be observed in T cell activation assays described herein.

EXAMPLE 29

Figure 35:
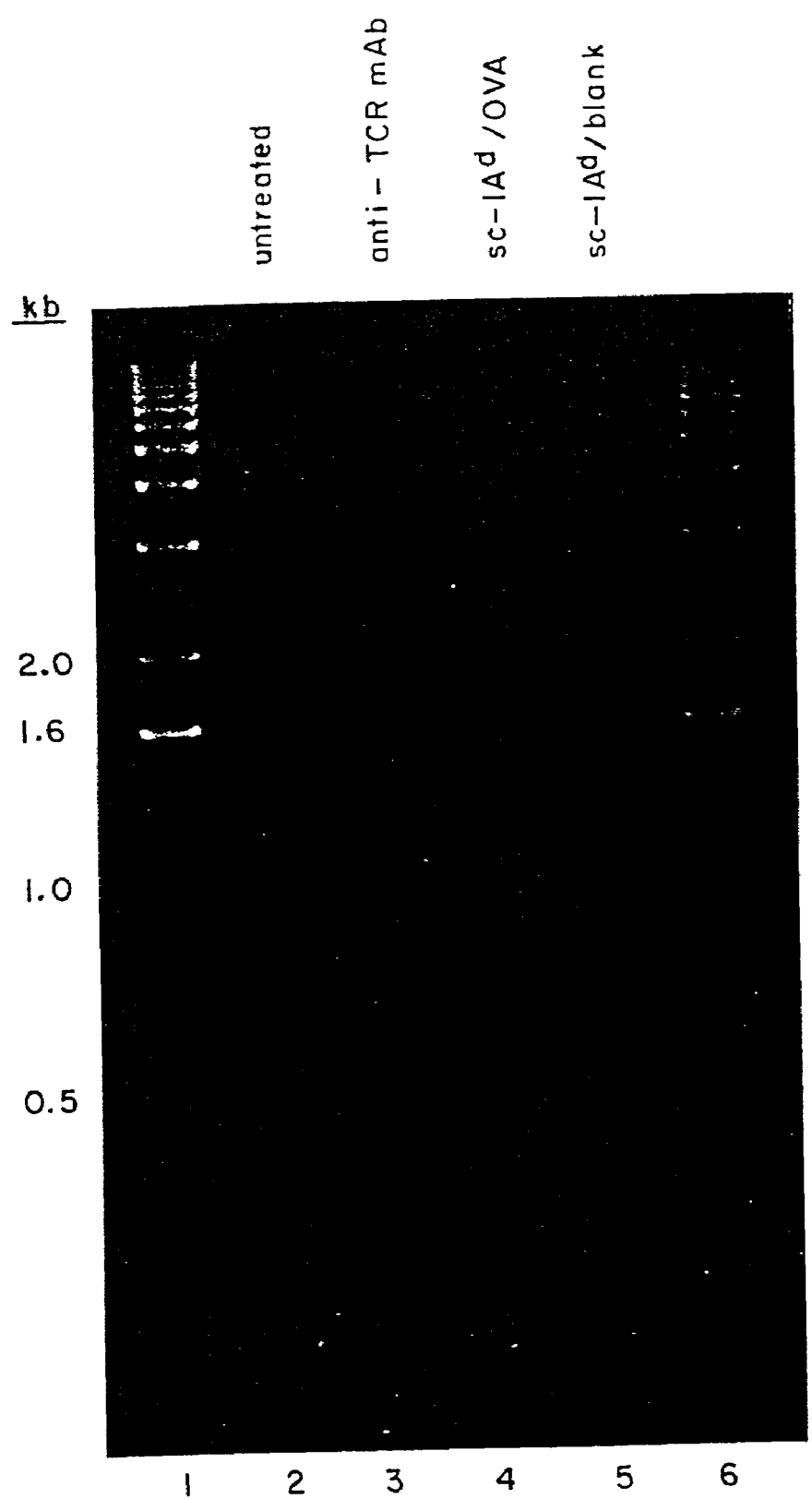
FIG. 35 is a photograph of an ethidium bromide stained gel showing that anti-T cell receptor antibody (anti-TCR mAb) or sc-$IA^d$/OVA can induce T cell apoptosis. The nucleosome ladder in lanes 3 and 4 is a hallmark of apoptosis.

Soluble sc-IA$^d$/peptide Fusion Complexes Activate T Cells and Induce Apoptosis DO11.10 cells were used to test the ability of soluble sc-IA$^d$ fusion molecules to induce T cell apoptosis. After an overnight incubation with the soluble sc-IA$^d$/OVA molecule described above, DO11.10 cells showed marked changes in cell morphology, including nuclear condensation, the appearance of apoptotic bodies and degradation of the DNA into oligonucleosomal bands (FIG. 35, lane 4). These changes are characteristic of apoptosis [P. Walker et al., *BioTechniques*, 15:1032 (1993)]. Similar effects were observed in cells incubated with anti-TCR and anti-CD3 mAbs, whereas no changes in cell morphology or DNA degradation were observed in the cell incubated with immobilized sc-IA$^d$/blank (compare lanes 3 and 5 of FIG. 35).

FIG. 35 is explained as follows: DO11.10 cells were incubated in untreated wells or in wells coated with 100 ng/well anti-TCR mAb (H57-597, PharMingen), or 250 ng/well sc-IA$^d$ molecules. After 24 hours, the cells (1.2× 10$^6$/sample) were harvested and Triton X-100 soluble/ DNA was isolated [P. Walker et al., *Bio Techniques*, 15:1032 (1993)]. Samples were analyzed by 2% agarose gel electrophoresis and stained with ethidium bromide to detect chromosomal DNA laddering. Lane 2 is from untreated DO11.10 cells. Lanes 1 and 6 show DNA molecular weight markers.

EXAMPLE 30

Soluble sc-IA$^d$ MHC Fusion Molecules Suppress T Cell Expansion in vivo

At least two signals are needed for the activation of T cells, e.g., as in the proliferation of T cells. A single signal delivered to the T cell via the TCR and MHC class II/peptide fusion complex will kill or anergize the T cells. It was found that soluble sc-IA$^d$/OVA fusion molecules selectively kill antigen specific T cells in vivo in the absence of added co-stimulatory signals. These results indicate that single chain MHC molecules, particularly single chain MHC class II molecules, are well suited for suppressing immune system function in vivo. The results also indicate that immune system function can be induced when a single chain MHC molecule is co-expressed in cells with a co-stimulatory signal or, alternatively, when a single chain MHC molecule is expressed in cells where a suitable co-stimulatory signal already exists in the cells.

To suppress the clonal expansion of T cells in vivo, we used the mammalian expression vector pEE13 which can be modified to carry the sc-IA$^d$/OVA fusion gene by standard methods. Transcription of the sc-IA$^d$/OVA gene was driven by the CMV promoter of the expression vector. BALB/c mice were injected with 100 μg of plasmid DNA (1 mg/ml in PBS) intramuscularly (IM) in the hind legs. Injections were repeated two more times 14 and 28 days later. A control group was injected IM with saline on week 0 and 100 μg of a plasmid encoding sc-IA$^d$/blank on weeks 2 and 4.

Both groups were then injected subcutaneously at the base of the tail with OVA 323–339 peptide (100 μg/mouse in complete Freunds H37Ra adjuvant) at 23 and 30 days after the final DNA inoculation. One week later, the mice were killed and the inguinal and paraaortic lymph nodes collected. A lymph node cell suspension was prepared and depleted of antigen presenting cells by incubation on nylon wool and Sephadex G-10 columns, and the resulting purified T cell populations were incubated with APCs pulsed with the OVA 323–339 peptide. Splenic B cells from a BALB/c mouse served as APCs. These cells were fixed with mitomycin C (50 to 100 μg/ml in s suspension of 4×10$^6$ spleenocytes/ml) to inhibit proliferation of the B cells, washed extensively and added to purified T cells (2×10$^5$ cells/well) at 2×10$^5$ cells/well with the OVA 323–339 peptide (0 to 50 μg/well). The cells were allowed to proliferate in 96 well round bottom microtiter plates at 37 C, 5% CO$_2$ for 4 days. At this time, wells were pulsed with MTS (40 μl/well) (Promega) for 4 to 6 hours prior to termination of cultures. Incorporation of MTS was determined by measuring absorbance at 490 and is a measure of T cell proliferation.

FIG. 36A and FIG. 36B show the results of T cell proliferation assays using cells from injected and control mice. In FIG. 36A, the T cells were isolated from mice receiving IM injections of the sc-IA$^d$/blank plasmid (and saline). In FIG. 36B, mice received IM injections of the sc-IA$^d$/OVA plasmid. Mice were challenged twice with the OVA peptide and T cells were isolated from the lymph nodes one week later. OVA-specific T cell proliferation assays were carried out as described above. T cells isolated from mice injected with the sc-IA$^d$/OVA plasmid showed a significant reduction in the amount of OVA-specific proliferation compared those isolated from the control group injected with the sc-IA$^d$/blank plasmid. These results show that expression of soluble sc-IA$^d$/OVA molecules suppresses the clonal expansion of antigen-specific T cells in vivo.

Administration of soluble single chain MHC molecules (e.g., soluble sc-MHC class II peptide fusion complexes or soluble loaded sc-MHC class II complexes) or DNA expression vectors coding for these molecules will alleviate immune disorders in mammals, particularly humans, which involve the undesirable presence or expansion of antigen specific T cells. For example, soluble single chain MHC molecules (e.g., soluble sc-MHC class II peptide fusion complexes) or DNA expression vectors coding for these molecules can be admixed with a pharmaceutically acceptable carrier substance, e.g., physiological saline, and administered to a mammal, e.g., a human, suffering from or likely to suffer from an immune disorder which involves the undesirable presence or expansion of antigen specific T cells. Examples of other pharmaceutically acceptable carriers are well known (see e.g., *Remington's Pharmaceutical Sciences*, Mack Pub. Co., Easton, Pa., 1980). One particular mode of administration is intramuscular, although other modes may be used (e.g., oral, nasal, intravenous, parentaeral, or transdermal), which mode will depend upon the condition being treated and the general status of the animal and will be apparent to those skilled in the art. The dosage of the soluble single chain MHC fusion molecule will also vary, depending on such factors as the type and severity of the immune disease, but will generally be at a dosage sufficient to suppress the in vivo expansion of immune cells such as antigen specific T cells. A typical dosage range would be 1 ng to 10 mg of the soluble MHC class II molecule per kg body weight. Treatment may be repeated as deemed necessary, e.g., each day.

It will also be understood that cells bearing all or most MHC molecules of the invention can be adminstered to a mammal at a dosage sufficient to suppress or induce T cells. T cell activity can be detected by assays described herein.

It will be apparent that other soluble loaded single chain MHC molecules can be used to treat the undesirable presence or expansion of antigen specific T cells in vivo. For example, a presenting peptide of about 6 to 30 amino acids (inclusive) can be mixed in at least an equimolar ratio with a suitable soluble empty single chain MHC molecule to form the corresponding loaded molecule. The loaded molecule can then be admixed with a pharmaceutically acceptable carrier and administered to a mammal, e.g., a human, to treat an immune system disorder as described above.

EXAMPLE 31

Construction and Use of Transgenic Mice Bearing a Single Chain MHC Complex

A transgenic mouse can be constructed which bears one or more genes encoding any of the single chain MHC molecules of the invention. As examples of preferred single chain MHC molecules, single chain MHC class II peptide fusion molecules with a single transmembrane domain in the α or β chain (or portion thereof), soluble single chain MHC class II peptide fusion molecules, and single chain MHC class II molecules bearing one or more hydrophilic amino acids to increase solubility (e.g., the 6×His tag, supra) can each be used to construct transgenic mouse strains. Such mouse strains will serve as valuable in vivo models for, e.g., the suppression or expansion of antigen specific T cells. In addition, cells derived from such transgenic animals can be used to establish an immortal cell line that retains at least some of its differentiated characteristics while proliferating indefinitely in vivo.

A transgenic mouse can be made which bears a soluble single chain MHC class II peptide fusion molecule. For example, DNA constructs encoding soluble sc-IA$^d$/OVA or sc-IA$^d$/gD molecules, supra, can be linked to a selected cell or tissue specific promoter and/or enhancer and the resultant hybrid gene introduced, by standard methods (e.g., as described by Leder et al., U.S. Pat. No. 4,736,866, Wagner et al. U.S. Pat. No. 4,873,191, and Ohashi in *The Immunologist*, 2, 87–92, herein incorporated by reference), into an animal embryo at an early developmental stage (e.g., the fertilized oocyte stage), to produce a transgenic animal which expresses elevated levels of the desired activity in selected cells or tissues (e.g., T cells or neuroectodermal, endothelial or angiogenic tissues).

Transgene-positive animals (founder animals) will be mated with non-transgenic animals and the progeny (f1 animals) are screened for transmission of the transgene DNA. The f1 transgene-positive animals are hemizygous for the transgene DNA and homozygous transgenic animals can be generated by suitable sibling matings. Each founder animal and its transgenic progeny are unique in comparison to other transgenci mice established with same transgene. Integration of the transgene DNA into mouse genomic DNA is random and the site of integration can profoundly effect the levels, and the tissue and developmental patterns of transgene expression. Consequently, a number of transgenic mouse lines will be established and screened for selection of those animals with the most appropriate expression patterns.

Transgenic lines are evaluated by the levels of transgene expression and the T cell assays described herein. Expression at the RNA level is determined initially to identify and quantitate expression-positive animals. Standard techniques for RNA analysis are employed and include PCR amplification assays using oligonucleotide primers designed to amplify only transgene RNA templates and solution hybridization assays using transgene-specific probes (see, e.g., Ausbel et al. supra). The RNA-positive animals are then analyzed for protein expression by Western immunoblot using, e.g, IA$^d$ or OVA specific antibodies (see, e.g., Ausubel et al. supra). In addition, in situ hybridization and immunocytochemistry can be suitably employed using transgene-specific nucleotide probes and antibodies, respectively, to localize sites of expression within transgenic tissue.

In accordance with the methods described herein it will be possible to reduce the activity of OVA or gD specific T cells in selected transgenic mouse strains. The form of DNA utilized can be one which encodes an MHC molecule similar to the animal species used, or it can encode the homolog of a different species (e.g., human). The level of T cells in the transgenic animal can be evaluated by T cell assays described herein.

It will be understood that by "transgenee" is meant DNA which is entirely heterologous (i.e., foreign) to the transgenic mouse, and which is inserted into the mouse genome.

It will also be understood that by "promoter" is meant a segment of DNA to which a transcriptional enzyme complex binds prior to initiating transcription of the gene. For construction of transgenic mice, preferred promoters include the IA$^d$ promoter and the rat insulin promter described by Ohashi et al. in Cell 65, 305–317 (1991).

The invention has been described with reference to preferred embodiments thereof. However, it will be appreciated that those skilled in the art, upon consideration of this disclosure, may make modifications and improvements within the spirit and scope of the invention.

What is claimed is:

1. A single chain class II MHC molecule comprising:
a peptide-binding groove and
covalently linked in sequence: 1) a class II β chain, 2) a single chain linker, and 3) a class II α chain,
wherein the chain of both 1) and 3) lack a transmembrane domain; and further wherein the single chain class II MHC molecule is empty.

2. The MHC molecule of claim 1, wherein the MHC molecule is soluble.

3. The MHC molecule of claim 1, wherein the chain of 1) comprises a β1 domain and the chain of 3) comprises an α1 domain.

4. The MHC molecule of claim 1, wherein the single chain linker is linked between the carboxyl terminus of the β chain and the amino terminus of the α chain.

5. The MHC molecule of claim 1, wherein the β and α chains are each independently selected from the group consisting of IE, IA, DR, DQ and DP proteins.

6. The MHC molecule of claim 1 wherein the MHC molecule is modified to carry a detectable tag.

7. A multivalent MHC complex comprising two or more linked MHC molecules of claim 1.

8. A MHC complex of claim 7 wherein the MHC molecules are linked to immunoglobulin domains.

9. A MHC complex of claim 7 wherein the MHC complex is modified to carry a detectable tag.

10. A single chain MHC class II-peptide complex comprising:
a peptide-binding groove;
covalently linked in sequence: 1) a class II β chain, 2) a single chain linker, and 3) a class II α chain, wherein the chain of both 1) and 3) lack a transmembrane domain; and
a presenting peptide being covalently linked to the MHC molecule and non-covalently bound to the peptide binding groove of the MHC molecule.

11. The MHC complex of claim 10, wherein the complex is soluble.

12. The MHC complex of claim 10, wherein the chains of 1) and 3) comprise a β1 domain and α1 domain, respectively.

13. The MHC complex of claim 10, wherein the MHC class II molecule comprises the presenting peptide covalently linked to the β chain.

14. The MHC complex of claim 10, wherein a presenting peptide linker sequence is interposed between the presenting peptide and the MHC molecule.

15. The MHC complex of claim 10, wherein the β and α chains are each independently selected from the group consisting of IE, IA, DR, DQ and DP proteins.

16. The MHC complex of claim 10, wherein the MHC molecule is modified to carry a detectable tag.

17. A multivalent MHC complex comprising two or more linked MHC molecules of claim 10.

18. The MHC complex of claim 17, wherein the MHC molecules are linked to immunoglobulin domains.

19. The MHC complex of claim 17, wherein the MHC complex is modified to carry a detectable tag.

20. A loaded single chain MHC class II-peptide complex comprising:
a peptide-binding groove;
covalently linked in sequence: 1) a class II β chain, 2) a single chain linker, and 3) a class II α chain, wherein the chain of both 1) and 3) lack a transmembrane domain; and
a presenting peptide being non-covalently linked to the MHC molecule and non-covalently bound to the peptide binding groove of the MHC molecule,
wherein the loaded single chain MHC class II-peptide complex can be recognized by a CD4+ T cell.

21. The MHC complex of claim 20, wherein the MHC molecule is soluble.

22. The MHC complex of claim 20, wherein the chain of 1) comprises a β1 domain and the chain of 3) comprises an α1 domain.

23. The MHC complex of claim 20, wherein the single chain linker is linked between the carboxyl terminus of the β chain and the amino terminus of the α chain.

24. The MHC complex of claim 20, wherein the β and α chains are each independently selected from the group consisting of IE, IA, DR, DQ and DP proteins.

25. The MHC complex of claim 20 wherein the MHC molecule is modified to carry a detectable tag.

26. A multivalent MHC complex comprising two or more linked MHC complexes of claim 20.

27. The multivalent MHC complex of claim 26 wherein the MHC complexes are linked to immunoglobulin domains.

28. A multivalent MHC complex of claim 26 wherein the MHC complex is modified to carry a detectable tag.

* * * * *

SEQUENCE LISTING (1) GENERAL INFORMATION:

(iii) NUMBER OF SEQUENCES: 124

(2) INFORMATION FOR SEQ ID NO: 1:

(i) SEQUENCE CHARACTERISTICS:
      (A) LENGTH: 10 amino acids
      (B) TYPE: amino acid
      (C) STRANDEDNESS: unknown
      (D) TOPOLOGY: unknown (xi) SEQUENCE DESCRIPTION: SEQ ID NO: 1:

Ala Ser Gly Gly Gly Gly Ser Gly Gly Gly
1             5                10

(2) INFORMATION FOR SEQ ID NO: 2:

(i) SEQUENCE CHARACTERISTICS:
      (A) LENGTH: 8 base pairs
      (B) TYPE: nucleic acid
      (C) STRANDEDNESS: unknown
      (D) TOPOLOGY: unknown (xi) SEQUENCE DESCRIPTION: SEQ ID NO: 2:

CCACCATG                                                                             8

(2) INFORMATION FOR SEQ ID NO: 3:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (xi) SEQUENCE DESCRIPTION: SEQ ID NO: 3:

Ser Ile Ser Gln Ala Val His Ala Ala His Ala Glu Ile Asn Glu Al
1               5                   10                  15

Gly Arg (2) INFORMATION FOR SEQ ID NO: 4:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (xi) SEQUENCE DESCRIPTION: SEQ ID NO: 4:

Ser Ile Ser Gln Ala Val His Ala Ala Arg Ala Glu Ile Asn Glu Al
1               5                   10                  15

Gly Arg (2) INFORMATION FOR SEQ ID NO: 5:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (xi) SEQUENCE DESCRIPTION: SEQ ID NO: 5:

Ser Ile Ser Gln Ala Val His Ala Ala His Tyr Glu Ile Asn Glu Al
1               5                   10                  15

Gly Arg (2) INFORMATION FOR SEQ ID NO: 6:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 6:

Asn Leu Cys Asn Ile Pro Cys Ser Ala Leu Leu Ser Ser
1               5                   10

(2) INFORMATION FOR SEQ ID NO: 7:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (xi) SEQUENCE DESCRIPTION: SEQ ID NO: 7:

Gln Ile Ser Val Gln Pro Ala Phe Ser Val Gln
1               5                   10

(2) INFORMATION FOR SEQ ID NO: 8:

(i) SEQUENCE CHARACTERISTICS:

```
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 8:

Pro Lys Tyr Val Lys Gln Asn Thr Leu Lys Leu Ala Thr
1               5                   10

(2) INFORMATION FOR SEQ ID NO: 9:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 9:

His Tyr Gly Ser Leu Pro Gln Lys Ser Gln His Gly Arg
1               5                   10

(2) INFORMATION FOR SEQ ID NO: 10:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (xi) SEQUENCE DESCRIPTION: SEQ ID NO: 10:

His Ser Leu Gly Lys Trp Leu Gly His Pro Asp Lys Phe
1               5                   10

(2) INFORMATION FOR SEQ ID NO: 11:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (xi) SEQUENCE DESCRIPTION: SEQ ID NO: 11:

Met Ala Ser Gln Lys Arg Pro Ser Gln Arg Ser Lys Tyr Leu
1               5                   10

(2) INFORMATION FOR SEQ ID NO: 12:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (xi) SEQUENCE DESCRIPTION: SEQ ID NO: 12:

GCAGAAGAAT TCGAGCTCGG CCCCCAG                                27

(2) INFORMATION FOR SEQ ID NO: 13:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO: 13:

GATGATATCA GAGAGAAATA CATACTAACA CAC                         33
```

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (xi) SEQUENCE DESCRIPTION: SEQ ID NO: 14:

CGGAAGAAAG AGACTTCGGC CGCTACTTAC                                                      30

(2) INFORMATION FOR SEQ ID NO: 15:

(i) SEQUENCE CHARACTERISTICS:
        (A) LENGTH: 47 base pairs
        (B) TYPE: nucleic acid
        (C) STRANDEDNESS: unknown
        (D) TOPOLOGY: unknown (xi) SEQUENCE DESCRIPTION: SEQ ID NO: 15:

GTGTGTTAGT ATGTATTTCT CTCTGATATC TTCAGCTTCC AGCAGTG                          47

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (xi) SEQUENCE DESCRIPTION: SEQ ID NO: 16:

TCTTCTAGAA GACCACGCTA C                                                                    21

(2) INFORMATION FOR SEQ ID NO: 17:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 17:

GATGATATCC GGCCGAAGTC TCTTTCTTCC GTTGTC                                  36

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (xi) SEQUENCE DESCRIPTION: SEQ ID NO: 18:

CAGGGTTATC AACACCCTGA AAAC                                                    24

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (xi) SEQUENCE DESCRIPTION: SEQ ID NO: 19:

GTCACAGTTA TCCACTCTGT C                                                                    21

(2) INFORMATION FOR SEQ ID NO: 20:

(i) SEQUENCE CHARACTERISTICS:
            (A) LENGTH: 38 base pairs
            (B) TYPE: nucleic acid
            (C) STRANDEDNESS: unknown
            (D) TOPOLOGY: unknown (xi) SEQUENCE DESCRIPTION: SEQ ID NO: 20:

CCGTCTCCTC AGGTACGGCC GGCCTCTCCA GGTCTTCG                                    38

(2) INFORMATION FOR SEQ ID NO: 21:

(i) SEQUENCE CHARACTERISTICS:
            (A) LENGTH: 39 base pairs
            (B) TYPE: nucleic acid
            (C) STRANDEDNESS: unknown
            (D) TOPOLOGY: unknown (xi) SEQUENCE DESCRIPTION: SEQ ID NO: 21:

CACAGTTATC CACTCTGTCT TTGATATCAC AGGTGTCCT                                   39

(2) INFORMATION FOR SEQ ID NO: 22:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (xi) SEQUENCE DESCRIPTION: SEQ ID NO: 22:

His Ser Leu Gly Lys Tyr Leu Gly His Pro Asp Lys Phe
1               5                   10

(2) INFORMATION FOR SEQ ID NO: 23:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (xi) SEQUENCE DESCRIPTION: SEQ ID NO: 23:

His Ser Leu Gly Lys Leu Leu Gly His Pro Asp Lys Phe
1               5                   10

(2) INFORMATION FOR SEQ ID NO: 24:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (xi) SEQUENCE DESCRIPTION: SEQ ID NO: 24:

Ser Ile Ser Gln Ala Val His Ala Ala His Ala Glu Ile Asn Glu Ar
1               5                   10                  15
Arg (2) INFORMATION FOR SEQ ID NO: 25:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (xi) SEQUENCE DESCRIPTION: SEQ ID NO: 25:

```
Asn Leu Cys Asn Ile Pro Ser Cys Ala Leu Leu Ser Ser
1               5                   10
```

(2) INFORMATION FOR SEQ ID NO: 26:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 26:

GGGGGGGCCA TGGCCGAAGA CGACATTGAG GCCGAC                        36

(2) INFORMATION FOR SEQ ID NO: 27:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO: 27:

GCGGCGACTA GTCCAGTGTT TCAGAACCGG CTC                           33

(2) INFORMATION FOR SEQ ID NO: 28:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (xi) SEQUENCE DESCRIPTION: SEQ ID NO: 28:

CCCCCCGATA TCTCAGCTTC AGCAGTGGA GACGACATTG AG               42

(2) INFORMATION FOR SEQ ID NO: 29:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (xi) SEQUENCE DESCRIPTION: SEQ ID NO: 29:

CCCCCCCGGC CGCTACTTAC GTTTCCAGTG TTTCAGAACC GG               42

(2) INFORMATION FOR SEQ ID NO: 30:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (xi) SEQUENCE DESCRIPTION: SEQ ID NO: 30:

GGGGGGGCCA TGGCCGGAAA CTCCGAAAGG CATTTCG                    37

(2) INFORMATION FOR SEQ ID NO: 31:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (xi) SEQUENCE DESCRIPTION: SEQ ID NO: 31:

GCGGCGACTA GTCCACTCCA CAGTGATGGG GC  32

(2) INFORMATION FOR SEQ ID NO: 32:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 32

CCCCCCCGGC CGTACCTGAG GACCACTCCA CAGTGATGG  39

(2) INFORMATION FOR SEQ ID NO: 33:

(i) SEQUENCE CHARACTERISTICS:
        (A) LENGTH: 78 base pairs
        (B) TYPE: nucleic acid
        (C) STRANDEDNESS: unknown
        (D) TOPOLOGY: unknown (xi) SEQUENCE DESCRIPTION: SEQ ID NO: 33:

CCCCCCGATA TCACAGGTGT CTTAAGTGCT AGCGGAGGGG GCGGAAGCGG CGGAGGGGGA  60

AACTCCGAAA GGCATTTC  78

(2) INFORMATION FOR SEQ ID NO: 34:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (xi) SEQUENCE DESCRIPTION: SEQ ID NO: 34:

AGCTTGATAT CACAGGTGTC TTAAGTGGAG  30

(2) INFORMATION FOR SEQ ID NO: 35:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (xi) SEQUENCE DESCRIPTION: SEQ ID NO: 35:

CTAGCTCCAC TTAAGACACC TGTGATATCA  30

(2) INFORMATION FOR SEQ ID NO: 36:

(i) SEQUENCE CHARACTERISTICS:
        (A) LENGTH: 34 base pairs
        (B) TYPE: nucleic acid
        (C) STRANDEDNESS: unknown
        (D) TOPOLOGY: unknown (xi) SEQUENCE DESCRIPTION: SEQ ID NO: 36:

TCCGGAGGCG GCGGAGACTC CGAAAGGCAT TTCG  34

(2) INFORMATION FOR SEQ ID NO: 37:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 37:

CGATCGCTAG CGGCGGTGGT GGTTCCGGTG GCGGCGGAG                                39

(2) INFORMATION FOR SEQ ID NO: 38:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (xi) SEQUENCE DESCRIPTION: SEQ ID NO: 38:

CCCCCCAGGC TTCCCGGGCC ACCATGCCGT GCAGCAGAGC TC                            42

(2) INFORMATION FOR SEQ ID NO: 39:

(i) SEQUENCE CHARACTERISTICS:
        (A) LENGTH: 40 base pairs
        (B) TYPE: nucleic acid
        (C) STRANDEDNESS: unknown
        (D) TOPOLOGY: unknown (xi) SEQUENCE DESCRIPTION: SEQ ID NO: 39:

CCCCCCGAGC TCGAATTCTC ATAAAGGCCC TGGGTGTCTG                               40

(2) INFORMATION FOR SEQ ID NO: 40:

(i) SEQUENCE CHARACTERISTICS:
        (A) LENGTH: 44 base pairs
        (B) TYPE: nucleic acid
        (C) STRANDEDNESS: unknown
        (D) TOPOLOGY: unknown (xi) SEQUENCE DESCRIPTION: SEQ ID NO: 40:

CCCCCCAAGC TTCCCGGGCC ACCATGGCTC TGCAGATCCC CAGC                          44

(2) INFORMATION FOR SEQ ID NO: 41:

(i) SEQUENCE CHARACTERISTICS:
        (A) LENGTH: 34 base pairs
        (B) TYPE: nucleic acid
        (C) STRANDEDNESS: unknown
        (D) TOPOLOGY: unknown (xi) SEQUENCE DESCRIPTION: SEQ ID NO: 41:

CCCCCCACTT AAGGTCCTTG GGCTGCTCAG CACC                                     34

(2) INFORMATION FOR SEQ ID NO: 42:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (xi) SEQUENCE DESCRIPTION: SEQ ID NO: 42:

CCCCCCCCAT CACTGTGGAG TGGAGGG                                             27

(2) INFORMATION FOR SEQ ID NO: 43:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 43:

```
CCCCCCGAGC TCGAATTCTC ACTGCAGGAG CCCTGCTGG                                    39

(2) INFORMATION FOR SEQ ID NO: 44:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 44:

GGGGGGAAGC TTATGATCAA AGAAGAACAT GTGATCATC                                    39

(2) INFORMATION FOR SEQ ID NO: 45:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 45:

GCGGCGGGAT CCGTTCTCTG TAGTCTCTGG GAGAGG                                       36

(2) INFORMATION FOR SEQ ID NO: 46:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 46:

GGGGGGAAGC TTATGGGGGA CACCCGACCA CGTTTCTTGT GGCAGC                            46

(2) INFORMATION FOR SEQ ID NO: 47:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 47:

GGGGGGGCCA TGGCCATCAA AGAAGAACAT GTGATCATC                                    39

(2) INFORMATION FOR SEQ ID NO: 48:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 48:

GCGGCGACTA GTGTTCTCTG TAGTCTCTGG GAGAGG                                       36

(2) INFORMATION FOR SEQ ID NO: 49:

(i) SEQUENCE CHARACTERISTICS:
        (A) LENGTH: 57 base pairs
        (B) TYPE: nucleic acid
        (C) STRANDEDNESS: unknown
        (D) TOPOLOGY: unknown (xi) SEQUENCE DESCRIPTION: SEQ ID NO: 49:

GGGGGGAAGC TTGATATCTC AGCTTCCAGC AGTAGTATCA AAGAAGAACA TGTGATC               57
```

(2) INFORMATION FOR SEQ ID NO: 50:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (xi) SEQUENCE DESCRIPTION: SEQ ID NO: 50:

GGGGGGCGGC CGCTACTTAC GTTTCTCTGG GAGAGGGCTT GGAGC                45

(2) INFORMATION FOR SEQ ID NO: 51:

(i) SEQUENCE CHARACTERISTICS:
        (A) LENGTH: 35 base pairs
        (B) TYPE: nucleic acid
        (C) STRANDEDNESS: unknown
        (D) TOPOLOGY: unknown (xi) SEQUENCE DESCRIPTION: SEQ ID NO: 51:

GCGGCGGGAT CCCTTGCTCT GTGCAGATTC AGACC                           35

(2) INFORMATION FOR SEQ ID NO: 52:

(i) SEQUENCE CHARACTERISTICS:
        (A) LENGTH: 51 base pairs
        (B) TYPE: nucleic acid
        (C) STRANDEDNESS: unknown
        (D) TOPOLOGY: unknown (xi) SEQUENCE DESCRIPTION: SEQ ID NO: 52:

GGGGGGGCCA TGGCCGGATC CGCTAGCGGG GACACCCGAC CACGTTTCTT G         51

(2) INFORMATION FOR SEQ ID NO: 53:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 53:

GCGGCGACTA GTCTTGCTCT GTGCAGATTC AGACCG                          36

(2) INFORMATION FOR SEQ ID NO: 54:

(i) SEQUENCE CHARACTERISTICS:
        (A) LENGTH: 56 base pairs
        (B) TYPE: nucleic acid
        (C) STRANDEDNESS: unknown
        (D) TOPOLOGY: unknown (xi) SEQUENCE DESCRIPTION: SEQ ID NO: 54:

GTTGTCTTAA GTGGAGCTAG CGGAGGGGGC GGGTCCGGAG GTGGTGGGGA CACCCG    56

(2) INFORMATION FOR SEQ ID NO: 55:

(i) SEQUENCE CHARACTERISTICS:
        (A) LENGTH: 57 base pairs
        (B) TYPE: nucleic acid
        (C) STRANDEDNESS: unknown
        (D) TOPOLOGY: unknown (xi) SEQUENCE DESCRIPTION: SEQ ID NO: 55:

GAAATGACAT TCAAACTTCA GCTGCCACAA GAAACGTGGT CGGGTGTCCC CACCACC   57

(2) INFORMATION FOR SEQ ID NO: 56:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (xi) SEQUENCE DESCRIPTION: SEQ ID NO: 56:

GGGGGGCGGC CGTACCTGAG GACTTGCTCT GTGCAGATTC AG                  42

(2) INFORMATION FOR SEQ ID NO: 57:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 57:

TTAAGTATCT CTCAGGCTGT TCACGCTGCT CACGCTGAAA TCAACGAAGC TGGTCGTG       58

(2) INFORMATION FOR SEQ ID NO: 58:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 58:

CTAGCACGAC CAGCTTCGTT GATTTCAGCC TGAGCAGCGT GAACAGCCTG AGAGATAC       58

(2) INFORMATION FOR SEQ ID NO: 59:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 59:

TTAAGTATCT CTCAGGCTGT TCACGCTGCT CGGGCTGAAA TCAACGAAGC TGGTCGTG       58

(2) INFORMATION FOR SEQ ID NO: 60:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 60:

CTAGCACGAC CAGCTTCGTT GATTTCAGCC CGAGCAGCGT GAACAGCCTG AGAGATAC       58

(2) INFORMATION FOR SEQ ID NO: 61:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 61:

TTAAGTATCT CTCAGGCTGT TCACGCTGCT CACTACGAAA TCAACGAAGC TGGTCGTG       58

(2) INFORMATION FOR SEQ ID NO: 62:

(i) SEQUENCE CHARACTERISTICS:
        (A) LENGTH: 58 base pairs
        (B) TYPE: nucleic acid
        (C) STRANDEDNESS: unknown
        (D) TOPOLOGY: unknown (xi) SEQUENCE DESCRIPTION: SEQ ID NO: 62:

CTAGCACGAC CAGCTTCGTT GATTTCATAG TGAGCAGCGT GAACAGCCTG AGAGATAC     58

(2) INFORMATION FOR SEQ ID NO: 63:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 63:

TTAAGTAACC TGTGCAACAT CCCCTGCAGC GCCCTGCTGA GCTCCG     46

(2) INFORMATION FOR SEQ ID NO: 64:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 64:

CTAGCGGAGC TCAGCAGGGC GCTGCAGGGG ATGTTGCACA GGTTAC     46

(2) INFORMATION FOR SEQ ID NO: 65:

(i) SEQUENCE CHARACTERISTICS:
        (A) LENGTH: 40 base pairs
        (B) TYPE: nucleic acid
        (C) STRANDEDNESS: unknown
        (D) TOPOLOGY: unknown (xi) SEQUENCE DESCRIPTION: SEQ ID NO: 65:

TTAAGTCAGA TCAGCGTGCA GCCCGCCTTC AGCGTGCAGG     40

(2) INFORMATION FOR SEQ ID NO: 66:

(i) SEQUENCE CHARACTERISTICS:
        (A) LENGTH: 40 base pairs
        (B) TYPE: nucleic acid
        (C) STRANDEDNESS: unknown
        (D) TOPOLOGY: unknown (xi) SEQUENCE DESCRIPTION: SEQ ID NO: 66:

CTAGCCTGCA CGCTGAAGGC GGGCTGAACG CTGATCTGAC     40

(2) INFORMATION FOR SEQ ID NO: 67:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 67:

TTAAGTCCCA AGTACGTGAA GCAGAACACC CTGAAGCTGG CCACCG     46

(2) INFORMATION FOR SEQ ID NO: 68:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 68:

CTAGCGGTGG CCAGCTTCAG GGTGTTCTGC TTCACGTACT TGGGAC                46

(2) INFORMATION FOR SEQ ID NO: 69:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 69:

TTAAGTCACT ATGGCTCCCT GCCGCAGAAG TCCCAGCACG GGCGCG                46

(2) INFORMATION FOR SEQ ID NO: 70:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 70:

CTAGCGCGCC CGTGCTGGGA CTTCTGCGGC AGGGAGCCAT AGTGAC                46

(2) INFORMATION FOR SEQ ID NO: 71:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 71:

TTACATCACT CCCTGGGCAA GTGGCTGGGC CACCCGGACA AGTTCG                46

(2) INFORMATION FOR SEQ ID NO: 72:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (xi) SEQUENCE DESCRIPTION: SEQ ID NO: 72:

CTAGCGAACT TGTTCGGGTG GCCCAGCCAC TTGCCCAGGG AGTGAC                46

(2) INFORMATION FOR SEQ ID NO: 73:

(i) SEQUENCE CHARACTERISTICS:
        (A) LENGTH: 49 base pairs
        (B) TYPE: nucleic acid
        (C) STRANDEDNESS: unknown
        (D) TOPOLOGY: unknown (xi) SEQUENCE DESCRIPTION: SEQ ID NO: 73:

TTAAGTATGG CATCCCAGAA GCGCCCGTCC CAGCGCTCCA AGTACCTGG             49

(2) INFORMATION FOR SEQ ID NO: 74:

(i) SEQUENCE CHARACTERISTICS:
        (A) LENGTH: 49 base pairs
        (B) TYPE: nucleic acid
        (C) STRANDEDNESS: unknown
        (D) TOPOLOGY: unknown (xi) SEQUENCE DESCRIPTION: SEQ ID NO: 74:

CTAGCCAGGT ACTTGGAGCG CTGGGACGGG CGCTTCTGGG ATGCCATAC        49

(2) INFORMATION FOR SEQ ID NO: 75:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (xi) SEQUENCE DESCRIPTION: SEQ ID NO: 75:

GATATCTCAG CTTCCAGCAG TGAAGACGAC ATTGAGGCCG ACCAC            45

(2) INFORMATION FOR SEQ ID NO: 76:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 76:

CCGGTTCTGA AACACTGGAA ACGTAAGTAG CGGCCG                      36

(2) INFORMATION FOR SEQ ID NO: 77:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (xi) SEQUENCE DESCRIPTION: SEQ ID NO: 77:

Ser Ser Ser Glu Asp Asp Ile Glu Ala Asp His
1               5                   10

(2) INFORMATION FOR SEQ ID NO: 78:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (xi) SEQUENCE DESCRIPTION: SEQ ID NO: 78:

Pro Val Leu Lys His Trp Lys Arg
1               5

(2) INFORMATION FOR SEQ ID NO: 79:

(i) SEQUENCE CHARACTERISTICS:
        (A) LENGTH: 72 base pairs
        (B) TYPE: nucleic acid
        (C) STRANDEDNESS: unknown
        (D) TOPOLOGY: unknown (xi) SEQUENCE DESCRIPTION: SEQ ID NO: 79:

GATATCACAG GTGTCTTAAG TGGAGCTAGC GGAGGGGCG GAAGCGGCGG AGGGGGAAAC    60

TCCGAAAGGC AT                                                       72

(2) INFORMATION FOR SEQ ID NO: 80:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO: 80:

ATCACTGTGG AGTGGTCCTC AGGTACGGCC GCC                     33

(2) INFORMATION FOR SEQ ID NO: 81:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (xi) SEQUENCE DESCRIPTION: SEQ ID NO: 81:

Val Leu Ser Gly Ala Ser Gly Gly Gly Ser Gly Gly Gly Gly As
1         5               10              15

Ser Glu Arg His
        20

(2) INFORMATION FOR SEQ ID NO: 82:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (xi) SEQUENCE DESCRIPTION: SEQ ID NO: 82:

Ile Thr Val Glu Trp Ser Ser
1             5

(2) INFORMATION FOR SEQ ID NO: 83:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (xi) SEQUENCE DESCRIPTION: SEQ ID NO: 83:

GATATCTCAG CTTCCAGCAG TGAAGACGAC ATTGAGGCCG ACCAC         45

(2) INFORMATION FOR SEQ ID NO: 84:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 84:

CCGGTTCTGA AACACTGGAA ACGTAAGTAG CGGCCG                  36

(2) INFORMATION FOR SEQ ID NO: 85:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (xi) SEQUENCE DESCRIPTION: SEQ ID NO: 85:

Ser Ser Ser Glu Asp Asp Ile Glu Ala Asp His
1               5                   10

(2) INFORMATION FOR SEQ ID NO: 86:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (xi) SEQUENCE DESCRIPTION: SEQ ID NO: 86:

Pro Val Leu Lys His Trp Lys Arg
1               5

(2) INFORMATION FOR SEQ ID NO: 87:

(i) SEQUENCE CHARACTERISTICS:
        (A) LENGTH: 72 base pairs
        (B) TYPE: nucleic acid
        (C) STRANDEDNESS: unknown
        (D) TOPOLOGY: unknown (xi) SEQUENCE DESCRIPTION: SEQ ID NO: 87:

GATATCACAG GTGTCTTAAG TGGAGCTAGC GGCGGTGGTG GTTCCGGTGG CGGCGGAGAC      60

TCCGAAAGGC AT                                                          72

(2) INFORMATION FOR SEQ ID NO: 88:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO: 88:

ATCACTGTGG AGTGGTCCTC AGGTACGGCC GCC                                   33

(2) INFORMATION FOR SEQ ID NO: 89:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (xi) SEQUENCE DESCRIPTION: SEQ ID NO: 89:

Val Leu Ser Gly Ala Ser Gly Gly Gly Gly Ser Gly Gly Gly Gly As
1               5                   10                  15

Ser Glu Arg His
            20

(2) INFORMATION FOR SEQ ID NO: 90:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (xi) SEQUENCE DESCRIPTION: SEQ ID NO: 90:

Ile Thr Val Glu Trp Ser Ser
1               5

(2) INFORMATION FOR SEQ ID NO: 91:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (xi) SEQUENCE DESCRIPTION: SEQ ID NO: 91:

```
GATATCTCAG CTTCCAGCAG TATCAAAGAA GAACATGTGA TCATC            45
```

(2) INFORMATION FOR SEQ ID NO: 92:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 92:

```
CCAGAGACTA CAGAGAACAA ACGTAAGTAG CGGCCG                      36
```

(2) INFORMATION FOR SEQ ID NO: 93:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (xi) SEQUENCE DESCRIPTION: SEQ ID NO: 93:

```
Ser Ser Ser Ile Lys Glu Glu His Val Ile Ile
1               5                   10
```

(2) INFORMATION FOR SEQ ID NO: 94:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (xi) SEQUENCE DESCRIPTION: SEQ ID NO: 94:

```
Pro Glu Thr Thr Glu Asn Lys Arg
1               5
```

(2) INFORMATION FOR SEQ ID NO: 95:

(i) SEQUENCE CHARACTERISTICS:
        (A) LENGTH: 90 base pairs
        (B) TYPE: nucleic acid
        (C) STRANDEDNESS: unknown
        (D) TOPOLOGY: unknown (xi) SEQUENCE DESCRIPTION: SEQ ID NO: 95:

```
GATATCACAG GTGTCTTAAG TGGAGCTAGC GGAGGGGGCG GGTTCGGAGG TGGTGGGGAC   60

ACCCGACCAC GTTTCTTGTG GCAGCTGAAG                                    90
```

(2) INFORMATION FOR SEQ ID NO: 96:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (xi) SEQUENCE DESCRIPTION: SEQ ID NO: 96:

```
TCTGAATCTG CACAGAGCAA GTCCTCAGGT ACGGCCG                              37
```

(2) INFORMATION FOR SEQ ID NO: 97:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (xi) SEQUENCE DESCRIPTION: SEQ ID NO: 97:

```
Val Leu Ser Gly Ala Ser Gly Gly Gly Ser Gly Gly Gly As
 1               5                  10                  15

Thr Arg Pro Arg Phe Leu Trp Gln Leu Lys
                20                  25
```

(2) INFORMATION FOR SEQ ID NO: 98:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (xi) SEQUENCE DESCRIPTION: SEQ ID NO: 98:

```
Ser Glu Ser Ala Gln Ser Lys Ser Ser
 1               5
```

(2) INFORMATION FOR SEQ ID NO: 99:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (xi) SEQUENCE DESCRIPTION: SEQ ID NO: 99:

```
GTCCAGCTGT CTTGTTTCAG TACTGATC                                       28
```

(2) INFORMATION FOR SEQ ID NO: 100:

(i) SEQUENCE CHARACTERISTICS:
        (A) LENGTH: 14 base pairs
        (B) TYPE: nucleic acid
        (C) STRANDEDNESS: unknown
        (D) TOPOLOGY: unknown (xi) SEQUENCE DESCRIPTION: SEQ ID NO: 100:

```
GTAAGTAGCG GCCG                                                      14
```

(2) INFORMATION FOR SEQ ID NO: 101:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (xi) SEQUENCE DESCRIPTION: SEQ ID NO: 101:

```
GGTATGTAAA AATAAACATC ACAG                                           24
```

(2) INFORMATION FOR SEQ ID NO: 102:

(i) SEQUENCE CHARACTERISTICS:
        (A) LENGTH: 21 base pairs
        (B) TYPE: nucleic acid
        (C) STRANDEDNESS: unknown (D) TOPOLOGY: unknown (xi) SEQUENCE DESCRIPTION: SEQ ID NO: 102:

GCTTTGCTTA CGGAGTTACT C                                              21

(2) INFORMATION FOR SEQ ID NO: 103:

(i) SEQUENCE CHARACTERISTICS:
        (A) LENGTH: 95 base pairs
        (B) TYPE: nucleic acid
        (C) STRANDEDNESS: unknown
        (D) TOPOLOGY: unknown (xi) SEQUENCE DESCRIPTION: SEQ ID NO: 103:

CCCGGGCCAC CATGCCGTGC AGCAGAGCTC TGATTCTGGG GGTCCTCGCC CTGAACACCA     60

TGCTCAGCCT CTGCGGAGGT GAAGACGACA TTGAG                               95

(2) INFORMATION FOR SEQ ID NO: 104:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (xi) SEQUENCE DESCRIPTION: SEQ ID NO: 104:

CGATCAGGTG GCACCTCCAG ACACCCAGGG CCTTTATGAG AATTC                    45

(2) INFORMATION FOR SEQ ID NO: 105:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (xi) SEQUENCE DESCRIPTION: SEQ ID NO: 105:

Met Pro Cys Ser Arg Ala Leu Ile Leu Gly Val Leu Ala Leu Asn Th
1               5                   10                  15

Met Leu Ser Leu Cys Gly Gly Glu Asp Asp Ile Glu
            20                  25

(2) INFORMATION FOR SEQ ID NO: 106:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (xi) SEQUENCE DESCRIPTION: SEQ ID NO: 106:

Arg Ser Gly Gly Thr Ser Arg His Pro Gly Pro Leu
1               5                   10

(2) INFORMATION FOR SEQ ID NO: 107:

(i) SEQUENCE CHARACTERISTICS:
        (A) LENGTH: 194 base pairs
        (B) TYPE: nucleic acid
        (C) STRANDEDNESS: unknown
        (D) TOPOLOGY: unknown (xi) SEQUENCE DESCRIPTION: SEQ ID NO: 107:

AAGCTTCCCG GGCCACCATG GCTCTGCAGA TCCCCAGCCT CCTCCTCTCA GCTGCTGTGG    60

TGGTGCTGAT GGTGCTGAGC AGCCCAAGGA CCTTAAGTAT CTCTCAGGCT GTTCACGCT    120

```
CTCACGCTGA AATCAACGAA GCTGGTCGTG CTAGCGGAGG GGGCGGAAGC GGCGGAGGG      180

GAAACTCCGA AAGG                                                       194
```

(2) INFORMATION FOR SEQ ID NO: 108:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (xi) SEQUENCE DESCRIPTION: SEQ ID NO: 108:

```
CCTCCTCCAG CAGGGCTCCT GCAGTGAGAA TTCGAGCTC                             39
```

(2) INFORMATION FOR SEQ ID NO: 109:

(i) SEQUENCE CHARACTERISTICS:
        (A) LENGTH: 59 amino acids
        (B) TYPE: amino acid
        (C) STRANDEDNESS: unknown
        (D) TOPOLOGY: unknown (xi) SEQUENCE DESCRIPTION: SEQ ID NO: 109:

```
Met Ala Leu Gln Ile Pro Ser Leu Leu Leu Ser Ala Ala Val Val Va
1               5                   10                  15

Leu Met Val Leu Ser Ser Pro Arg Thr Leu Ser Ile Ser Gln Ala Va
            20                  25                  30

His Ala Ala His Ala Glu Ile Asn Glu Ala Gly Arg Ala Ser Gly Gl
            35                  40                  45

Gly Gly Ser Gly Gly Gly Gly Asn Ser Glu Arg
    50                  55
```

(2) INFORMATION FOR SEQ ID NO: 110:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (xi) SEQUENCE DESCRIPTION: SEQ ID NO: 110:

```
Pro Pro Pro Ala Gly Leu Leu Gln
1               5
```

(2) INFORMATION FOR SEQ ID NO: 111:

(i) SEQUENCE CHARACTERISTICS:
        (A) LENGTH: 43 base pairs
        (B) TYPE: nucleic acid
        (C) STRANDEDNESS: unknown
        (D) TOPOLOGY: unknown (xi) SEQUENCE DESCRIPTION: SEQ ID NO: 111:

```
CCCCCCCCGC GGCCGCCCCA CCATGGGACT GAGTAACATT CTC                       43
```

(2) INFORMATION FOR SEQ ID NO: 112:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO: 112:

CCCCCCGCGG CCGCTTTAAA AACATGTATC ACTTTT                                      36

(2) INFORMATION FOR SEQ ID NO: 113:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 113:

CCCCCCGCCA TGGCCGCTAG CGGAGGGGGC GGAAGC                                      36

(2) INFORMATION FOR SEQ ID NO: 114:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 114:

CCCGGGGCCT CGAGTGAAGA CGACATTGAG GCCGAC                                      36

(2) INFORMATION FOR SEQ ID NO: 115:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (xi) SEQUENCE DESCRIPTION: SEQ ID NO: 115:

CCCCCCACTA GTCCACTCCA CAGTGATGGG GCT                                         33

(2) INFORMATION FOR SEQ ID NO: 116:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 116:

CCCCCCCCCG GGACCAGTGT TTCAGAACCG GCTCCTC                                     37

(2) INFORMATION FOR SEQ ID NO: 117:

(i) SEQUENCE CHARACTERISTICS:
        (A) LENGTH: 65 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 117:

TCGAGGAACC GCCACCGCCA GAACCGCCGC CACCGGAACC ACCACCGCCG CTGCCACCGC            60

CACCA                                                                        65

(2) INFORMATION FOR SEQ ID NO: 118:

(i) SEQUENCE CHARACTERISTICS:
        (A) LENGTH: 65 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 118:

CTAGTGGTGG CGGTGGCAGC GGCGGTGGTG GTTCCGGTGG CGGCGGTTCT GGCGGTGGCG    60

GTTCC                                                                65

(2) INFORMATION FOR SEQ ID NO: 119:

(i) SEQUENCE CHARACTERISTICS:
        (A) LENGTH: 22 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 119:

CTTGGGAATC TTGACTAAGA GG                                             22

(2) INFORMATION FOR SEQ ID NO: 120:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 120:

CAGGTCGAAT TCTCATTCCA TCGGCATGTA CTCTTCTTCC TCCCAGTGTT TCAGAACCGG    60

(2) INFORMATION FOR SEQ ID NO: 121:

(i) SEQUENCE CHARACTERISTICS:
        (A) LENGTH: 1385 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 6..1382

(xi) SEQUENCE DESCRIPTION: SEQ ID NO: 121:

CCACC ATG GCT CTG CAG ATC CCC AGC CTC CTC CTC TCA GCT GCT GTG         47
      Met Ala Leu Gln Ile Pro Ser Leu Leu Leu Ser Ala Ala Val
       1               5                  10

GTG GTG CTG ATG GTG CTG AGC AGC CCA AGG ACC TTA AGT ATC TCT CAG       95
Val Val Leu Met Val Leu Ser Ser Pro Arg Thr Leu Ser Ile Ser Gln
 15                  20                  25                  30

GCT GTT CAC GCT GCT CAC GCT GAA ATC AAC GAA GCT GGT CGT GCT AGC      143
Ala Val His Ala Ala His Ala Glu Ile Asn Glu Ala Gly Arg Ala Ser
                 35                  40                  45

GGA GGG GGC GGA AGC GGC GGA GGG GGA AAC TCC GAA AGG CAT TTC GTG      191
Gly Gly Gly Gly Ser Gly Gly Gly Gly Asn Ser Glu Arg His Phe Val
             50                  55                  60

-continued

| | |
|---|---|
| GTC CAG TTC AAG GGC GAG TGC TAC TAC ACC AAC GGG ACG CAG CGC ATA<br>Val Gln Phe Lys Gly Glu Cys Tyr Tyr Thr Asn Gly Thr Gln Arg Ile<br>        65                      70                  75 | 239 |
| CGG CTC GTG ACC AGA TAC ATC TAC AAC CGG GAG GAG TAC GTG CGC TAC<br>Arg Leu Val Thr Arg Tyr Ile Tyr Asn Arg Glu Glu Tyr Val Arg Tyr<br>        80                      85                  90 | 287 |
| GAC AGC GAC GTG GGC GAG TAC CGC GCG GTG ACC GAG CTG GGG CGG CCA<br>Asp Ser Asp Val Gly Glu Tyr Arg Ala Val Thr Glu Leu Gly Arg Pro<br>95                    100                 105               110 | 335 |
| GAC GCC GAG TAC TGG AAC AGC CAG CCG GAG ATC CTG GAG CGA ACG CGG<br>Asp Ala Glu Tyr Trp Asn Ser Gln Pro Glu Ile Leu Glu Arg Thr Arg<br>                115               120               125 | 383 |
| GCC GAG GTG GAC ACG GCG TGC AGA CAC AAC TAC GAG GGG CCG GAG ACC<br>Ala Glu Val Asp Thr Ala Cys Arg His Asn Tyr Glu Gly Pro Glu Thr<br>            130               135               140 | 431 |
| AGC ACC TCC CTG CGG CGG CTT GAA CAG CCC AAT GTC GCC ATC TCC CTG<br>Ser Thr Ser Leu Arg Arg Leu Glu Gln Pro Asn Val Ala Ile Ser Leu<br>          145               150               155 | 479 |
| TCC AGG ACA GAG GCC CTC AAC CAC CAC AAC ACT CTG GTC TGT TCG GTG<br>Ser Arg Thr Glu Ala Leu Asn His His Asn Thr Leu Val Cys Ser Val<br>160                   165               170 | 527 |
| ACA GAT TTC TAC CCA GCC AAG ATC AAA GTG CGC TGG TTC AGG AAT GGC<br>Thr Asp Phe Tyr Pro Ala Lys Ile Lys Val Arg Trp Phe Arg Asn Gly<br>175                   180               185               190 | 575 |
| CAG GAG GAG ACA GTG GGG GTC TCA TCC ACA CAG CTT ATT AGG AAT GGG<br>Gln Glu Glu Thr Val Gly Val Ser Ser Thr Gln Leu Ile Arg Asn Gly<br>                195               200               205 | 623 |
| GAC TGG ACC TTC CAG GTC CTG GTC ATG CTG GAG ATG ACC CCT CAT CAG<br>Asp Trp Thr Phe Gln Val Leu Val Met Leu Glu Met Thr Pro His Gln<br>            210               215               220 | 671 |
| GGA GAG GTC TAC ACC TGC CAT GTG GAG CAT CCC AGC CTG AAG AGC CCC<br>Gly Glu Val Tyr Thr Cys His Val Glu His Pro Ser Leu Lys Ser Pro<br>                225               230               235 | 719 |
| ATC ACT GTG GAG TGG ACT AGT GGT GGC GGT GGC AGC GGC GGT GGT GGT<br>Ile Thr Val Glu Trp Thr Ser Gly Gly Gly Gly Ser Gly Gly Gly Gly<br>        240               245               250 | 767 |
| TCC GGT GGC GGC GGT TCT GGC GGT GGC GGT TCC TCG AGT GAA GAC GAC<br>Ser Gly Gly Gly Gly Ser Gly Gly Gly Gly Ser Ser Ser Glu Asp Asp<br>255                   260               265               270 | 815 |
| ATT GAG GCC GAC CAC GTA GGC TTC TAT GGT ACA ACT GTT TAT CAG TCT<br>Ile Glu Ala Asp His Val Gly Phe Tyr Gly Thr Thr Val Tyr Gln Ser<br>                275               280               285 | 863 |
| CCT GGA GAC ATT GGC CAG TAC ACA CAT GAA TTT GAT GGT GAT GAG TTG<br>Pro Gly Asp Ile Gly Gln Tyr Thr His Glu Phe Asp Gly Asp Glu Leu<br>        290               295               300 | 911 |
| TTC TAT GTG GAC TTG GAT AAG AAG AAA ACT GTC TGG AGG CTT CCT GAG<br>Phe Tyr Val Asp Leu Asp Lys Lys Lys Thr Val Trp Arg Leu Pro Glu<br>          305               310               315 | 959 |
| TTT GGC CAA TTG ATA CTC TTT GAG CCC CAA GGT GGA CTG CAA AAC ATA<br>Phe Gly Gln Leu Ile Leu Phe Glu Pro Gln Gly Gly Leu Gln Asn Ile<br>320                   325               330 | 1007 |
| GCT GCA GAA AAA CAC AAC TTG GGA ATC TTG ACT AAG AGG TCA AAT TTC<br>Ala Ala Glu Lys His Asn Leu Gly Ile Leu Thr Lys Arg Ser Asn Phe<br>335                   340               345               350 | 1055 |
| ACC CCA GCT ACC AAT GAG GCT CCT CAA GCG ACT GTG TTC CCC AAG TCC<br>Thr Pro Ala Thr Asn Glu Ala Pro Gln Ala Thr Val Phe Pro Lys Ser<br>                355               360               365 | 1103 |
| CCT GTG CTG CTG GGT CAG CCC AAC ACC CTT ATC TGC TTT GTG GAC AAC<br>Pro Val Leu Leu Gly Gln Pro Asn Thr Leu Ile Cys Phe Val Asp Asn<br>                370               375               380 | 1151 |

```
ATC TTC CCA CCT GTG ATC AAC ATC ACA TGG CTC AGA AAT AGC AAG TCA      1199
Ile Phe Pro Pro Val Ile Asn Ile Thr Trp Leu Arg Asn Ser Lys Ser
            385                 390                 395

GTC ACA GAC GGC GTT TAT GAG ACC AGC TTC CTC GTC AAC CGT GAC CAT      1247
Val Thr Asp Gly Val Tyr Glu Thr Ser Phe Leu Val Asn Arg Asp His
400                 405                 410

TCC TTC CAC AAG CTG TCT TAT CTC ACC TTC ATC CCT TCT GAT GAT GAC      1295
Ser Phe His Lys Leu Ser Tyr Leu Thr Phe Ile Pro Ser Asp Asp Asp
415                 420                 425                 430

ATT TAT GAC TGC AAG GTG GAG CAC TGG GGC CTG GAG GAG CCG GTT CTG      1343
Ile Tyr Asp Cys Lys Val Glu His Trp Gly Leu Glu Glu Pro Val Leu
                435                 440                 445

AAA CAC TGG TCC CGG GCT AGT CAC CAT CAC CAT CAT CAC TAG              1385
Lys His Trp Ser Arg Ala Ser His His His His His His
            450                 455
```

(2) INFORMATION FOR SEQ ID NO: 122:

(i) SEQUENCE CHARACTERISTICS:
        (A) LENGTH: 1508 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 6..1505

(xi) SEQUENCE DESCRIPTION: SEQ ID NO: 122:

```
CCACC ATG GCT CTG CAG ATC CCC AGC CTC CTC CTC TCA GCT GCT GTG        47
      Met Ala Leu Gln Ile Pro Ser Leu Leu Leu Ser Ala Ala Val
      460                 465                 470

GTG GTG CTG ATG GTG CTG AGC AGC CCA AGG ACC TTA AGT ATC TCT CAG      95
Val Val Leu Met Val Leu Ser Ser Pro Arg Thr Leu Ser Ile Ser Gln
475                 480                 485

GCT GTT CAC GCT GCT CAC GCT GAA ATC AAC GAA GCT GGT CGT GCT AGC      143
Ala Val His Ala Ala His Ala Glu Ile Asn Glu Ala Gly Arg Ala Ser
490                 495                 500                 505

GGA GGG GGC GGA AGC GGC GGA GGG GGA AAC TCC GAA AGG CAT TTC GTG      191
Gly Gly Gly Gly Ser Gly Gly Gly Gly Asn Ser Glu Arg His Phe Val
                510                 515                 520

GTC CAG TTC AAG GGC GAG TGC TAC TAC ACC AAC GGG ACG CAG CGC ATA      239
Val Gln Phe Lys Gly Glu Cys Tyr Tyr Thr Asn Gly Thr Gln Arg Ile
            525                 530                 535

CGG CTC GTG ACC AGA TAC ATC TAC AAC CGG GAG GAG TAC GTG CGC TAC      287
Arg Leu Val Thr Arg Tyr Ile Tyr Asn Arg Glu Glu Tyr Val Arg Tyr
            540                 545                 550

GAC AGC GAC GTG GGC GAG TAC CGC GCG GTG ACC GAG CTG GGG CGG CCA      335
Asp Ser Asp Val Gly Glu Tyr Arg Ala Val Thr Glu Leu Gly Arg Pro
555                 560                 565

GAC GCC GAG TAC TGG AAC AGC CAG CCG GAG ATC CTG GAG CGA ACG CGG      383
Asp Ala Glu Tyr Trp Asn Ser Gln Pro Glu Ile Leu Glu Arg Thr Arg
570                 575                 580                 585

GCC GAG GTG GAC ACG GCG TGC AGA CAC AAC TAC GAG GGG CCG GAG ACC      431
Ala Glu Val Asp Thr Ala Cys Arg His Asn Tyr Glu Gly Pro Glu Thr
                590                 595                 600

AGC ACC TCC CTG CGG CGG CTT GAA CAG CCC AAT GTC GCC ATC TCC CTG      479
Ser Thr Ser Leu Arg Arg Leu Glu Gln Pro Asn Val Ala Ile Ser Leu
            605                 610                 615
```

-continued

| | | |
|---|---|---|
| TCC AGG ACA GAG GCC CTC AAC CAC CAC AAC ACT CTG GTC TGT TCG GTG<br>Ser Arg Thr Glu Ala Leu Asn His His Asn Thr Leu Val Cys Ser Val<br>      620                       625                       630 | 527 | |
| ACA GAT TTC TAC CCA GCC AAG ATC AAA GTG CGC TGG TTC AGG AAT GGC<br>Thr Asp Phe Tyr Pro Ala Lys Ile Lys Val Arg Trp Phe Arg Asn Gly<br>635                       640                       645 | 575 | |
| CAG GAG GAG ACA GTG GGG GTC TCA TCC ACA CAG CTT ATT AGG AAT GGG<br>Gln Glu Glu Thr Val Gly Val Ser Ser Thr Gln Leu Ile Arg Asn Gly<br>650                       655                       660                     665 | 623 | |
| GAC TGG ACC TTC CAG GTC CTG GTC ATG CTG GAG ATG ACC CCT CAT CAG<br>Asp Trp Thr Phe Gln Val Leu Val Met Leu Glu Met Thr Pro His Gln<br>                   670                       675                     680 | 671 | |
| GGA GAG GTC TAC ACC TGC CAT GTG GAG CAT CCC AGC CTG AAG AGC CCC<br>Gly Glu Val Tyr Thr Cys His Val Glu His Pro Ser Leu Lys Ser Pro<br>                   685                       690                     695 | 719 | |
| ATC ACT GTG GAG TGG ACT AGT GGT GGC GGT GGC AGC GGC GGT GGT GGT<br>Ile Thr Val Glu Trp Thr Ser Gly Gly Gly Gly Ser Gly Gly Gly Gly<br>               700                       705                     710 | 767 | |
| TCC GGT GGC GGC GGT TCT GGC GGT GGC GGT TCC TCG AGT GAA GAC GAC<br>Ser Gly Gly Gly Gly Ser Gly Gly Gly Gly Ser Ser Ser Glu Asp Asp<br>         715                       720                       725 | 815 | |
| ATT GAG GCC GAC CAC GTA GGC TTC TAT GGT ACA ACT GTT TAT CAG TCT<br>Ile Glu Ala Asp His Val Gly Phe Tyr Gly Thr Thr Val Tyr Gln Ser<br>730                       735                       740                     745 | 863 | |
| CCT GGA GAC ATT GGC CAG TAC ACA CAT GAA TTT GAT GGT GAT GAG TTG<br>Pro Gly Asp Ile Gly Gln Tyr Thr His Glu Phe Asp Gly Asp Glu Leu<br>                   750                       755                     760 | 911 | |
| TTC TAT GTG GAC TTG GAT AAG AAG AAA ACT GTC TGG AGG CTT CCT GAG<br>Phe Tyr Val Asp Leu Asp Lys Lys Lys Thr Val Trp Arg Leu Pro Glu<br>                   765                       770                     775 | 959 | |
| TTT GGC CAA TTG ATA CTC TTT GAG CCC CAA GGT GGA CTG CAA AAC ATA<br>Phe Gly Gln Leu Ile Leu Phe Glu Pro Gln Gly Gly Leu Gln Asn Ile<br>         780                       785                       790 | 1007 | |
| GCT GCA GAA AAA CAC AAC TTG GGA ATC TTG ACT AAG AGG TCA AAT TTC<br>Ala Ala Glu Lys His Asn Leu Gly Ile Leu Thr Lys Arg Ser Asn Phe<br>795                       800                       805 | 1055 | |
| ACC CCA GCT ACC AAT GAG GCT CCT CAA GCG ACT GTG TTC CCC AAG TCC<br>Thr Pro Ala Thr Asn Glu Ala Pro Gln Ala Thr Val Phe Pro Lys Ser<br>810                       815                       820                     825 | 1103 | |
| CCT GTG CTG CTG GGT CAG CCC AAC ACC CTT ATC TGC TTT GTG GAC AAC<br>Pro Val Leu Leu Gly Gln Pro Asn Thr Leu Ile Cys Phe Val Asp Asn<br>                   830                       835                     840 | 1151 | |
| ATC TTC CCA CCT GTG ATC AAC ATC ACA TGG CTC AGA AAT AGC AAG TCA<br>Ile Phe Pro Pro Val Ile Asn Ile Thr Trp Leu Arg Asn Ser Lys Ser<br>                   845                       850                     855 | 1199 | |
| GTC ACA GAC GGC GTT TAT GAG ACC AGC TTC CTC GTC AAC CGT GAC CAT<br>Val Thr Asp Gly Val Tyr Glu Thr Ser Phe Leu Val Asn Arg Asp His<br>                 860                       865                     870 | 1247 | |
| TCC TTC CAC AAG CTG TCT TAT CTC ACC TTC ATC CCT TCT GAT GAT GAC<br>Ser Phe His Lys Leu Ser Tyr Leu Thr Phe Ile Pro Ser Asp Asp Asp<br>875                       880                       885 | 1295 | |
| ATT TAT GAC TGC AAG GTG GAG CAC TGG GGC CTG GAG GAG CCG GTT CTG<br>Ile Tyr Asp Cys Lys Val Glu His Trp Gly Leu Glu Glu Pro Val Leu<br>890                       895                       900                     905 | 1343 | |
| AAA CAC TGG GAA CCT GAG ATT CCA GCC CCC ATG TCA GAG CTG ACA GAA<br>Lys His Trp Glu Pro Glu Ile Pro Ala Pro Met Ser Glu Leu Thr Glu<br>                   910                       915                     920 | 1391 | |
| ACT GTG GTG TGT GCC CTG GGG TTG TCT GTG GGC CTT GTG GGC ATC GTG<br>Thr Val Val Cys Ala Leu Gly Leu Ser Val Gly Leu Val Gly Ile Val<br>                   925                       930                     935 | 1439 | |

-continued

```
GTG GGC ACC ATC TTC ATC ATT CAA GGC CTG CGA TCA GGT GGC ACC TCC        1487
Val Gly Thr Ile Phe Ile Ile Gln Gly Leu Arg Ser Gly Gly Thr Ser
            940             945             950

AGA CAC CCA GGG CCT TTA TGA                                            1508
Arg His Pro Gly Pro Leu
    955
```

(2) INFORMATION FOR SEQ ID NO: 123:

(i) SEQUENCE CHARACTERISTICS:
        (A) LENGTH: 1382 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 6..1382

(xi) SEQUENCE DESCRIPTION: SEQ ID NO: 123:

```
CCACC ATG GCT CTG CAG ATC CCC AGC CTC CTC CTC TCA GCT GCT GTG           47
      Met Ala Leu Gln Ile Pro Ser Leu Leu Leu Ser Ala Ala Val
                        505                 510

GTG GTG CTG ATG GTG CTG AGC AGC CCA AGG ACC TTA AGT ATC TCT CAG         95
Val Val Leu Met Val Leu Ser Ser Pro Arg Thr Leu Ser Ile Ser Gln
515             520                 525                 530

GCT GTT CAC GCT GCT CAC GCT GAA ATC AAC GAA GCT GGT CGT GCT AGC        143
Ala Val His Ala Ala His Ala Glu Ile Asn Glu Ala Gly Arg Ala Ser
                535                 540                 545

GGA GGG GGC GGA AGC GGC GGA GGG GGA AAC TCC GAA AGG CAT TTC GTG        191
Gly Gly Gly Gly Ser Gly Gly Gly Gly Asn Ser Glu Arg His Phe Val
                550                 555                 560

GTC CAG TTC AAG GGC GAG TGC TAC TAC ACC AAC GGG ACG CAG CGC ATA        239
Val Gln Phe Lys Gly Glu Cys Tyr Tyr Thr Asn Gly Thr Gln Arg Ile
            565             570                 575

CGG CTC GTG ACC AGA TAC ATC TAC AAC CGG GAG GAG TAC GTG CGC TAC        287
Arg Leu Val Thr Arg Tyr Ile Tyr Asn Arg Glu Glu Tyr Val Arg Tyr
580                 585                 590

GAC AGC GAC GTG GGC GAG TAC CGC GCG GTG ACC GAG CTG GGG CGG CCA        335
Asp Ser Asp Val Gly Glu Tyr Arg Ala Val Thr Glu Leu Gly Arg Pro
595                 600                 605                 610

GAC GCC GAG TAC TGG AAC AGC CAG CCG GAG ATC CTG GAG CGA ACG CGG        383
Asp Ala Glu Tyr Trp Asn Ser Gln Pro Glu Ile Leu Glu Arg Thr Arg
                615                 620                 625

GCC GAG GTG GAC ACG GCG TGC AGA CAC AAC TAC GAG GGG CCG GAG ACC        431
Ala Glu Val Asp Thr Ala Cys Arg His Asn Tyr Glu Gly Pro Glu Thr
                630                 635                 640

AGC ACC TCC CTG CGG CGG CTT GAA CAG CCC AAT GTC GCC ATC TCC CTG        479
Ser Thr Ser Leu Arg Arg Leu Glu Gln Pro Asn Val Ala Ile Ser Leu
            645                 650                 655

TCC AGG ACA GAG GCC CTC AAC CAC CAC AAC ACT CTG GTC TGT TCG GTG        527
Ser Arg Thr Glu Ala Leu Asn His His Asn Thr Leu Val Cys Ser Val
660                 665                 670

ACA GAT TTC TAC CCA GCC AAG ATC AAA GTG CGC TGG TTC AGG AAT GGC        575
Thr Asp Phe Tyr Pro Ala Lys Ile Lys Val Arg Trp Phe Arg Asn Gly
675             680                 685                 690

CAG GAG GAG ACA GTG GGG GTC TCA TCC ACA CAG CTT ATT AGG AAT GGG        623
Gln Glu Glu Thr Val Gly Val Ser Ser Thr Gln Leu Ile Arg Asn Gly
                    695                 700                 705
```

-continued

```
GAC TGG ACC TTC CAG GTC CTG GTC ATG CTG GAG ATG ACC CCT CAT CAG        671
Asp Trp Thr Phe Gln Val Leu Val Met Leu Glu Met Thr Pro His Gln
            710                 715                 720

GGA GAG GTC TAC ACC TGC CAT GTG GAG CAT CCC AGC CTG AAG AGC CCC        719
Gly Glu Val Tyr Thr Cys His Val Glu His Pro Ser Leu Lys Ser Pro
                725                 730                 735

ATC ACT GTG GAG TGG ACT AGT GGT GGC GGT GGC AGC GGC GGT GGT GGT        767
Ile Thr Val Glu Trp Thr Ser Gly Gly Gly Gly Ser Gly Gly Gly Gly
    740                 745                 750

TCC GGT GGC GGC GGT TCT GGT GGC GGT TCC TCG AGT GAA GAC GAC            815
Ser Gly Gly Gly Gly Ser Gly Gly Gly Ser Ser Ser Glu Asp Asp
755                 760                 765                 770

ATT GAG GCC GAC CAC GTA GGC TTC TAT GGT ACA ACT GTT TAT CAG TCT        863
Ile Glu Ala Asp His Val Gly Phe Tyr Gly Thr Thr Val Tyr Gln Ser
                775                 780                 785

CCT GGA GAC ATT GGC CAG TAC ACA CAT GAA TTT GAT GGT GAT GAG TTG        911
Pro Gly Asp Ile Gly Gln Tyr Thr His Glu Phe Asp Gly Asp Glu Leu
            790                 795                 800

TTC TAT GTG GAC TTG GAT AAG AAG AAA ACT GTC TGG AGG CTT CCT GAG        959
Phe Tyr Val Asp Leu Asp Lys Lys Lys Thr Val Trp Arg Leu Pro Glu
                805                 810                 815

TTT GGC CAA TTG ATA CTC TTT GAG CCC CAA GGT GGA CTG CAA AAC ATA       1007
Phe Gly Gln Leu Ile Leu Phe Glu Pro Gln Gly Gly Leu Gln Asn Ile
    820                 825                 830

GCT GCA GAA AAA CAC AAC TTG GGA ATC TTG ACT AAG AGG TCA AAT TTC       1055
Ala Ala Glu Lys His Asn Leu Gly Ile Leu Thr Lys Arg Ser Asn Phe
835                 840                 845                 850

ACC CCA GCT ACC AAT GAG GCT CCT CAA GCG ACT GTG TTC CCC AAG TCC       1103
Thr Pro Ala Thr Asn Glu Ala Pro Gln Ala Thr Val Phe Pro Lys Ser
                855                 860                 865

CCT GTG CTG CTG GGT CAG CCC AAC ACC CTT ATC TGC TTT GTG GAC AAC       1151
Pro Val Leu Leu Gly Gln Pro Asn Thr Leu Ile Cys Phe Val Asp Asn
            870                 875                 880

ATC TTC CCA CCT GTG ATC AAC ATC ACA TGG CTC AGA AAT AGC AAG TCA       1199
Ile Phe Pro Pro Val Ile Asn Ile Thr Trp Leu Arg Asn Ser Lys Ser
                885                 890                 895

GTC ACA GAC GGC GTT TAT GAG ACC AGC TTC CTC GTC AAC CGT GAC CAT       1247
Val Thr Asp Gly Val Tyr Glu Thr Ser Phe Leu Val Asn Arg Asp His
    900                 905                 910

TCC TTC CAC AAG CTG TCT TAT CTC ACC TTC ATC CCT TCT GAT GAT GAC       1295
Ser Phe His Lys Leu Ser Tyr Leu Thr Phe Ile Pro Ser Asp Asp Asp
915                 920                 925                 930

ATT TAT GAC TGC AAG GTG GAG CAC TGG GGC CTG GAG GAG CCG GTT CTG       1343
Ile Tyr Asp Cys Lys Val Glu His Trp Gly Leu Glu Glu Pro Val Leu
                935                 940                 945

AAA CAC TGG GAG GAA GAA GAG TAC ATG CCG ATG GAA TGA                   1382
Lys His Trp Glu Glu Glu Glu Tyr Met Pro Met Glu *
            950                 955
```

(2) INFORMATION FOR SEQ ID NO: 124:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (xi) SEQUENCE DESCRIPTION: SEQ ID NO: 124:

```
Ala Pro Tyr Ser Thr Leu Leu Pro Pro Glu Leu Ser Glu Thr Pro
1               5                   10                  15
```